(12) United States Patent
Cubicciotti

(10) Patent No.: US 6,287,765 B1
(45) Date of Patent: Sep. 11, 2001

(54) METHODS FOR DETECTING AND IDENTIFYING SINGLE MOLECULES

(75) Inventor: Roger S. Cubicciotti, Montclair, NJ (US)

(73) Assignee: Molecular Machines, Inc., Montclair, NJ (US)

( * ) Notice: Subject to any disclaimer, the term of this patent is extended or adjusted under 35 U.S.C. 154(b) by 0 days.

(21) Appl. No.: 09/081,930

(22) Filed: May 20, 1998

(51) Int. Cl.$^7$ ............................. C12Q 1/08; C12P 19/34; C07M 21/02
(52) U.S. Cl. ......................... 435/6; 435/91.2; 536/22.1; 536/23.1; 536/24.3; 536/24.5
(58) Field of Search ..................... 435/6, 91.2; 536/22.1, 536/23.1, 24.3, 24.5

(56) References Cited

U.S. PATENT DOCUMENTS

| | | | |
|---|---|---|---|
| 5,118,801 | 6/1992 | Lizardi et al. | 536/27 |
| 5,168,057 | 12/1992 | Oh et al. | 435/174 |
| 5,270,163 | 12/1993 | Gold et al. | 435/6 |
| 5,372,930 | 12/1994 | Colton et al. | 435/6 |
| 5,475,096 | 12/1995 | Gold et al. | 546/23.1 |
| 5,558,998 | 9/1996 | Hammond et al. | 435/6 |
| 5,567,588 | 10/1996 | Gold et al. | 435/6 |
| 5,582,981 | 12/1996 | Toole et al. | 435/6 |
| 5,589,332 | 12/1996 | Shih et al. | 435/6 |
| 5,591,578 | 1/1997 | Meade et al. | 435/6 |
| 5,620,854 | 4/1997 | Holzrichter et al. | 435/6 |
| 5,631,146 | 5/1997 | Szostak et al. | 435/91.1 |
| 5,637,459 | 6/1997 | Burke et al. | 435/6 |
| 5,656,739 | 8/1997 | Cubicciotti | 536/23.1 |
| 5,661,019 | 8/1997 | Oh et al. | 435/174 |
| 5,663,064 | 9/1997 | Burke et al. | 435/172.3 |
| 5,674,743 | 10/1997 | Ulmer | 435/287.2 |
| 5,705,337 | 1/1998 | Gold et al. | 435/6 |
| 5,705,348 | 1/1998 | Meade et al. | 435/6 |
| 5,707,796 | 1/1998 | Gold et al. | 435/6 |
| 5,712,375 | 1/1998 | Jensen et al. | 530/412 |
| 5,723,289 | 3/1998 | Eaton et al. | 435/6 |
| 5,723,592 | 3/1998 | Eaton et al. | 536/23.1 |
| 5,730,940 | 3/1998 | Nakagawa | 422/68.1 |
| 5,756,291 | 5/1998 | Griffin et al. | 435/6 |
| 5,763,175 * | 6/1998 | Brenner | 435/6 |
| 5,763,192 | 6/1998 | Kauffman et al. | 435/7.1 |
| 5,773,598 * | 6/1998 | Burke et al. | 536/231 |
| 5,811,238 * | 9/1998 | Stemmer et al. | 435/6 |

OTHER PUBLICATIONS

Bruno et al, "In vitro selection of DNA to chloroaromatics using magnetic microbead affinity separation and fluorescence detection", Biochem. Biophys. Res. Comm. 234:117–120 (Nov. 1997).*

Davis et al, "Use of a high affinity DNA ligand in flow cytometry", Nucleic Acids Research 24(4):702–706 (1996).*

Allen MJ, et al., (1991), "Scanning Tunneling Microscope Images of Adenine and Thymine at Atomic Resolution", Scanning Microsc 5:625–630.

Allen MJ, et al., (1993), "Analysis of Synthetic DNAs and DNA–Protamine Complexes with the Scanning Tunneling microscope", Scanning Microsc 7:563–574.

Allen MJ, et al., (1997), "AMF analysis of DNA–protamine complexes bound to mica", Nucleic Acids Res 25:2221–2226.

Bock, et al., (1992) "Selection of single–stranded DNA molecules that bind and inhibit human thrombin", Nature 255:564–566.

Ellington, AD, et al., (1990), "In vitro selection of RNA molecules that bind specific ligands", Nature 346:818–822.

Famulok M., et al., (1993), "Nucleic Acids and Molecular Biology", Nucleic Acids and Molecular Biology (Eds. F. Eckstein and D.M.J. Lilley), Springer–Verlag, Berlin, pp. 271–284.

Fitzwater T., et al., (1996), "[17] A Selex Primer", Methods in Enzymology 267:271–284.

Gold L., et al., (1995), "Diversity of Oligonucleotide Functions", Annu. Rev. Biochem. 64:763–797.

Hansma H.G., et al., (1991), "Progress in sequencing deoxyribonucleic acide with an atomic force microscope", J. Vac. Sci. Techn. B 9:1282–1284.

Jing TW, et al., (1993), "Structure of hydrated oligonucleotides studied by in situ scanning tunneling microscopy", Proc Natl Acad Sci USA 90:8934–8938.

Kim Y, et al., (1991), "Scanning Tunneling Microscopy Imaging of Synthetic Oligonucleotides And Oligonucleotide–Metal Complexes", Scanning Microsc 5:311–316.

Morris KN, et al., (1998), "High affinity ligands from in vitro selection: Complex targets", Proc Natl Acad Sci USA 95:2902–2907.

(List continued on next page.)

Primary Examiner—Jeffrey Fredman
(74) Attorney, Agent, or Firm—Licata & Tyrrell P.C.

(57) ABSTRACT

Multimolecular devices and drug delivery systems prepared from synthetic heteropolymers, heteropolymeric discrete structures, multivalent heteropolymeric hybrid structures, aptameric multimolecular devices, multivalent imprints, tethered specific recognition devices, paired specific recognition devices, nonaptameric multimolecular devices and immobilized multimolecular structures are provided, including molecular adsorbents and multimolecular adherents, adhesives, transducers, switches, sensors and delivery systems. Methods for selecting single synthetic nucleotides, shape-specific probes and specifically attractive surfaces for use in these multimolecular devices are also provided. In addition, paired nucleotide-nonnucleotide mapping libraries for transposition of selected populations of selected nonoligonucleotide molecules into selected populations of replicatable nucleotide sequences are described.

27 Claims, No Drawings

OTHER PUBLICATIONS

Murray MN, et al., (1993), "Atomic force microscopy of biochemically tagged DNA", Proc Natl Acad Sci USA 90:3811–3814.

Sellergren B. (1997), "Noncovalent molecular imprinting: antibody–like molecular recognition in polymeric network materials", Trends Anal. Chem. 16:310–320.

Shea KJ, et al., (1993), "Polymer Complements to Nucleotide Bases. Selective binding of Adenine Derivatives to Imprinted Polymers", J. Am. Chem. Soc. 115:3368–3369.

Spivak DA, et al., (1998), "Binding of Nucleotide Bases by Imprinted Polymers", Macromolecules 31:2160–2165.

Tyagi S., et al., (1996), "Molecular Beacons:Probes that Fluoresce upon Hybridization", Nature (Biotechnol) 14:303–308.

Vant–Hull B., et al, (1998), "The Mathematics of SELEX Against complex Targets", J Mol Biol 278:579–597.

Wang K.Y., et al., (1993), "DNA Aptamer Which Binds to and Inhibits Thrombin Exhibits a New Structural Motif for DNA", Biochemistry 32:1899–1904.

Zareie MH, et al., (1998), "Interactions of DNA with fluorescent dyes: by scanning tunneling microscopy", Int J Biol Macromol 23:7–10.

Eigen M et al. (1994), "Sorting single molecules: Application to diagnostics and evolutionary biotechnology", Proc. Natl. Acad. Sci. USA 91:5740–5747.

* cited by examiner

METHODS FOR DETECTING AND IDENTIFYING SINGLE MOLECULES

FIELD OF THE INVENTION

The instant invention relates to multimolecular devices for use in pharmaceuticals, medical devices, diagnostics, cosmetics, dentistry, nutraceuticals, agriceuticals, environmental remediation, industrial polymers, packaging, microelectronics, nanofabrication and molecular manufacturing. Molecular adhesives, adherents, adsorbents and multimolecular switches, sensors, transducers and delivery systems are produced by template-directed molecular assembly and device integration.

BACKGROUND OF THE INVENTION

The development of effective and reliable multimolecular devices such as receptor-activated drug delivery systems molecular-scale sensors, switches, transducers and actuators requires control over the relative position of molecules within multimolecular structures. Molecules may be connected within multimolecular structures by covalent attachment (i.e., chemical bonds) or noncovalent means, including self-assembly, specific binding, hybridization of complementary nucleic acid sequences, ionic bonding, hydrophobic interactions, intercalation, chelation and coordination of metals. However, precise, reproducible and scalable methods for production of useful synthetic multimolecular devices with positional control at the molecular scale have heretofore been lacking.

Biological systems perform intricate functions through sophisticated molecular organization of complex molecules such as enzymes, antibodies, transmitters, receptors and regulatory proteins. Such intricate functions include signal transduction, information processing, cellular replication, growth and differentiation, biosynthesis, detoxification and transduction of chemical energy into heat and work. Wound healing, blood coagulation, muscle contraction, hormone secretion and complement-mediated immunity, for example, all represent biological functions that depend on multi-tiered cascades of biochemical reactions performed by organized molecules. Transport of ions and metabolites, gene expression and protein assembly represent a few of the many cellular functions that rely on concerted interaction of multiple organized biochemical systems. Efforts to simulate the productivity and efficiency of biomolecular machinery have been only marginally successful because of the inability to recreate the structural organization of molecules and groups of molecules inherent in highly ordered biological systems.

Biological systems have evolved two major capabilities that enable molecular manufacturing and nanomachinery far more sophisticated than chemical and biochemical methods developed by man. First, they have mastered the art of self-assembly, wherein discrete molecules either spontaneously organize or are chaperoned into supramolecular assemblies that perform complex functions through concerted interaction of the constituent molecules. Second, the rate and direction of biological reactions is manipulated through compartmentalization of reactants, catalysts and products, most commonly through physical segregation by cellular or subcellular membranes.

Efforts to develop self-assembling systems and micro-compartmentalized biochemical reactions have escalated over the past several years. Historically, experimental approaches to self-assembly have been modeled after spontaneous association of lipids into monolayers and bilayer membranes. More recently, self-assembly has been attempted using lipid-protein mixtures, engineered proteins, branched DNA, and supramolecular chemistry.

Compartmentalization has been attempted through a wide range of approaches, including liposomes, microimmobilization techniques (e.g., photolithography) and targeted delivery (e.g., therapeutic immunoconjugates). Microscopic arrays of peptides and oligonucleotides have been achieved through light-directed combinatorial in situ synthesis on silicon substrates. However, the resolution of this technique is about a million-fold inadequate for ordered molecular arrays. Discrete resolution and manipulation of matter at the atomic level is being pursued through scanning tunneling microscopy and atomic force microscopy, but these techniques have not been developed for production-scale preparation of molecular arrays.

In a related area of bimolecular engineering, several types of bifunctional or hybrid molecules have been developed for diagnostic imaging and targeted drug delivery. Some of these include: chimeric antibodies, particularly humanized antibodies designed to eliminate human anti-mouse immune responses upon in vivo administration; bispecific antibodies, produced through enzymatic digestion of parent antibodies and controlled reconstitution using Fab fragments obtained from two different parents; conventional immunoconjugates, composed of a drug, toxin or imaging agent covalently attached or chelated to an antibody or antibody fragment through established immunochemical methods; and fusion proteins, most commonly immunotoxins for cancer therapy, generated from hybrid genes developed and expressed through recombinant methods. While these hybrid molecules, especially fusion proteins, provide a practical approach to controlled production of hybrid gene products, none of the above methods provides a unified approach to directed multimolecular assembly.

Many methods have been described for site-directed attachment of effectors (e.g., enzymes, isotopes, drugs, fluorophores) to antibodies, antigens, haptens and nucleic acid probes. However, these methods represent bulk techniques that do not provide sufficient specificity for reproducible preparation of ordered molecular pairs, groups or arrays. Further, while these methods enable production of bifunctional conjugates, they do not provide for concerted interaction between the constituent moieties (e.g., probe and reporter molecules).

Branched DNA has been used as a carrier for accommodating large numbers of enzyme labels (e.g., alkaline phosphatase), thus enabling biochemical amplification of specific binding reactions in diagnostic assays. Scientists investigating branched DNA as a three-dimensional structural design system have speculated that natural mechanisms by which drugs and particular proteins recognize and bind to specific sites on DNA could be applied to attach molecular electronic components to DNA for development of memory devices (Seeman (1993) Clin. Chem. 39:722). Seeman has also suggested attaching conducting polymers, such as trans-polyacetylene or polyphenothiazine, a PTL-ruthenium switch, and a redox bit into branched DNA structures. However, they have not suggested using a single oligonucleotide or hybridized pairs of oligonucleotides for coordinated placement of two or more different molecules within a single DNA structure. They also have not suggested selecting or engineering nucleotides to achieve requisite affinity for molecules that have no natural mechanism for recognizing specific sites on DNA.

Recognition and self-assembly are the two critical properties of chemical structures being explored in the rapidly advancing field of supramolecular chemistry. This field focuses on the designed chemistry of intermolecular bonds. For example, 12-crown-4-ether contains a central cavity that is highly specific for lithium. In fact, the components of this ring structure will self-assemble when exposed to a solution of lithium. Crown ethers and related structures are being investigated for their utility as highly selective sensors, sieves, synthetic enzymes and energy transfer structures for use in artificial photosynthesis. Other emerging applications include molecular switches, diodes, transistors and molecular wires, and it has been proposed that supermolecule interactions on thin films may enable computers to be built around liquid-phase assembly reactions.

A general method is described in Cubicciotti, U.S. Pat. No. 5,656,739 which provides for controlled placement of two or more selected molecules in appropriate spatial proximity to produce cooperative molecular assemblies. This method yields self-assembling multimolecular heteropolymeric complexes through use of synthetic heteropolymers or multivalent heteropolymeric hybrid structures comprising nucleotides having defined sequence segments with affinities for identified molecules.

Cubicciotti, U.S. Pat. No. 5,656,739 describes the advantages of synthetic oligonucleotides as assembly templates. Template-ordered molecules cooperate when brought into close spatial proximity, much like ordered biological molecules in living systems. Nucleic acids are particularly useful assembly templates not just because they can be selected to specifically bind nonoligonucleotide target molecules with high affinity (e.g., Tuerk and Gold (1990) Science 249:505–510), nor because they can hybridize by complementary base pairing. More important, only nucleic acids are capable roth of hybridizing other nucleic acids and specifically binding nonoligonucleotide molecules. Both forms of recognition can be programmably synthesized into in a single molecule or hybridized into a single discrete structure. A single nucleic acid molecule with two different binding specificities (i.e., a synthetic heteropolymer) can be synthesized at the push of a button and two or more synthetic heteropolymers can be hybridizably linked to one another.

Nucleotide-directed molecular assembly provides a general solution to the problem of molecular positioning by exploiting several key attributes of synthetic oligonucleotides. First, oligonucleotides can be designed or selected, e.g., by combinatorial methods, to specifically bind molecules of nearly any size and shape with high affinity, not simply other nucleic acids as once thought. Second, the informational properties of nucleotides enable reproducible synthesis of single oligonucleotides having two or more specific binding sites in defined spatial proximity within a single molecule. Third, the base pairing properties of nucleotides enable the splicing of any two useful binding sequences into a single discrete structure (i.e., a bifunctional hybrid structure) by programmable self-assembly (i.e., hybridization). Fourth, oligonucleotides comprising modified nucleotides can be used to attach selected molecules (e.g., ligands, receptors, structural or effector molecules) at the 3' or 5' ends or at defined positions along the nucleotide sequence. Multivalent assembly structures can therefore be designed to specifically recognize different effector molecules and position them to perform cooperative functions such as energy transfer, signal transduction, multistep enzymatic processing, molecular sensing, molecular switching and targeted or triggered molecular delivery, release and/or activation, e.g., as particularly useful in drug delivery. Designer oligonucleotides can be cost-effectively produced at large scale using automated synthesizers, and they can be conveniently attached to surfaces and nanostructures to permit self-assembly of immobilized devices and on-chip molecular arrays.

Unnatural bases and modified nucleotides comprising synthetic oligonucleotides are useful as diagnostic reagents, molecular biology tools and probes of nucleic acid structure and function (e.g., Goodchild (1990) Bioconjugate Chemistry 1:165–187;Beaucage et al. (1993) Tetrahedron 49:1925–1963). Prior art modified nucleotides include natural bases linked by spacers arms to molecular reporters (e.g., spin labels, fluorophores, quenchers, DNP, digoxigenin and biotin) and analogs designed to enhance duplex stability and chemical stability. Novel bases (i.e., analogs) include unnatural nucleotides designed to increase coding diversity (e.g., Piccirilli et al. (1990) Nature 343:33–37. Nucleic acids are useful materials for programmable self-assembly, because the bases and backbone can be extensively modified without compromising molecular recognition properties, stability or hybridization rates and without destroying the relatively rigid structure of short duplex oligonucleotides. Several nucleotide positions can be modified by addition of tethered substituents without significantly affecting duplex structure (e.g., the N2 and N7 positions of guanine, the N6 and N7 positions of adenine, C5 position of cytosine, thymidine and uracil, and the N4 position of cytosine).

It is well known that nucleotides can be modified by covalent attachment of ligands (e.g., DNP, digoxigenin, biotin) and receptors (e.g., antibodies), but the art is silent with respect to use of nucleotides as positioning devices for attachment of multiple specific binding pairs in suitable juxtaposition to enable functional coupling between, e.g., two specifically bound effector molecules.

The instant invention describes nucleotide-based and nonnucleotide multimolecular structures and multimolecular devices capable of positioning at least two specific recognition pairs (e.g., a pair of specific binding pairs, optionally including at least one shape recognition pair) within close spatial proximity (i.e., within functional coupling distance). extends the teachings of Disclosed herein are molecular templates comprising, imprinted from and/or mimicking multivalent nucleotides capable of positioning and functionally coupling multiple nucleotide or nonnucleotide molecules, at least one being a selected nonoligonucleotide molecule, to provide nucleotide-based and nonnucleotide multimolecular switches, multimolecular transducers, multimolecular sensors, molecular delivery systems, drug delivery systems, tethered recognition devices, molecular adsorbents, molecular adhesives and molecular adherents. Commercial applications include, e.g., therapeutics, diagnostics, cosmetics, agriceuticals, nutraceuticals, industrial materials, consumer electronics, molecular-scale batteries, packaging, environmental remediation, sensors, transducers and actuators for aeronautic and military use, smart polymers, adsorbents, adhesives, adherents, lubricants, biomimetically functionalized organic and inorganic semiconductors and carbon-based, silicon-based and gallium arsenide-based membranes, devices and systems. Nucleotide-based templates can be designed to recognize structural molecules comprising, e.g., surfaces, parts, products and packaging materials for use as willfully reversible and reusable molecular adhesives, adherents and adsorbents) and even biological surfaces. For example, template-directed delivery of selected molecules to keratin comprising hair and nails enables precise and specific, willfully reversible, application of safe, lasting, yet reversible cosmetic dyes, pigments, liners and structural elements. Selection of ligands, receptors, aptamers and shape recognition partners from diverse sequence, chemical and shape recognition libraries enables novel cosmeceutical formulations capable of specifically decorating, strengthening, protecting, lengthening and thickening hair, nails, eyebrows and eyelashes.

Templates comprising, e.g., synthetic heteropolymers and multimolecular devices may also be used as dopants, additives, active ingredients or smart polymers comprising commercial chemicals, materials, products and packages, particularly polymers, gels, foams, woven and nonwoven fibers, plastics, papers, rubbers, coatings, coverings, paints, powders, sealants, adhesives and even recycled materials, particularly as smart polymers capable of performing useful functions. Useful functions include, for example, stimulus-responsive molecular delivery, switching, sensing, transducing, and actuating changes in the internal or external environment or, alternatively, in the properties of the host material (e.g., shape, color, temperature, conductivity, porosity, rigidity, adhesiveness, odor).

The ability to intimately combine within a single multimolecular structure at least two specific recognition pairs with different specificities (i.e., with control over the relative positions of or distance between constituent molecules) enables the design and construction of molecular-scale devices including multimolecular switches, sensors, transducers, molecular delivery systems, adsorbents, adherents, adhesives and lubricants. Multivalent molecular structures of the instant invention enable controlled positioning and optionally covalent crosslinking of multiple specific recognition pairs within suitable intermolecular proximity to provide functional coupling between members of the recognition pairs. Selected effector molecules can be conjugated to defined positions of nucleotide or nonnucleotide scaffolds to enable both controlled intermolecular positioning and functional coupling of conjugated effector molecules and recognition pairs. Selected molecules positioned by specific recognition using affinity-based templates can subsequently be permanently or pseudoirreversibly attached to one another or to the template using well known chemical and enzymatic methods, e.g., covalent crosslinking reagents, ligases and synthetases. Alternatively, template-ordered molecules can be used as imprintable hosts for cast-and-mold printing of nonnucleotide (e.g., plastic) templates and assemblies shaped by templated guest molecules. Two members of a specific binding or shape recognition pair or even two different specific recognition pairs can be tethered by pseudoirreversible (e.g., covalent, avidin/biotin-based, or hybridization-based) incorporation within a nucleotide-based, aptameric, heteropolymeric or nonnucleotide device in such manner that specific binding and unbinding between covalently connected molecules provides a useful, potentially reversible function (e.g., stimulus-responsive binary switching) without dissociative or diffusional loss or dilution of participating binding partners. The same tethering principle is applied in hybridization-based multimolecular switches comprising two (or more) pairs of complementary defined sequence segments, all four constituent defined sequence segments being covalently attached to one another within a single discrete structure, wherein either one pair or the other is hybridized at any given time. Such tethered specific recognition devices may be nucleotide-based (i.e., relying on nucleotides for molecular positioning), or they may be constructed using a nonnucleotide scaffold, preferably a copolymer or heteropolymer or flexible polymer comprising folds, bends, joints, hinges or branchpoints. Nucleotide-directed functional coupling between selected molecules or specific recognition pairs can be used as a screening and selection criterion for identification of defined sequence segments with desired recognition properties.

OBJECTS OF THE INVENTION

An object of the present invention is to provide synthetic heteropolymers which comprise a first synthetic defined sequence segment capable of specifically recognizing and covalently attaching a first selected nonoligonucleotide molecule and a second defined sequence segment attached to the first synthetic defined sequence segment with the proviso that the second defined sequence segment is not a fixed, unconjugated primer-annealing sequence. The first and second defined sequence segments may be attached directly or via a nucleotide spacer. The first selected nonoligonucleotide molecule recognized by the first synthetic defined sequence segment may comprise a specific binding partner of the first synthetic defined sequence segment or a specifically attractive surface feature. The second defined sequence segment is capable of specifically recognizing a second selected nonoligonucleotide molecule such as a specific binding partner or specifically attractive surface feature or specifically recognizing a selected nucleic acid sequence. In this structure, the second defined sequence segment may also be capable of hybridizing to a selected nucleic acid sequence or may comprise a conjugated defined sequence segment.

Another object of the present invention is to provide heteropolymeric discrete structures which comprise a synthetic aptamer and a defined sequence segment attached to the synthetic aptamer. In this structure, the defined sequence segment may comprise an aptamer, a nucleotide sequence which specifically binds or hybridizes to a selected nucleic acid sequence, or a conjugated defined sequence segment. The defined sequence segment can be attached directly to the synthetic aptamer or via a nucleotide spacer.

Another object of the present invention is to provide molecular adsorbents which comprise a solid phase and a multivalent template having a first specific recognition element specifically attached via the first specific recognition element to the solid phase. The solid phase comprises an amphibious or specifically attractive surface. It is preferred that the multivalent template of the molecular adsorbent have at least one other second specific recognition element capable of specifically recognizing a selected nonoligonucleotide molecule or of specifically hybridizing a selected nucleic acid sequence.

Another object of the present invention is to provide multimolecular adherents which comprise a specific recognition element and a first selected molecule attached to the specific recognition element. The specific recognition element specifically attaches, via specific binding or shape-specific recognition, the first selected molecule to a second selected molecule of an amphibious or specifically attractive surface. Thus, in one embodiment the second selected molecule comprises a specific binding partner of the specific recognition element while in a second embodiment, the second selected molecule comprises a specifically attractive surface feature.

Another object of the present invention is to provide multimolecular adhesives which comprise at least two specific recognition elements capable of specifically attaching and joining at least two surfaces. At least one of the specific recognition elements of the molecular adhesive specifically recognizes an amphibious or specifically attractive surface. Specific recognition of the specific recognition element may result from specific binding of the recognition element to a selected molecule of an amphibious surface, specific recognition of a surface feature of a specifically attractive surface or hybridization to a nucleic acid sequence immobilized to the amphibious or specifically attractive surface.

Another object of the present invention is to provide multivalent heteropolymeric hybrid structures which comprise a first synthetic heteropolymer hybridizably linked to a second synthetic heteropolymer. Each synthetic heteropolymer of this structure comprises at least two defined sequence segments. At least one defined sequence segment of the first synthetic heteropolymer specifically recognizes a selected nonoligonucleotide molecule which may be a specific binding partner of this defined sequence segment or a specifically attractive surface feature specifically recognized by this defined sequence segment. In one embodiment of this structure, at least one defined sequence segment of the second synthetic heteropolymer either specifically recognizes a selected nonoligonucleotide molecule such as a specific binding partner of this defined sequence segment or a specifically attractive surface feature specifically recognized by this defined sequence segment or specifically binds a selected nucleic acid sequence. In another embodiment of this structure, at least two defined sequence segments of the second synthetic heteropolymer hybridize to selected nucleic acid sequences. At least one defined sequence segment of the second synthetic heteropolymer may also comprise a conjugated defined sequence segment.

Another object of the present invention is to provide aptameric multimolecular devices which comprise a nonaptameric specific recognition pair and a synthetic aptamer which specifically binds or shape-specifically recognizes an aptamer target wherein a member of the nonaptameric specific recognition pair is conjugated to the aptamer to form a conjugated aptamer. In a preferred mode of operation, the conjugated aptamer positions the aptamer target for functional coupling with a member of the nonaptameric specific recognition pair. It is preferred that the conjugated aptamer or the aptamer target comprises an effector molecule. In one embodiment, the nonaptameric specific recognition pair comprises a nucleotide ligand or a nucleotide receptor. The aptamer target may comprise a specific binding partner of the synthetic aptamer or a surface feature of a specifically attractive surface.

Another object of the present invention is to provide tethered specific recognition devices which comprise a molecular scaffold and at least two members of a specific binding pair or shape-specific recognition pair. The members of the specific binding pair or shape-specific recognition pair are covalently or pseudoirreversibly attached to the molecular scaffold. The members of the specific binding pair or shape-specific recognition pair may also be specifically and directly attached to each other. It is preferred that at least one member of the specific binding pair or shape-specific recognition pair comprise an effector molecule. The molecular scaffold of the tethered specific recognition device may comprise a nonnucleotide molecule or a replicatable nucleotide. One or more members of the specific binding pair or shape-specific recognition pair of this device may also comprise an aptamer.

Another object of the present invention is to provide tethered specific recognition devices which comprise a molecular scaffold and at least four members of two specific recognition pairs. Each member of the specific recognition pairs is covalently or pseudoirreversibly attached to the molecular scaffold of the device. In this device at least one of the two specific recognition pairs comprises a specific binding pair, a shape-specific recognition pair or hybridizable selected nucleic acid sequences. Further, specific attachment of the two members of one specific recognition pair precludes specific attachment of the two members of another pair.

Another object of the present invention is to provide paired specific recognition devices which comprise a molecular scaffold and at least two different specific recognition pairs conjugated to the molecular scaffold. At least one specific recognition pair of this device is capable of specific binding or shape-specific recognition and it is preferred that at least one member of one of the two specific recognition pairs comprise an effector molecule. The molecular scaffold may comprise a nonnucleotide molecule or a replicatable nucleotide. The molecular scaffold of this device is preferably capable of positioning the specific recognition pairs for functional coupling between at least two members of the at least two specific recognition pairs. At least one member of the two specific recognition pairs may comprise an aptamer. In one embodiment of the paired specific recognition device at least one member of the at least two specific recognition pairs is specifically and directly attached to its specific recognition partner.

Another object of the present invention is to provide a nonaptameric multimolecular device which comprises a conjugated defined sequence segment and at least two different specific binding pairs or shape-specific recognition pairs. In this device, one member of each pair is conjugated to the conjugated defined sequence segment. The conjugated member of at least one of the pairs may comprise a modified nucleotide, a nucleotide ligand or nucleotide receptor The conjugated defined sequence segment of this device is capable of positioning the specific binding pairs or shape-specific recognition pairs for functional coupling between at least two members of the pairs.

Another object of the present invention is to provide multimolecular drug delivery systems which comprise a multimolecular structure selected from a group consisting of aptameric multimolecular devices, heteropolymeric discrete structures, multivalent heteropolymeric hybrid structures, synthetic heteropolymers, tethered specific recognition devices, paired specific recognition devices, nonaptameric multimolecular devices, multivalent imprints, and immobilized multimolecular delivery systems wherein the multimolecular structure contains a synthetic receptor that specifically recognizes a drug or a selected target.

Another object of the present invention is to provide immobilized multimolecular structures which comprise a solid support and a multimolecular structure immobilized to the solid support wherein the multimolecular structure is selected from the group consisting of aptameric multimolecular devices, heteropolymeric discrete structures, multivalent heteropolymeric hybrid structures, synthetic heteropolymers, tethered specific recognition devices, paired specific recognition devices, nonaptameric multimolecular devices, multivalent molecular structures, multivalent imprints, and multimolecular drug delivery systems.

Another object of the present invention is to provide shape-specific probes which comprise a nucleotide-based or nonnucleotide recognition element capable of recognizing a specifically attractive surface feature. Preferably, the recognition element comprises an aptamer, a nucleotide ligand or nucleotide receptor, or a selectable nonoligonucleotide molecule. Another object of the present invention is to provide multivalent imprints of multimolecular structures which comprise at least two specific recognition elements imprinted from the multimolecular structure. Multimolecular structures for preparation of these imprints may comprise aptameric multimolecular devices, heteropolymeric discrete structures, multivalent heteropolymeric hybrid structures, synthetic heteropolymers, or nonaptameric multimolecular devices. In one embodiment of the multivalent imprint, the imprinted specific recognition elements from the multimolecular structure mimic the specific recognition elements of the multimolecular structure. In another embodiment, the imprinted specific recognition elements from the multimolecular structure are capable of specifically recognizing the specific recognition elements of the multimolecular structure.

Another object of the present invention is to provide paired nucleotide-nonnucleotide mapping libraries which comprise a plurality of selected specific recognition partners capable of transposing a selected population of selected nonoligonucleotide molecules into replicatable nucleotide sequences.

Another object of the present invention is to provide methods for selecting a single synthetic nucleotide molecule capable of recognizing a selected target molecule comprising detecting a signal resulting from the proximity or functional coupling between the single synthetic nucleotide and the selected target molecule. In this method, it is preferred that the single synthetic nucleotide be selected from a nucleotide library. The single synthetic nucleotide molecule may comprise an aptamer that specifically recognizes the selected target molecule and is capable of forming a single discrete structure comprising the aptamer and the selected target molecule or an aptamer-effector conjugate that specifically recognizes the selected target molecule and is capable of forming a single discrete structure comprising the aptamer-effector conjugate and the selected target molecule while the selected target molecule may comprise an effector molecule. In one embodiment, the single synthetic nucleotide molecule comprises a catalytic nucleotide such as a ribozyme, a catalytic DNA molecule or a nucleotide catalyst. In another embodiment, the single synthetic nucleotide molecule comprises a shape-specific probe that specifically recognizes a surface feature of a specifically attractive surface. In this method the signal may be detected by a variety of techniques including, but not limited to, optical microscopy, flow cytometry or detection of a photon emitted by a signal-generating species. In a preferred embodiment, the signal is detected by single-molecule detection via scanning probe microscopy. These methods may further comprise amplification of the selected single synthetic nucleotide molecule and nucleotide sequence determination of the selected single synthetic nucleotide molecule.

Another object of the present invention is to provide methods for identifying a specifically attractive surface feature which comprises contacting a surface library with a selected shape-specific recognition partner and detecting attachment of the selected shape-specific recognition partner to a specifically attractive surface feature of the surface library. In a preferred embodiment, the shape-specific recognition partner is detectably labeled and attachment is detected by single-molecule detection.

SUMMARY OF THE INVENTION

The present invention extends the teachings of Cubicciotti, U.S. Pat. No. 5,656,739 by providing specifically and optionally covalently assembled multimolecular structures and multimolecular devices comprising MOLECULAR MACHINES. The term MOLECULAR MACHINES is used herein to describe claimed compositions and methods of the instant invention, including aptameric multimolecular devices, heteropolymeric discrete structures, multimolecular delivery systems, multivalent molecular structures, molecular adsorbents, multimolecular adherents, multimolecular adhesives, multivalent heteropolymeric hybrid structures, synthetic heteropolymers, tethered specific recognition devices, paired specific recognition devices, nonaptameric multimolecular devices, multivalent imprints, multimolecular drug delivery systems, shape-specific probes, paired nucleotide-nonnucleotide mapping libraries, paired nucleotide-nonnucleotide library-selected single synthetic nucleotides, paired nucleotide-nonnucleotide library-selected single synthetic nucleotide imprints, immobilized multimolecular structures, specifically attractive surface features, multimolecular switches, multimolecular sensors, multimolecular transducers, paired templates and paired MOLECULAR MACHINES.

Importantly, the instant invention discloses methods and devices which transpose the useful products and properties described by Cubicciotti, U.S. Pat. No. 5,656,739 into nonnucleotide multimolecular devices, including multivalent imprints of nucleotide-based multimolecular structures and specifically recognizable surface features comprising heretofore chemically bland, optionally inorganic substrates, e.g., silicon and gallium arsenide.

A variety of molecular-scale switches, sensors, transducers, molecular delivery systems and specific, willfully reversible, adsorbents, adhesives and adherents are assembled from multivalent templates and scaffolds. The multivalent property of the templates provides control over the relative positions of molecules within cooperative molecular assemblies comprising useful multimolecular devices. Innovative properties and products are achieved by template-directed assembly of cooperative pairs and groups of molecules. Synthetic heteropolymers are particularly well-suited template materials. This invention is not specifically drawn to the properties of the template material, itself, but to the wealth of useful devices that can be assembled by combining selected molecules within a single multimolecular structure. A central inventive step of this disclosure is demonstration of the variety of different devices that can be prepared by either 1) tethering two members of at least one specific binding or shape-specific recognition pair to a common molecular scaffold, so the recognition partners may exist in either of two states (e.g., specifically bound or dissociated) or 2) combining at least two different specific recognition pairs within a single multimolecular structure, i.e., a pair of specific recognition pairs, each pair having two members.

Combining a selected pair of selected specific recognition pairs within a single multimolecular structure provides a vast array of useful MOLECULAR MACHINES. What is truly surprising is the diversity or novel designs, functions and properties that can be achieved by applying this single unifying principle. Disclosed herein are multimolecular switches, multimolecular sensors, multimolecular transducers and multimolecular drug delivery systems prepared from paired specific recognition pairs. Multimolecular devices preferably comprise or mimic synthetic heteropolymers disclosed in Cubicciotti, U.S. Pat. No. 5,656,739. Nonnucleotide molecular scaffolds and templates are preferably bivalent, multivalent or heterofunctional molecules or polymers prepared by chemical, enzymatic and/or biological methods or mechanochemical synthesis, e.g., by nanomanipulation using proximal probes (e.g., SPM). Precursors may be biological, nonbiological, natural or synthetic monomers, polymers and/or selected molecules.

Multimolecular switches, sensors, transducers, adhesives, adherents, adsorbents and delivery systems are prepared from multimolecular structures which can be imprinted or transposed between nucleotide and nonnucleotide molecular media via paired nucleotide-nonnucleotide libraries.

Multimolecular drug delivery systems comprising receptor-targeted prodrugs and tethered prodrug delivery configurations, provide the art with highly specific control over drug action by combining prodrug compositions with receptor targeting, triggered release and localized activation mechanisms. They are particularly useful, e.g., for improving safety, targeting efficiency, compliance and efficacy for indications benefiting from single-dose, prolonged action or tissue-specific formulations, e.g., allergy, asthma, cancer, infection, vascular occlusion, psoriasis, arthritis and fibrosis.

Tethered specific recognition devices provide the benefits of specific recognition without the variability and limitations of diffusible binding partners. They are particularly useful, e.g., for molecular counting, search-and-destroy and sense-and-actuate applications, e.g., drug delivery and environmental remediation.

Multimolecular adhesives provide the art with surface bonding products relying on specific binding, complementary base pairing and specific surface attractivity. They are particularly useful, e.g., for precise bonding of micromachined and/or nanofabricated surfaces in proper register and for willfully reversible assembly of products and packages.

Multimolecular adherents provide the art with products that specifically attach a selected molecule or molecular function to a selected structure or surface, advantageously in a willfully reversible manner. They are particularly useful, e.g., for feature-directed patterning of electroactive and photoactive molecules on semiconductors, CDs and DVDs; safe and reversible targeting of cosmetics to hair and nails; and site-specific repair of skin irregularities, scars, wrinkles and discolorations using target-directed cosmeceuticals, structural molecules and pigments.

Molecular adsorbents provide the art with materials and surfaces having specifically attractive surface features, i.e., structural shapes capable of specifically recognizing and attaching selected molecules (i.e., ligands, receptors, structural molecules and effector molecules). They are particularly useful, e.g., as semiconductor substrates and separation media for industrial purification and processing.

The invention also provides the art with single-molecule selection methods that enable a heretofore unknown recognition property to be identified with single-molecule resolution from a highly diverse nucleic acid library, including isolation, characterization and sequencing of the individual selected nucleotide. Single-molecule selection methods are particularly useful, e.g., for selecting aptameric and catalytic nucleotides for assembly of functionally coupled multimolecular devices and MOLECULAR MACHINES of the invention.

The invention also provides the art with a method for screening and selecting diverse nucleotide libraries for functional coupling between a donor and an acceptor species. Selection based upon functional coupling is particularly useful, e.g., for identifying cooperative molecular interactions (i.e., energy transfer, enzyme channeling) that cannot be resolved with prior art screening and selection methods.

The invention also provides the art with methods for transposing or imprinting nucleotide-based MOLECULAR MACHINES into diverse (i.e., plastic) nonnucleotide molecular media. Nucleotide-nonnucleotide imprinting and transposition are particularly useful, e.g., for development of MOLECULAR MACHINES for industrial use, i.e., nonbiomedical applications.

The invention also provides the art with a method to select a nucleotide-based mapping library capable of encoding the recognition properties of a selected population of selected nonnucleotide molecules in the form of a library of amplifiable nucleotide sequences. Mapping libraries are particularly useful, e.g., for amplifying, archiving and monitoring the recognition properties of a clinically relevant population of selected nonnucleotide molecules, e.g., antibodies, disease markers or T cell antigens.

DETAILED DESCRIPTION OF THE INVENTION

Following is a glossary of terms used to describe the instant invention. Where the specification is unclear or incomplete, the definitions set forth in the glossary are intended to prevail.

GLOSSARY

The term "actuator" means a device or process capable of providing or performing useful work (i.e., a desirable result) in response to a stimulus, e.g., an input from a user, operator, system, environment, sensor or transducer, including, but not limited to, useful work resulting from, accompanying or mediated by the binding or activity of a nucleotide or nonnucleotide molecule comprising or capable of attaching to a nucleotide-based or nonnucleotide multimolecular device. Actuators of the present invention include devices which comprise, attach, are functionally coupled to or are capable of functionally coupling to multimolecular structures, MOLECULAR MACHINES, paired MOLECULAR MACHINES and systems comprising pairs, groups or networks of paired MOLECULAR MACHINES.

"AFM" is an abbreviation for "atomic force microscopy."

The term "amphibious surface" means a nonnucleotide surface that is able to operate in or on land, air, water, in a vacuum, or in a gaseous, liquid, aqueous or organic fluid, solution, glass or suspension, or in any combination of these environments, so long as the surface is not a reagent-binding or analyte-binding separation matrix of a specific binding or nucleic acid hybridization assay or a molecular recognition site capable of specifically binding or hybridizing a drug or hormone (i.e., a drug or hormone receptor or pathophysiological target). "Nonnucleotide surface," when used in reference to an amphibious surface, means a surface that does not comprise a heretofore known nucleotide-based molecular recognition partner unless and until modified by a multimolecular device of the instant invention. A nonnucleotide amphibious surface modified by attachment of a nucleotide-based multimolecular device of the instant invention remains an amphibious surface despite the attachment of nucleotides comprising the multimolecular device. Amphibious surfaces are limited to nonnucleotide surfaces to distinguish molecular adherent-modified and molecular adhesive-modified surfaces of the instant invention from biological and nonbiological hybridizable surfaces (e.g., immobilized nucleic acid probes and targets, in situ biological nucleic acids, and biological recognition sites comprising immobilized nucleic acids). Amphibious surfaces include, for example, surfaces of materials, parts, packaging, packing materials, people, products, vehicles, airports, train and bus stations, wholesale and retail establishments and media and communication systems used for research, development, manufacture, packaging, marketing, distribution, sales and support of commercial goods and services. Also included are surfaces comprising the homes, gardens, households, families and pets of consumers of commercial goods and services, excluding any home or office testing product surfaces to which molecular recognition reagents are immobilized for use in specific binding or hybridization assays and further excluding immobilized or membrane-associated drug and hormone receptors that specifically bind or hybridize to drugs or hormones. Docking surfaces of membrane-associated receptors for drugs and hormones that specifically bind or hybridize to pathophysiological targets are not amphibious surfaces, nor are solid supports comprising diagnostic or analytical antibodies, antigens, DNA probes, drugs, hormones or hormone receptors immobilized on latex particles, ELISA plates, chromatography supports, electrophoretic gels, polystyrene beads or immunochromatographic membranes (e.g., in home pregnancy tests). By contrast, the reagent surface of a home glucose test is an amphibious surface, as heretofore known home glucose tests do not comprise immobilized specific binding or hybridization reagents. A specifically attractive biological surface or structural shape is also an amphibious surface, so long as it is not a docking surface of a pathophysiological receptor that hybridizes or specifically binds a drug or hormone.

The terms "amplify" and "amplification," when used in reference to a molecule, nucleotide, target, population or library, refer to methods, processes, reagents or devices for increasing the amount, mass, concentration, detectability or number of copies of at least one molecule, group, sequence, member, subset or structure comprising the molecule, nucleotide, target, population or library.

The term "aptamer" means a single-stranded, partially single-stranded, partially double-stranded or double-stranded nucleotide sequence, advantageously a replicatable nucleotide sequence, capable of specifically recognizing a selected nonoligonucleotide molecule or group of molecules by a mechanism other than Watson-Crick base pairing or triplex formation. Aptamers disclosed herein include, without limitation, defined sequence segments and sequences comprising nucleotides, ribonucleotides, deoxyribonucleotides, nucleotide analogs, modified nucleotides and nucleotides comprising backbone modifications, branchpoints and nonnucleotide residues, groups or bridges. Aptamers of the invention include partially and fully single-stranded and double-stranded nucleotide molecules and sequences, synthetic RNA, DNA and chimeric nucleotides, hybrids, duplexes, heteroduplexes, and any ribonucleotide, deoxyribonucleotide or chimeric counterpart thereof and/or corresponding complementary sequence, promoter or primer-annealing sequence needed to amplify, transcribe or replicate all or part of the aptamer molecule or sequence. Unlike prior art aptamers that specifically bind to soluble, insoluble or immobilized selected molecules (e.g., ligands, receptors and effector molecules), the instant term "aptamer" includes nucleotides capable of shape-specific recognition of chemically bland surfaces by a mechanism distinctly different from specific binding. Aptamers of the instant invention may be selected to specifically recognize a structural shape or surface feature comprising a chemically bland surface (e.g., a silicon chip or carbon nanostructure) rather than the chemical identity of a selected target molecule (e.g., a ligand or receptor). An aptamer may be a molecule unto itself or a sequence segment comprising a nucleotide molecule or group of molecules, e.g., a defined sequence segment or aptameric sequence comprising a synthetic heteropolymer, multivalent heteropolymeric hybrid structure or aptameric multimolecular device.

The terms "aptamer-based" and "aptameric" mean comprising at least one synthetic aptamer.

The term "aptamer conjugate" means a conjugate comprising an aptamer and a second molecule and includes aptamers comprising nonnucleotide molecules or moieties introduced during as well as after nucleotide synthesis, e.g., by incorporation of derivatized nucleotides, nucleosides or nucleoside phosphates, labeled nucleotides, modified nucleotides, biotinylated nucleotides, nucleotide ligands, nucleotide receptors, conjugated nucleotides, nucleotides derivatized with nonnucleotide ligands or receptors, nonnucleotide molecules and the like. An aptamer conjugate is referred to herein as a synthetic aptamer if the conjugate is not heretofore known to occur in nature, regardless of the nucleotide sequence comprising the aptamer.

The term "aptameric device" means a discrete aptameric structure capable of providing functional coupling between a selected molecule which is not an aptamer target, preferably a ligand or receptor or a molecule conjugated to a ligand or receptor, and a selected molecule which is an aptamer target, preferably an effector molecule and more preferably a signal-generating species or a drug. Aptameric devices of the instant invention include multimolecular switches, multimolecular transducers, multimolecular sensors and multimolecular delivery systems comprising synthetic aptamers or aptamer conjugates.

The term "aptameric discrete structure" means a discrete structure comprising at least one aptamer.

The term "aptameric multimolecular complex" refers to a synthetic heteropolymer comprising two different aptamer molecules directly attached or conjugated to one another or indirectly attached via a linker (i.e., a nucleotide spacer, spacer molecule, oligonucleotide linker or nonnucleotide linker) that joins the aptamers to form a discrete heteropolymeric structure capable of specifically recognizing two different nonoligonucleotide molecules.

The term "aptameric multimolecular device" means a multimolecular device comprising at least one synthetic aptamer comprising a conjugated selected molecule which is not the aptamer target, preferably a conjugated nonaptameric specific recognition pair comprising a selected molecule capable of functional coupling with the aptamer target, preferably an effector molecule comprising the aptamer target. The synthetic aptamer is capable of specifically recognizing the aptamer target which preferably comprises an effector molecule so as to provide functional coupling between a selected molecule comprising the conjugated nonaptameric specific recognition pair and the aptamer target. The conjugated selected molecule may comprise a modified nucleotide, or it may be attached to a nucleotide comprising the aptamer, preferably by direct and site-specific attachment. In a preferred embodiment, the conjugated selected molecule comprises a nucleotide ligand or nucleotide receptor, i.e., a nucleotide library-selected modified nucleotide capable of specifically binding or shape-specifically recognizing a selected target which is not the aptamer target. In this way, the aptameric multimolecular device comprises at least two nucleotide library-selected recognition elements which specifically recognize two different selected molecules, i.e., an aptamer which specifically recognizes an aptamer target and a nucleotide ligand or receptor which specifically recognizes a selected molecule or a surface feature of a specifically attractive surface. Advantageously, the conjugated selected molecule (i.e., first conjugated selected molecule) is indirectly attached to the aptamer, e.g., by specific recognition of a second conjugated selected molecule which is directly and preferably site-specifically and covalently attached to a nucleotide comprising the aptamer. In this mode of operation, the aptameric multimolecular device comprises a paired specific recognition device, wherein the first and second conjugated selected molecules comprise a first specific recognition pair and the synthetic aptamer and its selected target molecule comprise a second specific recognition pair. The aptameric multimolecular device is advantageously capable of positioning a member of one specific recognition pair for functional coupling with a member of another specific recognition pair. At least one member of at least one specific recognition pair of an aptameric multimolecular device preferably comprises an effector molecule, more preferably a drug or a signal-generating species. An aptameric multimolecular device preferably comprises at least one replicatable nucleotide sequence.

The term "aptameric tethered specific recognition device" means an aptameric multimolecular device having two members of a nonaptameric specific recognition pair conjugated to an aptameric molecular scaffold. At least one member of the aptameric and/or nonaptameric specific recognition pair preferably comprises an effector molecule, e.g., the member is detectably labeled or specifically attached to a releasable or activatable effector (e.g., a prodrug or a signal-generating species).

The terms "aptamer target," "target," and "selected target," when used in reference to aptamer-target binding, means a selected molecule, group of molecules or surface feature specifically recognized by an aptamer. The terms "aptamer" and "aptamer target" as used herein are distinguished from "ligands" and "receptors." Although an aptamer and its target are specific binding partners and members of a specific binding pair, they are not referred to herein as ligands and receptors. The inventor's lexicography in this regard is intended to avoid conflict and contradiction arising from inconsistency and/or ambiguity in prior art usage of the terms ligand and receptor with respect to nucleic acids and aptamers. For example, the terms "nucleic acid ligand" "nucleic acid receptor," "nucleic acid antibody" and "aptamer" are sometimes used interchangeably or inclusively in the art, often without explicit, precise or commonly accepted definitions. The terms "aptamer," "ligand," "receptor" and "bispecific nucleic acid antibody" are independently and autonomously defined herein to avoid misinterpretation of the instant specification vis-a-vis prior art terminology.

The term "assortment" means a plurality comprising at least two different members.

The term "attachment site" refers to covalent and/or noncovalent site-directed attachment by methods including, but not limited to, specific recognition and site-specific chemical modification.

The terms "bifunctional," "trifunctional" and "multifunctional," when used in reference to a synthetic heteropolymer or multivalent heteropolymeric hybrid structure, mean bivalent, trivalent or multivalent, as the case may be, or comprising two, three or multiple specific recognition elements, defined sequence segments or attachment sites. When used in reference to a multivalent heteropolymeric hybrid structure, the terms "bifunctional," "trifunctional" and "multifunctional" refer to the number of available and/or unoccupied specific recognition sites, excluding the hybridized sequences joining the constituent synthetic heteropolymers. When used in reference to a molecule, linker or crosslinking reagent, the terms "bifunctional," "trifunctional" and "multifunctional" are used to describe the number of functional, chemical or reactive groups.

The terms "binding domain" and "recognition domain," when used in reference to a molecule or group of molecules, mean the portion or region of the molecule or group of molecules which is directly involved in binding or recognition.

The terms "binding element," "recognition element" and "element," when used in reference to a specified activity, recognition property or docking surface of a molecule, group, segment, template, scaffold, multimolecular structure or imprint, mean the operative site, region, epitope, binding domain, catalytic domain, selected molecule, defined sequence segment or nucleotide comprising the specified activity, recognition property or docking surface.

The term "binding partner" means a member of a specific recognition pair, each member of the specific recognition pair being a binding partner of the other member.

The term "biocompatible" means an exogenous substance that is relatively nonimmunogenic, nonallergenic and nontoxic when administered, contacted or attached to a biological organism.

The term "biological recognition site" means a catalytic site, hybridization site or specific binding site comprising a member of a heretofore known recognition pair whose members are biological molecules or biological nucleic acid sequences. A biological recognition site is the operative recognition site of a first biological molecule or biological nucleic acid sequence heretofore known to be a molecular recognition partner or catalytic recognition partner of a second biological molecule or biological nucleic acid sequence.

The term "biomimetic" means a nucleotide-based or nonnucleotide molecule, group, multimolecular structure or method that mimics a biological molecule, group of molecules, structure, system, process or principle, i.e., a mimetic of a biological composition, process or principle.

The term "bispecific nucleic acid antibody" means a bivalent or multivalent aptameric device, synthetic heteropolymer or multimolecular device which is capable of specifically recognizing at least two different target molecules.

The term "bivalent," when used in reference to nucleotide-based, aptameric and heteropolymeric discrete structures and nonnucleotide multimolecular structures, templates, scaffolds and molecules, means comprising at least two recognition sites or, in certain instances, precisely two specific recognition sites. When used in reference to a multivalent heteropolymeric hybrid structure, the terms "bivalent" and "bifunctional" mean precisely two defined sequence segments capable of specific recognition, excluding the hybridized sequences joining the constituent synthetic heteropolymers. In general, the term "bivalent" means at least bivalent and includes multivalent and multifunctional compositions, e.g., multivalent multimolecular structures.

The term "bivalent imprint" means a multivalent imprint comprising at least two recognition elements and optionally precisely two recognition elements.

The term "catalytic recognition partner" refers to a molecule or group of molecules capable of interacting selectively in a catalytic or enzymatic reaction, i.e., a reaction involving the making or breaking of covalent bonds which can be accelerated, facilitated, enhanced, modulated or practically enabled by a natural or synthetic enzyme or catalyst. Selective interaction means that a molecule preferentially modulates the activity of a particular enzyme or catalyst relative to other molecules in a reaction mixture or that catalytic or enzymatic activity is modulated by relatively low concentrations of the molecule, preferably less than about millimolar concentrations. Molecules capable of selective interaction in catalytic and enzymatic reactions include, without limitation, enzyme substrates, products, intermediates, coenzymes, cofactors, prosthetic groups, coordinated and chelated groups, regulatory factors, steric and allosteric modulators, inhibitors, mediators, and the like. Catalytic recognition partners include, without limitation, protein and nonprotein, nucleotide and nonnucleotide, organic and inorganic, specific, relatively unspecific and class-specific enzymes, catalysts, substrates, coenzymes, cofactors, inhibitors, regulatory factors and mimetics, imprints and conjugates thereof and progeny therefrom.

The term "catalytic recognition site" refers to a recognition site comprising a catalytic recognition partner, i.e., a molecule or group of molecules that interacts selectively in a catalytic or enzymatic reaction.

The term "chemically bland," when used in reference to a substance, structure, surface or material, means a composition comprising a nonbiological, synthetic, nonliving, planar or flat surface that is not heretofore known to comprise a specific binding, hybridization or catalytic recognition site or a plurality of different recognition sites or a number of different recognition sites which exceeds the number of different molecular species comprising the surface, structure or material. Chemically bland surfaces, structures and materials include, for example and without limitation, semiconductors, synthetic (organic) metals, synthetic semiconductors, insulators and dopants; metals, alloys, elements, compounds and minerals; synthetic, cleaved, etched, lithographed, printed, machined and microfabricated slides, substrates, devices, structures and surfaces; industrial polymers, plastics, membranes and substrates; silicon, silicates, glass, metals and ceramics; wood, paper, cardboard, cotton, wool, cloth, woven and nonwoven fibers, materials and fabrics; and amphibious surfaces, solid supports, nanostructures and microstructures unmodified by immobilization of recognition molecules.

The term "complementarity," when used in reference to nucleotides, means the stability, melting temperature or number, type or percent of complementary base pairs comprising a defined sequence segment, complementary sequence, duplex or hybridized pair of sequences, e.g., the length, number of base pairs, number of complementary nucleotides, percent base pairing or G-C content comprising a defined sequence segment.

The term "complex," when used in reference to a pair or group of molecules, means at least two molecules attached to one another either reversibly, quasireversibly or pseudoirreversibly.

The term "conjugate" means two or more molecules, at least one being a selected molecule, attached to one another in an irreversible or pseudoirreversible manner, typically by covalent and/or specific attachment. A first selected molecule may be conjugated to a second molecule or to a nucleic acid sequence either indirectly, e.g., through an intervening spacer arm, group, molecule, bridge, carrier, or specific recognition partner, or directly, i.e., without an intervening spacer arm, group, molecule, bridge, carrier or specific recognition partner, advantageously by direct covalent attachment. A selected molecule may be conjugated to a nucleotide via hybridization, provided the selected molecule is tagged with an oligonucleotide complementary to a selected nucleic acid sequence comprising the nucleotide. Other noncovalent means for conjugation of nucleotide and nonnucleotide molecules include, e.g., ionic bonding, hydrophobic interactions, ligand-nucleotide binding, chelating agent/metal ion pairs or specific binding pairs such as avidin/biotin, streptavidin/biotin, anti-fluorescein/ fluorescein, anti-2,4-dinitrophenol (DNP)/DNP, anti-peroxidase/peroxidase, anti-digoxigenin/digoxigenin or, more generally, receptor/ligand. For example, a reporter molecule such as alkaline phosphatase, horseradish peroxidase, β-galactosidase, urease, luciferase, rhodamine, fluorescein, phycoerythrin, luminol, isoluminol, an acridinium ester or a fluorescent microsphere which is attached, e.g., for labeling purposes, to a selected molecule or selected nucleic acid sequence using avidin/biotin, streptavidin/ biotin, anti-fluorescein/fluorescein, anti-peroxidase/ peroxidase, anti-DNP/DNP, anti-digoxigenin/digoxigenin or receptor/ligand (i.e., rather than being directly and covalently attached) is said to be conjugated to the selected molecule or selected nucleic acid sequence by means of a specific binding pair. The term "conjugate" does not include an unmodified sequence of nucleotides, referred to herein as a molecule, nucleic acid, nucleotide, defined sequence segment, nucleotide sequence or oligonucleotide. However, oligonucleotides, aptamers, synthetic heteropolymers, defined sequence segments and selected nucleic acid sequences may be referred to as conjugates if a nonnucleotide molecule, group or moiety (e.g., biotin, digoxigenin, fluorescein, rhodamine) is introduced as a nucleotide analog, modified nucleotide or nucleoside triphosphate before, during or after nucleic acid synthesis.

When used in reference to a first defined sequence segment or selected nucleic acid sequence attached to a second defined sequence segment or selected nucleic acid sequence, the terms "conjugation," "conjugate" and "conjugated" refer to covalent attachment. A pair or group of hybridized and/or specifically bound nucleic acids or nucleotide sequences is not referred to herein as a conjugate.

The term "conjugated aptamer" means an aptamer conjugate, e.g., an aptamer conjugated to a selected molecule or an aptamer comprising a conjugated nucleotide.

The terms "conjugated selected molecule" and "conjugated molecule," when used in reference to a defined sequence segment, also referred to herein as a "conjugated defined sequence segment," means either 1) a selected molecule or nonnucleotide molecule covalently or pseudoirreversibly attached to a defined sequence segment or 2) a defined sequence segment comprising a selected molecule or nonnucleotide molecule, e.g., a derivatized or modified nucleotide, nucleoside phosphate, nucleotide analog, nucleotide ligand or nucleotide receptor comprising a nonnucleotide molecule. Where a conjugated first defined sequence segment of a bifunctional synthetic heteropolymer or multivalent heteropolymeric hybrid structure is used to position a first selected molecule (i.e., the conjugated molecule) for functional coupling with a second selected molecule, the first and second selected molecules are different molecules and do not comprise a pseudoirreversibly or covalently attached ligand-receptor pair. In other words, a defined sequence segment and a conjugated defined sequence segment of a bifunctional synthetic heteropolymer or multivalent heteropolymeric hybrid structure are not directly attached (i.e., without intervening nucleotide or nonnucleotide molecules) to the same selected molecule or covalent or pseudoirreversible ligand-receptor conjugate. The two defined sequence segments directly attach to two different molecules whose assembly (i.e., attachment within a single discrete structure) is brought about by the molecular positioning property of the synthetic heteropolymer or multivalent heteropolymeric hybrid structure. Conjugated defined sequence segments may be produced by conventional nucleic acid synthesis using modified or derivatized nucleotides (e.g., using biotin, fluorescein, psoralen or acridine phosphoramidites) or by enzymatic labeling (e.g., using the modified nucleoside triphosphates biotin-11-dUTP, biotin-14-dATP or 8-aminohexyl-dATP) or chemical modification (e.g., using a diamine, bishydrazide or heterobifunctional crosslinker) of a defined sequence segment. The term "conjugated defined sequence segment" does not mean or include a defined sequence segment hybridized to a selected nucleic acid sequence, unless the unhybridized selected nucleic acid sequence or defined sequence segment is conjugated to a selected molecule. In other words, hybridized nucleotides sans attached nonnucleotide molecules are not referred to herein as conjugates. To position a conjugated selected molecule for functional coupling to a selected molecule specifically bound to a different defined sequence segment, 3' and/or 5' end-labeling of a defined-length sequence is preferred, particularly 5'-end labeling. The efficiency of functional coupling can then be optimized by varying the length, and optionally the composition, of the conjugated defined sequence segment. Defined sequence segments internally labeled or modified at defined nucleotide positions can also be used to effectively position conjugated selected molecules, as functional coupling can be optimized by varying the conjugation position. Conjugated defined sequence segments are synthetic defined sequence segments. In other words, a conjugated defined sequence segment is considered synthetic, regardless of the nucleotide sequence of the unconjugated nucleotide.

The terms "conjugated specific binding pair," "conjugated specific recognition pair" and "specific binding pair conjugate," when used in reference to a specific binding or shape recognition pair conjugated to a defined sequence segment, selected nucleic acid sequence, plastic segment, template, molecule or molecular scaffold comprising a multimolecular structure, mean at least one member of the specific binding or shape recognition pair, optionally an aptamer, is conjugated to the multimolecular structure by covalent or pseudoirreversible attachment. The other member of the pair is either specifically bound (or specifically attached) or capable of specifically binding (or specifically attaching) to its conjugated specific binding partner (or structural shape recognition partner). For example, when one member of a specific binding pair is conjugated to a segment, template or scaffold comprising a multimolecular structure, the specific binding pair is referred to as conjugated to the multimolecular structure if and when both members of the specific binding pair are specifically bound to one another or present and available for specific binding to one another. An aptamer-target pair comprising an aptameric or heteropolymeric multimolecular device is a conjugated specific binding pair, provided the aptamer or aptamer target is covalently or pseudoirreversibly attached to a molecule or scaffold other than its binding partner, e.g., a nucleotide comprising a second defined sequence segment of a synthetic heteropolymer. When used in reference to a nucleotide-based or nonnucleotide multimolecular device, "conjugated specific binding pair," and "specific binding pair conjugate," mean that operation of the multimolecular device requires the presence of both members of the specific binding pair or, in the case of certain analyte-dependent sensors or target-dependent molecular delivery systems, that the device does not respond to a stimulus or deliver its payload until both members of the specific binding pair are present. In either case, a nucleotide-based or nonnucleotide multimolecular device is said to comprise a specific binding pair if and only if a useful function is performed by the device when both members of the specific binding pair are present and available for specific binding. Hybridized nucleic acid sequences are not considered to be conjugated to one another, nor is a nucleic acid target considered to be conjugated or pseudoirreversibly attached to a nucleic acid probe. In other words, the term "conjugated specific recognition pair" does not mean or include a pair of hybridized nucleic acid sequences, i.e., a duplex or double-stranded nucleotide. Hybridization may be used to pseudoirreversibly conjugate an oligonucleotide-tagged selected nonoligonucleotide molecule to a nucleotide sequence, provided the oligonucleotide tag and nucleotide sequence comprise complementary sequence segments. However, the hybridized selected molecule-nucleotide product is referred to as a "conjugated selected molecule" or "conjugated defined sequence segment," not a conjugated specific recognition pair.

The terms "cooperating," "cooperative interactions" and "cooperativity," when used to describe molecules and the interactions between and among molecules, mean proximity-dependent intermolecular work or energy transfer and refer either to the ability of selected nucleotide or nonnucleotide molecules to interact positively or negatively to produce a desired result or to an effect on one molecule created by the presence of a second molecule or to an action or effect brought about by the proximity of two or more molecules or to the combined actions of two or more molecules on a third molecule or to a chemical, electrical, optical, thermal, mechanical, energetic or informational transformation of a system brought about by the additive or synergistic activities of at least two positionally controlled molecules. Cooperativity includes functional coupling between or among two or more molecules, reactions or processes.

The terms "defined position," "defined nucleotide position" and "positionally defined," when used in reference to a nucleotide sequence, mean an identified nucleotide, nucleotide analog, modified nucleotide, monomer, residue, functional group, recognition site or attachment site at the Nth monomer of a defined sequence segment or a plurality of identified nucleotides comprising a defined sequence segment beginning at the Nth monomer of a nucleotide sequence, where "N" is an integer representing the number of monomers from one end of the nucleotide sequence to the identified nucleotide or defined sequence segment. Defined sequence segments and selected nucleic acid sequences of the instant invention may be labeled or modified at defined positions by site-specific, site-directed and/or regiospecific attachment, conjugation and modification methods known in the art, including synthesis of oligonucleotides with modified nucleotides, conjugated nucleotides, nucleotide analogs and spacer modifiers at operator-specified positions. Uniformly, randomly or arbitrarily labeled or modified nucleotides are not considered herein to be labeled or modified at defined positions, i.e., they are not considered positionally defined nucleotides.

The term "defined sequence segment" means a selected, designed or identified sequence of nucleotides and includes single-stranded, double-stranded, partially single-stranded and partially double-stranded biological and synthetic nucleotide sequences, advantageously replicatable nucleotide sequences. When used in reference to synthetic heteropolymers of the instant invention, the term "defined sequence segment" refers to either 1) a nucleotide sequence having a defined number of nucleotides or 2) a nucleotide sequence comprising a nucleotide analog, modified nucleotide or conjugated nucleotide at a defined position or 3) a synthetic oligonucleotide or 4) a selected aptamer or 5) a selected, modified or designed sequence of monomers, preferably a single-stranded or double-stranded sequence of nucleotides, which is capable of specifically binding to an identified molecule or group of molecules or a selected nucleic acid sequence or of hybridizing to a selected nucleic acid sequence or of positioning a conjugated selected molecule or specific binding pair for single-molecule detection and/or functional coupling to a different molecule or specific binding pair. Defined sequence segments of the invention include partially and fully single-stranded and double-stranded nucleotide molecules and sequences, synthetic RNA, DNA and chimeric nucleotides, hybrids, duplexes, heteroduplexes, and any ribonucleotide, deoxyribonucleotide or chimeric counterpart thereof and/or corresponding complementary sequence, promoter or primer-annealing sequence needed to amplify, transcribe or replicate all or part of the defined sequence segment. Defined sequence segments as defined herein are not random-sequence nucleic acids or randomized sequences comprising nucleic acids, but they may be selected from mixtures of nucleic acids comprising random or randomized sequences. A nucleotide selected from a library comprising random-sequence nucleotides may be referred to herein as a defined sequence segment, even though the nucleotide sequence of the random-sequence nucleotide remains unknown unless and until the nucleotide is selected and characterized.

The terms "defined sequence segment capable of specifically binding to an identified molecule" and "defined sequence segment capable of specifically binding to a selected molecule," when used in reference to a synthetic heteropolymer or aptameric device, refer to a defined sequence segment comprising an aptamer capable of specifically recognizing a selected molecule or structural shape. Defined sequence segments of the instant invention include aptamers capable of specific shape recognition, i.e., specific recognition of a structural shape or surface feature. A synthetic defined sequence segment capable of specifically binding a selected molecule is a nonnaturally occurring defined sequence segment comprising either a synthetic aptamer, in the case of a synthetic heteropolymer or aptameric device, or a conjugated specific binding partner, in the case of a nonaptameric multimolecular device.

The terms "designer drug" and "designer drug delivery" refer to multimolecular structures and MOLECULAR MACHINES comprising designer receptors.

The term "designer receptor," alternatively called a "selected receptor" or "synthetic receptor," refers to a naturally occurring, recombinant, biological, biologically produced or synthetic nucleotide or nonnucleotide molecule or group of molecules comprising a specific recognition partner selected from the group consisting of specific binding partners, hybridizable nucleic acid sequences, shape recognition partners, specifically attractive surfaces and specific recognition pairs. Designer receptors are preferably capable of specifically recognizing a drug or therapeutic receptor and advantageously include mimetic specific recognition partners (i.e., a receptor mimetics) that mimic or approximate the recognition specificity of a selected target (e.g., a therapeutic receptor) for its recognition partner (e.g., a drug, hormone or transmitter). Designer receptors may further comprise or attach to catalytic recognition partners selected from the group consisting of enzymes, catalysts, biological recognition sites, biomimetics, enzyme mimetics and selected molecules and selected nucleic acid sequences capable of participating in catalytic recognition reactions. Designer receptors are not limited to receptors comprising selected molecules, which receptors are defined herein to be nonoligonucleotide molecules. Rather, designer receptors include not only nonoligonucleotide molecules (e.g., ligands and receptors), but also nucleotides (e.g., nucleotide ligands and nucleotide receptors) and oligonucleotides (e.g., aptamers and defined sequence segments capable of specifically binding or hybridizing selected nucleic acid sequences).

The term "device(s)" means a device or system that optionally or advantageously comprises paired devices.

"Different molecular recognition pairs" means two molecular recognition or specific recognition pairs whose four members comprise at least three different chemical identities. When used in reference to MOLECULAR MACHINES or multivalent molecular structures capable of specifically recognizing a surface feature, "different molecular recognition pairs" means "different specific recognition pairs," i.e., two specific recognition pairs whose four members comprise at least three different chemical identities, wherein the members may be capable of specific shape recognition.

"Different specific binding pairs" means two specific binding pairs whose four members comprise at least three different chemical identities. Exemplary pairs of different specific binding pairs include, but are not limited to, two antigen/antibody pairs with different specificities (e.g., peroxidase/anti-peroxidase and fluorescein/anti-fluorescein); two ligand/receptor pairs with different specificities (e.g., D-mannose/concanavalin A and biotin/avidin); a ligand/receptor pair (e.g., biotin/avidin) and an antigen/antibody pair (e.g., digoxigenin/anti-digoxigenin); two different molecular effector conjugate/ligand pairs (e.g., avidin-peroxidase/biotin and avidin-glucose oxidase/biotin); and a nucleotide ligand-receptor pair and a nucleotide receptor-ligand pair, wherein the nucleotide ligand and nucleotide receptor are different modified nucleotides selected, e.g., by combinatorial methods, to specifically bind a selected target molecule or two different selected target molecules. Even biotin/streptavidin and biotin/avidin are different specific binding pairs as defined herein, because the two specific binding pairs comprise three distinguishable chemical identities (i.e., biotin, streptavidin and avidin). The difference in chemical identity between, e.g., streptavidin vs. avidin or avidin-peroxidase vs. avidin-glucose oxidase is not accompanied by a sufficient difference in biotin-binding specificity to enable positional control of specific binding pairs. In other words, a defined sequence segment which is biotinylated at each of two defined nucleotide positions does not provide the requisite chemical specificity to attach avidin and streptavidin, on the one hand, or two different avidin-effector conjugates, on the other hand, in an ordered and reproducible positional relationship to one another. Nucleotide-based templates and multimolecular devices disclosed herein, however, are capable of positioning different specific binding pairs having similar and even indistinguishable binding specificities. When used in reference to MOLECULAR MACHINES or multivalent molecular structures capable of specifically recognizing a surface feature, "different specific binding pairs" means "different specific recognition pairs," i.e., two specific recognition pairs whose four members comprise at least three different chemical identities, wherein the members may be capable of specific shape recognition.

"Different specific recognition pairs" means two specific recognition pairs whose four members comprise at least three different chemical identities.

The term "discoverable," when used in reference to molecules, matter, data, information, energy, methods, principles, processes, compositions or applications, means knowable and heretofore undiscovered, i.e., capable of becoming discovered and known.

The term "discrete structure" refers to any single molecule or to any group of molecules comprising nucleotides, wherein the molecules are bound to one another either covalently or through noncovalent interactions or, in the case of a multimolecular device, are required to specifically bind or dissociate during device function. Discrete structures of the present invention, also referred to herein as "discrete nucleotide structures" and "nucleotide-based discrete structures," include defined sequence segments, aptamers, aptamer-target complexes, nucleotide-based multimolecular devices, discrete aptameric structures, discrete heteropolymeric structures, synthetic heteropolymers, and multivalent heteropolymeric hybrid structures comprising two or more hybridized synthetic heteropolymers, and multimolecular heteropolymeric complexes comprising one or more nonoligonucleotide molecules specifically bound to one or more synthetic heteropolymers or multivalent heteropolymeric hybrid structures. A discrete structure comprising one synthetic defined sequence segment capable of specifically recognizing a nonoligonucleotide molecule and another defined sequence segment capable of specifically recognizing a nucleotide or nonnucleotide molecule is or comprises a synthetic heteropolymer, unless both defined sequence segments specifically recognize the same molecule or one unconjugated defined sequence segment hybridizes to an unconjugated primer used for amplification.

The term "discrete aptameric structure" means a discrete structure comprising at least one synthetic aptamer and includes aptamer conjugates, aptamer-target complexes, oligonucleotides comprising one or more copies of an aptamer sequence, aptameric devices and discrete heteropolymeric structures, optionally including promoter and primer-annealing sequences, e.g., for replication or amplification of a defined sequence segment comprising the discrete aptameric structure.

The term "discrete heteropolymeric structure" means a discrete structure comprising at least one synthetic heteropolymer and optionally including one or more attached nucleotide or nonnucleotide molecules, including, without limitation, spacer molecules, nucleotide spacers, linker oligonucleotides, nonnucleotide linkers, selected molecules and selected nucleic acid sequences. A discrete heteropolymeric structure comprises at least a first defined sequence segment comprising an aptamer and a second defined sequence segment which is capable of specific recognition or comprises a conjugated selected molecule. second defined sequence segment comprises either an aptamer, a single-stranded, double-stranded, partially single-stranded or partially double-stranded nucleotide sequence capable of hybridizing or specifically binding to a selected nucleic acid sequence, or a defined sequence segment capable of positioning a conjugated molecule within suitable proximity to provide single-molecule detection or functional coupling between the conjugated molecule and an aptamer target specifically bound to the first defined sequence segment. Discrete heteropolymeric structures of the invention include synthetic heteropolymers, multivalent heteropolymeric hybrid structures and multimolecular heteropolymeric complexes. All discrete heteropolymeric structures are also discrete aptameric structures, but the converse is not true, i.e., not all discrete aptameric structures are discrete heteropolymeric structures.

The term "disease target" means a therapeutic target or pathophysiological target and includes therapeutic receptors and pathophysiological receptors.

The term "divergent and self-sustaining," when used in reference to cycles of expressing and transposing. imprints and progeny of a selected target molecule or a selected population of selected target molecules using a polydiverse nucleotide library, refers to an iterative, parallel, simultaneous or sequential positive feedback process capable of generating an increasingly diverse assortment of molecular structures, shapes and activities without heretofore known limits on achievable diversity.

The term "docking surface," when used in reference to a member of a recognition pair, means the operative points of contact, atoms, fields of electrostatic attraction or Connolly surface(s) that interact with corresponding points, atoms, fields or surface(s) of a recognition partner.

The terms "donor" and "acceptor," when used in reference to functionally coupled libraries, are introduced herein as useful metaphors in respect of corresponding terms used to describe functionally coupled effector molecules. A donor library is capable of donating (i.e., providing or comprising) a member, property, activity or specificity that can be recognized or imprinted by a member comprising an acceptor library.

The term "drug" as used herein means a molecule, group of molecules, complex or substance administered to an organism for diagnostic, therapeutic, medical or veterinary purposes. Drugs include externally and internally administered topical, localized and systemic human and animal pharmaceuticals, treatments, remedies, nutraceuticals, cosmeceuticals, biologicals, devices, diagnostics and contraceptives, including preparations useful in clinical and veterinary screening, prevention, prophylaxis, healing, wellness, detection, imaging, diagnosis, therapy, surgery, monitoring, cosmetics, prosthetics and forensics. The term "drug" may optionally be used in reference to agriceutical, workplace, military, industrial and environmental therapeutics or remedies comprising selected molecules or selected nucleic acid sequences capable of recognizing cellular receptors, membrane receptors, hormone receptors, therapeutic receptors, microbes, viruses or selected targets comprising or capable of contacting plants, animals and/or humans.

"Effector molecules," also referred to as "effector species," "effectors" and "molecular effectors," are selected nonoligonucleotide molecules or groups, complexes or conjugates of selected nonoligonucleotide molecules capable of transforming energy into work, work into energy, work or energy into information, or information into work or energy and include, but are not limited to, signal-generating species, stimulus-response molecules, response-generating molecules, enzymes, synthetic enzymes, drugs, catalytic antibodies, catalysts, contractile proteins, transport proteins, regulatory proteins, redox proteins, redox enzymes, redox mediators, cytochromes, electroactive compounds, photoactive compounds, supermolecules, supramolecular devices and shape-memory structures.

"Electronic coupling" as used herein means functional coupling relying on the transfer of electrons and includes, for example and without limitation, single-electron transfer and coupling mediated by direct, through-space overlap of relevant donor and acceptor orbitals and by through-bond superexchange(s). Electronic coupling may occur by single-step or multistep processes within a molecule or between molecules positioned by noncovalent or covalent interaction(s), advantageously direct covalent bonding.

"Enhancing or modulating detectability" means, without limitation, controlling or influencing the size, shape, charge, structural properties, position, chemical composition, chemical identity, energy state, binding, activity or functional properties of a molecule; controlling or influencing the amount, mass, concentration, copy number or spatial location of a molecule, product, transcript, replicate, complex, particle or structure; or controlling or influencing the relative positions of at least two molecules or the functional coupling between them.

The terms "evolving" and "evolution," when used in reference to the information comprising or willfully accessible through paired or functionally coupled informational devices, mean learning. No effort is made to reconcile the instant use of the term "learning" with art-accepted definitions regarding machine learning, artificial intelligence or expert systems.

"Functional coupling" and "functionally coupled" mean that at least two processes are connected by a common reaction, event or intermediate or that at least two compositions, which may be molecules, species, substances, structures, devices, groups or combinations thereof, participate as donor and acceptor in the transfer of mass (e.g., molecules, atoms or subatomic particles) or energy (e.g., photons, electrons, kinetic or potential energy, entropy, enthalpy, work or heat), or that two processes or compositions act on a third process, composition, disease or condition in an additive, partially additive or subtractive, mutualistic, synergistic, cooperative, combined or interdependent manner. Examples of functional coupling are well known in the art (e.g., Gust et al. (1993) *Accounts of Chemical Research* 26:198–205; Sheeler et al. (1983) *Cell Biology: Structure, Biochemistry, and Function*, p. 203, John Wiley & Sons, Inc., New York; Saier (1987) *Enzymes in Metabolic Pathways: A comparative Study of Mechanism, Structure, Evolution, and Control*, pp. 48–59 and 132–136, Harper & Row Publishers, New York; Aidley (1989) *The Physiology of Excitable Cells*, Third Edition, p. 320, Cambridge University Press, Cambridge; Bray et al. (1957), *Kinetics and Thermodynamics in Biochemistry*, p. 135, Academic Press, New York; and Guyton (1971) *Textbook of Medical Physiology*, Fourth Edition, p. 786, W.B. Saunders Company, Philadelphia). Functional coupling includes cooperativity between or among two or more molecules.

When used in reference to the interaction between two recognition pairs, the terms "functional coupling" and "functionally coupled" mean that the binding or activity of a member of a first recognition pair influences the binding or activity of a member of a second recognition pair or that members of both recognition pairs bind to or act upon a common substance, disease, condition or process in an additive, partially additive, combined or cooperative manner. Members of both recognition pairs bind to or act upon a common disease or condition, for example, when two (or more) functionally coupled drugs and/or targeting elements bind or act in a combined, additive or synergistic manner at a single disease target or at two or more neighboring sites, receptors or targets.

When used in reference to single-molecule detection of an aptamer, "functional coupling" means to enable detection of an individual aptamer-target complex or multimolecular structure comprising a pair or group of molecules attached by nucleotides or, alternatively, to enable discrimination of an individual molecular complex or multimolecular structure from an uncomplexed nucleotide or nonnucleotide molecule or plurality of molecules.

The term "functionally coupled," when used in reference to paired libraries or a library pair, means that at least one molecule (i.e., product) selected from a first (i.e., donor) library (hereinafter a product of a donor library) is used as a selected target (i.e., precursor or substrate) for screening and/or selection of a second (i.e., acceptor) library.

The term "functional element," when used to describe a nucleotide, segment, template or selected molecule comprising a multimolecular structure or MOLECULAR MACHINE, refers to a nucleotide or nonnucleotide molecule, residue, site, sequence or group having a selected activity, property, specificity, structure or function. Functional elements include, without limitation, selected molecules, nucleotides, modified nucleotides, selected nucleic acid sequences, defined sequence segments, recognition sites and replicates, clones, mimetics, recognition elements, partners and imprints thereof and progeny therefrom.

The term "grafting," when used in reference to attachment of a segment, template, multimolecular structure or MOLECULAR MACHINE to a surface, means specific attachment in such manner that at least one recognition domain or functional element is displayed on the surface in an oriented or polarized manner that enables a useful function or desirable result, e.g., specific adsorption or extraction, solid phase separations, surface catalysis, specific recognition or catalytic recognition assays or processes, or scanning, imaging and/or mapping of a displayed recognition domain or functional element using an analytical tool, e.g., scanning probe microscopy, laser scanning or a hyphenated method.

The terms "group of" and "plurality of," when used in reference to molecules, elements, recognition partners, libraries, sequences, receptors, drugs, recognition pairs and multimolecular structures, means at least two. A member comprising a group or plurality of members may be either attached to another member or unattached.

The terms "heteropolymer-based" and "heteropolymeric" mean comprising at least one synthetic heteropolymer.

The term "heteropolymeric discrete structure" means a discrete structure comprising at least one synthetic heteropolymer, i.e., at least a first defined sequence segment comprising an aptamer and a second defined sequence segment which is a conjugated defined sequence segment or is capable of specific recognition, including imprints, progeny, replicates and mimetics of nucleotides comprising synthetic heteropolymers. Heteropolymeric discrete structures include, for example and without limitation, a synthetic heteropolymer; a multivalent synthetic heteropolymer; a multivalent heteropolymeric hybrid structure; a multimolecular complex; a pair or group of attached synthetic heteropolymers; a pair or group of attached nucleotides comprising a synthetic heteropolymer; a pair or group of attached nucleotide and nonnucleotide molecules comprising a synthetic heteropolymer; a synthetic heteropolymer attached to a nucleotide or nonnucleotide molecule; a synthetic aptamer attached to a defined sequence segment capable of specific recognition; a synthetic aptamer attached to a defined sequence segment comprising a conjugated molecule; a synthetic aptameric first defined sequence attached via a nucleotide spacer, spacer molecule, oligonucleotide linker or nonnucleotide linker to a second defined sequence segment capable of specific recognition; a synthetic aptameric defined sequence segment attached via a nucleotide spacer, spacer molecule, oligonucleotide linker or nonnucleotide linker to a conjugated defined sequence segment; a plurality of nucleotide or nonnucleotide molecules joined by at least one synthetic heteropolymer; a synthetic first aptamer and at least a second aptamer conjugated to the first aptamer; a plurality of aptamers capable of specifically recognizing different target molecules, wherein the aptamers are attached to one another either directly or indirectly; and any of these discrete structures comprising, attached to or capable of attaching to a molecule, nucleotide, complex, multimolecular structure, solid support or transducer surface.

"Hybridizing" refers to specific binding between two selected nucleic acid sequences through complementary base pairing, i.e., hybridization of complementary sequences. Such bonding is also referred to as Watson-Crick base pairing. The binding between complementary nucleic acid sequences is preferably referred to as "hybridizing" or "hybridization" rather than "specific binding." Conversely, binding between noncomplementary nucleotide sequences is referred to as "specific binding," "specific recognition" or "molecular recognition." Hybridized, hybridizable, annealed and/or complementary nucleic acid sequences (e.g., strands comprising or capable of forming hybrids, duplexes or double-stranded regions) are not referred to herein as "specific binding partners" or "members of a specific binding pair," but instead as "hybridized," "hybridizable" or "complementary" nucleotides. For hybridization, a sufficient degree of complementarity is required such that stable and/or reproducible binding occurs between two selected nucleic acid sequences. However, perfect complementarity is not required and may not be preferred for embodiments relying on dissociation of a hybridized nucleic acid sequence, e.g., dissociation of a selected nucleic acid sequence from a defined sequence segment of a multimolecular device concomitant either with hybridization of the defined sequence segment to a more complementary selected nucleic acid sequence or with high-affinity specific binding to a selected molecule or selected nucleic acid sequence. "More complementary" means a second selected nucleic acid sequence having a relatively higher melting temperature, greater number of complementary nucleotides, longer complementary sequence segment, higher percent base pairing, higher G-C content or percent, or greater stability in hybridized form than a first selected nucleic acid sequence.

The term "immobilized" means insoluble, insolubilized or comprising, attached to or operatively associated with an insoluble, partially insoluble, colloidal, particulate, dispersed, suspended and/or dehydrated substance or a molecule or solid phase comprising or attached to a solid support. When used in reference to a multimolecular drug delivery system of the instant invention (e.g., a multimolecular structure comprising a designer drug, smaRTdrug, tethered recognition device, prodrug complex or multimolecular device) the term "immobilized" refers either to a multimolecular structure that is itself insoluble or to a multimolecular structure that is rendered insoluble by attachment to a biological or biocompatible solid support. For example, a drug delivery composition may be immobilized to a biocompatible solid support before administration, or it may be immobilized to a biological solid support during or after administration.

The term "immobilized multimolecular structure" means a MOLECULAR MACHINE of the invention which comprises or attaches to a solid support. In the case of multimolecular structures comprising a molecular adsorbent, multimolecular adherent or multimolecular adhesive, the solid support preferably comprises an amphibious or specifically attractive surface, optionally a chemically bland surface.

The terms "imprint" and "imprinted," when used in reference to the process or product of imprinting a selected target, print molecule or multimolecular structure, refer to an antiidiotypic or anti-antiidiotypic (i.e., idiotypic) recognition partner and any recognition partner thereof comprising a corresponding antiidiotypic or idiotypic specificity, i.e., a recognition partner that is capable of mimicking or recognizing the selected target, print molecule or multimolecular structure. "Imprinting" means any process for producing an imprint or recognition partner of a molecule or multimolecular structure or an imprint or recognition partner thereof, including, without limitation, polymeric casting and molding, library selection of target-specific recognition elements, and transposition of a selected target through paired libraries, preferably paired libraries comprising a nucleotide library. The imprint or recognition partner may be a first, second or subsequent generation imprint or imprinted imprint, idiotype or antiidiotype, mimetic or antimimetic of a target recognition element, all of which generations are referred to herein as imprints. An imprint may faithfully reflect, recognize, mimic, replicate or approximate the recognition properties (e.g., specificity, affinity, kinetics) of a parent recognition element. Alternatively, an imprint may be a weak, strong or moderate competitor, crossreactant, structural or functional analog, partial or mixed agonist or antagonist compared with its parent recognition element or a mimetic, recognition partner, replicate or mutation thereof or progeny therefrom, e.g., a product of molecular imprinting, combinatorial selection, amplification or transposition through a nucleotide library.

The term "imprint library" means a mixture of molecules designed, selected, collected, evolved or modified to comprise an idiotypic or antiidiotypic imprint molecule (i.e., a mimetic or antimimetic molecule) capable of mimicking, approximating, crossreacting with, competing with or recognizing a selected target comprising a selected molecule, selected nucleic acid sequence or surface feature.

"Independent operability," when used in reference to a defined sequence segment comprising a synthetic heteropolymer, means that the defined sequence segment comprising the synthetic heteropolymer retains the binding specificity for which it was selected or designed, i.e., the desired specificity of the defined sequence segment is not lost with incorporation into the synthetic heteropolymer. In other words, the defined sequence segment remains operable independent of its incorporation within the synthetic heteropolymer.

The term "information" means the knowledge comprising a set of data and all interactions among the data, including, e.g., implications and actionable results comprising interactions among the data. "Known information" means information that is willfully accessible. Unknown information may be either knowable (i.e., discoverable) or unknowable (i.e., undiscoverable).

The term "informational device" refers to a synthetic device, composition, product, medium, machine, program, code, process, library, database or means for marking, displaying, representing, mapping, transposing, imprinting, embodying, storing, copying, imaging, simulating, modeling, replicating, archiving, comparing, analyzing, contrasting, searching, researching, conveying or transmitting data, information or instructions, particularly including molecular modeling, biocomputing, multifactorial search engines and hardware and software designed for ultrafast, high-capacity, high-performance approaches to interrogating, analyzing, comparing, contrasting, integrating, interpreting, mapping, transposing, modeling and simulating molecular structure, function and dynamics, including chemical composition, polymer sequence, secondary, tertiary and quaternary structure, three-dimensional shape, docking surfaces, intermolecular dynamics, activity, catalysis and quantitative structure-activity relationships (QSAR).

The term "information space" means the set of all sets of information, including known information and unknown information.

The term "informational system" means a pair of functionally coupled informational devices, i.e., paired informational devices.

The term "instructions" refers to written or nonwritten letters, words, numbers or numerals, recordings, transmissions, replicas, representations, facsimiles, pictures, signs, symbols, digital or analog data or code, static or dynamic images, audio, visual, tactile, olfactory or other sensory, perceptible, detectable or interpretable messages, data or information. Detection, deciphering, decoding, deconvolution or interpretation of instructions may be accomplished by sensory means or may require suitable instrumentation, e.g., a light source, laser, scanner, reader, transmitter, detector, sensor, transducer, transformer, amplifier, actuator, magnifier, decoder, microphone, recorder, imaging system or the like.

The term "intelligent," when used in reference to an informational device(s) or system(s), means capable of learning. When used in reference to learning for willful purpose(s), intelligence requires either a functionally coupled system comprising an informational device and a human (and/or humanly introduced information source) or a functionally coupled paired informational device comprising, attaching to, or capable of attaching to an external information source.

The term "knowable," when used in reference to molecules, matter, data, information, energy, methods, principles, processes, compositions or applications, means capable of being known or discovered, i.e., not unknowable.

The terms "knowable alternatives" and "knowable," when used to describe a preferred embodiment, composition, method or use of the instant invention, mean the inventor is aware that present and future alternatives and discoveries will extend and improve the described embodiment, composition, method or use, such alternatives being predictable and likely derivatives or progeny of the instant invention.

The terms "knowledge" and "known information" refer to information that is known, i.e., willfully accessible. "Knowledge" and "known information" are synonymous.

The term "learning," when used in reference to an informational device(s) or system(s), means that the domain of informational space comprehended by the device(s) or system(s) (i.e., device or system information) evolves in parallel with the evolving information domain encompassed by the term "heretofore known" (i.e., knowledge).

The term "library" refers to a random or nonrandom mixture, collection or assortment of molecules, materials, surfaces, structural shapes, surface features or, optionally and without limitation, monomers, polymers, structures, functions, precursors, products, modifications, derivatives, substances, conformations, arrangements, shapes, features, activities, properties, energies, conditions, treatments, parameters, methods, processes, data or information.

The term "(libraries)$^N$" refers to nucleoplastic libraries and members of the set of all possible nucleoplastic libraries comprising nucleotide, nonnucleotide and paired libraries.

The terms "library pair" and "paired libraries" refer to at least two libraries capable of being functionally coupled, i.e., linked by a recognition pair, member or library comprising a target or probe, precursor or product, donor or acceptor which connects the libraries in diversity space. A paired nucleotide-nonnucleotide library is a paired library comprising a nucleotide library functionally coupled to a nonnucleotide library.

The terms "library-selected" and "library selection," when used in reference to a molecule, probe, product or imprint, refer to a heretofore unknown or unidentified nucleotide or nonnucleotide molecule (i.e., a selectable molecule) which becomes identified by screening and/or selection of a library. Library-selected molecules include, e.g., selected molecules, defined sequence segments, selected nucleic acid sequences, shape-specific probes, modified nucleotides, nucleotide ligands and nucleotide receptors identified by library screening and/or selection, preferably screening and selection of nucleic acid libraries, modified nucleotide libraries and nucleotide-encoded chemical libraries. Heretofore known selected molecules, by contrast, are themselves used as targets for screening and selection of nucleotides comprising aptamers, nucleotide ligands, nucleotide receptors, nucleotide catalysts, catalytic nucleotides and structural shape recognition probes. Once a library-selected molecule is identified and therefore becomes known, it may, in turn, be used as a selected target molecule for screening and selection of a nucleic acid library or nucleotide-encoded chemical library to identify heretofore unknown aptamers, nucleotide ligands, nucleotide receptors, nucleotide catalysts, catalytic nucleotides and structural shape-recognition probes.

The term "library-selected nucleic acid sequence" refers to a selected sequence, three-dimensional structure or activity comprising a nucleic acid, nucleotide and/or nucleotide-encoded nonnucleotide molecule selected from a mixture comprising synthetic and/or biologically derived nucleotides, conjugated nucleotides and/or immobilized nucleotides. Library-selected nucleic acid sequences include, without limitation, any heretofore unknown nucleic acid sequence, structure, activity, nucleotide analog, modified nucleotide or nonnucleotide molecule, particularly including aptamers, ribozymes, catalytic nucleotides, nucleotide ligands, nucleotide receptors, nucleotide catalysts, structural shape probes and sequences or structures comprising at least two recognition elements. Also included is any nucleic acid sequence comprising or attaching to a nucleotide or nonnucleotide molecule that is capable of functional coupling with another nucleotide or nonnucleotide molecule comprising a library. Importantly, screening and selection of a nucleotide library for a nucleotide, nucleotide replicate, imprint, clone, derivative, mimetic or conjugate may be achieved by single-molecule detection methods disclosed herein. Also, selected molecules identified by screening and selection of a nonnucleotide library by single-molecule detection may be advantageously transposed into nucleotide space, enabling amplification, sequencing, digital encoding, characterization and archiving of nucleotide imprints of nonnucleotide molecules and libraries. The importance of this capability will be apparent to the skilled artisan on reading this disclosure.

The term "ligand" means a selected nonoligonucleotide molecule capable of specifically binding to a receptor by affinity-based attraction that does not involve complementary base pairing. Ligands include, but are not limited to, receptor agonists, partial agonists, mixed agonists, antagonists, response-inducing or stimulus molecules, drugs, hormones, pheromones, transmitters, autacoids, growth factors, cytokines, prosthetic groups, coenzymes, cofactors, substrates, precursors, vitamins, toxins, regulatory factors, antigens, haptens, carbohydrates, molecular mimics, print molecules, structural molecules, effector molecules, selectable molecules, biotin, digoxigenin, and congeners, crossreactants, analogs, competitors or derivatives of these molecules as well as library-selected nonoligonucleotide molecules capable of specifically binding to selected targets and conjugates formed by attaching any of these molecules to a second molecule.

The terms "linker" and "linker molecule" refer to molecules or groups which are capable of joining two molecules and include, as the case may be, linker oligonucleotides, nucleotide spacers, spacer molecules, linker molecules and nonnucleotide linkers.

The terms "linker molecule," "linker" and "nonnucleotide linker," when used in reference to nonnucleotide molecules that link nucleotides, mean molecules and groups of molecules capable of joining at least two nucleotides either covalently or noncovalently. Nonnucleotide linkers include, for instance and without limitation, spacer molecules, selected molecules capable of attaching two aptamers (i.e., joining the two aptamers to form an aptameric multimolecular complex or synthetic heteropolymer), nonnucleotide dendrimers, dendrons, peptides, proteins, nonnucleotide linkages and bridges, nonnucleotide monomers, dimers and polymers, ligands (e.g., biotin, digoxigenin, FITC, DNP and peroxidase) and receptors (e.g., avidin, streptavidin and anti-digoxigenin, anti-FITC, anti-DNP and anti-peroxidase antibodies), lipids, sugars, polyethylene glycols, cholesterol, fusion proteins, bispecific antibodies, chelating agents, intercalating agents, crosslinking agents, and nonnucleotide molecules comprising bifunctional, heterofunctional and multifunctional molecules and oligonucleotide linkers.

The term "linker oligonucleotide," also referred to herein as an "oligonucleotide linker," refers to an oligonucleotide sequence, plurality of oligonucleotide sequences, monomers or polymers, or a linker molecule capable of specifically binding or hybridizing to two or more conjugated defined sequence segments or to second defined sequence segments of two or more synthetic heteropolymers, thus joining the conjugated defined sequence segments or synthetic heteropolymers into a discrete structure. An oligonucleotide linker may also join two or more nucleotides covalently or a first nucleotide covalently and a second nucleotide noncovalently. Oligonucleotide linkers conjugated to selected molecules may also join pairs or groups of nucleotides by specific binding or by a combination of specific binding, hybridization and covalent attachment. Alternatively, linker oligonucleotides may first noncovalently attach two or more nucleotides (e.g., by specific binding or hybridization) followed by covalent attachment. Examples of the linker oligonucleotide include, but are not limited to: an oligonucleotide; a stem-loop, bulged or pseudoknot structure having single-stranded ends capable of hybridizing to the second defined sequence segments; a duplex, triplex or quadruplex structure having single-stranded ends capable of hybridizing to the second defined sequence segments; a branched-chain or branched-comb structure having defined sequence segments capable of hybridizing to the second defined sequence segments; a nucleic acid dendron or dendrimer (e.g., Tomalia et al. (1993) In: *Topics in Current Chemistry*, pp. 193–245 Springer, Berlin) or a dendron, dendrimer or other branched or hyperbranched structure attached to nucleotides comprising defined sequence segments capable of hybridizing to the second defined sequence segments; a nonoligonucleotide dimer, multimer or polymer comprising monomeric subunits attached to defined sequence segments of nucleotides capable of hybridizing to the second defined sequence segments; a heteroconjugate comprising a nonoligonucleotide molecule or group of molecules attached to defined sequence segments of nucleotides capable of hybridizing to the second defined sequence segments; a single-stranded or partially single-stranded nucleic acid molecule or group of molecules having a defined topology comprising defined sequence segments capable of specifically binding or hybridizing to the second defined sequence segments; a double-stranded or partially double-stranded nucleic acid molecule or group of molecules having a defined topology comprising defined sequence segments capable of specifically binding or hybridizing to the second defined sequence segments; and a cyclic oligonucleotide or circular structure having defined sequences capable of hybridizing to the second defined sequence segments. Oligonucleotide linkers advantageously comprise replicatable nucleotides.

The terms "machine," "machine learning," "machine-directed" and "machine-intelligence," when used in reference to an informational device or system, refer to products and processes comprising or enabled, facilitated or accelerated by informational devices of the invention, preferably paired informational devices comprising informational systems, more preferably informational systems comprising or capable of attaching to an evolving information source or expert system.

The term "mapping library" means a library comprising a plurality of selected recognition partners identified, collected or accumulated by screening and/or selection of imprint libraries, preferably a diverse plurality of imprint libraries, to map, imprint, transpose, evaluate or characterize the recognition properties of a plurality of target molecules, preferably a selected population of selected molecules. In other words, a preferably diverse plurality of selected nucleotides comprising a mapping library is used to transpose (i.e., imprint) the recognition properties of a selected population of selected molecules into a selected population of selected nucleotides (i.e., a "receptive audience") comprising the mapping library. The mapping library is optionally selected and evolved over time by accumulating selected imprint library members capable of recognizing at least one target molecule comprising a selected population of selected molecules, e.g., the set of immunoglobulin light chains or CD antigens comprising a fractionated pool of umbilical cord blood. Selection and accumulation of the selected population of selected nucleotide recognition partners comprising a mapping library from a plurality of imprint libraries may be viewed as a process of rejecting imprint library members that do not recognize at least one member comprising a selected population of selected molecules, advantageously subjecting selected members to iterative cycles of rejection under conditions of variable and increasing stringency and/or selection pressure. Mapping libraries include the set of nonrejected members following iterative screening and selection of imprintable nucleotide libraries for specific binding and shape-specific recognition elements, optionally including selected specific recognition elements from nucleotide-encoded chemical libraries, e.g., nucleotide ligands and nucleotide receptors.

The terms "materials," "selected materials" and "identified materials," when used in reference to attractive surfaces and the selection of materials having heretofore unknown recognition properties, refers to chemically bland substances, amphibious surfaces and compositions comprising selectable structural shapes and surface features made up of molecules, as distinct from the chemical identities or recognition properties of the constituent selected molecules themselves. The term "recognition property," when used to describe a selected material, refers to the specific attractivity of a structural shape or surface feature and does not include the heretofore known recognition properties of the selected molecules comprising the material. Materials, structures, structural shapes, surfaces and surface features of the instant invention can be selected for the ability to recognize and specifically attach selected molecules and nucleotides. Conversely, selected molecules and nucleotides of the invention are capable of recognizing and specifically attaching to selected materials, structures, structural shapes, surfaces and surface features. A selected molecule with heretofore known recognition properties which attaches or makes up a material or surface is preferably referred to herein as, e.g., an immobilized molecule or a solid support, solid phase or solid phase reagent.

The term "mixture" means a composition comprising a plurality of molecules or at least two different substances that are not chemically bound to each other.

The terms "modified nucleotide" and "derivatized nucleotide" mean synthetic bases, i.e., nonnaturally occurring nucleotides and nucleosides, particularly modified or derivatized adenine, guanine, cytosine, thymidine, uracil and minor bases. Although there is substantial overlap between the terms "modified" and "derivatized," modification tends to relate broadly to any difference or alteration compared to a corresponding natural base, whereas derivatization refers more specifically to the addition or presence of different chemical groups, i.e., modification by the addition of chemical groups, functional groups and/or molecules. Although there is also overlap between the terms "modified nucleotide" and "nucleotide analog" as used herein, "modified nucleotide" typically refers to congeners of adenine, guanine, cytosine, thymidine, uracil and minor bases, whereas "nucleotide analog" further refers to synthetic bases that may not comprise adenine, guanine, cytosine, thymidine, uracil or minor bases, i.e., novel bases.

The terms "molecular adsorbent" and "mimetic adsorbent" refer to an amphibious, chemically bland, specifically attractive, modified or imprinted solid phase, material, surface or structure comprising or specifically attaching a multimolecular structure or multimolecular device, preferably a multimolecular structure comprising a multivalent template, or having a recognition property introduced by grafting, templating, copying, imprinting or transposing a segment, conjugated segment, multivalent template or multimolecular structure, or having a recognition property identified by screening and/or selection of a surface library for a specifically attractive surface feature.

The term "molecular attractor" means a plastic segment or plastic template used to generate and test hypotheses regarding the prospective participation of selected template recognition sites and template-ordered recognition partners in cooperative molecular interactions.

The term "molecular binding specificity," when used in reference to specific binding, means molecular recognition between specific binding partners and does not include specific surface attractivity or structural shape recognition.

The term "molecular complex," when used in reference to a pair or group of molecules, means at least two molecules attached to one another either reversibly, quasireversibly or pseudoirreversibly.

The terms "molecular delivery" and "molecular delivery system" refer to a multimolecular structure capable of specifically recognizing, binding or storing, and transporting, carrying, providing, presenting, delivering and/or releasing a nucleotide or nonnucleotide molecule to a selected target, receptor, site, region, proximity or destination. A molecular delivery system comprises at least two different recognition sites or pairs capable of functioning in an additive or cooperative manner, e.g., to deliver a selected molecule or selected nucleic acid sequence to a selected target and/or to modulate the structure or activity of the selected target.

The term "molecular diversity" refers to the realm of molecular structure-activity space and includes any set or subset of known and/or knowable molecules comprising the diversity space encompassed by the set of all molecules, known and unknown, excluding specifically attractive surfaces (i.e., structural shapes and surface features). The term "art-accepted molecular diversity" means structure-activity space.

The terms "MOLECULAR MACHINE" and "MOLECULAR MACHINES" refer to claimed methods and devices of the instant invention, including, without limitation, nucleotide-based and nonnucleotide aptameric multimolecular devices, heteropolymeric discrete structures, multimolecular delivery systems, promolecular delivery devices, multivalent molecular structures, molecular adsorbents, multimolecular adherents, multimolecular adhesives, molecular lubricants, multivalent heteropolymeric hybrid structures, synthetic heteropolymers, tethered specific recognition devices, paired specific recognition devices, nonaptameric multimolecular devices, multivalent imprints, multimolecular drug delivery systems, designer drugs, smaRTdrugs, shape-specific probes, paired nucleotide-nonnucleotide mapping libraries, recognition elements comprising synthetic nucleotides selected by single-molecule detection, library-selected imprints of synthetic nucleotides selected by single-molecule detection, immobilized multimolecular structures, surface libraries, specifically attractive surface features, multimolecular switches, multimolecular sensors, multimolecular transducers, paired templates, paired recognition pairs, paired MOLECULAR MACHINES and nucleotide-based or nonnucleotide precursors, products, progeny, combinations, clones, replicates, imprints, mimetics and conjugates thereof and progeny therefrom, including any of these MOLECULAR MACHINES operatively attached or functionally coupled to a molecule, nucleotide, molecular scaffold, multimolecular structure, solid support, transducer surface and/or informational device.

The terms "MOLECULAR MACHINE pair" and "paired MOLECULAR MACHINES" refer to pairs comprising at least two MOLECULAR MACHINES, optionally pairs of pairs or networks of pairs or paired pairs, comprising at least two MOLECULAR MACHINES, wherein the two members of a MOLECULAR MACHINE pair function collectively or cooperatively to achieve a desired result. Advantageously, the two members comprising a MOLECULAR MACHINE pair are functionally coupled. Two members of a functionally coupled MOLECULAR MACHINE pair may be attached to each another directly or indirectly, or they may be functionally coupled by means of a mobile substance, e.g., a pheromone, chemical transmitter, mediator or shuttle species.

The term "molecular matrix," when used in reference to imprinting or transposing a property, specificity, shape, structure or function from a molecule into a matrix, refers to a specifically attractive surface, structure, substrate or material, e.g., a chemically bland surface comprising a specifically recognizable surface feature. It will be appreciated by the skilled artisan on reading this disclosure that the distinction between chemically bland surfaces and chemically diverse molecules will become blurred as chemically bland surfaces are endowed with recognition properties as described herein, e.g., by surface library selection, grafting, imprinting and transposition.

The term "molecular medium," when used in reference to imprinting or transposing a property, specificity, shape, structure or function from one molecule into another, means a nucleotide or nonnucleotide molecule comprising an imprint or imprint library.

"Molecular mimics" and "mimetics" are natural or synthetic nucleotide or nonnucleotide molecules or groups of molecules designed, selected, manufactured, modified or engineered to have a structure or function equivalent or similar to the structure or function of another molecule or group of molecules, e.g., a naturally occurring, biological or selectable molecule. Molecular mimics include molecules and multimolecular structures capable of functioning as replacements, alternatives, upgrades, improvements, structural analogs or functional analogs to natural, synthetic, selectable or biological molecules.

The term "molecular recognition," when used in reference to heretofore known binding reactions, pairs, partners and complexes, means specific binding or hybridization and includes 1) specific binding between a ligand and receptor, 2) specific binding between a defined sequence segment and a nonoligonucleotide molecule, 3) specific binding between defined sequence segments and/or selected nucleic acid sequences, and 4) hybridization between complementary nucleic acid sequences and/or defined sequence segments. The terms "molecular recognition" and "specific recognition" may be used interchangeably in certain instances. For example, when used in reference to recognition of a specifically attractive surface feature, "molecular recognition" means and includes specific recognition, i.e., structural shape recognition as well as specific binding and hybridization. However, shape-specific recognition of a structural shape or surface feature by a shape-specific probe of the instant invention is preferably referred to as specific recognition rather than molecular recognition.

When used in reference to synthetic defined sequence segments, synthetic aptamers, synthetic heteropolymers, nucleotide ligands, nucleotide receptors, shape recognition elements, specifically attractive surfaces and MOLECULAR MACHINES disclosed herein, the term "molecular recognition" may include and does not necessarily exclude specific recognition of structural shapes and surface features.

The terms "molecular recognition partners" and "members of a molecular recognition pair" refer to pairs of molecules capable of specifically binding or hybridizing to one another, i.e., members of a specific binding pair or a pair of hybridizable nucleic acid sequences and include, without limitation, ligands, receptors, aptamers, aptamer targets, hybridizable nucleotides, nucleotide ligands, nucleotide receptors, defined sequence segments, linker oligonucleotides, nonnucleotide linkers, selected nucleic acid sequences, selected molecules and molecular recognition sites comprising molecular scaffolds and multimolecular structures. MOLECULAR MACHINES and multivalent molecular structures disclosed herein may further be capable of structural shape recognition, i.e., specific recognition of a surface feature. The terms "molecular recognition partner" and "specific recognition partner" may in certain cases be used interchangeably. A surface feature recognized by a specific recognition site of a MOLECULAR MACHINE or multivalent molecular structure is preferably referred to as a specific recognition partner rather than a molecular recognition partner.

The term "molecular recognition pair" means two molecular recognition partners that specifically bind or hybridize to one another.

The term "molecular recognition site" means the operative specific binding site, docking site, receptor site, epitope, defined sequence segment, nucleotide or complementary sequence of a member of a molecular recognition pair. In the case of a MOLECULAR MACHINE or multimolecular structure capable of specifically recognizing a structural shape or surface feature, "molecular recognition site" means and includes a shape-specific recognition element, i.e., a shape-specific probe. A surface feature recognized by a molecular recognition site of a MOLECULAR MACHINE or multivalent molecular structure is preferably referred to as a specific recognition partner or shape recognition partner rather than a molecular recognition partner or specific binding partner.

The term "molecular recognition unit" (MRU) is a term of art that refers to a (preferably diminutive) portion or subset of an antibody, Fab fragment or peptide that retains binding or effector functions of the parent antibody, Fab fragment or peptide, optionally referring to the minimally operative amino acid sequence of said antibody, Fab fragment or peptide.

The terms "molecular search engine" and "search engine," when used in reference to molecular diversity, diversity space, molecular space, shape space, structural space, surface space, chemical space, catalytic space, surface attractivity space, positional space, and the like, means an informational device(s) capable of searching and analyzing information regarding the structure, function and dynamics of molecules and materials, preferably an evolving informational system comprising at least one member of a set of networked, massively parallel informational device (s) comprising pairs of paired informational devices, processors and/or switches.

The term "molecular shape" refers to molecular structure and function, particularly the molecular recognition and catalytic recognition properties of molecules as distinguished from the structure and function of surface features and structural shapes.

The term "molecular shape space" refers to the diversity of molecular shape and is equivalent to structure-activity space. "Molecular shape" and "molecular shape space" are used preferentially in certain instances to highlight the molecular recognition properties of individual molecules, as distinct from either 1) structural shapes and recognition properties comprising specifically attractive surfaces or 2) intermolecular interactions comprising positional space, particularly the functional coupling achieved by multimolecular devices of the instant invention.

The terms "molecular template" and "template" refer to nucleotide-based or nonnucleotide templates.

The term "molecule" refers to single atoms, groups of atoms, molecules, compounds, species, free radicals, ions, salts and the like which may exist as individual molecules, groups of molecules, molecular species, substances or conjugates comprising molecules.

The terms "multimolecular adherent" and "molecular adherent" mean a specific recognition device capable of specifically attaching a selected molecule to an amphibious surface or a specifically attractive surface. A multimolecular adherent comprises at least a specific recognition element attached to a first selected molecule, wherein the specific recognition element is capable of specifically attaching the first selected molecule to a second selected molecule comprising an amphibious surface or a specifically attractive surface. In a preferred aspect of the invention, the second selected molecule is a structural molecule comprising an amphibious surface. In another preferred aspect, the second selected molecule comprises a specifically recognizable surface feature (i.e., structural shape) and the specific recognition element is a shape-specific probe. Recognition of a surface feature is preferably referred to herein as specific recognition rather than specific binding or molecular recognition. Exceptions are discretionary.

The terms "multimolecular adhesive" and "molecular adhesive" mean a multimolecular structure comprising at least two specific recognition elements capable of specifically attaching two surfaces, at least one surface being an amphibious or specifically attractive surface. A multimolecular adhesive comprises at least a bivalent molecule, template or scaffold comprising or connecting two specific recognition sites, at least one being capable of specifically recognizing a selected molecule and at least one being capable of specifically recognizing an amphibious surface or a specifically attractive surface. Two surfaces can be specifically attached by a single multimolecular structure comprising a multimolecular adhesive that specifically recognizes two surfaces. Alternatively, two surfaces can be specifically attached by a multimolecular adhesive comprising a pair or group of molecules or multimolecular structures that each bind a different surface or different molecule capable of attaching to a surface. In this case, the simultaneous or sequential attachment of the molecules or multimolecular structures to the two surfaces and to each other (i.e., by self-assembly) results in the formation of multimolecular adhesive that attaches the two surfaces to one another.

The term "multimolecular complex" or "multimolecular heteropolymeric complex" refers to a synthetic heteropolymer or multivalent heteropolymeric hybrid structure having at least one identified molecule specifically bound or at least two different aptamer molecules bound to the same target molecule or attached to a common nucleotide spacer, spacer molecule, oligonucleotide linker or nonnucleotide linker molecule. A multimolecular complex comprises at least one synthetic aptameric defined sequence segment, at least one other defined sequence segment which is a conjugated defined sequence segment or is capable of specific recognition, and at least one specifically attached selected nonoligonucleotide molecule. When used in reference to a complex comprising a synthetic heteropolymer, the term "multimolecular heteropolymeric complex" is preferred. When used in reference to a complex comprising at least two aptamers, the term "aptameric multimolecular complex" is also used. Two different aptamer molecules joined to one another either directly or via a linker molecule (i.e., a nucleotide spacer, spacer molecule, oligonucleotide linker or nonnucleotide linker) to form a discrete structure capable of specifically binding two different nonoligonucleotide molecules may be referred to as either as a synthetic heteropolymer or as an aptameric multimolecular complex. Similarly, a discrete structure comprising an aptameric defined sequence segment attached indirectly via a linker molecule to a second defined sequence segment may be referred to as a synthetic heteropolymer, if the discrete structure is capable of specifically recognizing a first, nonoligonucleotide molecule and of hybridizing a second, oligonucleotide molecule comprising a selected nucleic acid sequence.

The terms "multimolecular delivery system," "nucleotide-based delivery system," and "nucleotide-based molecular delivery system," as used herein, refer to discrete structures capable of specifically recognizing, binding or storing and transporting, carrying, providing, presenting, delivering or releasing a selected molecule or nucleic acid sequence to a selected target, receptor, site, region, proximity or destination. Like multimolecular switches, transducers and sensors, multimolecular delivery systems comprise at least two specific recognition pairs or two defined sequence segments connected and functionally coupled by nucleotide-dependent positioning of the corresponding specific recognition sites. Unlike multimolecular switches, transducers and sensors, however, a preferred embodiment of the multimolecular delivery system provides additive, combined or synergistic functional coupling of a first and second selected molecule or nucleic acid sequence to a third object (i.e., a selected target) comprising a molecule, group of molecules, process, disease or condition. In other words, a preferred form of functional coupling for multimolecular delivery systems does not involve the exchange of matter or energy between two specific recognition pairs connected by nucleotides, but instead relies on the combined binding or activity of two specific recognition pairs positioned by nucleotides to modulate the binding or activity of a selected target. The term "multimolecular delivery system" further includes replicates, progeny, imprints and mimetics of nucleotide-based molecular delivery systems, including nonnucleotide imprints and mimetics, i.e., nonnucleotide multimolecular delivery systems.

The term "multimolecular device" means a novel and useful synthetic multimolecular structure comprising at least one synthetic defined sequence segment and a second molecule (e.g., a multimolecular switch, transducer, sensor or molecular delivery system, a tethered recognition device or a MOLECULAR MACHINE) or, alternatively, a novel and useful replicate, progeny, imprint or mimetic of a multimolecular structure that comprises at least one synthetic defined sequence segment and a second molecule, e.g., a nonnucleotide imprint or mimetic of a nucleotide-based multimolecular device. The term "nucleotide-based multimolecular device" refers to synthetic nucleotide-based, aptamer-based or heteropolymer-based discrete structures comprising at least two molecules and includes, without limitation, nucleotide-based multimolecular switches, multimolecular sensors, multimolecular transducers, multimolecular drug delivery systems, molecular delivery systems, multimolecular adhesives, multimolecular adherents and tethered recognition devices. Nucleotide-based multimolecular devices are optionally referred to simply as multimolecular devices. The term "multimolecular device" further includes replicates, progeny, imprints and mimetics of nucleotide-based multimolecular devices, including nonnucleotide imprints and mimetics, i.e., nonnucleotide multimolecular devices. A nucleotide or nonnucleotide multimolecular device may be referred to as a "multimolecular structure" or "multivalent molecular structure." Nucleotide-based multimolecular devices advantageously comprise replicatable nucleotides.

The terms "multimolecular drug delivery system" and "multimolecular drug delivery device" refer to a nucleotide-based or nonnucleotide multimolecular device capable of facilitating, enhancing, enabling or modulating the administration, delivery, dosing, safety, efficacy, release, activation, clearance, transport, pharmacodynamics or pharmacokinetics of at least one drug or prodrug administered to or contacting an organism. Advantageously, one drug or prodrug is specifically attached to a first specific recognition element (e.g., an aptamer or designer receptor) comprising the multimolecular drug delivery system. A second specific recognition element comprises or specifically recognizes a second drug or prodrug or a selected target. Specific interaction of the second specific recognition element with a selected target results in target-specific delivery, release and/or activation of the specifically attached drug or prodrug at or near its therapeutic receptor. Alternatively, where the second specific recognition element comprises or specifically attaches a second drug or prodrug, the multimolecular drug delivery system is capable of combination therapy, e.g., delivery of two different drugs to neighboring therapeutic targets or receptors. A multimolecular drug delivery system may be specifically, covalently, pseudoirreversibly or quasireversibly conjugated to a biological or biocompatible substance or immobilized to a biological or biocompatible solid support (e.g., a cell, surface, tissue, polymer, device or carrier). Useful synthetic solid supports comprising immobilized multimolecular drug delivery systems include, without limitation, artificial organs, artificial cells, artificial skin, implantable devices, controlled release polymers, gels, foams, insoluble polymers, bioerodible polymers, transdermal devices, pumps, infusion devices, indwelling sensors, vascular grafts, artificial valves, artificial joints, prosthetic devices, endoscopes, optical fibers, imaging devices, ablation devices, catheters, guidewires, surgical equipment, diagnostic devices and monitoring devices. Preferred multimolecular drug delivery systems of the instant invention include smaRTdrugs, multimolecular complexes, promolecular delivery devices and tethered recognition devices comprising targeted, tethered or triggered release prodrug complexes. In a preferred embodiment, designer receptors comprising multimolecular drug delivery systems are selected for the ability to mimic the specificity of a therapeutic receptor for a drug.

The term "multimolecular heteropolymeric complex" means a multimolecular complex comprising a synthetic heteropolymer, i.e., a multimolecular complex comprising at least one synthetic aptameric defined sequence segment, at least one other defined sequence segment which is a conjugated defined sequence segment or is capable of specific recognition and at least one specifically attached nonoligonucleotide molecule.

The terms "multimolecular lubricant" and "molecular lubricant" refer to a multimolecular structure or multimolecular device that separates two surfaces, preferably amphibious or specifically attractive surfaces, by attaching to one or both surfaces and reduces the friction, adhesion, traction or direct interaction between the surfaces. Separation of the surfaces is achieved by template-directed attachment of a selected molecule, nucleotide or conjugate, preferably a structural molecule (e.g., a fullerene, buckyball, carbon nanotube, carbon nanorod, polymer, surfactant or glass) or an effector molecule (e.g., a colloid, nanosphere, microsphere or molecular ball bearing) to a first surface. The first surface-attached selected molecule, nucleotide or conjugate may further comprise or attach to a specific recognition element (e.g., a ligand, receptor or oligonucleotide sequence) that is capable of specifically attaching to the second surface, e.g., by specific recognition of a selected molecule, selected nucleic acid sequence or surface feature comprising the second surface. Specific attachment of a multimolecular lubricant to one or both surfaces is advantageously quasireversible, wherein dissociation and reassociation of one or more recognition elements enables movement of the multimolecular lubricant relative to one or both surfaces, i.e., movement of the surface(s) relative to the multimolecular lubricant.

The term "multimolecular sensor" means a multimolecular device comprising a sensor, optionally including a multimolecular transducer and/or a multimolecular switch, which is capable of sensing, detecting, measuring, monitoring, determining or quantifying one or more substances, events, activities or properties.

The terms "multimolecular structure" and "multivalent molecular structure" refer to a synthetic multimolecular or multivalent nucleotide or nonnucleotide molecule or complex, e.g., a discrete structure, molecular complex, molecule or molecular scaffold comprising at least two molecules and/or two recognition sites attached to one another either noncovalently or covalently. A multimolecular structure comprising a defined sequence segment (i.e., a nucleotide-based multimolecular structure) is a discrete structure. A multimolecular structure lacking a nucleotide is a nonnucleotide multimolecular structure and is not a discrete structure. Multimolecular structures include, without limitation, molecular complexes, conjugates, multivalent templates, multivalent molecules and multivalent molecular scaffolds, aptameric and heteropolymeric discrete structures, and nucleotide-based and nonnucleotide multimolecular devices.

The term "multimolecular switch" means a multimolecular device comprising at least two defined sequence segments or specific recognition pairs capable of participating in stimulus-response coupling.

The term "multimolecular transducer" means a multimolecular device capable of performing a desired function, i.e., transducing an input into a desired output, by means of functional coupling between or among two or more selected molecules or between at least one selected molecule and one selected nucleic acid sequence, e.g., by molecular channeling, electronic coupling or energy transfer. The function of a multimolecular transducer depends on additive or partially additive, combined, simultaneous, cooperative or synergistic functional coupling between or among selected molecules and/or selected nucleic acid sequences comprising or recognized by the multimolecular transducer.

The terms "multivalent" and "multisite," when used in reference to nucleotide-based, aptameric, heteropolymeric and nonnucleotide devices, templates, scaffolds and molecules, means comprising at least two specific recognition sites.

The term "multivalent," when used in reference to a multivalent heteropolymeric hybrid structure, means having at least two specific recognition sites in addition to the hybridizable defined sequence segments joining the synthetic heteropolymers that form the multivalent heteropolymeric hybrid structure, i.e., having at least two available and/or unoccupied valencies. In other words, at least two specific recognition sites comprising a multivalent heteropolymeric hybrid structure are capable of specifically recognizing selected molecules or selected nucleic acid sequences other than the synthetic heteropolymers that form the multivalent heteropolymeric hybrid structure itself. For example, a multivalent heteropolymeric hybrid structure consisting of two hybridized bifunctional synthetic heteropolymers is a bifunctional (i.e., bivalent) multivalent heteropolymeric hybrid structure having two available valencies and two hybridized (i.e., occupied) defined sequence segments.

The term "multivalent heteropolymeric hybrid structure" refers to two or more synthetic heteropolymers hybridizably linked. Each heteropolymer comprises nucleotides, preferably oligonucleotides, having at least two defined sequence segments. A first defined sequence segment of at least one heteropolymer is capable of specifically binding to a nonoligonucleotide molecule or group of molecules, preferably a receptor, ligand, structural molecule or molecular effector. The first defined sequence segments of other synthetic heteropolymers comprising the multivalent heteropolymeric hybrid structure are capable either of specifically binding to a selected molecule or of specifically binding or hybridizing to a selected nucleic acid sequence or of positioning a conjugated selected molecule within functional coupling distance of a nonoligonucleotide molecule specifically bound to the first defined sequence segment of the first synthetic heteropolymer, thereby enabling functional coupling between the conjugated selected molecule and the specifically bound nonoligonucleotide molecule. Functional coupling of a conjugated selected molecule includes detection of target molecule binding (i.e., to form a multimolecular complex) by molecular proximity-dependent single-molecule detection. Where the first defined sequence segment of the second synthetic heteropolymer is designed or selected to position a conjugated selected molecule for functional coupling to a specifically bound nonoligonucleotide molecule, the specifically bound nonoligonucleotide molecule is preferably an effector molecule and more preferably a signal-generating species or a drug. The specifically bound nonoligonucleotide molecule is not a ligand or receptor covalently or pseudoirreversibly attached to the conjugated selected molecule. In other words, the two defined sequence segments of a bifunctional multivalent heteropolymeric hybrid structure that are specifically bound and/or conjugated to nonoligonucleotide molecules are not directly attached to the same nonoligonucleotide molecule, one specifically and the other covalently or pseudoirreversibly. Nor are they directly attached to the same covalently or pseudoirreversibly conjugated pair or group of molecules, e.g., a tightly bound or covalently crosslinked ligand-receptor pair. These defined sequence segments of a bifunctional multivalent heteropolymeric hybrid structure are directly attached to two different molecules, thereby assembling and positioning the specifically bound molecule and the conjugated molecule for functional coupling. Stated differently, the two different attached molecules are site-specifically attached to two different defined sequence segments of two different, hybridizably linked synthetic heteropolymers. Second defined sequence segments of the synthetic heteropolymers comprising a multivalent heteropolymeric hybrid structure are capable of hybridizing to each other or to a linker oligonucleotide, optionally forming a double-stranded recognition site (e.g., an aptamer, immunoreactive epitope or biological recognition site) or intercalation site (e.g., for a drug, a dye or, more generally, an intercalating agent) between the first defined sequence segment of a first synthetic heteropolymer and the first defined sequence segment of a second synthetic heteropolymer.

The terms "multivalent imprint" and "bivalent imprint" refer to a bivalent and/or multivalent multimolecular structure comprising an idiotypic or antiidiotypic imprint, replicate, mimetic, clone or mutant of a multivalent molecular structure or a plurality of positionally ordered molecules comprising a multimolecular structure or multimolecular device. When used in reference to parent molecule(s) or multimolecular structure(s) comprising a plurality of recognition elements, the terms "multivalent imprint" and "bivalent imprint" mean a selected, imprinted, transposed, mimetic or progeny molecule or multimolecular structure comprising a plurality of antiidiotypic or idiotypic recognition elements capable of recognizing, competing with, cross-reacting with, mimicking or approximating the corresponding recognition element(s) of the parent molecule(s) or multimolecular structure(s). In other words, each imprint or progeny recognition element is either an idiotype or an antiidiotype of a corresponding precursor or parent recognition element. When used in reference to imprinting or transposing a parent multivalent template or multimolecular structure having a plurality of recognition elements, "imprint" and "transposition" refer to a progeny multivalent template or multimolecular structure capable of mimicking the parent or an imprint of the parent, i.e., the progeny multivalent template or multimolecular structure has recognition elements that correspond either idiotypically or anti-idiotypically to each recognition element of the parent multivalent template or multimolecular structure.

The term "multivalent molecular structure" means a multimolecular structure.

The term "mutation," when used in reference to transposing, transforming, imprinting or mimicking a non-nucleotide molecule or selected population of nonnucleotide molecules refers to a variation or change in structure, shape, activity, function, properties or diversity of the product compared to the precursor, e.g., an approximation or variant rather than a perfectly faithful imprint or copy.

The terms "native," "in nature", "natural," "naturally occurring," "biological" and "organism," refer to spontaneously occurring substances or beings that are not willful products of human-directed recombinant or transgenic technologies. In the case of hybrid plants and animals that have been identified and/or perpetuated by cross-breeding, selective breeding, cross-pollination, stem or limb grafting and the like, the terms "native," "in nature", "natural," "naturally occurring," "biological" and "organism" mean and include only heretofore known strains. Where the distinction between natural and synthetic is ambiguous, a heretofore known substance, being or strain shall be considered natural for purposes of this disclosure, and a heretofore unknown substance, being or strain shall be considered synthetic.

The term "networked," when used in reference to search engines, means multiple interconnected informational devices comprising an informational system. The informational system preferably comprises multiple application-specific search engines functionally coupled to one another and to an information source, e.g., a database comprising known information.

The term "nonaptameric," when used in reference to a nucleotide-based multimolecular device, means a discrete structure that does not comprise a nucleotide sequence heretofore known to be an aptamer.

The term "nonaptameric," when used in reference to a multimolecular structure, means a nonnucleotide multimolecular structure or a nucleotide-based multimolecular structure (i.e., a discrete structure) which is not known to comprise an aptamer or to rely on the recognition properties of an aptamer. In the event a nucleotide sequence comprising a nucleotide-based multimolecular structure is subsequently discovered to comprise a previously undiscovered aptamer, the multimolecular structure is considered to be a nonaptameric multimolecular structure, unless and until the aptameric sequence of the multimolecular structure specifically recognizes its target under conditions of use, thereby forming a multimolecular structure comprising an aptamer-target complex. A nonnucleotide multimolecular structure is also a nonaptameric multimolecular structure. When used in reference to a multimolecular device, the term "nonaptameric" similarly means a nonnucleotide multimolecular device or a nucleotide-based multimolecular device which is not known to comprise an aptamer or to rely on the recognition properties of an aptamer. In the event a nucleotide sequence comprising a nucleotide-based multimolecular device is subsequently discovered to comprise a previously undiscovered aptamer, the multimolecular device is considered to be a nonaptameric multimolecular device, unless and until the aptameric sequence of the multimolecular device specifically recognizes its target under conditions of use, thereby forming a multimolecular device comprising an aptamer-target complex. A nonnucleotide multimolecular device is also a nonaptameric multimolecular device.

The term "nonaptameric multimolecular device" refers to a nucleotide-based or nonnucleotide multimolecular device (e.g., a multimolecular switch, multimolecular sensor, multimolecular transducer, multimolecular delivery system, paired specific recognition device, tethered specific recognition device, multimolecular adherent, multimolecular adhesive, molecular adsorbent or MOLECULAR MACHINE) which does not comprise a known and/or operative aptamer. A nucleotide-based nonaptameric multimolecular device comprises either 1) at least two different specific binding pairs connected by a single defined sequence segment, each specific binding pair being attached in a controlled manner to a defined site or nucleotide position or 2) at least two different defined sequence segments and at least two different specific binding pairs, each specific binding pair being conjugated to a different defined sequence segment, wherein the two conjugated defined sequence segments are hybridized to a linker oligonucleotide which thus joins and positions the two conjugated defined sequence segments within a single discrete structure or 3) at least two members of a specific binding pair or four members of two specific recognition pairs covalently or pseudoirreversibly attached to a molecular scaffold. Nonaptameric multimolecular devices that do not comprise a nucleotide are nonnucleotide multimolecular devices and include, e.g., nonnucleotide paired specific recognition devices, nonnucleotide tethered specific recognition devices, nonnucleotide molecular adsorbents and nonnucleotide multimolecular adherents, multimolecular adhesives, multimolecular switches, multimolecular sensors, multimolecular transducers and multimolecular delivery systems.

The terms "nonoligonucleotide" and "nonoligonucleotide molecule" mean a molecule or group of molecules which is not an oligonucleotide or, in the case of a conjugate comprising a first molecule that is an oligonucleotide attached to a second molecule that is not an oligonucleotide, the portion of the conjugate originating from or consisting of the second molecule.

The term "nonnucleic acid molecule" means a molecule or group of molecules that is not a nucleic acid.

The terms "nonnucleotide" and "nonnucleotide molecule," when used in reference to a molecule, residue, moiety or group, means the molecule, residue, moiety, or group in question is not a nucleotide. When used in reference to an amphibious surface, the term "nonnucleotide" means the surface does not comprise a heretofore known nucleotide-based molecular recognition partner unless and until modified by a multimolecular device of the instant invention. A nonnucleotide amphibious surface modified by a nucleotide-based multimolecular device of the instant invention is referred to as an amphibious surface or a nucleotide-based amphibious surface. "Nonnucleotide surface," when used in reference to an amphibious surface, means a surface that does not comprise a heretofore known nucleotide-based molecular recognition partner unless and until modified by a multimolecular device of the instant invention. A nonnucleotide amphibious surface modified by attachment of a nucleotide-based multimolecular device of the instant invention may be referred to as an amphibious surface or a nucleotide-based amphibious surface.

The term "nucleotide-nonnucleotide" refers to a pair comprising a first nucleotide or nucleotide-based member and a second nonnucleotide or nonnucleotide-based member. A "nucleotide-nonnucleotide library" or "paired nucleotide-nonnucleotide library" is a paired library comprising a nucleotide library functionally coupled to a nonnucleotide library.

The terms "nucleotide or nonnucleotide," "nucleotide and nonnucleotide," "nucleotide-based or nonnucleotide" and "nucleotide-based and nonnucleotide," when used in reference to methods, compositions and devices disclosed herein, mean consisting of or comprising any type of molecule, i.e., nucleotide and/or nonnucleotide molecules.

The term "nonnucleotide library" means a mixture of molecules which does not comprise nucleotides or a library that is not a nucleotide library, or a pair, group or library of libraries that are not nucleotide libraries. Typically, nonnucleotide libraries of the invention are diverse mixtures of molecules of a particular nonnucleotide type or class, e.g., peptides, proteins, small molecules, lipids, carbohydrates, acrylates, polyalcohols, polyesters, polystyrenes, polyolefins, glycols, dendrons, antibodies, amino acids, engineered antibodies, oligosaccharides, and organic polymers such as polyhydroxyalkanoates, polyphenols, poylphosphates and polysulfates.

The terms "nonnucleotide multimolecular device" and "nonnucleotide-based multimolecular device" mean a multimolecular device that does not comprise a synthetic heteropolymer, aptamer or defined sequence segment.

The terms "nucleic acid amplification" and "nucleic acid amplification system" refer to processes and/or reagent means for amplifying nucleotides, including, without limitation, biological, enzymatic, in vivo, in vitro and in situ methods relying on thermal cycling, isothermal methods, cloning, nucleotide vectors, parasites, self-sustained reactions and the like, e.g., PCR, LCR, Q-beta replicase, 3SR, TAS, RCR, CPR, ribonuclease H and reAMP methods.

The term "nucleic acid molecule" refers to biological, naturally occurring, nonbiological and synthetic nucleotides, oligonucleotides and selected nucleic acid sequences which may optionally be conjugated to one or more nonoligonucleotide molecules.

The term "nucleolibrary-directed" refers to a product or process comprising, relating to or depending on from screening and/or selection of a nucleotide library, preferably a paired library comprising a nucleotide library functionally coupled to a nonnucleotide libraries.

The terms "nucleoplastic" and "plasticity," when used to describe synthetic nucleotides, nucleotide libraries, progenic molecules, segments, templates, progeny, mimics, imprints, clones, conjugates, copies, simulations, modifications and products and progeny therefrom, refers to the diversity of members of the set of all nucleoplastic libraries comprising nucleotide and nonnucleotide libraries and paired libraries, also referred to herein as (libraries)$^N$, wherein the composition and/or sequence, if applicable, of a heretofore unknown plastic nucleoprobe becomes known following library selection.

The terms "nucleoplastic library," "nucleodiverse library," "nucleotide library" and "(libraries)$^N$" refer to the set of all possible pairs of parent and progeny molecular libraries comprising a first member which is a nucleotide library and a second member which is a nonnucleotide library, wherein the first and second libraries are capable of being functionally coupled, including the set of all molecular libraries and members of molecular libraries that evolve from said parent or progeny molecular libraries. The terms also refer, as the case may be, to any set or subset of plastic segments or templates and any set or subset of libraries comprising a nucleoplastic library.

The term "nucleoprobe" refers to a nucleotide comprising a specific recognition element or, in the case of a plastic nucleoprobe, a parent nucleotide, replicate, progeny, imprint or mimetic comprising a specific recognition element. Nucleoprobes include, without limitation, nucleotide-based specific recognition elements and synthetic heteropolymers, multimolecular devices, imprints, progeny, replicates and mimetics comprising or originating from at least one nucleotide-based recognition element.

The term "nucleotide" includes nucleotides and nucleotide analogs, preferably groups of nucleotides comprising oligonucleotides, and refers to any compound containing a heterocyclic compound bound to a phosphorylated sugar by an N-glycosyl link or any monomer capable of complementary base pairing or any polymer capable of hybridizing to an oligonucleotide.

The term "nucleotide analog" refers to molecules that can be used in place of naturally occurring bases in nucleic acid synthesis and processing, preferably enzymatic as well as chemical synthesis and processing, particularly modified nucleotides capable of base pairing and optionally synthetic bases that do not comprise adenine, guanine, cytosine, thymidine, uracil or minor bases. This term includes, but is not limited to, modified purines and pyrimidines, minor bases, convertible nucleosides, structural analogs of purines and pyrimidines, labeled, derivatized and modified nucleosides and nucleotides, conjugated nucleosides and nucleotides, sequence modifiers, terminus modifiers, spacer modifiers, and nucleotides with backbone modifications, including, but not limited to, ribose-modified nucleotides, phosphoramidates, phosphorothioates, phosphonamidites, methyl phosphonates, methyl phosphoramidites, methyl phosphonamidites, 5'-β-cyanoethyl phosphoramidites, methylenephosphonates, phosphorodithioates, peptide nucleic acids, achiral and neutral internucleotidic linkages and nonnucleotide bridges such as polyethylene glycol, aromatic polyamides and lipids. These and other nucleotide and nucleoside derivatives, analogs and backbone modifications are known in the art (e.g., Piccirilli J. A. et al. (1990) *Nature* 343:33–37; Sanghvi et al (1993) In: *Nucleosides and Nucleotides as Antitumor and Antiviral Agents*, (Eds. C. K. Chu and D. C. Baker) Plenum, New York, pp. 311–323; Goodchild J. (1990) *Bioconjugate Chemistry* 1:165–187; Beaucage et al. (1993) *Tetrahedron* 49:1925–1963).

The term "nucleotide-based," when used in reference to a multimolecular device, multimolecular switch, multimolecular transducer, multimolecular sensor, multimolecular delivery system, multimolecular drug delivery system, tethered recognition device or molecular scaffold, means comprising at least one defined sequence segment.

The term "nucleotide catalyst" means a synthetic nucleotide or nucleotide-encoded nonnucleotide molecule comprising a catalytic recognition partner, preferably a nucleic acid, nucleotide or nonnucleotide molecule identified by screening and selection of a preferably diverse mixture comprising nucleic acid molecules, nucleotides, modified nucleotides or nucleotide-encoded nonnucleotide molecules, advantageously a diverse library comprising soluble, conjugated or immobilized molecules.

The term "nucleotide-dependent functional coupling" means functional coupling between or among nucleotide or nonnucleotide molecules which depends on or is brought about by attachment of at least one molecule to at least one nucleotide comprising a discrete structure.

The terms "nucleotide-dependent molecular positioning," "nucleotide-dependent positioning" and "nucleotide-positioned" means molecular positioning that depends on either 1) attachment of a molecule or group to a nucleotide comprising a defined sequence segment or 2) attachment of a molecule or group to a defined sequence segment comprising a nucleotide or 3) attachment of a molecule or group to a nucleotide comprising a defined sequence segment comprising a nucleotide-based multimolecular device, wherein the position of the attached molecule or group depends on the position of the nucleotide comprising the defined sequence segment or the position of the defined sequence segment comprising the multimolecular device.

The terms "nucleotide-directed," "nucleotide-ordered," and "nucleotide template-ordered" refer to nucleotide-dependent molecular positioning, nucleotide-dependent functional coupling and/or the preparation, properties and use of multimolecular devices. Nucleotide-ordered multimolecular devices include nucleotide and nonnucleotide replicates, clones, mimetics, imprints, progeny and conjugates of nucleotide-ordered multimolecular devices, including replicates, clones, mimetics, imprints, progeny and conjugates thereof and progeny therefrom.

The term "nucleotide library" means a library, paired library or group of libraries comprising nucleotides or nucleotide mimetics, including, without limitation, nucleic acid libraries, nucleotide libraries, modified nucleotide libraries, libraries comprising nucleotide analogs or nucleotide mimetics, nucleotide-encoded libraries, nucleotide-ordered molecular libraries, paired nucleotide libraries, nucleotide-nonnucleotide libraries, libraries of nucleotide libraries, libraries of libraries comprising nucleotides or nucleotide libraries, and any library comprising nucleotide and nonnucleotide molecules, wherein a nucleotide molecule comprises, attaches to or is capable of attaching to a nonnucleotide molecule.

The terms "nucleotide ligand" and "nucleotide receptor" refer to molecules or functional groups comprising or attaching to modified nucleotides, derivatized nucleotides, nucleotide analogs, nucleotide-encoded molecules or nucleotide-encoded chemical, shape or sequence libraries. Nucleotide ligands and nucleotide receptors are preferably derivatized monomers, optionally dimers or trimers, selected for the ability to specifically recognize an identified molecule or structural shape. Specific recognition properties are residue-dependent or modification-dependent, as distinct from sequence-dependent aptamer-based specific recognition. Preferably, a nucleotide ligand or nucleotide receptor comprising a derivatized nucleotide is selected for the ability to specifically recognize an identified molecule that is not heretofore known to specifically recognize the underivatized nucleotide. In other words, specific recognition is a property of the derivative or derivatized nucleotide, not the underivatized nucleotide. Thus, a nucleotide receptor that is a member of a first specific binding pair (i.e., the nucleotide receptor and its ligand) may also be a member of a second specific binding pair, e.g., the nucleotide receptor may be specifically recognized by a receptor (e.g., an antibody) or an aptamer. In other words, a nucleotide receptor may also be a ligand. Conversely, a nucleotide ligand may also be a receptor. Where there is overlap or potential ambiguity in the use of these terms, "nucleotide ligand" and "nucleotide receptor" may be used interchangeably.

The term "nucleotide mimetic" means a nucleotide analog or a nonnucleotide molecule capable of being replicated by nucleic acid cloning, replication or amplification methods known in the art, i.e., a nucleotide analog or a molecule capable of mimicking a replicatable nucleotide.

The term "nucleotide space" means the dimensionless product of all molecular and surface diversity spaces encompassed by all nucleotide libraries, including members of molecular libraries and surface libraries comprising or attaching to members of nucleotide libraries.

The terms "nucleotide spacer" and "spacer nucleotide" refer to one or more nucleotides, spacer arms, spacer molecules or groups selected or designed to join at least two nucleotides, defined sequence segments and/or a nucleotide and a nonnucleotide molecule, preferably to alter or adjust the distance between the two nucleotides, defined sequence segments and/or nucleotide and nonnucleotide molecules, and include individual nucleotides, groups of nucleotides, nucleotide analogs, modified nucleotides, spacer modifiers, spacer sequences, spacer molecules, linker molecules, linker oligonucleotides, nonnucleotide linkers and mutually hybridizable defined sequence segments comprising synthetic heteropolymers, multivalent heteropolymeric hybrid structures, discrete heteropolymeric structures and nucleotide-based multimolecular devices. Nucleotide spacers may also comprise contiguous or interspersed groups of molecules comprising a defined sequence segment or joining two defined sequence segments and may advantageously comprise replicatable nucleotides.

The term "nucleotide template" means a defined sequence segment capable of attaching at least two selected molecules to one another, wherein the template is capable of specifically binding at least one of the selected molecules. The other selected molecule may be specifically bound, covalently attached or pseudoirreversibly attached to the template. Also included are nucleotide and nonnucleotide clones, replicates, mimetics, imprints, progeny and conjugates of nucleotide templates, including clones, replicates, mimetics, imprints and conjugates thereof and progeny therefrom.

The term "oligonucleotide" means a naturally occurring or synthetic polymer of nucleotides, preferably a polymer comprising at least three nucleotides and more preferably a polymer capable of hybridization. Oligonucleotides may be single-stranded, double-stranded, partially single-stranded or partially double-stranded ribonucleic or deoxyribonucleic acids, including selected nucleic acid sequences, heteroduplexes, chimeric and hybridized nucleotides and oligonucleotides conjugated to one or more nonoligonucleotide molecules.

The terms "oligonucleotide conjugate" and "conjugated oligonucleotide" mean an oligonucleotide conjugated to, incorporating or comprising a nonoligonucleotide molecule or a nonoligonucleotide molecule covalently or pseudoirreversibly attached to an oligonucleotide.

The term "paired nucleotide-nonnucleotide library" means a paired library comprising a nucleotide library functionally coupled to a nonnucleotide library.

The term "paired nucleotide-nonnucleotide mapping library" refers to a mapping library comprising a paired nucleotide-nonnucleotide library, i.e., a paired nucleotide-nonnucleotide library comprising a plurality of selected recognition partners identified, collected or accumulated by screening and/or selection of at least one imprint library, preferably a plurality of imprint libraries, to map, imprint, transpose, evaluate or characterize the recognition properties of a plurality of target molecules, preferably a selected population of selected molecules.

The terms "paired recognition pair" and "paired recognition device" mean a multimolecular structure comprising at least two different recognition pairs, each recognition pair comprising two members.

The terms "paired specific recognition pair," "paired specific recognition device," "paired molecular recognition pair" and "paired molecular recognition device" mean a synthetic multimolecular structure comprising at least two different specific recognition pairs conjugated to a molecule, synthetic nucleotide, or molecular scaffold or comprising a nucleotide-based multimolecular device, each specific recognition pair comprising two specific recognition partners. advantageously, the specific recognition pairs are positioned for functional coupling by site-directed attachment to the same molecule, molecular scaffold or nucleotide, e.g., the binding or activity of a member of one specific binding pair can modulate the binding or activity of a member of the other specific binding pair. Paired specific recognition devices include, without limitation, heteropolymeric, aptameric, nonaptameric and nonnucleotide multimolecular devices comprising at least two different specific recognition pairs and multimolecular structures capable of mimicking multimolecular devices comprising at least two different specific recognition pairs, including replicates, imprints, mimetics and progeny thereof. Biological proteins, antibodies, and heretofore known bispecific, bivalent and multivalent synthetic, recombinant and engineered antibodies, antibody fragments, peptides, proteins, bacteriophage, immunoadhesins and fusion proteins are not paired specific recognition devices.

The term "pair of specific recognition pairs" means two different specific recognition pairs.

The terms "pair of specific binding pairs" and "paired specific binding pair" refer to a pair of specific recognition pairs whose members are capable of specific binding or structural shape recognition (i.e., any form of specific recognition except hybridization). "Paired specific binding pairs" means the specific binding pairs comprise a paired specific recognition device, i.e., they are attached to a common molecule, molecular scaffold or nucleotide, advantageously within functional coupling distance.

The term "paired templates" means at least two templates that are related to one another as parent and progeny or by one or more cycles of replication, transcription, conjugation, cloning, imprinting or transposition, transformation, projection, reflection or passage through a nucleotide library, optionally a paired nucleotide-nonnucleotide library.

The terms "payload" and "payload molecule," when used in reference to a promolecular delivery device or promolecule complex, mean a nucleotide or nonnucleotide molecule specifically attached to a designer receptor, i.e., a specific recognition partner of a designer receptor. Payload molecules may include, without limitation, selected molecules, nucleotides, selected nucleic acid sequences, structural shapes and surface features. Delivery of a payload molecule to a selected target by a promolecular delivery device provides a desired result caused or mediated by the binding or activity of the payload molecule at or near the selected target or by interaction between payload and target molecules.

The term "photosystem" as used herein means a photosynthetic molecule or group of molecules that serves as a functionally coupled energy transfer acceptor from a reaction center and includes, without limitation, molecules comprising photosystem I and photosystem II.

The term "plastic," when used in reference to segments, templates, libraries, recognition elements, MOLECULAR MACHINES and the imprinting, transposition and transformation of recognition elements, templates, molecular media, materials, surface features and MOLECULAR MACHINES, refers to plasticity, i.e., comprising, relating to or originating from a diverse mixture, medium, library, population, source, material, process or set of alternatives, preferably a diverse library, a paired library or a library of libraries, more preferably a nucleotide library. Alternatively, when used to describe heretofore known industrial materials (i.e., plastics), the term "plastic" means the family of cast and mold substances available for use in product design and commercial manufacturing, typically polymers capable of being shaped, formed, molded, extruded, cast into shapes or films, or drawn into filaments.

The terms "plastic nucleoprobe" and "nucleoplastic probe" refer to 1) a specific recognition element comprising a parent nucleotide or a replicate, progeny, imprint or mimetic thereof or 2) a specific recognition element selected from a nucleotide library, optionally a paired nucleotide-nonnucleotide library, including replicates, progeny, imprints or mimetics thereof.

The terms "polydiverse" and "nucleodiverse," when used in reference to a mixture, library or molecular medium, refer to multidimensional diversity in structure-activity space, preferably diversity in at least three dimensions, e.g., a nucleotide library diversified in chemical space, sequence space and positional space.

The term "positional space" refers to the two-dimensional positional relationships between and among members of pairs and groups of molecules comprising or attaching to nucleotide-defined positions of multisite templates, including imprints, progeny, replicates and mimetics of nucleotide-based templates. Positional space is approximated as the dimensionless product of possible positional relationships of Z recognition elements comprising X sequences of Y length, i.e., the combinatorial product of diversities comprising 1) variable sequence length and 2) variable distance between two recognition elements comprising a sequence and 3) variable distance between a third recognition element comprising a sequence and each of two optionally preselected and positionally fixed recognition elements and 4) variable distance between an Nth recognition element comprising a sequence and each of N−1 optionally preselected and positionally fixed recognition elements. Positional space as used herein does not refer to the axial, polar or three-dimensional position of nonnucleotide groups tethered to nucleotides comprising nucleotide ligands, nucleotide receptors, modified nucleotides, selected molecules conjugated to nucleotides, nucleotide-encoded chemical groups, and the like, which three-dimensional diversity is a subset of molecular shape space. Instead, positional space is a representation of the diversity space reflecting potential interactions between at least two recognition elements comprising either a nucleotide or an imprint, progeny or mimetic of a nucleotide. Sequence length is included as a dimension in positional space substantially to emphasize the bookend utility of 3' and 5' nucleotide modifications in mapping the positional preference landscape of first and second selected molecules (e.g., ligands, receptors and effector molecules) comprising, attached or tethered to members of nucleoplastic libraries. The user-definable distance between 3' and 5' ends of a nucleotide strand provides a convenient tool for mapping the "proximity space" or "functional coupling space" of a selected pair of selected molecules (e.g., donor and acceptor fluorophores) from a first plastic medium (e.g., a nucleotide library) into a second plastic medium (e.g., selectable nonnucleotide molecules or polymers).

The terms "precursor," "substrate" and "product," when used in reference to functionally coupled libraries, are introduced herein as useful metaphors in respect of corresponding terms used to describe functionally coupled paired effectors comprising, e.g., enzymatic, photonic and electronic donor and acceptor species (cf. Example 5 and Example 6, vide infra). A precursor library is capable of donating (i.e., providing or comprising) a member, property, activity or specificity that can be recognized or imprinted by a member comprising an acceptor library.

The terms "probe" and "probing," when used to describe a selected molecule, segment, template, nucleotide or library, refer to a specific recognition element or a plurality of specific recognition elements. Unlike prior art nucleic acid probes, the probes comprising synthetic heteropolymers, multimolecular devices and MOLECULAR MACHINES may specifically recognize nucleotide or nonnucleotide molecules or structural shapes.

The term "prodrug" means a drug, drug precursor or modified drug that is not fully active or available until converted in vivo or in situ to its therapeutically active or available form. Prodrugs comprising multimolecular devices and MOLECULAR MACHINES of the instant invention include targeted and triggered-release prodrug complexes, e.g., multimolecular drug delivery systems and promolecular delivery devices.

The term "prodrug complex" refers to a promolecule complex or payload-receptor complex comprising a drug specifically attached in inactive or unavailable form to a designer receptor, whereupon dissociation of the drug from the designer receptor renders the drug molecule active or available for interaction with a selected target or pathophysiological receptor. Prodrug complexes may comprise a pair or plurality of drugs specifically bound to a pair or plurality of designer receptors. Prodrug complexes may also be operatively attached to biological or biocompatible structures, microstructures or nanostructures free to distribute in or to one or more anatomical or physiological compartments. Useful synthetic solid supports comprising immobilized prodrug complexes include, without limitation, artificial organs, artificial cells, artificial skin, implantable devices, controlled release polymers, gels, foams, insoluble polymers, bioerodible polymers, transdermal devices, pumps, infusion devices, indwelling sensors, vascular grafts, artificial valves, artificial joints, prosthetic devices, endoscopes, optical fibers, imaging devices, ablation devices, catheters, guidewires, surgical, diagnostic and monitoring devices. Useful synthetic solid supports comprising immobilized multimolecular drug delivery systems include, without limitation, artificial organs, artificial cells, artificial skin, implantable devices, controlled release polymers, gels, foams, insoluble polymers, bioerodible polymers, transdermal devices, pumps, infusion devices, indwelling sensors, vascular grafts, artificial valves, artificial joints, prosthetic devices, endoscopes, optical fibers, imaging devices, ablation devices, catheters, guidewires, surgical equipment and in vivo, in situ and extracorporeal diagnostic, monitoring and delivery devices. Prodrug complexes may also attach to solid tissues or anatomically confined biologic or biocompatible structures, or they may be willfully attached to cells, tissues or organs, optionally reversibly or by a willfully biodegradable, cleavable and/or metabolizable linkage. Prodrug complexes may be stored, confined or released in selected physiological or anatomical compartments or, alternatively, transported, delivered and/or confined to a selected physiological or anatomical compartment, site or target.

The term "progeny," when used in reference to a molecule, nucleotide, segment, template or group of molecules, nucleotides, segments or templates, means originating ultimately from a replicatable synthetic nucleotide (i.e., a parent) either by replication, cloning, amplification, modification, imprinting or transposition. The parent synthetic nucleotide and progeny nucleotide or nonnucleotide molecules, segments, templates or progeny therefrom may be enzymatically, chemically or physically modified, derivatized, imprinted, transposed, replicated, cloned, simulated, copied, approximated, conjugated, complexed, assembled, amplified, mutated and the like, all with variable and preferably willful control over the fidelity of the replication, imprinting, simulation and/or modification process.

The term "promolecular delivery device" means a targeted and/or triggered-release (i.e., smart) molecular delivery system comprising a bivalent or multivalent molecule, template, scaffold or multimolecular device capable of specifically recognizing, storing, preserving, stabilizing or attaching a payload molecule and/or carrying, transporting, delivering, releasing, activating or attaching the payload molecule to or near a selected target. The payload molecule is specifically attached in inactive and/or unavailable form to a designer receptor, providing a complex referred to herein as a "promolecule complex," "payload-designer receptor complex" or "payload-receptor complex." Upon dissociation of the payload-receptor complex, the released payload molecule becomes active or available for interaction with a selected target. A promolecular delivery device further comprises a second, optionally allosteric, recognition site capable of delivering, attaching, activating and/or releasing the payload molecule to or near a selected molecule, surface feature or selected nucleic acid sequence comprising, attaching to or neighboring the selected target. The payload molecule can also be tethered to a molecule or scaffold comprising or attaching to the designer receptor, providing a tethered promolecular delivery device. In this mode of operation, the payload molecule is not only specifically attached, but also pseudoirreversibly or covalently attached (i.e., tethered) to the designer receptor, optionally in a selectively cleavable manner (e.g., cleavable by enzymatic, catalytic or photodynamic degradation of a selected covalent bond).

The term "promolecule," when used in reference to a promolecule complex or molecular delivery system, means a nucleotide or nonnucleotide molecule or group of molecules having a selected property, structure, function or activity that is not expressed, active or available unless or until the molecule or group of molecules is released or activated, i.e., by dissociation from a promolecule complex.

The terms "promolecule complex," "payload-designer receptor complex" and "payload-receptor complex" refer to a molecular complex comprising a promolecule or payload molecule specifically attached in inactive or unavailable form to a designer receptor, whereupon dissociation of the payload molecule from the designer receptor renders the payload molecule active or available for interaction with a selected target.

The terms "proximity space" and "functional coupling space," when used in reference to plastic nucleoprobes, templates and nucleotide libraries, refer to the structural and functional correlates of positional space with respect to the ability of at least two molecules or groups to interact in a functionally coupled manner, e.g., as donor and acceptor species comprising a functionally coupled donor-acceptor pair.

The term "pseudoirreversible" means a binding event, bond, association, complex or specific recognition pair comprising a selected molecule which cannot be dissociated, displaced, reversed, separated or detached under normal conditions of use and which is not formed during operation, as distinct from manufacture, of a multimolecular structure or multimolecular device. For purposes of the present invention, noncovalent, pseudoirreversible attachment of a selected molecule to a multimolecular device is functionally equivalent to covalent attachment in terms of the stability and permanence of attachment, so long as the pseudoirreversibly attached molecule is attached during multimolecular device manufacture and remains inseparable during device operation. An unconjugated oligonucleotide hybridized to a defined sequence segment of a multimolecular device is said to be hybridized, not pseudoirreversibly attached, regardless of the melting temperature of the hybridized duplex. Pseudoirreversible attachment of selected molecules may be achieved by a number of methods well known in the art, preferably by avidin/biotin or streptavidin/biotin conjugation or by hybridization of conjugated defined sequence segments having a high degree of complementarity (i.e., to form a stable hybrid), and further including, without limitation, ionic bonding, surface adsorption, intercalation, triplex formation, chelation, coordination, hydrophobic binding and high-affinity specific binding, optionally followed by UV irradiation or treatment with a noncovalent stabilizer, covalent crosslinking reagent and/or photoactivatable reagent. Pseudoirreversible attachment may also be achieved by threading a ring-shaped or circular molecule (e.g., a rotaxane) with a linear molecule (e.g., a polymer with knotted or bulky ends) or by caging or entrapping a guest molecule using, e.g., a spherical or hollow polymer, host or cage molecule (e.g., a cyclodextrin). Noncovalent, site-specific conjugation of a selected molecule to a multimolecular device may be accomplished by pseudoirreversible attachment, preferably by hybridization of an oligonucleotide conjugate to a defined sequence segment or by specific binding of an avidin or streptavidin conjugate to a biotinylated molecule or defined sequence segment. A member of a molecular recognition pair that specifically binds or hybridizes a selected target (e.g., a clinical analyte) during multimolecular device operation is not considered pseudoirreversibly attached to the selected target, even if both members are required for device function, e.g., as may be the case with a conjugated specific binding pair comprising a multimolecular sensor. A target nucleic acid sequence detected by hybridization to a DNA probe comprising a multimolecular sensor, for example, is considered hybridized to the multimolecular sensor, not pseudoirreversibly attached.

The term "quasireversible," when used in reference to specific recognition, means specific binding, hybridization or shape-specific recognition that, following association, can be dissociated, displaced or reversed under conditions of use. Quasireversible attachment means specific attachment and/or noncovalent attachment.

The term "reaction center" means a natural or synthetic photosynthetic molecule or group of molecules in which photoinitiated electron transfer culminates in a relatively long-lived, charge-separated state.

The term "receptor" means a selected nonoligonucleotide molecule capable of specifically binding to a ligand by affinity-based interactions that do not involve complementary base pairing. Whereas a ligand and its corresponding receptor are referred to herein as members of a specific binding pair, complementary nucleic acid sequences are simply referred to as "complementary" or "hybridizable" or "members of a molecular recognition pair." "Receptors" include, but are not limited to, biological, synthetic or engineered membrane receptors, hormone receptors, drug receptors, transmitter receptors, autacoid receptors, pheromone receptors, stimulus-response coupling or receptive molecules, antibodies, antibody fragments, engineered antibodies, antibody mimics or mimetics, molecular mimics, molecular imprints, molecular recognition units, adhesion molecules, agglutinins, lectins, selecting, cellular receptors, avidin and streptavidin, and congeners, analogs, competitors or derivatives of these molecules as well as nonoligonucleotide molecules selected, e.g., by combinatorial methods and/or library screening, to specifically bind other selected molecules and conjugates formed by attaching any of these molecules to a second molecule. Receptors further include selected molecules capable of specifically recognizing structural molecules, effector molecules and selectable molecules comprising ligands.

The term "recognition," when used in reference to molecular diversity or structure-shape-activity space or when used without classification as specific recognition, molecular recognition, catalytic recognition or structural shape recognition, includes all forms of recognition disclosed in the instant application, including molecular recognition, structural shape recognition, catalytic recognition and specific surface attractivity. "Molecular recognition" means specific binding or hybridization. "Specific recognition" means molecular recognition, structural shape recognition or specific attractivity. "Recognition" means specific recognition or catalytic recognition, i.e., specific binding, hybridization, structural shape recognition, catalytic recognition or specific surface attractivity.

The terms "recognition element," "recognition partner," "recognition molecule" and "recognition," when used to describe a nucleotide, segment, template or selected molecule comprising a multimolecular structure, synthetic heteropolymer, multimolecular device or MOLECULAR MACHINE, refers to a molecule, residue, sequence or group that is capable of recognizing another molecule, residue, sequence or group or a structural shape or surface feature by molecular recognition, structural shape recognition or catalytic recognition. Recognition elements include, without limitation, ligands, receptors, selected nucleic acid sequences, defined sequence segments and replicates, clones, mimetics, recognition partners and imprints thereof and progeny therefrom.

When used in reference to an imprint of a first (i.e., print, parent or idiotype) recognition element comprising a first (i.e., print, parent or idiotype) multimolecular structure, the terms "recognition element" and "recognition site" mean a second (i.e., imprint or progeny) recognition element comprising a second, different multimolecular structure, wherein the second, progeny recognition element is either an idiotype or antiidiotype that is capable of either mimicking or recognizing the first, parent recognition element. The progeny recognition element may be a first, second or subsequent generation imprint or imprinted imprint, idiotype or antiidiotype, mimetic or antimimetic of the first, parent recognition element, all of which generations are referred to herein as imprints.

The term "recognition site" means a recognition element comprising a site, position, functional group, molecule, residue or sequence comprising, e.g., a template, scaffold, multimolecular structure or multimolecular device.

The terms "recognize" and "recognition," when used in reference to a surface feature or structural shape, include specific attractivity, structural shape recognition and catalytic recognition.

The terms "replicatable nucleotide" and "replicatable nucleotide sequence," when used in reference to a synthetic nucleotide, defined sequence segment, selected nucleic acid sequence, linker oligonucleotide, spacer nucleotide, aptameric, heteropolymeric or nucleotide-based multimolecular device, mean a nucleotide, nucleotide analog, nucleic acid, defined sequence segment or discrete structure that can be cloned, replicated, amplified, transcribed or copied, preferably by enzymatic and/or biological methods known in the art. Replicatable nucleotides include RNA, DNA, chimeric, parent and progeny nucleotide sequences comprising or complementary to a selected parent or progeny nucleotide, including corresponding RNA, DNA or chimeric sequences (e.g., a DNA sequence corresponding to an RNA parent or an RNA sequence corresponding to a DNA parent) which can be replicated, transcribed or amplified either in vivo or in vitro.

The term "replicatable sequences of nucleotides," when used in reference to a synthetic heteropolymer or multimolecular device, means any RNA or DNA or chimeric nucleotide sequence comprising or complementary to a synthetic heteropolymer and any corresponding RNA or DNA or chimeric sequence (e.g., a DNA sequence corresponding to an RNA synthetic heteropolymer or an RNA sequence corresponding to a DNA synthetic heteropolymer) which can be replicated or amplified either in vivo or in vitro.

"RT," as used in "smaRTdrug," is an abbreviation for "receptor-triggered," "receptor-targeted" or, as the case may be, "receptor-tethered." Receptor-triggered, receptor-targeted and receptor-tethered mechanisms refer not only to receptors comprising selected nonoligonucleotide molecules, but also to specific recognition partners comprising nucleotides, e.g., nucleotide ligands, nucleotide receptors, defined sequence segments and selected nucleic acid sequences. In other words, the abbreviation "RT" refers to products and processes comprising designer receptors.

"SAS" is an acronym for "structure-activity space."

The terms "scaffold," "molecular scaffold," and "polymer scaffold" mean a discrete structure or multimolecular structure, preferably a synthetic discrete structure or synthetic multimolecular structure, or an individual molecule, monomer, polymer or pair or group of attached molecules, monomers or polymers comprising a linear, curved, branched, circular, polygonal, bent, folded, looped, jointed, hinged, resilient, elastic and/or flexible molecule, complex, nanostructure or microstructure, advantageously a molecule, monomer, polymer or pair or group of attached molecules, monomers or polymers comprising a synthetic multimolecular structure, multimolecular device, paired specific recognition device or tethered specific recognition device. A molecular scaffold comprising a synthetic defined sequence segment is referred to as a "nucleotide-based molecular scaffold" or "nucleotide-based scaffold." A molecular scaffold comprising an aptamer is referred to as an "aptameric molecular scaffold" or a "conjugated aptamer." An aptameric tethered specific recognition device is formed by two members of a nonaptameric specific recognition pair conjugated to an aptameric molecular scaffold wherein at least one member of the aptameric and/or nonaptameric specific recognition pair preferably comprises an effector molecule, e.g., a signal-generating species or a drug. A molecular scaffold comprising a tethered specific recognition device preferably comprises a bifunctional, trifunctional or multifunctional molecule, more preferably a heterofunctional, heterobifunctional or heterotrifunctional molecule, polymer, copolymer or defined sequence segment. The scaffold is optionally designed, selected or engineered to provide suitable spacing and/or flexibility between functional elements (e.g., tethered members of a specific recognition pair) to permit interaction between the functional elements (e.g., specific binding between tethered specific binding partners) under defined conditions, e.g., conditional upon the absence of a dissociative stimulus (e.g., an allosteric ligand or competitor). A molecular scaffold may further comprise or attach to a solid support.

The term "selectable," when used in reference to a molecule, sequence or surface feature, refers to a substance or property that is knowable but heretofore unknown or unidentified, i.e., discoverable or identifiable. Selectable molecules, sequences and surface features are preferably discovered or identified by screening and/or selection of a library.

The terms "selected" and "identified," when used in reference to a surface, feature, structure or shape (e.g., an attractive surface, surface feature, structure or structural shape), refer to surface features that can be specifically recognized by a shape-specific recognition partner, i.e., a shape-specific probe.

"Selected molecules" or "identified molecules," also referred to herein as "selected nonoligonucleotide molecules" and "identified nonoligonucleotide molecules," are nonoligonucleotide molecules which include, but are not limited to, receptors, ligands, structural molecules and effector molecules which may exist as single molecules, conjugates or groups of molecules, multimolecular structures or multimolecular devices, including mimetics, imprints and conjugates of any of these molecules, and mimetics, imprints and conjugates thereof. Selected molecules also include library-selected molecules, e.g., unknown or unidentified nucleotide ligands, nucleotide receptors, modified nucleotides, nucleotide analogs, shape recognition molecules and nonoligonucleotide molecules identified or discovered by screening and selection of nucleotide and nonnucleotide libraries and nucleotide-encoded chemical libraries. In other words, selected molecules include selectable molecules that are knowable but heretofore unknown or unidentified, i.e., molecules that remain to be discovered or identified. When used in reference to a conjugate comprising a first molecule that is an oligonucleotide attached to a second molecule that is not an oligonucleotide, the terms "selected molecule," "identified molecule," "selected nonoligonucleotide molecule" and "identified nonoligonucleotide molecule" refer to the portion of the conjugate originating from or consisting of the second molecule.

"Selected nucleic acid sequences" include, but are not limited to, defined sequence segments of synthetic heteropolymers and discrete structures, heteropolymeric, aptameric and nonaptameric nucleotide-based devices, oligonucleotides, and RNA, DNA or denatured RNA or DNA sequences, including wild-type, mutant and recombinant biological nucleic acid sequences; biological, recombinant, engineered and synthetic nucleic acids comprising specific or catalytic recognition sites or properties, e.g., aptamers, catalytic DNA, ribozymes, nucleic acid ligands, nucleic acid receptors, nucleic acid antibodies and nucleic acid molecules capable of participating in specific recognition, catalytic and enzymatic reactions; genomic, plasmid, cellular and transcribed or complementary nucleic acids, including DNA, cDNA and RNA; natural and synthetic coding, noncoding, initiation, termination, promoter and regulatory sequences, including natural, synthetic, native or nonnative biological recognition sites and therapeutic targets; natural and synthetic oligonucleotides with defined topology, secondary or tertiary structure or three-dimensional shape, including rolling and circular nucleic acids, nucleic acid loops, stems, bulges, knots, pseudoknots, polygons, spheres, pyramids, cubes, and higher order three-dimensional shapes; immobilized, conjugated, labeled and insolubilized nucleic acids, including nucleic acids hybridized or specifically bound to other soluble, insoluble, immobilized, conjugated or labeled nucleic acids; nucleic acid probes, targets and templates; sense, antisense and antigene nucleic acid strands; conjugated defined sequence segments and conjugated oligonucleotides, including oligonucleotides that are internally conjugated to provide closed-loop, single-ended or double-ended loop structures; branched, branched-chain, branched-comb, multi-chain and "Christmas tree" oligonucleotides; nucleic acid dendrons, dendrimers and nucleic acid conjugates formed by coulombic, affinity-based or covalent interactions with dendrons, dendrimers and other branched and hyper-branched structures; nucleotides comprising or capable of forming single-stranded, double-stranded, partially single-stranded, partially double-stranded, heteroduplex, triplex, quadruplex, chimeric and hybrid structures comprising natural or synthetic RNA, DNA or oligonucleotides comprising nucleotide analogs, derivatized nucleotides, nucleosides, nucleoside phosphates or backbone modifications. Selected nucleic acid sequences hybridized to bifunctional synthetic heteropolymers do not include unconjugated primers that hybridize to fixed primer-annealing sequences of aptamers selected from mixtures of random-sequence nucleic acids.

The terms "selected target," "selected target molecule" and "targeted molecule" refer to a nucleotide or nonnucleotide molecule or group of molecules comprising a target or an identified member of a recognition pair (e.g., a selected molecule, selected nucleic acid sequence, recognizable surface feature, selectable molecule or selectable surface feature), an identified composition, process, disease or condition, or the object, acceptor or substrate of a selected molecule (e.g., an enzyme, drug, dye, energy or electron donor) or desired result (e.g., catalysis, labeling, energy transfer or electron transfer) and include nucleotide and nonnucleotide molecules, structural shapes and surface features. The terms "selected target molecule" and "selected target," when used in reference to the process of identifying a recognition partner, e.g., by selecting a single synthetic nucleotide molecule capable of recognizing the selected target or by screening and selection of a library, means an identified or known target molecule for which a recognition partner is being sought. A selected target may be a heretofore unknown target, so long as the target is selectable (i.e., discoverable) and is identified at the time a recognition partner for the target is selected. Selected targets include, e.g., targets, aptamer targets, therapeutic targets, target molecules, targeted molecules and sequences, selected molecules, target sequences, selected nucleic acid sequences and specifically attractive surface features.

The term "selection of a recognition property," when used in reference to a surface library, structure library or material library, means identifying one or more structural shapes or surface features capable of recognition, preferably structural shape recognition or catalytic recognition.

The term "sensor" means and includes any device capable of sensing, detecting, measuring, monitoring, determining or quantifying one or more substances or events including, without limitation, mechanical sensors, force and mass sensors, velocity sensors, pressure sensors, acoustic sensors, temperature and thermal sensors, chemical sensors, biosensors, electrochemical sensors, optical sensors, electromagnetic sensors, electrical sensors, electronic sensors, optoelectronic sensors, motion sensors, photodetectors, gas sensors, liquid sensors, liquid and solid level sensors as well as multimolecular devices and tethered recognition devices of the instant invention, e.g., multimolecular sensors and multimolecular switches. Sensors of the invention further include devices which comprise, attach, are functionally coupled to or are capable of functionally coupling to MOLECULAR MACHINES of the invention, optionally paired MOLECULAR MACHINES or systems comprising pairs or networks of paired MOLECULAR MACHINES. A multimolecular sensor is a multimolecular device capable of sensing, detecting, measuring, monitoring, determining or quantifying one or more substances or events or a sensor comprising a multimolecular device.

The term "shape," when used in reference to a surface, structure or shape-specific recognition element, means structural shape, as distinct from molecular shape.

The term "shape recognition library" means a preferably diverse mixture of molecules synthesized, collected or pooled for library selection of one or more shape-specific recognition elements, e.g., a shape-specific probe or shape recognition template.

The term "shape-specific" refers to specific recognition of a structural shape comprising a chemically bland or specifically attractive surface by a shape recognition element, wherein a neighboring or distant region of the surface having the same chemical composition as the specifically recognized structural shape is not recognized by the shape recognition element. In other words, specific recognition of the structural shape by a shape-specific recognition element is not competitively inhibited by another surface or region that is heretofore chemically indistinguishable from the specifically recognized structural shape.

The terms "shape-specific probe," "shape-specific partner," "shape-specific recognition element," "shape-specific element," "shape-specific molecule" and "shape-specific recognition" refer to a nucleotide-based or non-nucleotide specific recognition partner of a structural shape, specifically attractive structure, surface or surface feature. A shape-specific probe and the corresponding specifically recognized structural shape are members of a specific recognition pair.

The terms "shape-specific template" and "shape recognition template" mean a bivalent or multivalent template comprising at least one shape-specific probe.

The terms "signal-generating molecule" and "signal-generating species" refer to a selected molecule, species or group comprising selected molecules capable of generating a detectable signal or enhancing or modulating the detectability of a substance or transducing an energy, activity, output or signal of a substance into a qualitatively, quantitatively or detectably different energy, activity, output, signal, state or form. Signal-generating species include, but are not limited to, molecules, groups of molecules, conjugates and complexes comprising detectable (and optionally dyed, modified, conjugated, labeled or derivatized) tags, tracers, radioisotopes, labels, reporters, polymers, light-harvesting complexes, antenna structures, natural and synthetic and biomimetic photosynthetic molecules, reaction centers, photosystems, signal transduction pathways, molecular cascades, macromolecules, microparticles, nanoparticles, colloids, metals, dyes, fluorophores, phosphors and other photon-absorbing, photon-emitting and photosensitive molecules, including molecules or groups that enhance, attenuate, modulate or quench the photon-absorbing or photon-emitting properties of another molecule or group, energy transfer donors and acceptors, enzymes, coenzymes, cofactors, catalytic antibodies, synthetic enzymes and catalysts, molecular mimics and mimetics, luminescent, triboluminescent, sonoluminescent, electroluminescent, chemiluminescent and bioluminescent molecules, electron transfer donors and acceptors, oxidizing and reducing compounds, mediators and other electroactive molecules, metabolic, photoactive, signaling and signal processing molecules used to capture and transduce energy in biological and biomimetic processes and systems, optionally including natural, synthetic or mimetic scaffold, organizational and coupling molecules, chaperones and accessory biological or biomimetic molecules or groups of molecules involved in the transduction of a first form of energy or information into a second form of energy or information.

The term "single-molecule," as used in reference to single-molecule detection, single-molecule isolation, single-molecule characterization, single-molecule identification, single-molecule amplification and single-molecule sequencing, relates to an individual or selected molecule, an individual pair or group of molecules or selected molecules attached to one another or an individual molecular complex, supramolecular assembly, discrete structure or multimolecular structure. When used in reference to single molecules and single-molecule detection, the term "molecule" means an individual molecule, selected molecule, discrete structure, multimolecular structure, complex or conjugate comprising a selected molecule, nucleotide, pair or group of molecules and not an indefinite plurality of molecules, e.g., an unknown and/or uncountable number of molecules.

The terms "single-molecule detection" and "single-molecule detection method" refer to a method capable of detecting an individual or selected molecule, an individual pair or group of molecules or selected molecules attached to one another, a molecule or multimolecular structure attached to a surface feature or an individual molecular complex, supramolecular assembly, discrete structure or multimolecular structure. Molecules detectable by single-molecule methods include nucleotide and nonnucleotide molecules, conjugates, complexes, selectable and selected molecules, selectable and selected nucleic acid sequences and replicates, imprints, clones, mimetics, conjugates and progeny thereof. Single-molecule detection methods and devices of the instant invention include, without limitation, optical force fields, optical tweezers, optical trapping, laser scanning and laser trapping; scanning probe techniques including scanning probe microscopy, scanning tunneling microscopy, scanning force microscopy, atomic force microscopy, scanning electrochemical microscopy and hybrid scanning probe techniques; spectroscopy, kromoscopy and mass spectrometry; capillary electrophoresis, microelectrophoresis, on-chip electrophoresis and multiplexed and arrayed electrophoretic methods and detectors; microminaturized and nanofabricated optical, spectroscopic, spectrometric, electrochemical, optoelectronic and electronic detectors; microsensors, nanosensors and integrated on-chip detectors, sensors, transducers and arrays; molecular detectors, sensors and transducers; and multimolecular devices comprising multimolecular sensors, multimolecular switches, multimolecular transducers and tethered recognition devices.

The term "site," when used in reference to a molecule, polymer, template, scaffold, multivalent molecular structure, multimolecular device or MOLECULAR MACHINE, means a chemical group, functional group, charged group, electrostatic field, three-dimensional shape, docking surface, residue, position, moiety, atom, group of atoms, topological location, region, defined sequence segment, nucleotide, functional element or recognition partner. When used in reference to a recognition site comprising a recognition partner, e.g., a catalytic site, specific binding site, hybridization site or shape recognition site, the term "site" means the operative binding element, recognition element or docking surface comprising the recognition partner.

The terms "site-specific," "site-directed" and "regiospecific," when used in reference to attachment to or modification of a molecule or group of molecules, mean covalent or noncovalent attachment at chemically, functionally or topologically defined site(s). Site-specific and site-directed attachment typically imply attachment to a particular chemical moiety, residue, reactive group, specific recognition site or epitope, while regiospecific attachment typically relates to the topological position, region or portion of a molecule or surface occupied by an attached species rather than the particular chemical site. However, the art recognizes some overlap between these terms.

The term "smart" refers to a multimolecular structure or multimolecular device capable of performing a useful function in response to a selected target or stimulus through the combined actions of at least two different functional elements, e.g., a recognition element and an effector element. For example, a smart polymer may comprise a first (e.g., structural) element that changes shape in response to interaction of a second (i.e., recognition) element with a selected target or stimulus. Smart multimolecular devices of the instant invention include, without limitation, promolecular delivery devices, multimolecular drug delivery systems, multimolecular sensors, multimolecular switches, multimolecular transducers, tethered recognition devices, multimolecular lubricants, molecular adhesives, molecular adherents and smaRTdrugs.

The term "smaRTdrugs" refers to smart multimolecular drug delivery systems, promolecular delivery devices and tethered recognition devices having utility in human and veterinary medicine comprising at least a designer receptor and a second recognition site comprising a targeting site, a triggered release or activation site, an allosteric site, or a tethered recognition pair, optionally a cleavably tethered recognition pair. Preferred smaRTdrug compositions of the invention comprise multimolecular drug delivery systems, tethered molecular delivery devices, receptor-targeted prodrugs and triggered release prodrug complexes.

The term "solid support" means a composition comprising an immobilization matrix, insolubilized substance, solid phase, surface, substrate, layer, coating, transducer, transducer surface, woven or nonwoven fiber, matrix, crystal, membrane, liposome, vesicle, gel, sol, colloid, insoluble polymer, plastic, glass, biological or biocompatible or bioerodible or biodegradable polymer or matrix, suspension, precipitate, microparticle or nanoparticle. Solid supports include, for example and without limitation, monolayers, bilayers, vesicles, liposomes, cell membranes, fixed cells, commercial membranes, resins, matrices, fibers, separation media, chromatography supports, hydrogels, foams, polymers, plastics, glass, mica, gold, beads, microspheres, nanospheres, silicon, gallium arsenide, organic and inorganic metals, semiconductors, insulators, microstructures and nanostructures. Microstructures and nanostructures include, without limitation, microminiaturized, nanometer-scale and supramolecular probes, tips, bars, pegs, plugs, rods, sleeves, wires, filaments, tubes, ropes, tentacles, tethers, chains, capillaries, vessels, walls, edges, corners, seals, pumps, channels, lips, sippers, lattices, trellises, grids, arrays, cantilevers, gears, rollers, knobs, steps, steppers, rotors, arms, teeth, ratchets, zippers, fasteners, clutches, bearings, sprockets, pulleys, levers, inclined planes, cords, belts, cams, cranks, wheels, axles, rotating wheels, springs, nuts, screws, bolts, shafts, pistons, cylinders, bearings, motors, generators, gates, locks, keys, solenoids, coils, switches, sensors, transducers, actuators, insulators, capacitors, transistors, resistors, semiconductors, diodes, electrodes, cells, antennae, appendages, cages, hosts, capsules, sieves, coatings, knedels, ultrafine particles, powders and micromachined and nanofabricated substrates, surfaces, layers, films, polymers, membranes and parts, including stationary, mobile, attached, tethered, ratcheted and robotic structures, devices, machines, components, elements and features. Solid supports useful in drug delivery comprise, for example and without limitation, artificial organs, artificial cells, artificial skin, implantable devices, controlled release polymers, gels, foams, insoluble polymers, bioerodible polymers, transdermal devices, pumps, infusion devices, indwelling sensors, vascular grafts, artificial valves, artificial joints, prosthetic devices, endoscopes, optical fibers, imaging devices, ablation devices, catheters, guidewires, surgical equipment and diagnostic devices.

The term "spacer molecule" refers to one or more nucleotide and/or nonnucleotide molecules, groups or spacer arms selected or designed to join two nucleotide or nonnucleotide molecules and preferably to alter or adjust the distance between the two nucleotide or nonnucleotide molecules.

The term "spacer nucleotide" means a nucleotide spacer comprising a nucleotide, i.e., a nucleotide spacer that is a nucleotide or joins at least two nucleotides or comprises a sequence of nucleotides, e.g., a defined sequence segment.

The terms "specifically attach," "specific attachment" and "specifically recognize" refer to specific recognition and include specific binding, hybridization, structural shape recognition and specific attractivity. The terms "site-specifically attach," "site-specific attachment" and "attachment site" refer to site-directed covalent and/or noncovalent attachment by methods including, but not limited to, specific recognition.

The terms "specifically attractive," "specifically attractive surface," "specific attractivity" and "specific surface attractivity," when used in reference to a surface, structure, surface feature or structural shape, mean specifically recognizable by a shape-specific recognition partner, i.e., a member of a specific recognition pair comprising a shape-specific element, shape-specific molecule, shape-specific partner or shape-specific probe.

The term "specifically recognizable," when used in reference to a surface or structure, means a specifically attractive surface comprising a surface feature or structural shape capable of being specifically recognized by a shape-specific recognition partner, i.e., a shape-specific element, shape-specific molecule, shape-specific partner or shape-specific probe.

The term "specific binding" refers to a measurable and reproducible degree of attraction between a ligand and a receptor or between a defined sequence segment and a selected molecule or selected nucleic acid sequence. The degree of attraction need not be maximized to be optimal. Weak, moderate or strong attractions may be appropriate for different applications. The specific binding which occurs in these interactions is well known to those skilled in the art. When used in reference to synthetic defined sequence segments, synthetic aptamers, synthetic heteropolymers, nucleotide ligands, nucleotide receptors, shape recognition elements, specifically attractive surfaces and MOLECULAR MACHINES disclosed herein, the term "specific binding" may include specific recognition of structural shapes and surface features. Otherwise, specific binding refers explicitly to the specific, saturable, noncovalent interaction between two molecules (i.e., specific binding partners) that can be competitively inhibited by a third molecule (i.e., competitor) sharing a chemical identity (i.e., one or more identical chemical groups) or molecular recognition property (i.e., molecular binding specificity) with either specific binding partner. The competitor may be, e.g., a crossreactant, analog or congener of an antibody or its antigen, a ligand or its receptor, or an aptamer or its target. Specific binding between an antibody and its antigen, for example, can be competitively inhibited either by a cross-reacting antibody or by a crossreacting antigen. By contrast, surface-specific attachment of a shape-specific probe to a structural shape (e.g., a surface feature of a silicon or carbon surface) cannot be competitively inhibited by amorphous silicon or carbon. Shape-specific surface recognition does not involve specific binding or molecular binding specificity as defined herein. However, the term "specific binding" may be used for convenience to approximate or abbreviate a subset of specific recognition that includes both specific binding and structural shape recognition. Specific binding between a ligand and receptor means affinity-based interaction related to the secondary, tertiary and quaternary structure and charge of the participating molecules and does not include the hybridization of complementary nucleic acid sequences due to Watson-Crick base pairing. When used in reference to a defined sequence segment, the term "specifically binding to a selected nucleic acid sequence" means a measurable and reproducible degree of attraction between the defined sequence segment and a selected nucleic acid sequence which may involve hybridization if participating sequences are complementary or alternative mechanisms if sequences are noncomplementary. Where the attraction between nucleotide sequences is known to depend on complementary base pairing, binding is preferably referred to as "hybridization." Where the attraction does not depend on complementary base pairing, binding between nucleotide sequences is referred to as "specific binding," "specific recognition" or "molecular recognition." Nonhybridization-based specific binding between noncomplementary nucleic acid sequences depends not on base pairing, but on the secondary, tertiary and quaternary structures and electrostatic fields comprising participating sequences. Nucleic acid binding reactions known to involve mechanisms other than hybridization include, e.g., antisense, triplex, quadruplex and aptamer interactions. When used in reference to an aptamer, the term "specific binding" means recognition of the aptamer target and does not refer to a nucleic acid sequence capable of hybridizing to the aptamer or a ligand or receptor capable of specifically binding to a corresponding receptor or ligand conjugated to or incorporated in the aptamer, e.g., a particular nucleoside, derivative, analog, modified nucleotide, nucleotide ligand, nucleotide receptor, conjugated nucleotide or conjugated selected molecule comprising the aptamer.

The term "specific binding" may in some instances be used as an abbreviation for the phrase "specific binding and structural shape recognition." Although "specific binding" differs from "structural shape recognition" as defined herein, the terms may in some cases be used interchangeably or inclusively for clarity or convenience.

The term "specific binding pair" means two specific binding partners that specifically bind to one another, e.g., a ligand and its receptor or an aptamer and its target.

The terms "specific binding partner" and "specific binding pair" mean a ligand capable of specifically binding a receptor, an aptamer capable of specifically binding an aptamer target, a defined sequence segment capable of specifically binding a selected molecule, or a defined sequence segment capable of specifically binding a selected nucleic acid sequence and does not include hybridized, hybridizable or complementary nucleic acid sequences. The term "specific binding partner," when used in reference to an aptamer, means the aptamer target and does not refer to either 1) a nucleic acid sequence capable of hybridizing to the aptamer or 2) a ligand or receptor capable of specifically binding to a receptor or ligand comprising the aptamer, e.g., a particular nucleoside, nucleotide, analog, derivative, modified nucleotide, conjugated nucleotide, nucleotide ligand or nucleotide receptor. "Specific binding partner" and "specific binding pair" may also be used as abbreviations for the phrases "specific binding or structural shape recognition pair" and "specific binding or structural shape recognition partner." Although a "specific binding partner" differs from a "structural shape recognition partner" as defined herein, the terms may in some cases be used interchangeably or inclusively for clarity or convenience.

The terms "specific recognition," "specific recognition pair" and "specific recognition partner" mean and include specific binding, hybridization, structural shape recognition and specific attractivity.

The terms "specific recognition pair" means two specific recognition partners that specifically recognize one another.

The terms "specific shape recognition," "shape-specific recognition," "shape recognition," "surface recognition" and "surface feature recognition" mean capable of discriminating one structural shape or surface feature from another. Discriminating means binding a first surface feature and not binding a second surface feature having the same chemical composition. Perfect specificity is not required. A certain degree of nonspecific surface association may be expected, as occurs with specific binding and hybridization reactions. The practical limits on achievable discrimination by shape-specific recognition relate to the precision of nanostructure synthesis and surface fabrication techniques (e.g., surface machining, molecular and atomic-scale assembly, nanofabrication, mechanochemical synthesis and preparation of diamondoid materials and nanostructures, e.g., fullerenes, nanorods and nanotubes) and the purity, affinity, stability and reproducibility of shape-specific probes.

"SASS" is an acronym for "structure-activity-surface space" which refers to the combinatorial product of structure-activity space (SAS) and structural shape space (SSS). Symbolically, SASS=SAS×SSS=space.

"SECM" is an abbreviation for "scanning electrochemical microscopy."

"SPM" is an abbreviation for "scanning probe microscopy."

"SSS" is an acronym for "structural shape space" which is equivalent to surface attractivity space.

"STM" is an abbreviation for "scanning tunneling microscopy."

The terms "stimulus-response coupling" and "stimulus-responsive" refer to functional coupling between or among molecules, wherein an input of matter or energy (i.e., a stimulus) to a first defined sequence segment, selected molecule or specific recognition pair results in a stimulus-specific, effector-mediated response at or by a second defined sequence segment, selected molecule or specific recognition pair. The effector-mediated response may result from the binding or activity of a selected molecule comprising an effector molecule or a functional element comprising a nucleotide or nonnucleotide molecule, e.g., an enzyme, ribozyme, conjugate, imprint or mimetic.

The term "stimulus-specific" means that a definitive effector-mediated response is elicited only by stimuli comprising a specified type or group of molecules or form or level of energy or combination thereof and is not intended or known to be elicited by unspecified molecules or energies.

The terms "structural attractivity" and "surface attractivity" refer to specific recognition of a nucleotide or nonnucleotide molecule by a surface feature or structural shape, optionally a surface feature or structural shape comprising a chemically bland or amphibious surface. A structurally attractive surface comprises a surface feature or structural shape which is a specific recognition partner of a shape recognition molecule (i.e., a shape-specific probe or shape recognition element).

The terms "structural attractivity space," "surface space" and "materials space" refer to selectable recognition properties of chemically bland or amphibious surfaces, materials, structures structural shapes, surface features and material substrates, as distinct from the molecular recognition properties of selected molecules and selected nucleic acid sequences.

The term "structural molecules" refers to selected nonoligonucleotide molecules that may lack heretofore known specific binding or effector properties and includes, but is not limited to, selected molecules comprising structural shapes and surface features and selected molecules comprising elements, atoms, molecules, ions, and compounds comprising surfaces, amphibious surfaces, inorganic and organic materials such as carbon, silicon, glass, organic and inorganic crystals, selected solvents, selected solutes, natural, biomimetic and synthetic nanostructures and microstructures, fibers, filaments, silks, molecular scaffolds, nanotubes, nanorods, fullerenes, buckyballs, diamondoid molecules, semiconductors, insulators, metals, plastics, elastomers, polymers, detergents, lubricants, waxes, oils, powders, fillers, excipients, fibers, tableting ingredients, packaging materials, papers, industrial plastics, cyclic and polycyclic molecules, dendrons, dendrimers, electrolytes and polyelectrolytes, salts, hydrocarbons, ceramics and biological, biocompatible, biomimetic, biodegradable and imprintable monomers, multimers and polymers, e.g., fatty acids, lipids, surfactants, amino acids, peptides, proteins, polyamines, polyacids, sugars, starches, cellulose, glycosylated molecules, glycopolymers and conjugates thereof.

The terms "structural shape," "structural feature," "surface feature" and "surface shape" refer to natural, synthetic, designed or selected surfaces or structures having a two-dimensional or three-dimensional shape, contour, texture, characteristic, pattern, distribution, property, configuration, arrangement, organization, order, lack of organization or order, form, trait or peculiarity that can be specifically recognized by a shape-specific recognition element.

The terms "structural shape recognition," "shape recognition," "shape recognition partner," "shape recognition probe," "shape probe" and "surface feature recognition," when used in reference to a material, surface, surface feature, structure or structural shape, refer to specific recognition of a structural shape or surface feature.

The term "structure-activity space," also referred to herein as "art-accepted molecular diversity" or "molecular diversity," means the diversity space comprising the set of all molecules, known and unknown, net of the diversity space of specifically attractive surfaces (i.e., structural shapes and surface features). The combinatorial product of structure-activity space (SAS) and structural shape space (SSS) is the set of all heretofore known and unknown (molecular and surface) diversity spaces and is referred to herein as "molecular space," "diversity space" or simply "space." Symbolically, SAS×SSS=space.

The term "structure-activity-surface space" (SASS) refers to the dimensionless combinatorial product of molecular recognition space, catalytic recognition space, surface recognition space and surface attractivity space, i.e., all forms of recognition disclosed herein. Structure-activity-surface surface space is equivalent to the combinatorial product of structure-activity space and structural shape space, i.e., SASS=SAS×SSS=space.

The terms "substrate" and "material substrate," when used in reference to materials, surfaces and surface space, refer to a substratum, structural layer or foundation, as distinct from an enzyme substrate, and do not relate to catalytic recognition. A material substrate may, however, optionally comprise an enzyme substrate or catalytic recognition property. Advantageously, novel catalytic and molecular recognition properties can be conferred on heretofore chemically bland substrates by transposition through a nucleotide library, preferably a paired nucleotide-nonnucleotide library.

The term "surface" means a boundary in two-dimensional or three-dimensional space. When used in reference to a molecular adsorbent, multimolecular adhesive or multimolecular adherent, the term "surface" means an amphibious surface, a chemically bland surface or a specifically attractive surface.

The terms "surface feature" and "specifically attractive surface feature" refer to a structural shape or structural feature of a specifically attractive surface, i.e., a specifically recognizable structural feature of a surface. Surface features include natural, synthetic, designed or selected structures or surfaces, preferably subnanometer- to submicron-sized surface contours, having a two-dimensional or three-dimensional shape, contour, texture, characteristic, pattern, distribution, property, configuration, arrangement, organization, order, lack of organization or order, form, trait or peculiarity that can be specifically recognized by a shape-specific recognition element.

The terms "surface library," "structure library" and "material library" refer to a random or nonrandom assortment of structural shapes or surface features comprising a structure, surface or material or a random or nonrandom assortment of structures, surfaces or materials.

The term "surface template" means a template specifically attached by one recognition element to a surface in such manner that a second recognition element is displayed on the surface in a preferred orientation, i.e., an orientation enabling the second recognition element to effectively and efficiently perform a desired function. Desired functions include, e.g., solid phase catalysis, separations, multimolecular synthesis, purification and/or detection of selected molecules, and scanning, imaging and/or characterization of displayed recognition elements by an analytical system, e.g., STM, optical scope, laser scanning device or hybrid system.

The term "synthetic," when used to describe a defined sequence segment, means nonnaturally occurring, i.e., the defined sequence segment is not heretofore known to occur in nature (sans human biotechnologic intervention) and is not heretofore known to be a biological recognition site. The term "synthetic," when used in reference to a synthetic heteropolymer, means that 1) the synthetic heteropolymer is not derived from a heretofore known biological organism and 2) the nucleotide sequence of the synthetic heteropolymer is not heretofore known to occur in nature and 3) at least one defined sequence segment comprising the synthetic heteropolymer is selected from a source other than a heretofore known biological organism, biological polymer or collection of biological polymers and 4) the nucleotide sequence of at least one defined sequence segment comprising the synthetic heteropolymer is not heretofore known to occur in nature. At least one defined sequence segment of a synthetic heteropolymer is typically selected either 1) from an experimental or willfully designed mixture, population, pool, library or assortment of sequences, preferably a diverse mixture, population, pool, library or assortment or 2) by means of a computer simulation, model, search engine or virtual experiment or 3) by in vitro evolution or directed evolution. In each case, the selection criteria are established to identify sequences capable of either specifically binding to a selected nonoligonucleotide molecule or nucleic acid sequence or hybridizing to a selected nucleic acid sequence or positioning a conjugated molecule (e.g., by hybridization, ligation or specific binding of a conjugate or ab initio synthesis of a synthetic heteropolymer comprising a conjugated defined sequence segment) within functional coupling distance of a selected molecule capable of specifically binding another defined sequence segment and/or within suitable proximity of the selected molecule to enable single-molecule detection.

The term "synthetic aptamer" means an aptamer or aptameric sequence that is not heretofore known to occur in nature and function as a biological recognition site or an aptamer conjugate.

The term "synthetic defined sequence segment" refers to a nonnaturally occurring defined sequence segment, meaning either 1) a defined sequence segment which is not a biological recognition site and whose nucleotide sequence is not heretofore known to occur in nature (i.e., sans genetic engineering) or 2) a conjugated defined sequence segment, wherein the corresponding unconjugated sequence segment is not a biological recognition site for the conjugated molecule or 3) a sequence of nucleotides comprising a modified nucleotide, nucleotide analog, nucleotide ligand, nucleotide receptor or nucleotide catalyst. When used in reference to a synthetic heteropolymer or aptameric device, the term "synthetic defined sequence segment capable of specifically binding to a selected molecule," means a synthetic aptamer. Where a nonaptameric nucleotide-based multimolecular device is capable of specifically binding a selected molecule, the operative recognition element is not an aptamer, but a defined sequence segment conjugated to a specific binding partner, e.g., a ligand, receptor or modified nucleotide, optionally a nucleotide ligand or nucleotide receptor.

The term "synthetic heteropolymer" means a nonnaturally occurring heteropolymer and refers to nucleotides, particularly nucleic acids and replicatable nucleotides (including partially and fully double-stranded and single-stranded nucleotides, synthetic RNA, DNA and chimeric nucleotides, hybrids, duplexes, heteroduplexes, and any ribonucleotide, deoxyribonucleotide or chimeric counterpart thereof and/or corresponding complementary sequence, promoter or primer-annealing sequence needed to amplify, transcribe or replicate all or part of the synthetic heteropolymer), having at least two defined sequence segments, wherein at least one defined sequence segment per discrete structure is a synthetic defined sequence segment capable of specifically binding (or shape-specifically recognizing) and optionally covalently attaching a selected nonoligonucleotide molecule or group of molecules. The second defined sequence is capable of either specifically binding (or shape-specifically recognizing) and optionally covalently attaching a different, selected nonoligonucleotide molecule or selected nucleic acid sequence or of hybridization or of positioning a conjugated molecule within suitable distance of a selected molecule specifically bound to a first defined sequence segment to enable single-molecule detection or functional coupling between the conjugated molecule and the selected molecule. In other words, a synthetic heteropolymer comprises at least a synthetic aptameric first defined sequence segment which is capable of specific recognition and a second defined sequence segment which is a conjugated defined sequence segment or is capable of specific recognition. Where a second defined sequence segment is designed or selected to position a conjugated molecule for functional coupling to a specifically bound selected molecule, the selected molecule is preferably an effector molecule and more preferably a signal-generating species or a drug. A convenient method to position a molecule conjugated to one defined sequence segment for functional coupling to a selected nonoligonucleotide molecule specifically bound to another defined sequence segment of a synthetic heteropolymer involves 3' and/or 5' end-labeling of a defined-length sequence, particularly 5'-end labeling. The efficiency of functional coupling (i.e., the distance between attached selected molecules) can then be adjusted by varying the length of the conjugated defined sequence segment (and optionally the composition of the intervening nucleotide sequence). Defined sequence segments internally labeled or modified at defined nucleotide positions can also be used to effectively position conjugated selected molecules. In this case, functional coupling efficiency is optimized by adjusting the conjugation position of the selected molecules. Where the second defined sequence segment is designed or selected to position a conjugated molecule within suitable proximity of a specifically bound molecule to enable single-molecule detection, the conjugated molecule comprises a selected molecule, preferably an effector molecule, macromolecule, group of molecules or signal-generating species. A multisite heteropolymer selected from a random-sequence nucleic acid library to position and/or functionally couple selected molecules is referred to herein as a synthetic heteropolymer, even though the random sequence segment is not strictly a defined sequence segment until the selected heteropolymer is characterized. The second defined sequence segment of a synthetic heteropolymer comprising an aptameric first defined sequence segment may be a conjugated defined sequence segment capable of hybridizing a selected nucleic acid sequence comprising a primer or may alternatively be an unconjugated defined sequence segment capable of hybridizing a selected nucleic acid sequence comprising a conjugated primer. However, a nucleic acid molecule comprising a randomized sequence and one or more fixed, unconjugated primer-annealing sequences is not a synthetic heteropolymer, nor is an aptamer comprising one or more unconjugated primer-annealing sequences for unconjugated primers. So long as a synthetic heteropolymer comprises at least two defined sequence segments capable of specifically binding, hybridizing or positioning a selected nonoligonucleotide molecule or selected nucleic acid sequence, wherein at least one synthetic defined sequence segment is capable of specifically binding a nonoligonucleotide molecule, there is no upper limit to the number of defined sequence segments per synthetic heteropolymer. Any nucleotide-based discrete structure that comprises a synthetic first defined sequence segment capable of specifically recognizing a first (nonoligonucleotide) molecule and a second defined sequence segment capable of specifically recognizing a second (nucleotide or nonnucleotide) molecule is or comprises a synthetic heteropolymer, so long as the first and second molecules are different molecules and the second defined sequence segment is not an unconjugated primer-annealing sequence. Two different aptamer molecules joined to one another either directly or indirectly via a linker (i.e., a nucleotide spacer, spacer molecule, oligonucleotide linker or nonnucleotide linker) to form a discrete structure capable of specifically recognizing two different nonoligonucleotide molecules is a synthetic heteropolymer, alternatively referred to herein as an aptameric multimolecular complex. A discrete structure comprising an aptameric defined sequence segment attached indirectly via a linker to a second defined sequence segment is also a synthetic heteropolymer if the discrete structure is capable of specifically recognizing a nonoligonucleotide first molecule and of hybridizing to an oligonucleotide second molecule comprising a selected nucleic acid sequence.

"Synthetic photosynthetic molecules" refers to artificial photosynthesis as known in the art (e.g., Gust et al. (1993) *Accounts of Chemical Research* 26:198–205), and includes synthetic energy conversion systems that mimic the natural process of photosynthesis.

The term "synthetic reaction center" means a molecule or group of molecules capable of existing in a light-induced, charge-separated state, thereby mimicking the function of a natural photosynthetic reaction center.

The term "synthetic receptor" means a "designer receptor," i.e., a naturally occurring, recombinant, biological, biologically produced or synthetic nucleotide or nonnucleotide molecule or group of molecules comprising a specific recognition partner selected from the group consisting of specific binding partners, hybridizable nucleic acid sequences, shape recognition partners, specifically attractive surfaces and specific recognition pairs, advantageously a mimetic specific recognition partner (i.e., a receptor mimetic) that mimics or approximates the binding specificity of a selected target or receptor (e.g., a therapeutic target) for its recognition partner (e.g., a drug, hormone or transmitter) or a selected receptor that specifically recognizes a drug or a therapeutic receptor.

The term "system(s)" means a system that optionally or advantageously comprises paired systems.

The term "target," when used in reference to a recognition element, shape-specific probe, multimolecular structure, multimolecular device or MOLECULAR MACHINE, means a selected target, aptamer target, therapeutic target, target molecule, selected molecule, target sequence, selected nucleic acid sequence or, in the case of a shape-specific probe, a specifically attractive surface feature. When used in reference to molecular delivery devices described herein, the terms "target" and "target molecule" mean a selected target or any identified substance, structure, process, device or object capable of being acted upon by a selected molecule or selected nucleic acid sequence including, without limitation, selected molecules, structural shapes and surface features, selected nucleic acid sequences, therapeutic receptors, pathological, physiological and anatomical sites, disease markers, diagnostic analytes, cells, cell surface antigens, cytoplasmic, subcellular, genetic and genomic markers, biological recognition sites, environmental markers, pollutants, pests and pathogens, agricultural products, strains, symbiotes, pests, pesticides, pathogens and contaminants, industrial feedstock, products, byproducts, wastes, process and quality control analytes, chemical weapons, biological weapons and selected sites, recognition elements and recognizable features comprising materials, substrates, transducer surfaces, amphibious surfaces, specifically attractive surfaces, chemically bland surfaces, solid supports, arrays, biochips and microminiaturized and nanofabricated devices.

The terms "target sequence" and "targeted sequence" refer to selected targets comprising selected nucleic acid sequences.

The term "template" means a bivalent or multivalent nucleotide or nonnucleotide molecule or molecular scaffold capable of positioning at least two molecules, preferably a multivalent molecular structure comprising a MOLECULAR MACHINE.

The terms "template-directed," "template-based" and "templating" refer either to a nucleotide-directed process or product or to specific attachment of one selected molecule or surface to another selected molecule or surface by means of a nucleotide-based or nonnucleotide template or molecular scaffold capable of specifically recognizing at least one of the selected molecules or surfaces.

The term "tethered," when used in reference to a tethered recognition device or specific recognition pair, means that two members of a recognition pair comprising a synthetic multimolecular structure remain connected to one another by covalent or pseudoirreversible and preferably site-specific attachment to a common molecular scaffold or multimolecular structure, regardless of whether the recognition partners are directly attached to one another or not. For example, tethered members of a specific recognition pair covalently or pseudoirreversibly attached to a common molecular scaffold may be either specifically attached to one another (e.g., hybridized or specifically bound) or not specifically attached to one another (e.g., unhybridized, dissociated or unbound).

The terms "tethered specific recognition device," "tethered recognition device," "tethered molecular recognition device," "tethered device" and "tethered specific recognition pair" refer to stimulus-responsive synthetic devices comprising a molecular scaffold, optionally a synthetic nucleotide or a nonnucleotide multimolecular structure, and at least two members of a specific binding pair or four members of two different specific recognition pairs, each member being covalently or pseudoirreversibly attached in a site-specific manner to the molecular scaffold. Each member of a specific recognition pair comprising a tethered recognition device is covalently or pseudoirreversibly tethered to its specific recognition partner by attachment to a common scaffold, so the specific recognition partners remain connected (i.e., indirectly attached) even when they are not specifically bound or hybridized to one another (i.e., not specifically and directly attached). Unlike prior art tethered compositions, each tethered device of the instant invention is capable of existing in either of two functionally different states (e.g., "on" or "off") depending on whether a selected target is present. The instant tethered devices are therefore stimulus-responsive, i.e., specifically responsive to a selected target. For example, specific recognition of a selected target molecule by a tethered recognition device results in generation of a detectable signal or targeted delivery of a payload molecule, e.g., an effector molecule or drug. Advantageously, the molecular scaffold to which members of a specific recognition pair are tethered may comprise a conjugated aptamer. In other words, an aptameric multimolecular device having two members of a nonaptameric specific recognition pair conjugated to an aptameric molecular scaffold is an aptameric tethered specific recognition device. In this embodiment, at least one member of the aptameric and/or nonaptameric specific recognition pair further comprises an effector molecule, e.g., the member is detectably labeled or specifically attached to a releasable or activatable effector (e.g., a prodrug). The terms "tethered recognition device," "tethered recognition pair" and "tethered device" may also refer to stimulus-responsive devices that alternatively comprise two members of a catalytic recognition pair covalently or pseudoirreversibly attached to a molecular scaffold. The interaction between first and second molecules comprising the catalytic recognition pair may be modulated by the binding or activity of a third molecule comprising or capable of recognizing a functional element of the tethered recognition device.

The terms "therapeutic receptor," "target receptor" and "pathophysiological receptor," when used in reference to drug delivery methods and devices disclosed herein, mean nucleotide and nonnucleotide targets of drug, hormone and transmitter action, including selected molecules, selected nucleic acid sequences and structural shapes.

The terms "therapeutic target," "pathophysiological target," "pathological target," and "disease target," refer to the physiological, pathological and anatomical sites of drug action and include therapeutic receptors, targeted molecules and receptors, target molecules and receptors, groups of target molecules or receptors, and cells or groups of cells comprising target molecules or receptors.

"Tight coupling" and "efficient coupling," when used in reference to the functional coupling of machine intelligence to a process, domain or system, means that data and/or information are effectively comprehended in a usefully timely manner. Perfect effectiveness means comprehension of all information with absolute fidelity. Perfect timeliness means immediate or instantaneous. For any given application or process, "Tight" and "efficient" are relative terms, i.e., quantitative standards vary for different applications. For purposes disclosed herein, these terms refer to a degree or efficiency of functional coupling that is practically useful and sustainable, preferably increasing with time, i.e., growing more efficient and thus becoming more effective. Any degree of functional coupling may be useful. Absence of functional coupling means that two substances, processes, devices or systems function independently or autonomously, i.e., they are functionally uncoupled. Loose coupling means an intermediate or partial degree of cooperation between two substances, processes, devices or systems which may or may not be practically useful. Particularly useful loosely coupled substances, processes, devices and systems are those in which the degree of functional coupling increases with time, i.e., the substances, processes, devices or systems evolve toward tight and efficient functional coupling, thereby approaching perfect functional coupling. The terms "tight coupling" and "efficient coupling," when used in reference to the functionally coupled substances, processes, devices and systems, shall be interpreted and understood by analogy to corresponding terms describing informational devices. Conversely, the term "functional coupling," when used in reference to informational devices, machine intelligence and library selection, is to be interpreted and understood as a metaphor in respect of the functional coupling between molecules comprising multimolecular devices.

"TR," as apparent in "gurdTRams" (i.e., the mirror image of "smaRTdrug"), is an abbreviation for "triggered release," "target-responsive" or, as the case may be, "tethered receptor." "Tethered receptor" refers not only to receptors comprising selected nonoligonucleotide molecules, but also to ligands and specific recognition elements comprising nucleotides and nucleotide-based multimolecular devices, e.g., nucleotide ligands, nucleotide receptors and defined sequence segments. In other words, "tethered receptor" refers to a designer receptor.

"Transduce" means to convert, transform, transfer, modify, send, receive or interconnect from one substance, process, state, form, unit or level of matter, information, order or energy to another or between two substances, processes, states, forms, units or levels of matter, information, order or energy, typically by means of a change in the relative energy state, velocity or position of two molecules or a molecule and its environment, particularly a change that occurs in response to a thermal gradient, electrical, chemical or electromagnetic potential, mechanical force, specific stimulus or recognition event.

The terms "transducer" and "transducer surface," when used in reference to an immobilized substance or specifically attractive surface, refer to surfaces, solid supports and devices capable of converting an output of a molecule, multimolecular structure or multimolecular device (e.g., matter, energy and/or heat) into a qualitatively or quantitatively different form, wherein the conversion produces useful work or a detectable signal. Functional coupling between a multimolecular device of the invention (e.g., a multimolecular transducer, multimolecular switch or multimolecular sensor) and a transducer surface can be accomplished, e.g., by the transfer of mass, energy, electrons or photons or by coupled chemical or enzymatic reactions that share a common intermediate, mediator or shuttle species.

The terms "transpose," "transposing" and "transposition," when used in reference to nucleotide library-mediated processes and products, refer to mapping, imprinting, transforming, expressing, reflecting, bouncing, passaging, passing, projecting, or converting a first property, shape, structure or activity comprising a first molecule, material, molecular medium, library or selected population within, through, on, off, or into a second molecule, material, medium, population, library or region of diversity space. Transposition may be used to create an imprint, antiimprint, antiidiotype, idiotype or mimetic of a nucleotide or nonnucleotide target or an imprint, replicate, mimetic or progeny thereof.

The term "undiscoverable" means either already discovered or unknown and unknowable.

The term "unknowable," when used in reference to molecules, matter, data, information, energy, methods, principles, processes, compositions or applications, means not known and not capable of being known or discovered.

The terms "unknown" and "unknown information" refer to information that is not heretofore known, including information capable of becoming known (i.e., knowable and discoverable information) and information not capable of becoming known (i.e., unknowable information).

The terms "willful" and "willfully" refer to human will, intent, design, or purpose.

This invention relates to methods and structures for coupling the activities of two or more molecules or groups of molecules, preferably molecules with defined activities, to perform functions dependent on the spatial proximity of constituent molecules. Whereas Cubicciotti, U.S. Pat. No. 5,656,739 discloses a method for specifically and noncovalently assembling selected molecules into a single multimolecular structure through use of synthetic heteropolymers or multivalent heteropolymeric hybrid structures comprised of hybridizably linked synthetic heteropolymers, the instant invention further provides template-ordered multimolecular devices which are covalently or pseudoirreversibly stabilized. Also provided are nonnucleotide multimolecular devices comprising imprints and mimetics of synthetic heteropolymers.

Each synthetic heteropolymer disclosed herein comprises nucleotides having at least a first and a second defined sequence segment. One defined sequence segment of a synthetic heteropolymer or multivalent heteropolymeric hybrid structure is capable of specifically binding to a selected nonoligonucleotide molecule or group of molecules, preferably a receptor, ligand, structural molecule or effector molecule, or specifically recognizing a surface feature of a specifically attractive surface. The other defined sequence segments are capable of either specifically binding to a different nonoligonucleotide molecule, group of molecules or selected nucleic acid sequence or of specifically recognizing a surface feature of a specifically attractive surface or of hybridization or of participating by means of a conjugated molecule, optionally a conjugated nucleic acid molecule, in functional coupling to a selected nonoligonucleotide molecule or group of molecules specifically bound to a first defined sequence segment.

The present invention represents a novel approach to assembling ordered pairs, groups and arrays of molecules that capitalizes on two important features of nucleotides, preferably groups of nucleotides comprising oligonucleotides, advantageously nonnucleotide molecular templates and multivalent molecular structures that mimic the molecular positioning properties of nucleotides. First, nucleotides, preferably groups of nucleotides comprising oligonucleotides, can be selected or engineered to recognize a wide range of molecular targets with high affinity. Second, nucleotides, preferably groups of nucleotides comprising oligonucleotides, can be synthesized with defined sequence segments that enable reproducible combination of two or more monofunctional heteropolymers into a single, bifunctional or multifunctional hybrid referred to herein as a multivalent heteropolymeric hybrid structure. These features provide the ability to reproducibly engineer the assembly of limitless combinations of biological and nonbiological molecules with substantial control over both the design and production of desired complexes. The advantage of this approach over prior efforts to coax lipids and proteins into self-assembly is control over the assembly process. The present invention teaches methods to engineer defined sequence segments into a sequence of nucleotides, modified nucleotides or nucleotide analogs that control the proximity of two or more selected molecules by the relative positions of defined sequence segments along the sequence and further provides covalently stabilized devices prepared from nucleotide-directed molecular assemblies. Also provided are nonnucleotide multimolecular devices comprising multivalent imprints and mimetics of nucleotide-based multimolecular devices.

Useful multimolecular devices of the invention include switches, sensors, transducers and drug delivery systems produced using both the covalent and noncovalent binding capabilities of nucleotide polymers, selected molecules and conjugates thereof, including, hybridization of complementary nucleotide sequences, aptamer recognition of nonnucleotide molecules, specific binding between ligands and receptors, specific binding between noncomplementary nucleic acid sequences, and even self-assembly of MOLECULAR MACHINES using nucleotide-based templates. Nucleotides of the instant invention, particularly defined sequence segments, aptamers, specific binding pairs, shape recognition pairs and conjugates thereof, also combinations of defined sequence segments comprising synthetic heteropolymers, and even combinations of multiple synthetic heteropolymers comprising multivalent heteropolymeric hybrid structures, are shown herein to provide control over the relative positions of specifically and covalently bound molecules. The resulting switches, sensors, transducers and drug delivery devices function in a highly efficient manner due to the spatially ordered arrangement of molecules within multimolecular devices.

In a preferred aspect of the invention, multimolecular devices comprise at least two different specific recognition pairs positioned by nucleotides in suitable spatial proximity to enable either functional coupling between the specific recognition pairs or, in the case of certain molecular delivery devices, concerted action of two or more selected molecules (e.g., drugs) at a selected target (e.g., a therapeutic target). The positioning capability of defined sequence segments described herein refers to functional coupling both between different molecules connected by nucleotides and between nucleotide-positioned molecules and selected targets. The benefits of functional coupling between and among molecules comprising and targeted by nucleotide-based multimolecular devices in many ways parallel the structural and functional efficiencies realized through biological evolution and self-organization.

Nucleotide-based templates can be also be designed or selected to specifically recognize structural molecules of surfaces, parts, products, articles of manufacture, containers, packaging and packing materials for use as reversible and reusable adhesive coatings. Specific binding of a bivalent template to at least one of two surfaces allows the surfaces to be bonded, optionally reversibly and repetitively. A first ligand, receptor or defined sequence segment of the bivalent template, optionally two or more hybridized nucleotide sequences binds the first surface. A second ligand, receptor or defined sequence segment of the bivalent template binds the second surface. Reversible surface bonding is achieved by specific template binding to structural molecules comprising the surfaces, optionally aided by hybridization of two or more defined sequence segments.

If the composition of the two surface is different (i.e., foil on leather or vinyl on cardboard), a bivalent adhesive applied to one surface orients in a sided and reproducible manner. Each member of a plurality of templates also orients in a sided and reproducible orientation. Once a selected second surface is plated upon the template-modified first surface, the templates thus consort in bonding the surfaces. A plurality of weak-binding templates can effectively and reversibly bond the two surfaces due to their collective binding strength. Because the bound templates share a common bivalent specificity and are uniformly oriented, their collective binding strength can be specifically and efficiently reversed by a specific and convenient intervention, e.g., application of a selected laser or electromagnetic frequency.

If the composition of the two surfaces is the same (i.e., two flaps or panels of a cardboard box), the structure of the template is designed to provide specific, efficient and uniform binding to the surfaces. Collective binding is achieved, e.g., using dendrimeric or spherical polymeric templates having surface-binding ligands uniformly attached in a site-directed manner. Advantageously, linear polymers of defined length may be used, preferably with surface-binding ligands positionally controlled in both Cartesian and polar coordinates. Modified helical DNA is well suited of this application. Alternatively, bivalent or multivalent DNA-ligand templates may be used as imprint molecules. A plastic adhesive capable of joining two surfaces in a specific and reversible manner can then be prepared in two sequential generations of cast-and-mold imprinting.

Adhesive templates and adherent probes of the invention can even be designed to specifically recognize a particular structural shape or surface feature (i.e., a shape, texture, contour or other localized property) on the structure or surface, e.g., for specific attachment of selected molecules to microminiaturized devices and/or nanofabricated features. Shape-specificity is distinct from ligand-receptor binding as known in the art. Shape-specific adhesive templates or adherent probes specifically recognize one surface feature (e.g., an edge) without binding others (e.g., a face). Two surfaces having the same composition but a different surface feature, optionally male and female contours, can be aligned by a shape-specific bivalent template. Shape-specific recognition of a first part, edge or face by a shape-specific template enables specific adhesion (bonding) to a second part, edge or surface, optionally also treated. Shape-specific adhesion between surfaces is advantageously reversible. Precise and specific feature-to-feature registration of first and second surfaces and parts enables nanofabrication of hybrid devices with molecular-scale resolution.

Multiply patterned surfaces may also be prepared by selecting and specifically attaching at least two, different shape recognition probes or templates to a surface, preferably to each of two surfaces. Feature-specific attachment of bivalent templates to two different male features on a first surface corresponding to equivalently spaced female features on a second surface enables precise and unique registration of the surfaces. Advantageously, bivalent nucleotide-based templates feature-specifically attached to the male surface may be hybridized to complementary bivalent nucleotide-based templates feature-specifically attached to the female surface. The surfaces may be reversibly bonded and willfully separated. Alternatively, they may be covalently and permanently attached, e.g., by photoactivated crosslinking.

Whereas molecular adhesives of the instant invention are used to specifically attach two surfaces, molecular adherents are used to attach a first selected molecule to a second selected molecule comprising a surface. For example, a single nanofabricated surface may be functionalized by template-directed and feature-specific attachment of MOLECULAR MACHINES disclosed herein. For example, A selected molecule (e.g., a signal-generating molecule) or a multimolecular device (e.g., a fluorescence energy transfer complex) may be site-specifically delivered, e.g., to a selected, specifically attractive surface feature (e.g., an edge, pit, vertex, directrix or nadir). Advantageously, nonselected surfaces or parts need not be modified, even if they have the same chemical composition as selected surface features. Nonselected surfaces are not specifically attractive and therefore not specifically recognized. Because shape recognition is specific for a surface feature and not its chemical identity, monolithic nanoscale features on micromachined surfaces can be specifically decorated with useful MOLECULAR MACHINES. Feature-specific delivery of MOLECULAR MACHINES to nanofabricated shapes (e.g., diamondoid features of a carbon, silicon or gallium arsenide device) enables precise structural and functional integration of organic and inorganic surfaces and device components. Alternatively, optoelectronic MOLECULAR MACHINES patterned in a feature-directed manner to pits comprising CD and DVD surfaces can be used as marking devices for antipiracy and anticounterfeiting purposes.

Molecular adherents of the instant invention can be used not only to attach a first selected molecule (i.e., the delivered or targeted molecule) to a target surface, they can also be used to degrade, digest, detoxify or remove a second selected molecule (i.e., a selected target molecule) comprising or attaching the target surface. For example, a molecular adherent designed to prevent or treat microbial corrosion of a nuclear reactor surface may comprise a first recognition element (i.e., a specific recognition site) that specifically attaches to a molecule or surface feature comprising the corroded surface (e.g., a biofilm-modified metal). A second recognition element of the molecular adherent, e.g., an antimicrobial enzyme or drug, may then kill and/or degrade the causative microbe. Alternatively, a surface active effector molecule (e.g., an oxidoreductase or electroactive catalyst) may directly modify the properties of the corroded surface. Related applications include, e.g., prevention, remediation, treatment or surface removal of dental plaque, bacterial contamination, mold, mildew, dust, pollens, mites, allergens, toxins, rust, tarnish, oils, films, paints and coatings.

The development of molecular adhesives and adherents is enabled by the ability to either 1) identify a selected molecule capable of specifically recognizing the surface, either by specific binding, hybridization to a nucleotide-modified surface (i.e., in the case of molecular adhesives), structural shape recognition or, alternatively, 2) selection of a surface feature capable of recognizing an identified molecule. Selection of specific recognition molecules or surfaces (i.e., structural shapes, surface features or selected molecules comprising a surface) may be accomplished by identifying a heretofore known selected molecule (e.g., a known ligand, receptor, effector molecule or structural molecule) having a desirable property or activity, preferably using an informational device(s) comprising a paired molecular search engine (s). A first molecular search engine explores a first multidimensional, evolving knowledge base encompassing heretofore known (i.e., heretofore identified) molecules and their properties, activities, interactions, sourcing and production/processing data. A second structural shape search engine explores a multidimensional, evolving knowledge base encompassing heretofore known structures and surfaces (e.g., substrates and/or feedstock materials comprising potentially useful structural shapes and surface features), including heretofore known properties, activities, interactions, sourcing, production and processing considerations. The informational system (paired search engines) is functionally coupled in a closed-loop, divergent (i.e., positive) feedback control system, wherein the learning of one system at one and the same time advances and is advanced by the expanded comprehension of the other. In addition, the molecular knowledge base search engine (i.e., molecular knowledge base) is functionally coupled to an information source, preferably a willful datastream comprising not only heretofore available, but also emerging molecule and structures/surfaces data. In this way, the identities, properties, activities, interactions and use-considerations of heretofore known molecules and materials is correlated within an evolving informational system, preferably comprising, attaching to or capable of attaching to an expert system, intelligent machine and/or willful director. Similarly, novel catalytic properties may be introduced to a surface by either 1) attaching a catalytic selected molecule or nucleic acid sequence to the surface using a bivalent or multivalent template or, alternatively, 2) selecting a surface library for a surface feature having a selected catalytic recognition property.

Plastic segments of the instant invention deriving from functionally coupled nucleotide-nonnucleotide libraries enable transposition of the binding properties of structural shapes (i.e., surface features) into molecular and catalytic recognition partners and vice versa. A surface feature previously confined to the diversity domain limited by chemical blandness can now be transposed into molecular structure-activity-shape space by imprinting to a paired library. Conversely, a structural shapes can be endowed or adorned with molecular diversity by at least two heretofore unknown methods.

First, a diverse structural space library (i.e., surface library or material library) can be created by random, randomized, or rational, preferably combinatorial nanofabrication techniques (e.g., emerging MEMS, NEMS, lithographic, ion beam and electrospray techniques). A selected specific recognition partner (e.g., a plastic segment), optionally a selected library of selected plastic segments) can be displayed on a chemically bland substrate (e.g., freshly cleaved mica) in a structurally oriented manner, e.g., by site-directed covalent attachment. Alternatively, using a chemically bland surface comprising a selected or designed surface feature (e.g., nanometer-scale concave pits or conical tips comprising uniquely shaped nadirs, vertices and directricies), specific attachment can be achieved using molecular adherents comprising bivalent plastic templates disclosed herein, the plastic templates having a binding domain (e.g., defined sequence segment imprint) capable of specifically recognizing the selected surface feature. The second binding domain of the plastic segment is then displayed in a controlled, preferred and uniform orientation. Whether by site-directed covalent attachment of a plastic segment or feature-specific recognition by a bivalent template, the result is a modified surface displaying a selected molecular shape or an assortment or array, random or ordered in the two dimensions comprising a planar surface, of selected segments or paired segment templates comprising a selected library. This shape-modified surface (i.e., surface template or specifically grafted surface) can then be scanned by single-molecule detection techniques described herein, preferably SPM, more preferably AFM, advantageously multiplexed AFM comprising multiple cantilevered probe tips operating in parallel. Information from this surface template is then used as a knowledge base defining three-dimensional shape(s) of displayed segment(s) to be correlated with similarly determined surface features comprising the surface library. In this way, selected surface features can be identified which mimic the recognition properties of a molecular shape. The selected surface features can then be transposed through a nucleotide-nonnucleotide library into a newly selected molecular medium (i.e., a preferred and/or compositionally diverse molecular matrix) by paired imprinting, e.g., a two-step imprinting process generating firstly antiidiotypic and secondly idiotypic imprints of the selected surface feature. Advantageously, the newly selected (i.e., evolved) molecular medium comprises a suitably compact, compressed, rigid and/or defined structure and shape to enable precise and informative three-dimensional AFM imaging of surface-displayed template features. It will be apparent to the skilled artisan that an analogous method can be applied to biological surface-displayed molecular and structural shapes as well (e.g., phage displayed peptides, complement determining antigens, Fc receptors, drug receptors, hormone receptors and the like, optionally displayed in self-assembling films, surface coatings, layers or membranes).

Second, bivalent plastic templates can be used to modify surfaces by adherence without scanning and transposing of a desired molecular shape into the surface material itself. For biomedical devices such as hearing aids comprising microcantilever-bound MOLECULAR MACHINES functionally coupled to cochlear cells of the inner ear, biological and biomimetic materials are preferred. Microcantilevers may have dimensions on the order of typical AFM probes (e.g., about 100–200 microns long×20–40 microns wide× 0.3–3.0 microns thick). Alternatively, further miniaturization to micron and even submicron dimensions (e.g., 1.0× 0.3×0.1 microns) enables honing of device responsiveness (i.e., sensitivity) to the attogram scale. Biomimetic materials are optionally selected by imprinting defined sequence segments comprising nucleotides into plastic segments, preferably by transposing a nonbiomimetic but otherwise attractive precursor through a nucleotide library followed by selection of a plastic segment or template from a second, biomimetic molecular medium (vide infra). For microelectronic applications, e.g., attractive materials include metals, semiconductors, synthetic (organic) metals and synthetic semiconductors, including insulators and Mott insulators and further comprising dopants. For example, a bivalent plastic template is imprinted from a synthetic heteropolymer into a semi-rigid polymeric matrix, e.g., polyacrylate, by paired library transposition or by molecular imprinting methods known in the art (e.g., Shea et al. (1993) *J. Am. Chem. Soc.* 115:3368–3369;Ramstrbm et al.(1993) *J. Org. Chem.* 58:7562–7564; Vlatakis et al. (1993) *Nature* 361:645–647). This bivalent imprint template is then transposed by a second imprinting step into a second molecular medium, preferably a relatively compressed and ordered rigid polymeric structure having conductive, semiconductive or insulating properties compatible, advantageously synergistic, with the structure and function of the microelectronic device. For example, to functionalize a field effect transistor e.g., a 0.1 micron MOSFET switch, a plastic molecular adherent is imprinted or transposed from a bivalent aptameric or heteropolymeric template into a corresponding antiidiotype plastic template comprising a first binding domain specific for the conjunction between the planar surface surrounding the FET device and the channel wall (i.e., ledge junction). The second domain of the plastic template may be a binding domain, a catalytic domain or an alternative effector (e.g., a redox, photonic, or electroluminescent domain). In this way, new functionalities heretofore presumed to occur only in the realm of molecular shape space (i.e., molecular and catalytic recognition as distinct from specific surface attractivity) are introduced to chemically bland surfaces. Template-directed attachment of a heat sink and/or thermally triggered switch may enable, e.g., development of a molecular coolants or surge protector to prevent overheating of densely packed printed circuits (i.e., feature sizes in the 1–100 nm range). Alternatively, in situ amplification of a negatively charged nucleotide polymer may be used to generate an electrochemical potential or electromotive force (i.e., a molecular battery), e.g., by polymer replication-induced partitioning of charged monomeric nucleotides across a semipermeable membrane, channel, matrix or gate to which the replicated polymer is impermeable.

Surface template, when used in reference to a template or MOLECULAR MACHINE comprising a surface, means a template having at least one functional element displayed on the surface, advantageously oriented in such manner that displayed recognition properties are useful in solid phase catalysis, separations, binding or catalytic assays or processes, or can be scanned, imaged and/or mapped by an analytical system, e.g., an STM, optical scope, laser scanning device or hybrid system.

Grafting, when used in reference to attachment of a segment, template or MOLECULAR MACHINE to a surface, means site-directed attachment in such manner that at least one binding domain or recognition element is displayed on the surface in an oriented or polarized manner useful in solid phase catalysis, separations or recognition-based assays or processes, or can be scanned, imaged and/or mapped by an analytical system, e.g., an STM, optical scope, laser scanning device or hybrid system.

The melding of surface space and recognition space has important commercial implications. For example, seamless integration of biomimetic and semiconductor functionalities into hybrid devices and systems can now be achieved. This hybridization provides the art with a path to biosensors, biochips and molecular arrays capitalizing on the most useful and powerful attributes of materials and molecules heretofore refractory to sustained and meaningful camaraderie. While efforts to achieve intimate contact and functional coupling between biologicals and inorganic substrates have long been in development (e.g., biosensors, biochips, hearing aids, implantable drug delivery systems), achieving stable, tightly coupled integration has been impaired by the differing needs and interests of participating compositions. For example, biologicals tend to prefer wet, salty, proteinaceous solutions. Semiconductors, metal, and insulators, by contrast, are favor dry, clean, crystalline and particle-free. Semiconductors, FETS and switches are fabricated from bulk materials with 0.1 to 1.0 micron feature sizes, evolving toward and below the 100 nm scale. Biological and biomimetic recognition reagents are molecules, supramolecular assemblies at best, having molecular sizes up to about the 10 nm scale. Structural shape (i.e., surface feature) selection from diversely modified surfaces, as described herein, and nucleotide-library mediated diversification and imprinting of identified surface features will bridge this gap between the 0.01–10 nm molecular playground and the 100–1000 nm world.

The instant invention also enables innovative functionalization of emerging diamondoid structures and shapes comprising fullerenes, buckyballs and related carbon-based nanostructures, e.g., carbon nanotubes, nanorods, and the like, doubtless to be followed by novel silicon and gallium arsenide devices and heretofore unknown ceramics. Plastic segments (i.e., plastic bits) and templates (i.e., paired bits) disclosed herein can be used as adherents to decorate such diamondoid structures with specific recognition and catalytic recognition properties or to enhance connectivity, e.g., to molecular wires and molecular switches. Alternatively, bivalent plastic templates can be used as adhesives to integrate carbon nanotubes, nanorods, nanolevers and other emerging nanostructures with emerging submicron-scale photolithographic features. Alternatively, nucleoplastic templates comprising nucleotides, optionally encapsulated in glassy matrices can be used to perform on-board processes heretofore known only to nucleotides, e.g., programmable self-assembly, replication, amplification and combinatorial mutation.

Mapping libraries are preferably diverse libraries of selected recognition partners, preferably nucleotides selected from a diverse plurality of nucleotide libraries, used to transpose the recognition properties of a selected population of selected nonoligonucleotide molecules into a selected population of replicatable nucleotides which can be sequenced and archived. Mapping libraries may be used to create an antiidiotypic or idiotypic image of a selected population of selected molecules through one or more imprinting steps. An antiidiotypic imprint may be obtained in a single step to or from a nucleotide library. For example, a template may be imprinted in a single step to create an antiidiotype which is idiotypic to one or more selected molecules capable of recognizing the parent template. Alternatively, a nonnucleotide receptor may be imprinted in a single step to create an antiidiotypic ligand. In a second imprinting step, the antiidiotypic ligand may be imprinted using a nucleotide library to create a nucleotide idiotype of the parent receptor. The corresponding nucleotide library can be 1) sequenced with single-molecule resolution, 2) replicated with approximately perfect fidelity, 3) digitally archived in the form of sequence information comprising a searchable knowledge base of an informational system (e.g., search engine), 4) archived as matter, e.g., replicated clones of the parent mapping library, 5) amplified with variable fidelity to generate diverse brethren libraries useful in searching functionally defined regions of molecular diversity space, 6) transposed by imprinting into alternative molecular media expressing different structural and functional dimensions of the parent mapping library, and 7), functionally characterized by single-molecule detection methods as disclosed herein, e.g., detection of specific binding proclivities to selected molecules using, e.g., AFM and/or optical scanning/microscopy. The specific binding proclivity of a library is preferably determined by massively parallel scanning of a selected array of selected molecules by optically guided, multiplexed SPM techniques presently becoming known to the art. These individual and collective embodiments of transposition, enable the exploration, expression, amplification, display, archiving, permutation and combinatorial correlation a selected population of selected molecules first in molecular space and second in functionally coupled informational space. Imprint library means a mixture of molecules prospectively comprising a recognition partner for an identified target.

Single-molecule detection, isolation, amplification and/or sequencing can be applied not only to aptamer screening, but to identification and characterization of other synthetic nucleotides having commercially useful properties or potentially useful activities that can be adapted or evolved in vitro for commercial use, e.g., ribozymes, catalytic DNA, and library-generated nucleotides having a specific binding or surface feature binding property or catalytic activity (i.e., catalytic recognition). In a preferred aspect of the invention, a library of random-sequence nucleotides, each random-sequence nucleotide comprising or attaching to a first selected molecule (preferably a first molecular effector or selected nucleic acid sequence having a first selected activity) is screened and selected for the ability to recognize a target comprising a second selected molecule (preferably a second molecular effector capable of cooperating with the first, preattached selected molecule). Random-sequence nucleotides capable of recognizing the second selected molecule (e.g., effector molecule) or nucleic acid sequence (e.g., conjugate, ribozyme, catalytic DNA, recognition site) are then selected by single-molecule detection of functionally coupled nucleotide-target molecules. Unlike single chromosome imaging and excision as known in the art, the instant methods provide a means for harvesting potentially valuable synthetic nucleotides from synthetic libraries based on functional activities, e.g., specific binding, specific attractivity and catalytic recognition. Also unlike heretofore known scanning probe chromosomal dissection efforts, the instant invention discloses not only single-molecule amplification followed by large-scale sequencing, but also a single-molecule sequencing modality. The instant methods are advantageously applied to single-stranded as well as double-stranded synthetic nucleotides, including ribonucleotides, deoxyribonucleotides, hybrids and chimeric sequences, preferably nucleotides having as few as one two bases per sequence. Also disclosed herein is the use of single-molecule detection and sequencing to deconvolute nucleotide-encoded chemical libraries, particularly modified nucleotide libraries comprising nucleotide ligands, nucleotide receptors and nucleotide catalysts.

Single-molecule detection, amplification and sequencing methods disclosed herein are not drawn to analysis, mapping or sequencing of chromosomal DNA or genomic nucleic acids or to natural replication, transcription or translation of biological nucleic acids to yield natural, recombinant or transgenic proteins. These and other applications of nucleic acids, nucleic acid analysis, single-molecule imaging and single-molecule sequencing are known in the art and outside the scope of this invention. However, as will be apparent to the skilled artisan on reading the instant disclosure, MOLECULAR MACHINES designed and selected using single-molecule detection methods provide highly sensitive, specific and well-defined multimolecular compositions capable of molecular counting, DNA diagnostics, pseudoimmunodiagnostics, clinical chemistry and high-throughput screening (e.g., for drug discovery), all with the potential to achieve single-molecule detection, characterization, diagnostics and monitoring. These and other single-molecule uses of MOLECULAR MACHINES, including the analysis, mapping and sequencing of genomic, microbial and plasmid nucleic acids, are fully within the purview of this invention.

The commercial potential of nucleotide-directed mapping libraries is almost unimaginable. Nucleotide-directed transposition of provides a general method for characterizing, cloning and archiving representations of any selected population of selected molecules both in molecular space and in information space. For example, a selected population comprising B cell, T cell or macrophage-engulfed antigens or antibodies; a selected population comprising lymphocytic leukemia-specific antigens or cell surface antigens comprising a fractionated tumor homogenate; a selected population of molecules capable of binding a selected surface; a selected population of molecules capable of catalyzing a selected chemical reaction; a selected population of molecules comprising a selected hazardous substance or spill; a selected population of molecules comprising the set of willfully accessible DNA intercalators; a selected population of surface features comprising the surface of a scar; a selected population of molecules capable of recognizing smoke particles; a selected population of molecules capable of binding a selected microbe; a selected population of molecules capable of binding a selected population of selected microbes; a selected population of molecules capable of recognizing serotonergic or β-adrenergic or dopaminergic receptors; a selected population of molecules capable of recognizing avidin or cancanavalin A or protein A or protein G or the Fc region of IgG; and so forth. Any of these selected populations of selected molecules can be transposed into nucleotide space, characterized, digitally coded, archived, cloned, amplified with impunity or infidelity and comprehended in information space. Product may further be mapped into a selected nonnucleotide medium which may represent a similar or entirely different region of molecular diversity space from the parent, nucleotide-mapped, selected population of molecules.

This staggering and ramifying array of potential utility is exponentially compounded by the herein disclosed ability to map molecular space (i.e., recognition space) into surface space (i.e., surface feature or materials space). In fact, the ability to transpose surface features (e.g., scars, MOSFET channel junctions) into molecular shape space and vice versa, enables the mapping of any knowable population comprising surface features or selected molecules into nucleotide space. The ability to map nucleotide space into a second molecular medium enables the recognition properties of the parent population of selected molecules to be recast into a second molecular medium having different chemical and physical properties from the parent population.

Nucleotide-mediated digital encoding and deconvolution of the immune repertoire for real time monitoring of health status is one particularly attractive application of the diversity that can be achieved with the paired nucleotide-nonnucleotide diversity generator disclosed herein. Questions and skepticism will arise regarding the potential of a nucleotide library to achieve the diversity required to map a system as complex, e.g., as the human immune system or even a subset thereof, e.g., all CD antigens on a particular subset of T cells or all IgGs having a selected class specificity (e.g., for gram negative bacteria). These concerns are valid, in view of the molecular and informational complexity of these mapping functions. However, a divergent molecular diversity generator evolving toward infinite diversity can achieve adequate diversity to comprehend (i.e., map) any finite population. A selected population of selected molecules is a finite set. Also, willful selection of a selected population of selected molecules means that the diversity of the selected population can be reduced, e.g., by tightening the selection criteria, fractionating cells or antibodies, isolating or purifying molecules by willful selection. Thus, a selected population of selected molecules, no matter how diverse the parent source (e.g., the set of all human immunoglobulins), is a convergent set. Diversity can be controlled, reduced to whatever degree necessary or practical. A finite and potentially convergent selected population of selected molecules is intrinsically within the mapping purview of a higher order library of libraries coupled to an intelligent informational system, e.g., a divergent, multidimensional diversity generator comprising paired nucleotide-nonnucleotide libraries, optionally libraries of paired nucleotide libraries projected in molecular shape space.

Selection and evolution of a mapping library requires highly efficient means of exploring diverse libraries, preferably paired nucleotide-nonnucleotide libraries and more preferably libraries of paired libraries. Selection is preferably achieved in a combinatorial manner, e.g., using selected populations of selected molecules (i.e., selected targets) and paired library members (e.g., nucleic acids) conjugated to different signal-generating species, e.g., fluorescent particles differing in size, color and/or spectral properties. Advantageously, the paired library comprises a random-sequence nucleic acid library, wherein member nucleic acids each comprise fixed-position or fixed-sequence nucleotides conjugated to a second and optionally a third, fourth and $N^{th}$ different signal-generation species, each expressing a different signal (e.g., color, fluorescence emission, enzyme activity, luminescence). Preselection or counterselection against structurally conserved epitopes is important in selecting libraries for new recognition elements. Evolution of maximally informative mapping libraries requires muting, filtering or subtraction of redundant or uninformative specificities, e.g., epitopes comprising immunoglobulin hinge and disulfide bridge regions.

Capitalizing on both the plasticity and adherent properties of nucleoplastic templates, attractive applications include cosmetics and tissue repair. Examples include long-lasting and willfully removable cosmetics (vide infra) and mapping the shape space of a scar. By characterizing the surface attractivity and recognition properties of a healed, cosmetically imperfect facial scar, for example, biocompatible molecular adherents can be used to replace, enhance or supplement plastic surgery. A first machine-coupled paired nucleotide library serves as molecular diversity generator to produce a first set of libraries willfully and intelligently designed to map the molecular and structural shape contours of the scar. A second machine-coupled paired library generator expresses and explores structure-activity-shape space for suitable biocompatible structural and effector molecules (e.g., mimetics of epithelium, keratin, collagen, elastic and/or contractile proteins, pigments). Template-directed molecular assemblies with affinities for the scar surface are then coselected in proximity space by a willfully directed, machine-coupled consorting system. The template-ordered molecules or assemblies are stabilized by irradiation or site-directed heterobifunctional conjugation. The stabilized conjugate or assembly is then optionally transposed through a paired nucleotide-nonnucleotide library into a second molecular medium (e.g., into a collagenous medium by antiidiotypic and anti-antiidiotypic imprinting steps). The final product, optionally evolved through multiple automated cycles, is a patient-specific, customized, biocompatible adherent that coats and smoothes the fibrotic surface of a scarred wound. A similar selection process can be applied the design and evolution of molecular adherents for a variety of dermatologic and cosmetic applications, including smoothing, filling, plasticizing and coloring wrinkles, birth marks, acne-induced pock marks, pitting, dermabrasions and the like. Molecular adherents can also be formulated as topical smaRTdrugs comprising targeted and/or triggered release prodrug complexes that dissociate on binding of an allosteric recognition site to a selected therapeutic target (e.g., for treatment of psoriasis, dermatitis, melanoma, impetigo, urticaria and the like).

The instant mapping libraries and methods for mapping surface features into molecular shape space thus enable the transformation of recognition properties or surface features of a first material or molecular medium into a second material or molecular medium. This nucleotide-mediated molecular transposition process (i.e., transformation through nucleotide space) enables the properties of ordinary molecules to be represented, archived, amplified, and modulated in nucleotide space. Retrieval may then be achieved in a second or third or fourth molecular medium, advantageously a molecular medium selected on structurofunctional grounds by an intelligent informational system, preferably a functionally coupled network comprising information source(s), knowledge base(s), hypothesis-generating and hypothesis-testing search engines as described elsewhere in the instant disclosure.

Nucleotide-directed transformation enables a selected sterile molecule or population of molecules to proliferate in molecular diversity space and thereby populate diversity space through faithful mapping (i.e., replication) and unfaithful replication (e.g., drift, mutation or directed evolution via biased amplification) mediated by nucleotides, preferably paired nucleotide libraries comprising an automated, willfully directed process. Advantageously, transformation is achieved from a first selected molecule(s) to a second, improved selected molecule(s) by passing (i.e., transposing) the first selected molecule(s) through a nucleotide library.

In this way, a first selected population of selected molecules, optionally a single selected molecule, can be mapped into nucleotide space, transposed into an alternative molecular medium or material which can be retrieved and archived in nucleotide space, and, as desired reflected into and expressed in still new and different materials and media.

Nucleotide mapping libraries of the instant invention are surprisingly useful, particularly functionally coupled paired libraries comprising at least a library of first nucleotide libraries capable of representing a nonnucleotide library in nucleotide library space. This transposition of nonnucleotide molecules, preferably selected populations of selected molecules, enables the transformation of a heretofore sterile molecule or population of molecules into a replicatable, amplifiable, divergent molecular medium.

Various terms are used herein metaphorically to describe nucleotide library-mediated transposition. For example, the diversity of a first selected molecular medium confined to a particular region of diversity space (e.g., decapeptides or octapeptides or Arg-Gly-Asp-Ser conformers) may be expanded, enhanced, mutated, transformed, or transposed by bouncing the molecule(s) off a nucleotide library or reflecting a first library off a nucleotide library or passaging or passing a first molecule through nucleotide library or projecting or imaging a molecule or library in diversity space. These metaphors represent the inventor's attempt to articulate through visually tractable images a toolkit of methods and compositions that relate to N-dimensional space. These methods and compositions are best expressed in mathematical language(s) in which the instant inventor is not well versed.

An important aspect of instant invention is to provide a paired library comprising a nucleotide library and a nonnucleotide library (hereinafter nucleotide-nonnucleotide or paired nucleotide libraries) capable of functioning as a fertile molecular diversity generator, i.e., an automated process comprising paired nucleotide libraries capable of exploring diversity space on an application-specific basis through functional coupling with a diversity space search engine that is in turn functionally coupled to an information source (e.g., willfully acquired data, information or knowledge).

Another important aspect is the incorporation of a molecular diversity generator-search engine pair within a multicomponent system designed to create, assemble, imprint, transform and evolve useful molecules comprising multimolecular assemblies, preferably either 1) self-replicating, self-assembling nucleotide-based MOLECULAR MACHINES or 2) application-specific, plastic-casted imprints comprising multimolecular machines for industrial use. Components comprising the system include, for example, a molecular diversity generator (i.e., an evolution station with variable fidelity amplifier); a sorting station (i.e., library screening and selection of selectable molecules); a consorting station (i.e., a molecular proximity optimization or functional coupling station); a templating station (i.e., preparation of nucleotide and nonnucleotide templates); a first template-directed assembly station (i.e., self-assembly of nucleotide-based multimolecular devices and MOLECULAR MACHINES); a conjugation station (i.e., for covalent conjugation of a pair or group of template positioned molecules or for covalent stabilization of MOLECULAR MACHINES); a casting or imprinting station (i.e., for transposing templates and selected molecules into alternative molecular media); a second template-directed assembly station (i.e., self-assembly of MOLECULAR MACHINES comprising plastic templates and/or transposed selected molecules); a printing station (i.e., for plastic template-directed casting and molding of imprints and antiimprints). The precursors and products of each station (e.g., a template, selected molecule or assembled MOLECULAR MACHINE) may advantageously be recycled through the molecular diversity generator in successive automatable rounds of paired nucleotide library-directed molecular evolution. Products of the system are 1) covalent conjugates of template-positioned, functionally coupled selected molecules, 2) self-assembling, advantageously self-replicating nucleotide-based MOLECULAR MACHINES, optionally covalently stabilized, and 3) self-assembling nonnucleotide MOLECULAR MACHINES, optionally covalently stabilized. Selected molecules comprising conjugates and MOLECULAR MACHINES may be heretofore known molecules, or they may be identified and/or evolved by the molecular diversity generator.

Nucleotide space means the dimensionless product of all molecular diversity spaces encompassed by molecules, molecular libraries, materials, and materials libraries comprising, attaching to or capable of attaching to a nucleotide library.

Transpose and transposition, when used in reference to nucleotide library-mediated imprinting and mapping, means mapping, imprinting, expressing, reflection, bouncing, passaging, passing, projecting, transforming or converting a first molecular, structural or surface property, shape, structure or activity, particularly a recognition property or surface feature comprising a first material, molecular medium, library or selected population of selected molecules, into, through, on, off, or within a second molecule, material, population, library, plurality of libraries or region of diversity space. Transposition may be used to create an imprint, antiidiotype, antiimprint, idiotype or any successive offspring or descendant evolving from the parent molecule, segment, nucleotide, precursor, donor or target. In a particularly preferred mode of operation, the bivalent and multivalent recognition properties of synthetic heteropolymers are transposed into nonnucleotide molecular media by dual imprinting, creating anti-antiidiotypes or idiotypic mimetics of synthetic heteropolymers.

Synthetic heteropolymers are nonnaturally occurring heteropolymers comprising nucleotides, particularly replicatable nucleotide sequences, nucleic acids, chimeric sequences, heteroduplexes and hybrids and any ribonucleotide, deoxyribonucleotide or chimeric counterpart thereof and any corresponding complementary sequence or promoter or primer-annealing sequence needed to replicate all or part of the synthetic heteropolymer, having at least two defined sequence segments, wherein at least one defined sequence segment per discrete structure is a synthetic defined sequence segment capable of specifically binding and optionally covalently binding a selected nonoligonucleotide molecule or group of molecules. The second defined sequence is capable of either specifically and optionally covalently binding a different, selected nonoligonucleotide molecule or selected nucleic acid sequence or of hybridization or of positioning a conjugated molecule within suitable distance of a selected molecule specifically bound to a first defined sequence segment to enable single-molecule detection or functional coupling between the conjugated molecule and the selected molecule. Where a second defined sequence segment is designed or selected to position a conjugated molecule for functional coupling to a specifically bound selected molecule, the selected molecule is preferably an effector molecule and more preferably a signal-generating species or a drug. Where the second defined sequence segment is designed or selected to position a conjugated molecule within suitable proximity of a specifically bound molecule for single-molecule detection, the conjugated molecule comprises a selected molecule, preferably a macromolecule, group of molecules or signal-generating species. So long as a synthetic heteropolymer comprises at least two defined sequence segments capable of specifically binding (and optionally shape-specifically recognizing), hybridizing or positioning a selected nonoligonucleotide molecule or selected nucleic acid sequence, at least one synthetic defined sequence segment being capable of specifically binding or a nonoligonucleotide molecule or specifically recognizing a surface feature of a specifically attractive surface, there is no upper limit to the number of defined sequence segments per synthetic heteropolymer.

Synthetic heteropolymers disclosed by Cubicciotti, U.S. Pat. No. 5,656,739 comprise a single-stranded nucleic acid molecule having at least a first and a second defined sequence segment, wherein the first defined sequence segment is capable of specifically and noncovalently binding to a first nonoligonucleotide molecule having a selected activity and the second defined sequence segment is capable of specifically and noncovalently binding to a second, different nonoligonucleotide molecule having a selected activity, wherein said first and second defined sequence segments are not known to be biological recognition sites for said first and second nonoligonucleotide molecules. Synthetic heteropolymers of the instant invention differ from the synthetic heteropolymers disclosed by Cubicciotti, U.S. Pat. No. 5,656,739 in several respects, most importantly in comprising defined sequence segments capable of covalently binding to selected nonoligonucleotide molecules and groups of molecules as well as specifically and noncovalently binding.

Replicatable sequences of nucleotides, e.g., in reference to a synthetic heteropolymer, may be any RNA or DNA or chimeric nucleotide sequence comprising or complementary to a synthetic heteropolymer and any corresponding RNA or DNA or chimeric sequence (e.g., a DNA sequence corresponding to an RNA synthetic heteropolymer or an RNA sequence corresponding to a DNA synthetic heteropolymer) which can be replicated or amplified either in vivo or in vitro. Nucleotide sequences comprising synthetic heteropolymers may be produced, detected and/or characterized through use of amplification systems well known in the art, including, but not limited to, polymerase chain reaction (PCR), ligase chain reaction (LCR), Q-beta replicase, self-sustained replication (3SR), transcription-based amplification system (TAS), repair chain reaction (RCR), cycling probe reaction (CPR), ribonuclease H or reAMP methods. For amplification, defined sequence segments or selected nucleic acid sequences preferably comprise or adjoin at least one primer annealing sequence (e.g., for 3SR amplification and circular nucleotides) and optionally at least two primer-annealing sequences (e.g., for PCR amplification of nucleotides having at least two termini). However, degenerate oligonucleotide priming may also be used to amplify a nucleic acid molecule of unknown sequence or a member of a mixture or library comprising nucleic acids having unknown or randomized sequences. In a preferred aspect of the instant invention, synthetic heteropolymers and methods of making, using, detecting or characterizing heteropolymeric discrete structures described herein comprise not only defined sequence segments, but also nucleotide recognition sites, e.g., promoter and primer annealing sequences, and complementary sequences required or formed during amplification reactions. A selected molecule or selected nucleic acid sequence specifically bound or hybridized to a synthetic heteropolymer may be detected with high sensitivity by amplifying the synthetic heteropolymer or any sequence comprising the synthetic heteropolymer, preferably a defined sequence segment, provided specifically bound or hybridized synthetic heteropolymers can be distinguished from their unbound counterparts, e.g., by physical separation or homogeneous detection means.

Synthetic heteropolymers of the instant invention may be single-stranded, double-stranded, partially single-stranded, partially double-stranded, branched, hyperbranched or conjugated oligonucleotides and may comprise any polymer of nucleotides or combination of nucleotide sequences including RNA, DNA, ribonucleotides, deoxyribonucleotides, modified nucleotides and nucleotide analogs such as peptide nucleic acids and nucleotides with backbone modifications or novel bases, including DNA-RNA hybrids, heteroduplexes and other hybrid or chimeric nucleotides and even conjugates of any such nucleotide polymer with nonnucleotide molecules, groups or sequences, provided the defined sequence segments are sequences of nucleotides.

Synthetic, in reference to a synthetic heteropolymer, means that 1) the synthetic heteropolymer is not derived from a heretofore known biological organism and 2) the nucleotide sequence of the synthetic heteropolymer is not heretofore known to occur in nature and 3) at least one defined sequence segment comprising the synthetic heteropolymer is selected from a source other than a heretofore known biological organism or biological polymer or collection of biological polymers and 4) the nucleotide sequence of at least one defined sequence segment comprising the synthetic heteropolymer is not heretofore known to occur in nature. At least one defined sequence segment of a synthetic heteropolymer is typically selected either 1) from an experimental or willfully designed pool, mixture, population, library or assortment of sequences, preferably a diverse pool, mixture, population, library or assortment, or 2) by means of a computer simulation, model, database, spreadsheet or virtual experiment or 3) by in vitro evolution or directed evolution. In each case, the selection criteria are established to select for sequences capable of either specifically binding to a selected nonoligonucleotide molecule or nucleic acid sequence or hybridizing to a selected nucleic acid sequence or positioning a conjugated molecule (e.g., by hybridization, specific binding, ligation, or incorporation of the selected sequence during synthesis into a synthetic heteropolymer) within functional coupling distance of a selected molecule capable of specifically binding another defined sequence segment or, optionally, within suitable proximity of the selected molecule to enable single-molecule detection.

Synthetic heteropolymers described herein and discrete structures comprising two or more synthetic heteropolymers are capable of noncovalently binding selected molecules or nucleic acid sequences through specific binding or hybridization at defined sequence segments. In addition, one or more molecules or nucleic acid sequences, preferably selected molecules or selected nucleic acid sequences, may be covalently attached to one or more nucleotides or defined sequence segments of a synthetic heteropolymer or multivalent heteropolymeric hybrid structure, provided the ability of at least one defined sequence segment of a synthetic heteropolymer to specifically bind a nonoligonucleotide molecule is conferred not by the conjugated molecule itself, but by the synthetic heteropolymer or the three-dimensional structure of the conjugated synthetic heteropolymer. The specific binding property of a defined sequence segment of a synthetic heteropolymer is a property of the defined sequence segment itself, optionally conjugated to another molecule or nucleic acid sequence, and is not intrinsic to the molecule or nucleic acid to which it may be conjugated. In other words, the ability of a defined sequence segment of a synthetic heteropolymer to specifically bind a nonoligonucleotide molecule is a property of the defined sequence segment, optionally including modified, derivatized or conjugated nucleotides, and cannot be introduced simply by conjugating a ligand or a receptor to the synthetic heteropolymer or its constituent nucleotides.

The synthetic heteropolymers of the instant invention are not derived, selected or copied from wild-type biological nucleic acid molecules, sequences or groups of contiguous sequences, nor are they derived, isolated, selected or copied from heretofore known mutants, genetic variants or nucleic acid molecules or sequences therefrom. At least one defined sequence segment of each synthetic heteropolymer or multivalent heteropolymeric hybrid structure of the instant invention is not only capable of specifically binding a nonoligonucleotide molecule, but is also synthetic. When used to describe a defined sequence segment, synthetic means nonnaturally occurring, i.e., the defined sequence segment is not heretofore known to occur in nature (sans human biotechnologic intervention) and is not heretofore known to be a biological recognition site. Biological recognition site means a first biological molecule or nucleic acid sequence that is heretofore known to specifically bind or recognize a second biological molecule or nucleic acid sequence. Unless otherwise specified, artificial and synthetic refer to willful products of human technology. Native, in nature, natural, naturally occurring, biological and organism, by contrast, refer to spontaneously occurring substances or beings that are not willful products of human-directed recombinant or transgenic technologies. In the case of hybrid plants and animals that have been identified and/or perpetuated by cross-breeding, selective breeding, cross-pollination, stem or limb grafting and the like, native, in nature, natural, naturally occurring, biological and organism mean only heretofore known strains. Where the distinction between natural and synthetic is ambiguous, a heretofore known substance, being or strain shall be considered natural for purposes of this disclosure, and a heretofore unknown substance, being or strain shall be considered synthetic.

A selected molecule or nucleic acid sequence which is specifically and noncovalently bound or hybridized to a defined sequence segment of a synthetic heteropolymer can subsequently be permanently affixed to the synthetic heteropolymer by covalent attachment using bifunctional or multifunctional crosslinking reagents well known in the art (e.g., Wong, S. S. (1991) *Chemistry of Protein Conjugation and Crosslinking*, CRC Press, Boca Raton). Alternatively, crosslinking reagents reactive toward functional groups present on selected molecules and not present on synthetic heteropolymer nucleotides can be used with appropriate spacer arms to selectively and covalently attach molecules specifically bound to proximally spaced defined sequence segments without chemically modifying the synthetic heteropolymer. In this way, synthetic heteropolymers can be used as templates to position molecules for reproducible and regiospecific attachment to one another. Selective modification and conjugation of selected molecules and positioning templates can also be achieved enzymatically, e.g., using well known biosynthetic enzymes, ligases, and the like. It will therefore be apparent to one of skill in the art that a defined sequence segment of a synthetic heteropolymer which is capable of specifically and noncovalently binding a selected molecule can also be used as a site of covalent attachment for the same selected molecule. Alternatively, selected molecules that are specifically and noncovalently bound to defined sequence segments of a synthetic heteropolymer can subsequently be covalently attached to one another.

In a preferred aspect of the invention, bifunctional synthetic heteropolymers are used as templates to position selected molecules for covalent conjugation, optionally by regiospecific chemical modification and crosslinking techniques. Template-directed covalent conjugation of selected molecules, preferably site-specific conjugation of functionally coupled effector molecules, enables efficient transfer of energy, electrons and photons between donor and acceptor species, advantageously including resonance energy transfer, fluorescence energy transfer and direct electronic coupling. In another preferred embodiment, covalent crosslinkers, preferably heterobifunctional crosslinking reagents, are used to stabilize multimolecular devices by chemically attaching specifically bound ligands, receptors, structural molecules and effector molecules to nucleotides comprising defined sequence segments, preferably by site-directed chemical modification. In still another preferred embodiment, selected molecules positioned by specific binding to a nucleotide template and optionally covalently attached either to the template or to one another are used as print molecules (i.e., guests) for preparation of nonnucleotide templates (i.e., hosts) capable of specifically binding and assembling the guests, e.g., using molecular imprinting methods known in art (e.g., Vlatakis et al. (1993) *Nature* 361:645–647, Shea et al. (1993) *J. Am. Chem. Soc.* 115:3368–3369, Ramström et al. (1993) *J. Org. Chem.* 58:7562–7564). In this manner, the positioning capability of nucleotide-based templates described herein can be transposed into nonnucleotide materials (e.g., industrial polymers and plastics) with particular properties (e.g., thermal, optical, chemical and structural properties, availability, quality, reliability and cost) selected for compatibility with different commercial and industrial applications for which nucleotide polymers may not be ideally suited. In another preferred embodiment, libraries of nucleic acid libraries, preferably libraries of libraries comprising nucleic acid libraries, are screened and selected to identify, assemble (i.e., collect) and evolve a mapping library from imprint libraries of nucleotides that specifically recognize members of a selected population of selected nonnucleotide molecules. The evolved library comprises a diverse plurality of nucleic acids selected to map, transpose and/or image (i.e., imprint) the recognition properties of the selected population of selected nonnucleotide molecules into a corresponding mapping library. Advantageously, the diverse mapping library comprises nucleic acids which, unlike the selected population of selected nonnucleotide molecules, can be amplified, sequenced, quantitatively characterized, digitally represented and archived both as stored digital information and as a defined reagent library (e.g., analytical, diagnostic, prognostic and monitoring use).

Attachment of a first molecule or functional group to a second molecule or functional group, e.g., a nucleotide, a selected molecule, or a particular chemical group comprising a selected molecule or nucleotide may be site-specific, site-directed or regiospecific, for example, by derivatizing a particular portion of a selected molecule or nucleotide or by chemical, enzymatic or biological synthesis of a molecule, preferably a polymer, more preferably a heteropolymer and most preferably an oligonucleotide, comprising a selected molecule, modification, monomer or analog at a defined position. Site-specific, site-directed or regiospecific attachment or modification means preparation of a conjugate or derivatized molecule comprising a first molecule (e.g., a selected molecule or nucleotide) and a second species (e.g., a second molecule, a new chemical group, plurality of new chemical groups, or a solid support) wherein the second species is attached to the first molecule at chemically, functionally or topologically defined site(s). Site-specific and site-directed attachment typically involve attachment to a particular chemical moiety, such as a reactive group or site that specifically binds a ligand or receptor (i.e., an epitope), while regiospecific attachment typically related to the topological position of the attached species rather than on the particular chemical site. However, the art recognizes some overlap between these terms.

Nucleotide means nucleotides and nucleotide analogs, preferably groups of nucleotides comprising oligonucleotides, and refers to any compound containing a heterocyclic compound bound to a phosphorylated sugar by an N-glycosyl link or any monomer capable of complementary base pairing or any polymer capable of hybridizing to an oligonucleotide. Nucleotide analog includes, but is not limited to, modified purines and pyrimidines, minor bases, convertible nucleosides, structural analogs of purines and pyrimidines, labeled, derivatized and modified nucleosides and nucleotides, conjugated nucleosides and nucleotides, sequence modifiers, terminus modifiers, spacer modifiers, and nucleotides with backbone modifications, including, but not limited to, ribose-modified nucleotides, phosphoramidates, phosphorothioates, phosphonamidites, methyl phosphonates, methyl phosphoramidites, methyl phosphonamidites, 5'-β-cyanoethyl phosphoramidites, methylenephosphonates, phosphorodithioates, peptide nucleic acids, achiral and neutral internucleotidic linkages and nonnucleotide bridges such as polyethylene glycol, aromatic polyamides and lipids. These and other nucleotide and nucleoside derivatives, analogs and backbone modifications are known in the art (e.g., Piccirilli J. A. et al. (1990) *Nature* 343:33–37; Sanghvi et al (1993) In: *Nucleosides and Nucleotides as Antitumor and Antiviral Agents*, (Eds. C. K. Chu and D. C. Baker) Plenum, N.Y., pp. 311–323; Goodchild J. (1990) *Bioconjugate Chemistry* 1:165–187; Beaucage et al. (1993) *Tetrahedron* 49:1925–1963).

Modified nucleotides and derivatized nucleotides are synthetic bases, i.e., nonnaturally occurring nucleotides and nucleosides, particularly modified or derivatized adenine, guanine, cytosine, thymidine, uracil and minor bases. Although there is substantial overlap between the two terms as used herein in reference to nucleotides, modified tends to mean altered or different from corresponding natural bases, whereas derivatized tends to imply the addition of groups, i.e., derivatization by the addition of chemical groups, functional groups and/or molecules.

Nucleotide analog means a molecule that can be used in place of a naturally occurring base in nucleic acid synthesis and processing, preferably enzymatic as well as chemical synthesis and processing, particularly modified nucleotides capable of base pairing and more particularly synthetic bases that do not comprise adenine, guanine, cytosine, thymidine, uracil or minor bases. Although there is some overlap between the terms as used herein, modified nucleotide typically refers to congeners of adenine, guanine, cytosine, thymidine, uracil and minor bases, whereas nucleotide analog typically refers to synthetic bases which may not comprise adenine, guanine, cytosine, thymidine, uracil or minor bases (i.e., novel bases).

Nucleotides described herein are replicatable and may exist in DNA, RNA and chimeric forms. Claimed nucleotide compositions and methods therefore include not only the described, preferred, selected or sense form of a specified nucleotide, but also any corresponding RNA or DNA or chimeric form and any corresponding sequence comprising backbone modifications, derivatized nucleotides or nucleotide analogs and any corresponding sequence further comprising one or more promoter or primer annealing sequences and any complementary sequence counterpart, e.g., as may be required or formed during replication. Nucleotide sequences and self-assembling groups of nucleotide sequences may be produced by biological and synthetic nucleic acid production techniques, including, but not limited to, recombinant methods, enzymatic methods and chemical methods, including automated nucleic acid synthesis. Amplification methods including, without limitation, PCR, LCR, Q-beta replicase, 3SR, TAS, RCR, CPR, ribonuclease H or reAMP methods may be used not only to synthesize or replicate, but also to detect, evaluate, characterize and sequence nucleotides described herein. In a preferred aspect of the invention, nucleotide-based compositions described and claimed herein comprise not only specified defined sequence segments required for specific binding and hybridization to selected molecules and nucleic acid sequences, but also effector recognition sites (e.g., promoter sequences) and/or annealing sequences (e.g., for PCR primers) for enzymatic modification, replication, amplification and/or detection of all or part of a constituent nucleotide.

Oligonucleotide means a naturally occurring or synthetic polymer of nucleotides, preferably a polymer comprising at least three nucleotides and more preferably a polymer capable of hybridization, and includes single-stranded, double-stranded, partially single-stranded and partially double-stranded ribonucleic and deoxyribonucleic acids, including selected nucleic acid sequences, heteroduplexes, chimeric and hybridized nucleotides, and optionally including nucleotides conjugated to one or more nonoligonucleotide molecules.

Nonoligonucleotide means a molecule or group of molecules which is not an oligonucleotide or, in the case of a conjugate comprising a first molecule that is an oligonucleotide attached to a second molecule that is not an oligonucleotide, the portion of the conjugate originating from or consisting of the second molecule. Nonnucleotide means a molecule or group of molecules which is not a nucleotide. Nucleotide or nonnucleotide (as well as nucleotide and nonnucleotide) means comprising or consisting of any molecule, i.e., either nucleotides or nonnucleotides.

Oligonucleotide conjugate and conjugated oligonucleotide mean an oligonucleotide conjugated to, incorporating or comprising a nonoligonucleotide molecule or a nonoligonucleotide molecule covalently or pseudoirreversibly attached to an oligonucleotide.

Nucleic acid molecules include biological, naturally occurring, nonbiological and synthetic nucleotides, oligonucleotides and selected nucleic acid sequences which may optionally be conjugated to one or more nonoligonucleotide molecules. Nonnucleic acid molecule means a molecule or group of molecules that is not a nucleic acid.

Discrete structures are single molecules or groups of molecules comprising nucleotides, wherein the molecules are bound to one another either covalently or through noncovalent interactions or, in the case of a multimolecular device, are required to specifically bind or dissociate during device function. Discrete structures of the present invention, also referred to herein as discrete nucleotide structures and nucleotide-based discrete structures, include defined sequence segments, aptamers, aptamer-target complexes, nucleotide-based multimolecular devices, discrete aptameric structures, discrete heteropolymeric structures, synthetic heteropolymers, and multivalent heteropolymeric hybrid structures comprising two or more hybridized synthetic heteropolymers, and multimolecular heteropolymeric complexes comprising one or more nonoligonucleotide molecules specifically bound to one or more synthetic heteropolymers or multivalent heteropolymeric hybrid structures.

Discrete structures of the invention may be partially or fully replicatable, meaning that one or more nucleotide sequences comprising a discrete structure may be synthesized, replicated, detected or characterized using a nucleic acid amplification system, e.g., PCR, LCR, Q-beta replicase, 3SR, TAS, RCR, CPR, ribonuclease H or reAMP methods to replicate and/or detect a defined sequence segment, a group of defined sequence segments or any portion thereof comprising suitable promoter and/or primer annealing sequences. Alternatively, degenerate oligonucleotide priming may be used to amplify nucleotides comprising randomized or undefined sequence segments.

Selected molecules or selected nucleic acid sequences specifically bound or hybridized to nucleotides, modified nucleotides or nucleotide analogs comprising a discrete structure of the invention may optionally be covalently attached to one another or to one or more nucleotides comprising a defined sequence segment of the discrete structure, e.g., using heterobifunctional crosslinking reagents and/or UV irradiation, to create a relatively stable, nondissociable and/or permanent discrete structure. Covalent attachment to a defined sequence segment comprising a discrete structure is preferably directed to a functional group comprising only one particular nucleotide, modified nucleotide, nucleotide position, nucleotide analog, type of nucleotide or group of nucleotides. Covalent attachment to a selected molecule, selected nucleic acid sequence or conjugate comprising multiple functional groups and/or multiple types of functional groups (e.g., a macromolecule, polymer or conjugate such as a protein or protein-ligand conjugate) may advantageously be directed to a single functional group, pair or group of functional groups that is uniquely represented, uniquely available or selectively accessible or addressable (e.g., for topological, positional, steric, electrostatic, kinetic or conformational reasons) in the selected molecule, selected nucleic acid sequence or conjugate. Alternatively, regiospecific covalent attachment of nucleotides to noncovalently bound molecules comprising multiple functional groups and/or multiple types of functional groups may be achieved without stringent chemical selectivity by adjusting reaction conditions (e.g., crosslinker selection, incubation time, temperature, pH and buffer conditions, reagent concentrations, photoactivation options)

to favor proximity-driven bonding between closest-approach reactive functional groups on the docking surfaces of the noncovalently bound molecules (e.g., the surface of a macromolecular selected molecule specifically bound to the surface of a defined sequence segment). In a preferred mode of operation, covalent attachment of nucleotides or selected molecules comprising a discrete structure is accomplished by selective modification of particular or unique functional groups on the nucleotide(s) and/or selected molecules to be covalently conjugated or by related site-directed or site-specific covalent modification methods known in the art, including enzymatic methods (e.g., Fisch et al. (1992) *Bioconjugate Chemistry* 3:147–153; Gaertner et al. (1992) *Bioconjugate Chemistry* 3:262–268; Offord (1990) In: *Protein Design and Development of New Therapeutics and Vaccines* (Eds. J. B. Hook and G. Paste), New York: Plenum, pp. 252–282).

Discrete aptameric structures are discrete structure comprising at least one synthetic aptamer and includes aptamer conjugates, aptamer-target complexes, oligonucleotides comprising one or more copies of an aptamer sequence, aptameric devices and discrete heteropolymeric structures, optionally including promoter and primer annealing sequences for replication. Aptameric devices are further capable of providing functional coupling between a selected molecule which is not an aptamer target, preferably a ligand or a receptor or a molecule conjugated to a ligand or receptor, and a selected molecule which is an aptamer target, preferably an effector molecule and more preferably a signal-generating species or a drug. Aptameric devices of the instant invention include multimolecular switches, multimolecular transducers, multimolecular sensors and multimolecular delivery systems comprising synthetic aptamers or aptamer conjugates.

Discrete heteropolymeric structures are discrete structures comprising at least two defined sequence segments, at least one of which comprises an aptamer, and optionally includes one or more linker oligonucleotides. The second defined sequence segment comprises either an aptamer, a single-stranded, double-stranded or partially double-stranded nucleotide sequence capable of hybridizing or specifically binding to a selected nucleic acid sequence, or a defined sequence segment capable of positioning a conjugated molecule within suitable proximity to provide single-molecule detection or functional coupling between the conjugated molecule and an aptamer target specifically bound to the first defined sequence segment. Discrete heteropolymeric structures of the invention include synthetic heteropolymers, multivalent heteropolymeric hybrid structures and multimolecular heteropolymeric complexes. All discrete heteropolymeric structures are also discrete aptameric structures, but the converse is not true, i.e., not all discrete aptameric structures are discrete heteropolymeric structures.

Aptamers are single-stranded, partially double-stranded or double-stranded nucleotide sequences capable of specifically recognizing a selected nonoligonucleotide molecule or group of molecules by mechanisms other than Watson-Crick base pairing or triplex formation. Aptamers disclosed herein include, without limitation, defined sequence segments, sequences comprising nucleotides, ribonucleotides, deoxyribonucleotides, nucleotide analogs and modified nucleotides, and nucleotides comprising backbone modifications, branchpoints and nonnucleotide bridges. Unlike aptamers known in the art, the instant term includes nucleotides capable of specifically recognizing a structural shape or surface feature of a selected target sans specific binding based upon the chemical identity of a selected molecule comprising the target. An aptamer may be a molecule unto itself or a sequence segment comprising a nucleotide molecule or group of molecules, e.g., a defined sequence segment or aptamer sequence comprising a synthetic heteropolymer or multivalent heteropolymeric hybrid structure. The molecule or group of molecules specifically recognized by an aptamer is referred to herein as the aptamer target, aptamer receptor, or aptamer binding partner. Synthetic aptamers are defined sequence segments or conjugated defined sequence segments not heretofore known to occur in nature and function as biological recognition sites which are capable of specifically binding a nonoligonucleotide molecule or group of molecules.

Aptamer conjugates are conjugates comprising an aptamer and a second molecule and includes aptamers comprising nonnucleotide molecules or moieties introduced during as well as after nucleotide synthesis, e.g., by incorporation of derivatized nucleotides or nucleoside triphosphates, labeled nucleotides, biotinylated nucleotides, nucleotide ligands, nucleotide receptors, conjugated nucleotides, nucleotides derivatized with nonnucleotide ligands or receptors, nonnucleotide molecules and the like. An aptamer conjugate is referred to herein as a synthetic aptamer if the conjugate is not heretofore known to occur in nature, regardless of the nucleotide sequence comprising the aptamer.

Nonaptameric multimolecular devices, which are either nonnucleotide multimolecular devices or nucleotide-based multimolecular devices lacking a sequence known to be an aptamer, are nonaptameric multimolecular structures or tethered specific recognition devices comprising either 1) at least two different specific binding or shape recognition pairs connected by a single defined sequence segment, each specific binding or shape recognition pair being attached in a controlled manner to a defined site or nucleotide position, or 2) at least two different defined sequence segments and at least two different specific binding or shape recognition pairs, each specific binding or shape recognition pair being conjugated to one defined sequence segment, and the two conjugated defined sequence segments being hybridized to a linker oligonucleotide which thus joins and positions the two conjugated defined sequence segments within a single discrete structure, or 3) at least two members of a specific binding or shape recognition pair or four members of two specific recognition pairs covalently or pseudoirreversibly attached to a molecular scaffold.

Tethered specific recognition devices are stimulus-responsive multimolecular structures comprising a molecular scaffold and at least two members of a specific binding or shape recognition pair or four members of two different specific recognition pairs, each member being covalently or pseudoirreversibly attached to the molecular scaffold. All nonaptameric, nucleotide-based multimolecular devices comprise at least either two specific binding or shape-specific recognition partners tethered to the molecular scaffold of a tethered specific recognition device or two conjugated specific binding or shape-specific recognition pairs brought together within a single multimolecular structure in a spatially controlled manner by site-specific or position-directed attachment to a sequence of nucleotides.

Different specific binding or shape recognition pairs means any two specific binding or shape recognition pairs whose four members comprise at least three different chemical identities. Representative pairs of different specific binding pairs include, for example, two antigen/antibody pairs with different specificities (e.g., peroxidase/anti-peroxidase and fluorescein/anti-fluorescein); two ligand/receptor pairs with different specificities (e.g., D-mannose/concanavalin A and biotin/avidin); a ligand/receptor pair (e.g., biotin/avidin) and an antigen/antibody pair (e.g., digoxigenin/anti-digoxigenin); two different molecular effector conjugate/ligand pairs (e.g., avidin-peroxidase/biotin and avidin-glucose oxidase/biotin); and two different nucleotide derivatives, each selected by combinatorial methods to specifically bind a different receptor. Even biotin/streptavidin and biotin/avidin are different specific binding pairs as defined herein, because the two specific binding pairs comprise three distinguishable chemical entities. The difference in chemical identity between, e.g., streptavidin vs. avidin or avidin-peroxidase vs. avidin-glucose oxidase is not accompanied by a sufficient difference in specificity to enable positional control of specific binding pairs. In other words, a defined sequence segment which is biotinylated at each of two defined nucleotide positions does not provide the requisite chemical specificity to attach avidin and streptavidin, on the one hand, or two different avidin-effector conjugates, on the other, in an ordered and reproducible positional relationship to one another. Nucleotide-based devices of the instant invention can, however, be used to position even multiple specific binding pairs with virtually indistinguishable specificities. For example, a receptor-first effector molecule conjugate can be specifically bound to a ligand-modified nucleotide at a first sequence position (e.g., a defined nucleotide position toward the 3' end of a sequence) during solid phase synthesis of a defined sequence segment. Unbound receptor-first effector molecule conjugate is then removed prior to continuing nucleotide synthesis in the 3' to 5' direction. A receptor-second effector molecule conjugate can then be specifically bound to a ligand-modified nucleotide at a second position (e.g., toward or at the 5' end). In this manner, different specific binding pairs with similar or identical specificities can be positioned along a defined sequence segment during synthesis. Similarly, a first ligand-conjugated defined sequence segment specifically bound via its ligand to a first molecular effector-receptor conjugate (e.g., defined sequence segment-biotin/avidin-peroxidase) can be ligated to a second ligand-conjugated defined sequence segment specifically bound via its ligand to a second molecular effector-receptor conjugate (e.g., defined sequence segment-biotin/avidin-glucose oxidase). In this case, controlled positioning of the two different, albeit closely related, specific binding pairs relies on the specificity provided by enzymatic ligation of two conjugated defined sequence segments. Another way to position two different specific binding pairs having indistinguishable specificities is to hybridize the two specific binding pair-defined sequence segment conjugates to a common linker oligonucleotide, thereby forming a discrete structure with nucleotide-ordered specific binding pairs.

In a preferred aspect of the instant invention, at least one nucleotide comprising a defined sequence segment is a modified nucleotide or nucleotide analog selected, preferably by combinatorial selection and/or high-throughput screening of a diverse library comprising modified nucleotides or nucleotide analogs, for the ability to specifically bind a selected molecule, e.g., a ligand, effector or receptor molecule. In this way, a specific binding partner, i.e., a modified nucleotide comprising a ligand or receptor, can be conjugated in a positionally defined manner to a defined sequence segment by chemically or enzymatically synthesizing the defined sequence segment and including the modified nucleotide or nucleotide analog at a defined position. Also, specific binding or shape recognition pairs can be conjugated to defined positions of a defined sequence segment by producing and/or ligating the defined sequence segment with modified nucleotides or nucleotide analogs comprising ligands or receptors, optionally modified nucleotides or nucleotide analogs identified by screening and/or selection of a diverse mixture or combinatorial library for candidates capable of specifically binding a selected molecule, preferably a ligand, receptor, or effector molecule. Inclusion of modified nucleotides or nucleotide analogs comprising selected molecules, e.g., ligands and receptors, in defined sequence segments provides a convenient method for conjugating ligands, receptors and specific binding or shape recognition pairs to nucleotide-based devices.

Nucleotide ligand and nucleotide receptor refer to molecules or functional groups comprising or attaching to derivatized nucleotides, nucleotide analogs, nucleotide-encoded chemicals and nucleotide-encoded chemical, shape and sequence libraries, preferably derivatized monomers, but optionally including derivatized dimers and even derivatized trimers, selected for the ability to specifically recognize an identified molecule or structural shape. Preferably, a nucleotide ligand or nucleotide receptor is selected for the ability to specifically recognize an identified molecule that is not heretofore known to specifically recognize the underivatized nucleotide that, once derivatized, specifically recognizes the identified molecule. Selection of a nucleotide ligand, nucleotide receptor, or a pair or group of nucleotide ligands and/or nucleotide receptors comprising a single nucleic acid molecule or a plurality of nucleic acid molecules is preferably achieved by screening or selection of a mixture of synthetic nucleotides, preferably a diverse library of chemically derivatized nucleotides, more preferably a diverse library of nucleic acid molecules comprising fixed or partially randomized sequences having at least one derivatized nucleotide per nucleic acid molecule and advantageously having at least two derivatized nucleotides per nucleic acid molecule, more preferably a nucleotide-encoded chemical library. Selection is preferably achieved by screening and selection of a library of diverse libraries, each diverse library diversified with respect to a different sequence, shape, chemical parameter so as to explore different regions (e.g., of chemical space) or dimensions (i.e., of diversity space) of chemical, shape or sequence space. Selection of templates for multimolecular devices and tethered recognition devices of the instant invention is optionally achieved by exploring positional space, i.e., by screening and selection of nucleotide libraries, advantageously nucleotide-encoded chemical libraries, comprising at least two preselected defined sequence segments, nucleotide ligands and/or nucleotide receptors, wherein the library is randomized with respect to the positions of pairs or groups of preselected defined sequence segments, nucleotide ligands and/or nucleotide receptors comprising member nucleic acids of the library.

Nucleotide catalyst means a synthetic nucleotide or nucleotide-encoded nonnucleotide molecule comprising a catalytic recognition partner, preferably a nucleic acid, nucleotide or nonnucleotide molecule identified by screening and selection of a diverse library comprising nucleic acid molecules, nucleotides, modified nucleotides or nucleotide-encoded nonnucleotide molecules, advantageously a diverse library comprising conjugated or immobilized molecules.

Although there is an extensive literature describing unnatural and modified nucleotides useful as diagnostic reagents and analytical tools (e.g., Goodchild (1990) *Bioconjugate Chemistry* 1:165–187; Beaucage et al. (1993) *Tetrahedron* 49:1925–1963), the prior art does not describe nucleotide analogs and modified nucleotides designed to introduce heretofore unknown ligands and receptors to enable functional coupling between pairs of specific binding pairs. Several nucleotide positions can be modified by addition of tethered substituents without significantly affecting duplex structure, including the N2 position of guanine, the N6 and N7 positions of adenine, the N7 position of guanine, the N4 and C5 positions of cytosine, and the C5 position of thymidine and uracil. Libraries described herein for selection of nucleotide ligands and nucleotide receptors are diversified in chemical space by derivatization at usefully modifiable positions of naturally occurring nucleotides (vide supra) and at novel sites comprising synthetic nucleotide analogs (i.e., novel bases).

A nucleotide ligand or nucleotide receptor may be selected to specifically bind an identified molecule comprising a ligand, receptor, structural molecule or a molecular effector. Where the identified molecule is a receptor, the selected specific binding partner is typically referred to herein as a nucleotide ligand. Where the identified molecule is a ligand, the selected specific binding partner is typically referred to herein as a nucleotide receptor. In preferred embodiments of the instant invention, paired specific recognition devices and tethered specific recognition devices comprise at least two specific recognition pairs, optionally at least two specific binding or shape recognition pairs (e.g., two ligand-receptor pairs), within a single multimolecular structure or multimolecular device. A nucleotide ligand comprising a first specific binding pair (i.e., a nucleotide ligand and its receptor) may also be a receptor comprising a second specific binding pair (i.e., an (aptamer) ligand and a (nucleic acid ligand) receptor). Similarly, a nucleotide receptor may also be a ligand. The distinction between nucleotide ligands and nucleotide receptors is therefore not compositional, but contextual, discretionary and optionally arbitrary.

Selection of nucleotide ligands and nucleotide receptors, e.g., by combinatorial synthesis and selection of a diverse library comprising derivatized nucleotides and/or derivatized nucleotide analogs, enables assembly of multimolecular devices with heretofore unknown specific recognition properties. In a particularly preferred embodiment, selected nucleotides with designer specificities (i.e., nucleotide ligands and nucleotide receptors) are incorporated into multimolecular drug delivery systems, multimolecular transducers, and multimolecular switches, particularly multimolecular sensors for detecting and characterizing heretofore unknown receptors and ligands, e.g., plant, animal, microbial and viral receptors discovered through genomic and proteomic research and corresponding newly discovered ligands, as well as multimolecular sensors for detecting and monitoring, e.g., hazardous waste, environmental pollutants, chemical and biological weaponry, agricultural diseases, pests and pesticides, food, chemical and biological contamination, analytes for monitoring industrial, chemical and food production and processing, and the like. In another preferred mode of operation, selected nucleotide ligands and nucleotide receptors comprising defined sequence segments are used to specifically recognize and assemble selected molecules and conjugated defined sequence segments into useful multimolecular devices, particularly multimolecular transducers, multimolecular switches and multimolecular sensors for industrial production, processing and testing, particularly for microelectronic and microfabricated devices, microelectromechanical systems and submicron-scale products and systems requiring nanofabrication and, preferably, molecular-scale manufacturing.

Sequences of nucleotides described herein, i.e., defined sequence segments comprising nucleotides, can also be selected for the ability to specifically bind selected nonoligonucleotide molecules not heretofore known to specifically bind the selected defined sequence segments. Defined sequence segments capable of specifically binding selected molecules, preferably ligands, receptors, structural molecules and effector molecules, are particularly useful and necessary constituents of aptameric and heteropolymeric multimolecular devices of the instant invention. Particularly preferred constituents of such devices are defined sequence segments capable of specifically binding effector molecules, particularly drugs and signal-generating species and more particularly drugs and signal-generating species not heretofore known to specifically bind nucleotides, thereby enabling nucleotide-based recognition and molecular positioning, preferably within functional coupling distance, of useful effector molecules, preferably pairs or groups of effector molecules that function cooperatively or collectively when brought into close spatial proximity, and optionally effector molecules in combination with other types of selected molecules (e.g., ligands, receptors or structural molecules). Of particular importance is the ability to select defined sequence segments comprising aptameric and heteropolymeric devices for the ability to specifically bind identified molecules, preferably effector molecules and more preferably signal-generating species, that have no heretofore known specific binding partners, thereby transposing said identified molecules into ligands or receptors. A particularly preferred method for selecting defined sequence segments for the ability to specifically bind identified molecules relies upon the selection criterion that a nucleic acid molecule from a diverse mixture comprising nucleic acids be capable of attaching two identified molecules comprising or attaching signal-generating species so as to render the two attached identified molecules detectable, preferably as a result of position-dependent functional coupling between two signal-generating species. Alternatively important is the selection of nucleotide ligands and nucleotide receptors, i.e., chemically derivatized nucleotides and nucleotide analogs capable of specifically binding identified molecules, particularly effector molecules and more particularly drugs and signal-generating species, thereby transposing the identified molecules into ligands and receptors. Selection of such heretofore unknown nucleotide ligands and nucleotide receptors enables nucleotide-directed positioning of limitless combinations of ligands, receptors and specifically bindable effector functions within useful MOLECULAR MACHINES.

Defined sequence segment, when used to describe synthetic heteropolymers of the invention, refers to either 1) a nucleotide sequence having a defined number of nucleotides, or 2) a nucleotide sequence comprising a nucleotide analog, modified nucleotide or conjugated nucleotide at a defined position, or 3) a synthetic oligonucleotide, or 4) a selected, modified or designed sequence of monomers, preferably a single-stranded or double-stranded sequence of nucleotides, which is capable of specifically binding to an identified molecule or group of molecules or a selected nucleic acid sequence or of hybridizing to a selected nucleic acid sequence or of positioning a conjugated selected molecule or specific binding or shape recognition pair for single-molecule detection and/or functional coupling to a different molecule or specific binding or shape recognition pair.

Defined sequence segments of the invention are imprintable, e.g., using a paired nucleotide-nonnucleotide library, i.e., an imprint library. Imprinting enables the transposition of a nucleotide-based defined sequence segment into an imprinted segment whose composition is dictated by the molecular medium of the imprint library. The compositional diversity of an imprinted segment approaches the knowable limits of molecular sequence and shape space, limited only by the diversity of the set of all molecular libraries that can be functionally coupled to a nucleic acid library, a modified nucleotide library or, more generally, a nucleotide library.

Nucleotide library means a library, paired library or group of libraries comprising nucleotides, including, without limitation, nucleic acid libraries, nucleotide libraries, modified nucleotide libraries, paired nucleotide libraries, nucleotide-nonnucleotide libraries, libraries of nucleotide libraries and libraries of libraries comprising nucleotides or nucleotide libraries.

Nonnucleotide library means a mixture of molecules which does not comprise nucleotides or a library that is not a nucleotide library, or a pair, group or library of libraries that are not nucleotide libraries. Typically, nonnucleotide libraries of the invention are diverse mixtures of molecules of a particular nonnucleotide type or class, e.g., peptides, proteins, small molecules, lipids, carbohydrates, acrylates, polyalcohols, polyesters, polystyrenes, polyolefins, glycols, dendrons, antibodies, amino acids, engineered antibodies, oligosaccharides, and organic polymers such as polyhydroxyalkanoates, polyphenols, poylphosphates and polysulfates.

The basic assembly units for MOLECULAR MACHINES are imprintable precursor or parent molecules or segments (i.e., plastic segments), optionally multivalent segments and/or multisegment segments comprising multivalent plastic templates, originating from a replicatable parent nucleotide sequence, wherein the lineage from parent to progeny is nonbiological, i.e., does not comprise a natural hereditary mechanism involving genetic replication, transcription and expression of heretofore known nucleic acid sequences.

Progeny means originating ultimately from a parent or replicatable synthetic nucleotide. The parent or replicatable synthetic nucleotide and the progeny nucleotide or nonnucleotide (i.e., nucleotide-nonnucleotide) molecules, segments or templates may be modified, derivatized, imprinted, replicated, cloned, chemically, enzymatically or physically simulated or modified, copied or approximated, conjugated, complexed, assembled, amplified, mutated, and the like, all with variable and advantageously willful control over the fidelity of the replication, reproduction, simulation and/or modification process.

Parent and progeny plastic segments and templates may comprise any combination of nucleotides and/or nonnucleotides attached by any known or knowable method, covalent or noncovalent, specific or nonspecific, ionic or nonionic, reversible or pseudoirreversible or irreversible, including binding, bonding, association, ionization, intercalation, coordination, hydrophobic interactions, chelation, incorporation by genetic, recombinant, transgenic, chemical, enzymatic and physical methods, e.g., nanomechanical synthesis and manipulation, without limitation.

Plastic segments comprising MOLECULAR MACHINES of the invention, preferably plastic segments identified by screening and selection of polydiverse libraries comprising nucleic acids, nucleotide and nucleotide-encoded nonnucleotide molecules, are capable of all forms of molecular and catalytic recognition between nucleotide and nonnucleotide molecules, including specific binding, hybridization, structural shape recognition and catalytic recognition. Also, as will become apparent on reading this disclosure, the recognition properties of structural shapes and surface features comprising substrates, structures and materials can be transposed into plastic segments and templates of the instant invention, erasing the definitional boundary between specific surface attractivity and molecular shape-based recognition. Plastic segments and templates thus comprise a universally plastic molecular structure-activity-surface medium capable of all types of surface attractivity and recognition. The ability to design, select, shape, engineer and advantageously evolve nucleoplastic segments and templates to encompass any an all selected recognition functions provides the basis for powerful and universal molecular attractors capable of assembling limitless forms and functions for development MOLECULAR MACHINES disclosed herein. The complementary Enabler is the Universe of useful molecules from which to identify and assemble cooperative consortia of functionally coupled selected molecules, i.e., ligands, receptors, structural molecules and effector molecules. Not only does the Universe of willfully known selectable molecules (i.e., selected molecules prior to selection) provide a diverse, multimedia palette for expression of bimolecular and multimolecular synergies by molecular attractors (i.e., plastic templates), this same abundant toolkit of selectable molecules provides a feedstock stream of molecular structures and activities capable of being cast and recast through a nucleotide library amplifier. The molecular structure-activity space of the feedstock stream can be expanded, projected, reflected, distorted, permuted and projected into heretofore unknown regions of diversity space.

Molecular attractor means a plastic segment or plastic template used to generate and test hypotheses regarding templating and templated participants in prospective cooperative molecular interactions. Advantageously, the molecular attractor and a functionally coupled informational system are used in a consorting station to explore and map proximity space and functional coupling space for different combinations of selected molecules and positioning templates.

At least two compositional dimensions of plastic segments and templates comprising MOLECULAR MACHINES distinguishes them from all art-known substances, and the practical, commercial ramifications are heretofore unimaginable. First is the heretofore unexplored positional diversity addressable by simultaneous or sequential covalent, noncovalent, specific, nonspecific, pseudoirreversible, reversible, small and large molecule modification and conjugation of molecules, sequences, polymers and templates at a plurality of sites or positions, (i.e., the realm of proximity space). Second is the plasticity of the instant plastic segments, i.e., plastic nucleoprobes or nucleoplastic probes.

Nucleoplastic and plasticity, when used to describe synthetic nucleotides, nucleotide libraries, segments, templates, progeny, mimics, imprints, clones, conjugates, copies, simulations, modifications and products and progeny therefrom, refer to the diversity of members of the set of all nucleoplastic libraries comprising paired libraries of nucleotide and nonnucleotide libraries, also referred to herein as (libraries)$^N$, wherein the composition and/or sequence, if applicable, of a heretofore unknown plastic nucleoprobe becomes known following library selection.

Plastic, when used in reference to segments, templates, libraries, MOLECULAR MACHINES, imprinting and transposition and transformation of molecules, templates, surfaces, MOLECULAR MACHINES, molecular media, structural shapes and surface features, refers to plasticity and means comprising, relating to or originating from a diverse mixture, medium, library, population, source, substance, process or set of alternatives, particularly a diverse library, preferably a paired library or library of libraries. Alternatively, when used to describe heretofore known industrial materials (i.e., plastics), plastic refers to the family of cast and mold substances heretofore used in manufacturing, typically polymers capable of being shaped, formed, molded, extruded, cast into shapes or films, or drawn into filaments.

Nucleoplastic libraries and paired nucleotide libraries refer to the set of all possible pairs of parent and progeny molecular libraries comprising a first member which is a nucleotide library and a second member which is a non-nucleotide library, wherein the first and second libraries are capable of being functionally coupled, including the set of all molecular libraries and members of molecular libraries that evolve from said parent or progeny molecular libraries. The terms also refer, as the case may be, to any set or subset of plastic segments or templates and any set or subset of libraries comprising a nucleoplastic library. Library means at least two different molecules. Functionally coupled, when used in reference to a library pair, means that at least one molecule (i.e., product) selected from a first (i.e., donor) library (hereinafter a product of a donor library) is used as a selected target (i.e., precursor or substrate) for screening and/or selection by a second (i.e., acceptor) library. Library pair and paired libraries refer to at least two libraries capable of being functionally coupled by a an intermediate member or library comprising a target or probe, precursor or product, donor or acceptor which connects the libraries in diversity space.

Precursor, substrate and product, when used in reference to functionally coupled libraries, are used metaphorically in respect of corresponding terms describing functionally coupled paired effectors comprising enzymatic, photonic and electronic donor and acceptor species (cf. Example 5 and Example 6, vide infra). Similarly, donor and acceptor are used metaphorically to describe the relationship between donor and acceptor libraries and corresponding donor and acceptor members of libraries comprising nucleoplastic library pairs.

Nucleotide library means comprising nucleotides or nucleotide mimetics and includes nucleic acid libraries, nucleotide libraries, modified nucleotide libraries, nucleotide-encoded chemical libraries and any of these libraries comprising a selected molecule comprising, attached to or capable of attaching to a member of the library. Nucleotide mimetic means a molecular capable of functioning as a useful nucleotide comprising a nucleotide library. Nonnucleotide library means a mixture of molecules which is not a nucleotide library.

Positional space refers to the two-dimensional positional relationship between pairs and groups of molecules comprising or attaching to nucleotide-defined or imprint-reflected positions comprising plastic nucleoprobes. Positional space is approximated as the dimensionless product of (diversity in sequence length) times (distance between at least two recognition elements comprising a sequence, at least one being positionally randomized) times (distance between a third recognition element comprising a sequence and two optionally preselected and positionally fixed recognition elements) to the appropriate Zth power, combinatorially permuted to represent all possible positional relationships of Z possible recognition elements comprising X sequences of Y length. Positional space as used herein does not refer to the axial, polar or N-dimensional position of nonnucleotide groups tethered to nucleotides comprising nucleotide ligands, nucleotide receptors, modified nucleotides, selected molecules conjugated to nucleotides, nucleotide-encoded chemical groups, and the like. The diversity planes represented by these parameters are encompassed within molecular shape space. Instead, positional space is a representation of the diversity space reflecting potential interactions between at least two recognition elements comprising a sequence of nucleotides or, alternatively, a nonnucleotide imprint of a sequence of nucleotides. Sequence length is included as a dimension in positional space substantially to emphasize the bookend utility of 3' and 5' nucleotide modifications (of single-stranded plastic nucleoprobes) in mapping the positional preference landscape of first and second selected molecules (e.g., ligands, receptors and effector molecules) tethered to members of plastic nucleoprobe libraries. The user-definable distance between 3' and 5' ends of a single-stranded nucleotide (i.e., plastic nucleoprobe) provides a convenient tool for mapping the proximity space (also functional coupling space) of a selected pair of selected molecules (e.g., donor and acceptor fluorophores) from a first plastic medium (i.e., nucleic acids) into a second plastic medium (i.e., peptides, phospholipids, polyacrylate).

Proximity space and functional coupling space, when used in reference to plastic nucleoprobes, refer to the structural and functional correlates of positional space with respect to the ability of at least a first selected molecule and a second selected molecule to interact in a functionally coupled manner, e.g., as donor and acceptor species comprising a donor-acceptor pair. Positional space in practice, as embodied herein, means the intersection between the proximity space of a nucleoplastic library of plastic nucleoprobes with the informational space comprehended by a massively parallel informational search engine. In other words, functional coupling of the nucleoplastic molecular diversity generator with a suitably (parallel)$^N$, fast and computationally intelligent search engine defines the field of positional space practically accessible to the willful artisan, preferably aided by automation, variation and selection of processing modalities and library-search engine feedback systems and evolution. Computational intelligence depends in large part on the sensitivity and specificity of the interrogation process, e.g., the human-machine interface. Advantageously, machine, generator and machine-generator evolution are possible and likely. Automation-enhanced variation and selection of search parameters, hypotheses, and library expression by the molecular diversity generator and search engine oscillating in paired and functionally coupled closed-loop feedback cycles provide the potential for divergent and self-sustained exploration of diversity planes included but not limited to positional space. Positional space as defined by the actualizable intersection between library-generated molecular space and machine-palpable informational space will depend in large part on the ultimate director. At issue is whether the functionally coupled (molecular/machine) diversity search will be nucleoplastic library-directed, search engine-directed, willfully directed, or some combination thereof. Or none of the above. Exploration is optionally guided by artificial intelligence and/or willful direction.

Structure-activity space (SAS), also referred to herein as molecular diversity, means the diversity space of the set of all molecules net of the diversity space of structural shapes as defined herein. The multidimensional diversity in structure-activity-shape space of the instant polydiverse nucleotide libraries distinguishes them from prior art nucleic acid libraries diversified only in sequence and/or nucleotide chemistry, e.g., for selection of aptamers, ribozymes or chemically modified nucleotides. Enhanced ribozyme activity has been demonstrated using a contiguous allosteric deoxynucleotide sequence and by 2'-O-methylation (Goodchild (1992) *Nucleic Acids Research* 10:4607–4612). A ribozyme-based diagnostic method capable of detecting nonoligonucleotide analytes has also been described (Bockman et al. (1993) International Conference on Nucleic Acid Medical Applications, Cancun, Mexico, January 26–30), implying use of a ribozyme with both catalytic and specific binding properties. An allosteric molecular switch comprising internally hybridizable switch sequences and a DNA-binding biological recognition site has also been described (i.e., Lizardi et al., U.S. Pat. No. 5,118,801). However, the prior art does not provide access to the diversity space encompassed by MOLECULAR MACHINES comprising defined sequence segments, plastic segments, synthetic templates and/or molecular scaffolds of the instant invention.

A surprisingly enabling inventive step of the instant disclosure which is lacking in the prior art is the diversity space encompassed by defined sequence segments comprising MOLECULAR MACHINES. Particularly and advantageously, defined sequence segments and combinations of defined sequence segments comprising different embodiments of MOLECULAR MACHINES and paired MOLECULAR MACHINES include nucleotide ligands, nucleotide receptors, nucleotide catalysts, aptamers, and conjugated nucleotides comprising ligands, receptors, effector molecules and structural molecules. Defined sequence segments comprising these multidimensional functionalities as well as ribozymes, catalytic nucleic acids and synthetic oligonucleotides known in the art, can be selected with single-molecule resolution by methods described herein. The instant single-molecule detection, amplification and sequencing methods are enabling for isolation and functional characterization of individual short, single-stranded or double-stranded, ribonucleotide, deoxyribonucleotide or chimeric, modified or unmodified, randomized or encoding (i.e., informational), conjugated or hybridized nucleotides or any combination thereof, e.g., a ribozyme functionally coupled to an aptamer-bound enzyme.

Importantly, the functional coupling between at least two defined sequence segments, selected nucleic acid sequences and/or selected molecules of the invention is best achieved by imaging and quantifying functional activity at the single-molecule level, i.e., by measuring catalysis, fluorescence, luminescence or electron transfer within or between single molecules or multimolecular structures. More particularly, and heretofore unknown in the art, are structural shape recognition probes comprising defined sequence segments selected for the ability to recognize surface features comprising chemically homogeneous and doped structural surfaces, e.g., carbon, silicon, gallium arsenide, plastics, glasses, polymers, semiconductors and synthetic semiconductors, metals and synthetic (i.e., organic) metals, insulators, Mott insulators, buckyballs, carbon nanotubes, carbon nanorods and emerging nonbiomimetic mimics of organic and inorganic surfaces. This ability of the defined sequence segments of the present invention enables grafting, templating and imprinting of heretofore chemically bland surfaces. Furthermore, plastic imprints (e.g., nonnucleotide molecules, monomers and polymers, including nucleotide-encoded nonnucleotides) and the progeny of paired nucleotide-nonnucleotide library evolution (i.e., (libraries)$^N$), enable the transposition of 1) nucleotide recognition properties into nonnucleotide recognition elements and 2) structural shapes (i.e., surface features) into molecular shapes. In turn, surface features (e.g., nanofabricated and micromachines features) can be identified by screening and selection of materials and patterning methods yielding structures polydiversif ied in surface attractivity. The implications of this heretofore unrecognized potential to exploit the interplay between molecular diversity and structural shape diversity, i.e., the mutually synergistic plasticities of chemically bland, structurally diverse surfaces (e.g., designed, selected or engineered surface features) and chemically diverse, structurally autonomous molecules are wondrously enabling for a daunting array of practical, commercially valuable applications. For example, the long-anticipated and heretofore unreconcilable marriage between biological/biomimetic effectors (renowned for diversity in structure-activity-shape space), and inorganic substrates, (renowned for surface uniformity, semiconductivity, structural integrity and atomistically precise sculptability, i.e., chemical blandness) can finally be envisioned as a harmonious coselection of specific surface attractivity against molecular specificity. The virtually limitless plasticity of chemical, sequence and shape space represented by defined sequence segments comprising defined sequence segments, plastic segments, templates and molecular scaffolds enables systematic, nucleotide-programmable and nucleolibrary-directed, willfully automated and supervised selection of novel biomimetic imprints of industrial surfaces, e.g., silicon chips, CDs and DVDs. Conversely and heretofore unknown in the art, industrial surfaces can be plasticized (e.g., diversified in structural shape space) to accommodate the specific attractivity preferences of a selected plastic, biomimetic matrix, e.g., a synthetic polymer, preferably a durable, scalable, process-friendly and inexpensive polymer, more preferably a polymer capable of self-assembling on the industrial surface, advantageously a smart polymer doped, supplemented or blended with a self-replicating, self-assembling MOLECULAR MACHINE.

Mimetic multimolecular structures and multimolecular devices of the instant invention may be designed and prepared using nucleolibrary-directed products and processes to create mimetic, imprinted, transposed, transcribed, replicated and complementary segments, templates, multimolecular structures and multimolecular devices, i.e., nucleotide-based and nonnucleotide replicates, clones, mimetics, imprints, conjugates and progeny of defined sequence segments comprising parent multimolecular structures. Replicates, imprints and mimetics may be prepared with varying degrees of fidelity ranging from identical or approximately identical clones to arbitrary, randomized, combinatorial and/or willfully evolved or directed variants and/or mutants.

Defined sequence segments comprising synthetic heteropolymers, multimolecular devices, discrete structures and nucleotide-based molecular scaffolds of the invention include replicatable nucleotides, meaning that all or part of one or more defined sequence segments can be synthesized or detected using amplification systems well known in the art. PCR, LCR, Q-beta replicase, 3SR, TAS, RCR, CPR, ribonuclease H or reAMP methods, for example, may be used to detect or amplify a defined sequence segment, a group of defined sequence segments or any portion thereof comprising suitable promoter and/or primer annealing sequences. A randomized nucleotide sequence is not a defined sequence segment unless and until it is identified as a recognition partner of a selected target, whereupon characterization and/or sequencing is imminent. Defined sequence segments capable of specifically binding identified or selected molecules are aptamers.

When used in reference to a defined sequence segment, defined position, defined nucleotide position and positionally defined mean an identified nucleotide, nucleotide analog, modified nucleotide, monomer, functional group, recognition or attachment site or plurality thereof at the $N^{th}$ monomer in a nucleotide sequence or comprising a defined number of monomers beginning at the $N^{th}$ monomer in a nucleotide sequence, where "N" is an integer representing the number of monomers from one end of the sequence to the identified site or monomer, inclusive. Defined sequence segments and selected nucleic acid sequence of the instant invention may be labeled or modified at defined positions by methods well known in the art as site-specific, site-directed and regiospecific attachment, conjugation and modification, including synthesis of oligonucleotides with modified nucleotides, conjugated nucleotides, nucleotide analogs and spacer modifiers at user-specified positions. Uniformly or arbitrarily labeled or modified nucleotides are not considered herein to be labeled or modified at defined positions.

Conjugated selected molecule, when used in reference to defined sequence segment, also referred to herein as a conjugated defined sequence segment, means a selected molecule covalently or pseudoirreversibly attached to a defined sequence segment or a defined sequence segment comprising a derivatized nucleotide or nucleoside triphosphate, a modified nucleotide or nucleotide analog comprising a selected molecule, or a nucleotide ligand or nucleotide receptor. Where a multivalent heteropolymeric hybrid structure comprises a first synthetic heteropolymer hybridized to a selected nucleic acid sequence which is a conjugated defined sequence segment, the conjugated molecule is not a ligand or receptor covalently attached to a nonoligonucleotide molecule specifically bound to the first defined sequence segment of the first synthetic heteropolymer. In other words, two defined sequence segments of a bifunctional multivalent heteropolymeric hybrid structure are not directly attached (i.e., intimately attached, without intervening nucleotides or molecules) to the same nonoligonucleotide molecule, one specifically and the other covalently. Conjugated defined sequence segments may be produced by conventional nucleic acid synthesis using modified or derivatized nucleotides (e.g., using biotin, fluorescein, psoralen or acridine phosphoramidites) or by enzymatic labeling (e.g., using the modified nucleoside triphosphates biotin-11-dUTP, biotin-14-dATP or 8-aminohexyl-dATP) or chemical modification (e.g., using a diamine, bis-hydrazide, or heterobifunctional crosslinker) of a defined sequence segment. Conjugated defined sequence segment does not mean a defined sequence segment hybridized to a selected nucleic acid sequence, unless the unhybridized selected nucleic acid sequence or defined sequence segment is conjugated to a selected molecule. To position a conjugated selected molecule for functional coupling to a selected molecule specifically bound to a different defined sequence segment, 3' and/or 5' end-labeling of a defined-length sequence is preferred, particularly 5'-end labeling. The efficiency of functional coupling can then be optimized by varying the length, and optionally the composition, of the conjugated defined sequence segment. Defined sequence segments internally labeled or modified at defined nucleotide positions can also be used to effectively position conjugated selected molecules, as functional coupling can be optimized by varying the conjugation position. Conjugated defined sequence segments described herein are considered to be synthetic defined sequence segments, regardless of their nucleotide sequence.

Synthetic defined sequence segment means a nonnaturally occurring defined sequence segment, meaning either a defined sequence segment which is not a biological recognition site and whose nucleotide sequence is not heretofore known to occur in nature (i.e., absent genetic engineering) or a conjugated defined sequence segment which is not a biological recognition site for the conjugated molecule or a sequence of nucleotides comprising a nucleotide ligand or a nucleotide receptor. Hybridizing refers to specific binding between two selected nucleic acid sequences through complementary base pairing. Such bonding is also referred to as Watson-Crick base pairing. For hybridization, a sufficient degree of complementarity is required such that stable and/or reproducible binding occurs between two selected nucleic acid sequences. However, perfect complementarity is not required and may not be preferred for embodiments relying on dissociation of a hybridized nucleic acid sequence, e.g., applications requiring dissociation of a hybridized defined sequence segment followed by hybridization to a more complementary selected nucleic acid sequence or specific binding to a selected molecule or a selected nucleic acid sequence. More complementary means having a greater number of complementary nucleotides, a longer complementary sequence segment, a greater percent base pairing or a higher G-C content within a particular sequence segment. The binding between hybridized nucleic acid sequences may be readily reversible, quasireversible or virtually irreversible depending, e.g., on the length and G-C content of the hybridized sequence segment, the number of complementary base pairs and the percent base pairing. A selected nucleic acid sequence may be used to pseudoirreversibly attach a selected molecule to a defined sequence segment or a multimolecular device by first conjugating the selected molecule to the selected nucleic acid sequence (i.e., an oligonucleotide) and then hybridizing the selected molecule-oligonucleotide conjugate to the defined sequence segment.

Quasireversibility refers to specific recognition that can be dissociated, displaced or reversed under certain conditions of use, whereas pseudoirreversibility refers to a binding event or bond, association, complex or specific recognition pair comprising a molecule that cannot be dissociated, displaced, separated, reversed or detached under normal conditions of use and which specific recognition pair complex is not formed during operation, as distinct from manufacture, of a multimolecular device. For purposes of the present invention, noncovalent, pseudoirreversible attachment of a selected molecule to a multimolecular device is functionally equivalent to covalent attachment in terms of the stability and permanence of attachment, so long as the pseudoirreversibly attached molecule is attached during multimolecular device manufacture and remains inseparable during device operation. An unconjugated oligonucleotide hybridized to a defined sequence segment of a multimolecular device is said to be hybridized, not pseudoirreversibly attached, regardless of the melting temperature of the hybridized duplex. Pseudoirreversible attachment of selected molecules may be achieved by a number of methods well known in the art, preferably by avidin/biotin or streptavidin/biotin conjugation or by hybridization of selected nucleic acid sequences and/or defined sequence segments having a high degree of complementarity, but also by methods including, without limitation, ionic bonding, surface adsorption, intercalation, triplex formation, chelation, coordination, hydrophobic binding and high-affinity specific binding, optionally followed by UV irradiation or treatment with a noncovalent stabilizer, covalent crosslinker and/or photoactivatable reagent. Noncovalent site-specific conjugation of a selected molecule to a multimolecular structure may be achieved by pseudoirreversible attachment, preferably by hybridization of an oligonucleotide conjugate to a defined sequence segment or by specific binding of an avidin or streptavidin conjugate to a biotinylated molecule or defined sequence segment. A member of a specific recognition pair that specifically binds or hybridizes during multimolecular device operation is not considered pseudoirreversibly attached, even if (as may be the case with a conjugated specific binding pair) the member is required for device function. A selected nucleic acid target detected by a multimolecular sensor, for example, is considered hybridized and not pseudoirreversibly attached to the multimolecular sensor.

Selected molecules, identified molecules, selected nonoligonucleotide molecules and identified nonoligonucleotide molecules are nonoligonucleotide molecules and groups of molecules which include, but are not limited to, receptors, ligands, structural molecules and effector molecules which may exist as single molecules, conjugates or groups of molecules, including molecules or groups of molecules comprising MOLECULAR MACHINES, as well as mimetics, imprints and conjugates of any of these molecules, and mimetics, imprints and conjugates of any selected molecule, conjugate, imprint or mimetic. Selected molecules also include heretofore unknown molecules comprising nucleotide ligands, nucleotide receptors, modified nucleotides, nucleotide analogs, shape recognition molecules and molecules identified by screening and selection of nucleic acid libraries and nucleotide-encoded chemical libraries, depicted herein as library-selected molecules. Selected molecules also include selectable molecules, which are knowable but heretofore unknown molecules, i.e., molecules that remain to be identified. Selected molecules may be identified from natural or synthetic sources, particularly by screening and selection of a library comprising natural or synthetic molecules. A selected molecule comprising a first MOLECULAR MACHINE may specifically recognize a selected molecule or selected nucleic acid sequence comprising a second MOLECULAR MACHINE, thereby attaching the two MOLECULAR MACHINES. The attached MOLECULAR MACHINES, which may be referred to as a single MOLECULAR MACHINE or a pair of MOLECULAR MACHINES, may further attach to other MOLECULAR MACHINES, e.g., by specific binding, hybridization, site-directed covalent attachment, pseudoirreversible attachment, to form pairs or groups of MOLECULAR MACHINES and optionally pairs or groups therefrom.

Library-selected molecules of the invention are heretofore unknown molecules identified by screening and/or selection of nucleotide and nonnucleotide libraries, including nucleic acid libraries, nucleotide libraries and nucleotide-encoded chemical libraries. Heretofore known selected molecules, by contrast, are themselves used as targets for screening and selection of nucleotides comprising aptamers, nucleotide ligands, nucleotide receptors, nucleotide catalysts, catalytic nucleotides and structural shape recognition probes. Once a library-selected molecule is identified and therefore becomes known, it may, in turn, be used as a selected target molecule for screening and selection of a nucleic acid library or nucleotide-encoded chemical library to identify heretofore unknown aptamers, nucleotide ligands, nucleotide receptors, nucleotide catalysts, catalytic nucleotides and structural shape-recognition probes.

This iterative and advantageously automatable process, i.e., iteratively selecting first a heretofore unknown probe for an identified target and second, the probe being identified, a heretofore unknown recognition partner (i.e., an imprint) for the library-selected probe, is both divergent and self-sustaining. By iteratively selecting library-selected product (s) of a first evolutionary selection process as target(s) for a second evolutionary selection process, the ensuing self-sustained cycling enables systematic evolution of the evolutionary process into heretofore unavailable regions of shape space. The cycle is divergent in exploring both nucleotide and nonnucleotide shape space with positive feedback, transcending the chemical and sequence bias of any single imprint medium.

This cyclic process enables identification of limitless novel, useful and heretofore unknown molecules comprising nucleotides, nonnucleotides and hybrid and chimeric combinations thereof. Each generation of precursor molecule (i.e., known, selected target) and product molecule (i.e., library-selected probe) is either itself replicatable, advantageously self-replicatable, or it is imprintable into replicatable partner (i.e., imprint or probe). In each generation of the cycle, new levels of diversity can be introduced by arbitrary, rational, randomized and/or combinatorial chemical, enzymatic and/or genetic methods, including, e.g., unfaithful replication.

The surprising, almost haunting, result that emerges with the ability to transpose a selected nonnucleotide target (i.e., precursor) into a library-selected nucleotide imprint (i.e., product) is that a first library can be coupled to second library, much as a donor effector species can be functionally coupled to an acceptor species (e.g., cf. Example 5 and Example 6, vide infra). By selecting a population of selected molecules (e.g., immunoglobulins of selected type or antibodies of selected specificity), it becomes possible through iterative screening and selection of a population of imprintable nucleotide and nucleotide-encoded libraries to evolve a mapping library comprising a set of nucleotide ligands, nucleotide receptors and aptamers, including shape-specific recognition partners, that correspond in molecular shape space (i.e., specific recognition diversity space) to an imprinted library of a selected population of nonnucleotide molecules, i.e., a receptive audience. In other words, screening and selection of vastly diverse libraries of diverse nucleotide and nucleotide-encoded libraries, enables selection, collection, and continued evolution of a receptive audience comprising the set of molecular and structural shape probes that recognize members of the selected population.

Evolution of a useful mapping library requires a vastly higher order of diversity of the collective imprint libraries (i.e., (probing libraries)$^N$) over the selected population of selected molecules (i.e., (selected targets)xN or selected population). This balancing of (probing library)$^N$ diversity (i.e., probing plasticity) against (selected targets)xN diversity is achieved simply, in principle, by 1) maximizing probing plasticity (e.g., by chemical, sequence and positional diversity and by self-sustained amplification with varying fidelity), and 2) minimizing the molecular and population diversity of the selected population (e.g., by limiting the population, optionally by willful selection, fractionation and/or purification), and 3) evolving the receptive audience in time, advantageously by willful and automatable self-sustained and divergent amplification and selection.

This initially laborious but ultimately automatable process of reciprocal transposition between selected populations of nonnucleotide targets and polydiverse nucleotide libraries is important, useful and enabling in several respects.

First, polydiverse nucleotide (libraries)$^N$ provide a uniquely plastic and high-resolution molecular diversity generator that enables vast regions of diversity space to be explored with single-molecule resolution.

Second, the replicative and mutational propensities of nucleotides, particularly divergent and self-sustained amplification with varying fidelity, enables novel shapes to be expressed and reflected off or into nonnucleotide shape media (e.g., (libraries)$^N$). Iterative cycles of expression and reflection enable comprehensive probing of heretofore inaccessible regions of molecular and structural shape space, i.e., regions unavailable within directed evolutionary time.

Third, imprinting of nonnucleotide populations into nucleotide libraries, enables single-molecule detection and identification of useful molecular shapes from any medium comprising a diversity of molecular shapes (e.g., random, randomized, combinatorial, natural or synthetic peptides, proteins, small molecules, monomers, dimers and polymers, including biologically diverse and biologically diversified sets).

Fourth, the single-molecule detection capability provided by nucleotide amplification enables a thorough and efficient probing of structural space, e.g., identification of specifically attractive surfaces by methods heretofore unknown in the art (e.g., the identification of shape recognition probes for inorganic materials, surfaces and structures, including nanostructures and microstructures (e.g., nanofabricated circuits, MEMS and NEMS devices, buckyballs, carbon nanotubes, carbon nanorods, and the like).

Fifth, the suitability of nucleotides for construction of, e.g., bivalent and multivalent nucleotides of the instant invention enables selection and imprinting of positioning templates capable of assembling a diverse array of useful MOLECULAR MACHINES comprising functionally coupled selected target molecules.

Sixth, template-based MOLECULAR MACHINES can then be imprinted into nonnucleotide materials selected for suitability to the intended purpose of the product. For in vivo applications, templates comprising, e.g., nucleotide, peptide, protein and dendritic polymers modified for oral availability and resistance to enzymatic degradation are preferred. Materials selection criteria will vary, e.g., for cosmeceutical, diagnostic, analytical, microelectronic, automotive, military, food processing, chemical processing, environmental, agricultural, consumer electronic, industrial polymers, paints and coatings, industrial enzyme reactors and packaging materials.

Seventh, the shape plasticity of polydiverse nucleotide (libraries)$^N$ amplified by temporal evolution enables transposition of highly diverse selected populations of selected nonnucleotide molecules into imprinted mapping libraries useful in, e.g., clinical diagnostics, monitoring and prognostic modalities (vide infra).

Furthermore, the combination of nucleotide-dependent replication and template-directed self-assembly provides a general approach for development of synthetic self-replicating and self-assembling MOLECULAR MACHINES.

Single-molecule selection using polydiverse nucleotide libraries enables comprehensive and efficient exploration of diversity space with single-molecule resolution that cannot be achieved using nonamplifiable, noncoded chemical libraries sans single-molecule analytical techniques. This single-molecule resolution is important in the selection and assembly (i.e., collection or accumulation) of (target)xN-specific receptive audience members as the selected mapping library evolves in time, preferably in a willful direction. Willful directions include, for example, mapping the immunoglobulin repertoire of an organism, advantageously monitoring ontogenetic dynamics and the response of the selected population to clinical and environmental factors, e.g., therapeutic intervention; identifying and characterizing the antigenic determinants comprising the set of all autoimmune antibodies in Hashimoto's thyroiditis; mapping the set of lymphocyte cell surface antigens comprising the cellular immune system and monitoring responses to disease and therapy; and monitoring the molecular and structural shape repertoire of dynamic elements comprising the human immune system, including cellular and humoral compartments.

In a particularly preferred willful direction of the instant invention, highly plastic, replicatable, digitally encoded and dynamic (e.g., willfully evolving) nucleotide mapping libraries are selected first to maternal selected population(s) prior to conception and subsequently to an embryonic and/or perinatal selected populations), advantageously including at least a first map of a selected population comprising immune globulins, immunoglobulin antibodies and lymphocytes comprising a defined fraction of umbilical cord blood. Selected maternal (target)xN-derived and umbilical cord (target)xN-derived mapping libraries are amplified, sequenced and digitally archived as a baseline imprint of the immune repertoire, as transposed into nucleotide-encoded (molecular and structural) shape space. Ontogenetic development of immune competence is then imaged over time by evolving the receptive audience, amplifying, sequencing, digitally encoding the information and comparing the digitally encoded shape space against baseline and cumulative molecular and structural shape images as transposed into information space. Using paired nucleotide-nonnucleotide libraries functionally coupled to an informational system, a product of a first library selection step is used as a target for a second library selection step. There is no heretofore known limit to the molecular diversity that can be explored, expressed and archived in this type of self-sustainable, divergent evolutionary process. The enabling tool for high-resolution mapping is transposition or imprinting of a non-nucleotide library into an amplifiable molecular medium (e.g., a nucleotide library).

When used in reference to a conjugate comprising a first molecule that is an oligonucleotide attached to a second molecule that is not an oligonucleotide, selected molecule, identified molecule, selected nonoligonucleotide molecule and identified nonoligonucleotide molecule mean the portion of the conjugate originating from or consisting of the second molecule. Molecules include single atoms, groups of atoms, molecules, compounds, species, free radicals, ions, salts and the like which may exist as individual molecules, groups of molecules, molecular species, substances or conjugates comprising molecules.

Single-molecule detection, single-molecule isolation, single-molecule characterization, single-molecule identification, single-molecule amplification and single-molecule sequencing relate to resolution at the level of an individual molecule, an individual pair or group of molecules attached to one another, an individual molecular complex, an individual supramolecular or multimolecular assembly or a discrete structure. Single-molecule detection and single-molecule methods refer to methods capable of detecting an individual molecule, an individual pair or group of molecules attached to one another, an individual molecular complex, an individual supramolecular or multimolecular assembly or a discrete structure. Single-molecule detection methods and devices of the instant invention include, without limitation, optical force fields, optical tweezers, optical trapping, laser scanning, laser trapping, scanning probe microscopy, scanning tunneling microscopy, scanning force microscopy, atomic force microscopy, scanning electrochemical microscopy, hybrid scanning probe microscopy techniques, mass spectrometry, spectroscopy, kromoscopy, capillary electrophoresis, microelectrophoresis, on-chip electrophoresis, multiplexed and arrayed electrophoretic methods and detectors; microminiaturized and nanofabricated optical, spectroscopic, spectrometric, electrochemical, optoelectronic and electronic detectors; microsensors, nanosensors, integrated on-chip detectors, sensors, transducers and arrays; molecular detectors, sensors and transducers; and multimolecular sensors, multimolecular transducers and tethered specific recognition devices.

Conjugate means two or more molecules, at least one being a selected molecule, attached to one another in an irreversible or pseudoirreversible manner, typically by covalent means. A first selected molecule may be conjugated to a second molecule or to a nucleic acid sequence either indirectly, e.g., by inclusion of an intervening spacer arm, spacer molecule, bridge, carrier, or specific binding partner, or directly, e.g., by direct covalent attachment without intervening spacer(s). Alternatively, a selected molecule may be conjugated to a selected nucleic acid sequence via hybridization, if the selected molecule is first tagged with an oligonucleotide complementary to the selected nucleic acid sequence, or via other noncovalent means, e.g., ionic bonding, hydrophobic interactions, ligand-nucleotide binding, a chelating agent/metal ion pair, or a specific binding pair such as avidin/biotin, streptavidin/biotin, fluorescein/anti-fluorescein, 2,4-dinitrophenol (DNP)/anti-DNP, peroxidase/anti-peroxidase, digoxigenin/anti-digoxigenin or, more generally, ligand/receptor. For example, a reporter molecule such as alkaline phosphatase, horseradish peroxidase, β-galactosidase, urease, luciferase, rhodamine, fluorescein, phycoerythrin, luminol, isoluminol or an acridinium ester which is attached, e.g., for labeling purposes, to a selected molecule or selected nucleic acid sequence using avidin/biotin, streptavidin/biotin, DNP/anti-DNP, fluorescein/anti-fluorescein, peroxidase/anti-peroxidase, or digoxigenin/anti-digoxigenin rather than being directly and covalently attached is said to be conjugated to the selected molecule or selected nucleic acid sequence by means of a specific binding pair. When used in reference to the attachment between a first defined sequence segment or selected nucleic acid sequence and a second defined sequence segment or selected nucleic acid sequence, conjugation, conjugate and conjugated mean covalent attachment. Hybridized and/or specifically bound nucleic acid sequences described herein are not considered to be conjugated. When used in reference to a defined sequence segment or selected nucleic acid sequence, conjugated specific binding pair and specific binding pair conjugate mean at least one member of a specific binding pair is conjugated to the defined sequence segment or selected nucleic acid sequence. The other member of the specific binding pair is either specifically bound or capable of specific binding to its conjugated specific binding partner. similarly, when one member of a specific binding pair is conjugated to a defined sequence segment, the specific binding pair may be referred to as conjugated if and when both members of the specific binding pair are either specifically bound to one another or present and available for specific binding to one another.

When used in reference to a multimolecular device, conjugated specific binding or shape recognition pair and specific binding or shape recognition pair conjugate mean that operation of the multimolecular device requires the presence of both members of the specific binding or shape recognition pair or, in the case of certain analyte-dependent sensors or target-dependent molecular delivery systems, that the device does not respond to a stimulus or deliver its payload until both members of the specific binding or shape recognition pair are present. In either case, a multimolecular device is said to comprise a specific binding or shape recognition pair if and only if a useful function is performed by the device when both members of the specific binding or shape recognition pair are present and available for specific binding. Hybridized nucleic acid sequences are not considered to be conjugated to one another, nor is a nucleic acid target considered to be conjugated or pseudoirreversibly attached to a nucleic acid probe. However, a selected molecule may be conjugated or pseudoirreversibly attached to a defined sequence segment by conjugation of the selected molecule to an oligonucleotide and hybridization of the selected molecule-oligonucleotide conjugate to the defined sequence segment.

A sequence of nucleotides (e.g., a selected nucleic acid sequence) is referred to herein, e.g., as a nucleotide molecule, nucleic acid, nucleotide, nucleotide sequence or oligonucleotide and not as a conjugate or as a polymer of conjugated nucleotides. However, nucleotides may be referred to as conjugates, e.g., if a nonnucleotide molecule, group or moiety (e.g., biotin, digoxigenin, fluorescein, rhodamine) is introduced either before, during or after nucleic acid synthesis, e.g., as a nucleotide analog, modified nucleotide or modified nucleoside triphosphate. Ligands are molecules capable of specifically binding to receptors by affinity-based attraction that does not involve base pairing between complementary nucleic acid sequences. Conversely, receptors are molecules capable of specifically binding to ligands. Whereas a ligand and its corresponding receptor are referred to herein as members of a specific binding pair, complementary nucleic acid sequences are referred to as complementary, hybridizable or members of a specific recognition pair but not as members of a specific binding pair. Molecular recognition means and includes specific binding and hybridization, but not specific recognition of a surface feature of a specifically attractive surface.

Ligands include, but are not limited to, receptor agonists, partial agonists, mixed agonists, antagonists, stimulus-response-inducing or stimulus molecules, drugs, hormones, pheromones, transmitters, autacoids, growth factors, cytokines, prosthetic groups, coenzymes, cofactors, substrates, precursors, vitamins, toxins, regulatory factors, antigens, haptens, anions, cations, polyelectrolytes, carbohydrates, molecular mimics, imprint molecules, biotin, digoxigenin, and congeners, analogs, competitors or derivatives of these molecules as well as nonoligonucleotide molecules selected by combinatorial methods to specifically bind other selected molecules and conjugates formed by attaching any of these molecules to a second molecule.

Receptors include, but are not limited to, biological, synthetic or engineered membrane receptors, hormone receptors, drug receptors, transmitter receptors, autacoid receptors, pheromone receptors, stimulus-response coupling or receptive molecules, antibodies, antibody fragments, engineered antibodies, antibody mimics or mimetics, molecular mimics, molecular imprints, molecular recognition units, adhesion molecules, agglutinins, lectins, selecting, cellular receptors, avidin and streptavidin, and congeners, analogs, competitors or derivatives of these molecules as well as nonoligonucleotide molecules selected by combinatorial methods to specifically bind other selected molecules and conjugates formed by attaching any of these molecules to a second molecule. A molecular recognition unit (MRU) is a (preferably diminutive) portion or subset of an antibody, Fab fragment or peptide that retains binding or effector functions of the parent antibody, Fab fragment or peptide (and optionally referring to the minimally operative amino acid sequence of said antibody, Fab fragment or peptide).

Structural molecules include, but are not limited to, molecules comprising structural shapes and elements, atoms, molecules, ions, and compounds comprising surfaces, amphibious surfaces, inorganic and organic materials such as carbon, silicon, glass, organic and inorganic crystals, selected solvents, selected solutes, natural, biomimetic and synthetic nanostructures and microstructures, molecular scaffolds, carbon nanotubes, nanorods and buckyballs, semiconductors, metals, plastics, polymers, detergents, lubricants, waxes, oils, powders, fillers, fibers, tableting ingredients, packaging materials, papers, industrial plastics, cyclic and polycyclic molecules, dendrons, dendrimers, electrolytes, salts, hydrocarbons, ceramics and biological, biocompatible, biodegradable, biomimetic and imprintable monomers, multimers and polymers such as fatty acids, lipids, surfactants, amino acids, peptides, proteins, polyamines, polyacids, sugars, starches, cellulose, glycosylated molecules, glycopolymers and conjugates thereof.

Overlap can exist among the terms ligand, receptor, effector molecule and structural molecule. The distinction between a ligand and receptor, a structural molecule and a ligand, or a structural molecule and an effector molecule, for example, may in some cases be discretionary. In other cases, a ligand may also be a receptor, a structural molecule and/or an effector molecule, and reciprocal cases are also possible. In still other cases, a selected molecule may function as a ligand or structural molecule in one context and a receptor or effector molecule in another. Although the meaning of these terms will be apparent to the skilled artisan on reading this disclosure, it will also be apparent that some contextual flexibility is required.

Amphibious surface means a surface that is either able to operate on land, in air, in vacuum, or in fluids including, but not limited to, gaseous, liquid, aqueous and organic solutions and suspensions or, alternatively, in some combination of these environments, so long as the surface is not the reagent-binding or analyte-binding separation matrix of a specific binding assay or a nucleic acid hybridization assay. Operate, when used in reference to an amphibious surface, means to perform a useful function. Amphibious surfaces include, for example, surfaces of materials, parts, packaging, packing materials, people, products, vehicles, airports, stations, wholesale and retail establishments and media and communication systems used for research, development, manufacture, packaging, marketing, distribution, sale and servicing of commercial goods and services. Also included are surfaces comprising the homes, gardens, households, families and pets of consumers of commercial goods and services, excluding any home or office testing product surfaces to which molecular recognition reagents are immobilized for use in specific binding or hybridization assays. Diagnostic and analytical antibodies, antigens, DNA probes, drugs, hormones and hormone receptors immobilized on latex particles, ELISA plates, chromatography supports, electrophoretic gels, and immunochromatographic membranes (e.g., in home pregnancy tests), for example, do not comprise amphibious surfaces. By contrast, the reagent surface of a home glucose test is an amphibious surface, as heretofore known home glucose tests not comprise immobilized specific binding or hybridization reagents.

Effector molecules, also referred to as effector species, effectors and molecular effectors, are molecules, groups of molecules, complexes or conjugates capable of transforming energy into work or work into energy and include, but are not limited to, signal-generating species, stimulus-response-generating or response molecules, enzymes, synthetic enzymes, drugs, catalytic antibodies, catalysts, contractile proteins, transport proteins, regulatory proteins, redox proteins, redox enzymes, redox mediators, cytochromes, electroactive compounds, photoactive compounds, supermolecules and shape-memory structures. Selected nucleic acid sequences include, but are not limited to, defined sequence segments of synthetic heteropolymers, MOLECULAR MACHINES, oligonucleotides, and RNA, DNA or denatured DNA sequences, including wild-type, mutant and recombinant biological nucleic acid sequences; biological, engineered and synthetic nucleic acid ligands, nucleic acid receptors, nucleic acid antibodies and nucleic acid sequences capable of participating in specific binding, catalytic and enzymatic reactions, e.g., aptamers, catalytic DNA and ribozymes; genomic, plasmid, cellular and transcribed or complementary nucleic acids, including DNA, cDNA and RNA; natural and synthetic coding, noncoding, initiation, termination, promoter and regulatory sequences, including natural, synthetic, native or nonnative biological recognition sequences and therapeutic targets; natural and synthetic oligonucleotides with defined topology, secondary or tertiary structure or three-dimensional shape, including rolling and circular nucleic acids, nucleic acid loops, stems, bulges, knots, pseudoknots, polygons, spheres, pyramids, cubes, and higher order three-dimensional shapes; immobilized, conjugated, labeled and insolubilized nucleic acids, including nucleic acids hybridized or specifically bound to other soluble, insoluble, immobilized, conjugated or labeled nucleic acids; nucleic acid probes, targets and templates; sense, antisense and antigene nucleic acid strands; conjugated defined sequence segments and conjugated oligonucleotides, including oligonucleotides that are internally conjugated to provide closed-loop or single-ended or double-ended loop structures; branched, branched-chain, branched-comb, multi-chain and Christmas tree oligonucleotides; nucleic acid dendrons, dendrimers and nucleic acid conjugates formed by coulombic, affinity-based or covalent interactions with dendrons, dendrimers and other branched and hyperbranched structures; single-stranded, double-stranded, partially single-stranded, partially double-stranded, heteroduplex, triplex, quadruplex, chimeric and hybrid structures comprising natural or synthetic RNA, DNA or oligonucleotides comprising nucleotide analogs, derivatized nucleotides or nucleoside triphosphates or backbone modifications. A defined sequence segment comprising a first MOLECULAR MACHINE may hybridize or specifically bind to a selected nucleic acid sequence or selected molecule comprising a second MOLECULAR MACHINE, thereby attaching the two MOLECULAR MACHINES. The resulting product, which may be referred to as a single MOLECULAR MACHINE or a pair of MOLECULAR MACHINES, may attach to other MOLECULAR MACHINES by methods described herein, including specific binding, hybridization, site-directed covalent attachment, pseudoirreversible attachment and the like.

Library-selected nucleic acid sequence means a selected sequence, shape or activity comprising a nucleic acid, nucleotide and/or nucleotide-encoded nonnucleotide molecule selected from a mixture comprising synthetic and/or biologically derived nucleotides, conjugated and/or immobilized nucleotides. Library-selected nucleic acid sequences include, without limitation, any heretofore unknown nucleic acid sequence, shape, activity, nucleotide, modified nucleotide or nonnucleotide molecule, particularly including aptamers, ribozymes, catalytic nucleotides, nucleotide ligands, nucleotide receptors, nucleotide catalysts, structural shape probes and sequences or shapes comprising at least two recognition elements. Also included is any second nucleotide or nonnucleotide molecule capable of functionally coupling with a first nucleotide or nonnucleotide molecule comprising a member of the mixture. Importantly, screening and selection of any nucleotide library for any nucleotide, nucleotide replicate, imprint, clone, derivative, mimetic or conjugate may be achieved by single-molecule detection methods disclosed herein. Also, selected molecules identified by screening and selection of a nonnucleotide library by single-molecule detection may be advantageously transposed into nucleotide space, enabling sequencing, characterization, digital encoding and archiving nucleotide imprints of nonnucleotide libraries. The importance of this capability will be apparent to the skilled artisan on reading this disclosure.

A nucleotide recognition element is any molecule, sequence or group of nucleotide or nonnucleotide molecules or residues capable of recognition, including, without limitation, molecular recognition, structural shape recognition, and catalytic recognition. A nucleic acid molecule comprising an unconjugated randomized sequence (e.g., a prospective aptamer sequence) and a fixed unconjugated primer-annealing sequence is not a synthetic heteropolymer. In other words, where a bifunctional synthetic heteropolymer comprises a first aptameric sequence segment and a second defined sequence segment capable of hybridizing, the second defined sequence segment is not an unconjugated primer-annealing sequence for an unconjugated primer. Conversely, selected nucleic acid sequences that hybridize bifunctional synthetic heteropolymers of the instant invention do not include unconjugated primers used to amplify nucleic acid molecules selected from mixtures, pools, or random-sequence libraries. Mixtures of nucleic acids having both fixed primer-annealing sequences and regions of randomized sequence are known in the art, including candidate mixtures from which regions of randomized sequence may be selected for the ability to specifically bind a selected nonoligonucleotide molecule (e.g., Ellington and Szostak (1990) *Nature* 346:818–822; Ellington and Szostak (1992) *Nature* 355:850–852; Famulok and Szostak (1992) In: *Nucleic Acids and Molecular Biology*, pp. 271–284 Springer-Verlag, Berlin; Famulok and Szostak (1993) *J. Am. Chem. Soc.* 114:3990–3991; Gold et al., U.S. Pat. No. 5,270,163; Green et al. (1990) *Nature* 346: 818–822; Jellinek et al. (1993) *Proc. Natl. Acad. Sci. USA* 90:11227–11231; Tuerk and Gold (1990) *Science* 249:505–510; Tuerk and MacDougal-Waugh (1993) *Gene* 137:33–39). Heteropolymeric selected nucleic acid sequences of the instant invention also do not include a conjugated oligonucleotide hybridized to a second defined sequence segment of a synthetic heteropolymer, wherein the oligonucleotide-conjugated molecule is a ligand or receptor covalently attached to a nonoligonucleotide molecule capable of specifically binding to the first defined sequence segment of the synthetic heteropolymer. In other words, the instant disclosure is not directed to bivalent nucleotides capable simply of specifically binding the nonoligonucleotide moiety (at a first sequence segment) and hybridizing the oligonucleotide moiety (at a second sequence segment) of an oligonucleotide conjugate comprising a nonoligonucleotide molecule conjugated to an oligonucleotide. Bifunctional, bivalent, multivalent and multifunctional relate to the recognition and attachment properties of nucleotide and nonnucleotide molecules, scaffolds and templates. Multivalent in the context of a multivalent heteropolymeric hybrid structure means having at least two specific recognition sites in addition to the hybridizable defined sequence segments joining the synthetic heteropolymers comprising the multivalent heteropolymeric hybrid structure. At least two specific recognition sites comprising a multivalent heteropolymeric hybrid structure are capable of specifically recognizing selected molecules or selected nucleic acid sequences which are not the synthetic heteropolymers that make up the multivalent heteropolymeric hybrid structure itself.

Structural shapes, structural features and surface features refer to specifically attractive surfaces, i.e., specifically recognizable structural features of a surface. Surface features include natural, synthetic, designed or selected structures or surfaces, preferably subnanometer- to submicron-sized surface contours, having a two-dimensional or three-dimensional shape, contour, texture, characteristic, pattern, distribution, property, configuration, arrangement, organization, order, lack of organization or order, form, trait or peculiarity that can be specifically recognized by a shape-specific recognition element. Structural shapes or surface features are optionally designed or selected to be specifically recognizable by a shape recognition partner, preferably a shape recognition partner selected from a diverse mixture of molecules comprising a library, advantageously a library of libraries. In a preferred mode of operation, surfaces are micromachined and/or nanofabricated with a variety of structural features, preferably a diversity of structural features, and coselected against shape recognition libraries. The shape recognition libraries are preferably nested combinatorial libraries of libraries exploring, e.g., nucleotide sequence, nucleotide charge, backbone modifications, sequence length, chemical modifications and optionally positional space (i.e., the relationship between pairs and groups of nucleotide modifications). Surface features that are specifically attractive, i.e., specifically recognizable by at least one member of a shape recognition library, are selected as useful prospects for template-directed assembly of MOLECULAR MACHINES. Alternatively, selected attractive features are used for surface-to-surface registration and bonding. In a particularly preferred aspect, diverse modifications are introduced in a single surface, preferably by randomized or combinatorial surface treatments, advantageously with nanoscale or atomic precision. Tagged molecules comprising diverse shape recognition libraries, preferably nucleic acid libraries or nucleotide-encoded chemical libraries, are then coselected against diverse surface features to identify useful specific pairs of specifically attractive surface shapes and shape-specific probes. Fluorescently tagged nucleic acids or nucleotide-encoded chemical libraries are preferred. surfaces are advantageously imaged by a combination of optical and scanning probe microscopy (SPM), preferably fluorescence and atomic force microscopy (AFM), before and after exposure to shape recognition libraries. Bound, fluorescently tagged molecules, preferably nucleotides, are then isolated and characterized, preferably by AFM extraction followed by single-molecule nucleic acid amplification and/or sequencing.

A structural shape recognition partner may, for convenience, be considered a special case of a specific binding partner, because the art has no suitable term for shape recognition sans specificity for chemical identity. As described herein, a shape recognition partner is the antithesis of a specific binding partner. The several differences between molecular recognition and shape recognition will become apparent to the skilled artisan on reading this disclosure. For example, structural shape recognition is specific for a surface feature comprising a selected material, not the chemical identity of a constituent selected molecule. Therefore, selected molecules having the same composition as the recognized surface feature do not necessarily compete, inhibit or crossreact, as would be the case in specific binding reactions known in the art. Nor do chemically related congeners crossreact. Nor do solution phase molecules or even other surface molecules having the same chemical identity as the shape recognition partner crossreact, unless they comprise the recognized structural shape.

Structural shape recognition, shape recognition, shape recognition partner, shape recognition probe, shape-specific probe and surface feature recognition refer to specific recognition of a structural shape or surface feature. Specifically attractivity or specific attractiveness refers to a surface, structure, surface feature or structural shape which is specifically recognizable by a shape-specific recognition partner, i.e., a shape-specific probe. Similarly, selected or identified surface features, shapes, structures or structural shapes (i.e., specifically attractive surfaces or features) are surface features that can be specifically recognized by a shape-specific recognition partner. Specific shape recognition, shape-specific recognition and shape recognition refer to discrimination of one structural shape or surface feature from another. Discrimination means binding a first surface feature and not binding a second surface feature having the same chemical composition. Perfect specificity is ideal. However, as in the case of molecular recognition (i.e., specific binding or hybridization), a certain degree of nonspecific surface association may be expected. The practical limits on achievable discrimination with shape-specific recognition related to the precision of surface fabrication techniques (e.g., surface machining; molecular and atomic-scale assembly) and by the purity and molecule-to-molecule uniformity of shape-specific probes. Shape recognition libraries are diverse mixtures of molecules designed or selected for screening and/or selection of shape-specific recognition partners or templates, i.e. shape-specific probes or templates. Shape-specific templates and shape recognition templates are bivalent or multivalent templates comprising at least one shape-specific probe.

Unlike a specific binding partner in the art-accepted use of the term, a shape recognition partner is capable of specifically recognizing a shape, texture, consistency, attribute, discontinuity, charge distribution, energy, property or feature of a surface or structure rather than the chemical identity of molecules comprising the surface or structure. A shape recognition partner that specifically recognizes a structural shape or surface feature is capable of doing so without binding to other surfaces or parts of the structure, even other surfaces or parts having the same chemical identity as the recognized structural shape. In other words, shape recognition is specific for the shape and not the chemical identity of the recognized structure. For example, a diamondoid conical tip comprises a structural shape, if the tip (i.e., a surface feature) can be recognized by a shape recognition partner that does not bind a flat diamondoid face or a graphite rod. If substantial binding (i.e., crossreactivity) to a flat surface occurs, binding is not shape specific. In one exception, it may be desirable to design or select shape recognition probes that specifically recognize only flat surfaces and do not crossreact with nonflat surface features. Structural shapes may comprise, without limitation, shapes, textures, surfaces, patterns, properties or features comprising solid supports, diamondoid structures, micromachined, microminiaturized and nanofabricated structures, molecular devices and MOLECULAR MACHINES, molecules and groups of molecules capable of existing in at least two conformations or states, transducers, microstructures and nanostructures.

Selected targets, selected target molecules, targeted molecules and target molecules refer to molecules or groups of molecules comprising either an identified member of a specific recognition pair (e.g., a nucleic acid target or therapeutic receptor) or an identified object of an effector molecule (e.g., the substrate of an enzyme) and include selected molecules and selected nucleic acid sequences. Target sequences and targeted sequences refer to selected targets comprising selected nucleic acid sequences. Disease targets, therapeutic targets, pathological targets and pathophysiological targets are physiological, pathological and/or anatomical sites of drug and hormone action, including target molecules, receptors, groups of target molecules or receptors, and cells or groups of cells comprising target molecules and receptors. A target may be any identified substance, structure, process, device or object capable of being acted upon by a selected molecule or selected nucleic acid sequence including, without limitation, therapeutic receptors, pathological, physiological and anatomical sites, disease markers, diagnostic analytes, cells, cell surface antigens, cytoplasmic, subcellular, genetic and genomic markers, biological recognition sites, environmental markers, pollutants, pests and pathogens, agricultural products, strains, symbiotes, pests, pesticides, pathogens and contaminants, industrial feedstock, products, byproducts, wastes, process and quality control analytes, chemical and biological weaponry and selected sites, receptors and features comprising molecular arrays, biochips and microminiaturized devices.

Signal-generating molecules and signal-generating species are molecules or functional groups capable of generating a detectable signal or enhancing or modulating the detectability of a selected molecule or transducing the energy, activity, output or signal of a selected molecule into a qualitatively or quantitatively different activity, output, signal or form of energy. Enhancing or modulating detectability means, without limitation, influencing the size, shape, charge, structural properties, chemical composition, energy state, activity, functional properties, number of molecules or complexes or particles or copies, spatial location or relative position of a selected molecule. Signal-generating species include, but are not limited to, molecules, groups of molecules, conjugates and complexes comprising detectable (and optionally dyed, modified, conjugated or labeled) tags, tracers, radioisotopes, labels, reporters, polymers, light-harvesting structures, photonic assemblies, antenna complexes, natural and synthetic photosynthetic molecules, natural and synthetic reaction centers, natural and synthetic photosystems, macromolecules, microparticles, nanoparticles, colloids, metals, dyes, fluorophores, phosphors and other photon-absorbing, photon-emitting and photosensitive molecules, including molecules or groups that enhance, attenuate, modulate or quench the photon-absorbing or photon-emitting properties of another molecule or group, enzymes, coenzymes, cofactors, catalytic antibodies, synthetic enzymes and catalysts, molecular mimics and mimetics, luminescent compounds such as triboluminescent, sonoluminescent, chemiluminescent, bioluminescent and electroluminescent molecules, electron transfer donors and acceptors, oxidizing and reducing compounds, mediators and other electroactive molecules, metabolic, photoactive, signal transduction and processing molecules used to capture or transduce energy in biological and biomimetic processes, optionally including natural scaffold, organizational and coupling molecules, chaperones and accessory biological or biomimetic molecules or groups of molecules involved in the transduction of a first form of energy or information into a second form of energy or information.

Transduction means to convert, transform, transfer, modify, send, receive or interconnect from one substance, process, state, form, unit or level of matter, information, order or energy to another or between two substances, processes, states, forms, units or levels of matter, information, order or energy, typically by means of a change in the relative energy state, velocity or position of two molecules or of one molecule and its environment, and more typically in response to a thermal gradient, electrical, chemical or electromagnetic potential or a mechanical force, binding interaction or catalytic event.

Molecular mimics, mimetics and biomimetics are customized, derivatized or engineered natural or synthetic molecules or groups of molecules designed, manufactured, modified or selected to perform an equivalent or similar function to that of a naturally occurring or biological molecule or group of molecules.

Ligands and receptors may also be structural molecules or molecular effectors. A drug, for example, is both a ligand for its therapeutic receptor and an effector molecule capable of stimulating, catalyzing or mediating a therapeutic response. An enzyme which is a therapeutic target may be a receptor for a drug. As will be apparent to one of skill in the art, a molecular effector may also be transformed into a ligand or receptor, e.g., by conjugation to a ligand or receptor. A molecular effector conjugated to a ligand is referred to herein as either a ligand, a molecular effector or, preferably, a molecular effector-ligand conjugate. Similarly, a molecular effector conjugated to a receptor is referred to herein as either a receptor, a molecular effector or, preferably, a molecular effector-receptor conjugate. Alternatively, by screening and selection for heretofore unknown specific binding partners, e.g., by combinatorial chemistry, in vitro evolution, directed molecular evolution and/or high-throughput screening, the identification of new compounds that specifically bind effector molecules provides a practical means of equipping a molecular effector with ligand or receptor properties.

Specific binding refers to a measurable and reproducible degree of attraction between a ligand, receptor or defined sequence segment and a selected molecule or nucleic acid sequence. The degree of attraction need not be maximized to be optimal. Weak, moderate or strong attractions may be appropriate for different applications. The specific binding which occurs in these interactions is well known to those skilled in the art. Specific binding is saturable, noncovalent interaction between two species that can be competitively inhibited by chemically identical or similar substances, i.e., analogs of the binding partners. Specific binding between a ligand and receptor means affinity-based interaction related to the three-dimensional shapes of the participating molecules and does not include the hybridization of complementary nucleic acid sequences due to Watson-Crick base pairing. When used in reference to a defined sequence segment, specific binding to a selected nucleic acid sequence refers to a measurable and reproducible degree of attraction between the defined sequence segment and a selected nucleic acid sequence which may involve hybridization if participating sequences are complementary or alternative mechanisms if sequences are noncomplementary. Nonhybridization based specific binding between noncomplementary nucleic acid sequences depends not on base pairing, but on the secondary and tertiary structures and charge distributions of participating sequences. Nucleic acid binding reactions known to involve mechanisms other than hybridization include, e.g., antisense, triplex, quadruplex and aptamer interactions. Specific binding pairs include ligand-receptor pairs and aptamer-target pairs and do not include pairs of hybridized nucleotides, i.e., hybridized, hybridizable or complementary nucleic acids or nucleic acid sequences.

Molecular recognition and molecular recognition pair mean the specific molecular interactions and complexes involving either specific binding or hybridization reactions. Different molecular recognition pairs means two molecular recognition pairs whose four members comprise at least three different chemical identities. A partner is a member of a recognition pair. Molecular recognition includes 1) specific binding between a ligand and receptor, 2) specific binding between a defined sequence segment and a nonoligonucleotide molecule, 3) specific binding between defined sequence segments and/or selected nucleic acid sequences, and 4) hybridization between complementary nucleic acid sequences and/or defined sequence segments. Molecular recognition does not include specific surface attractivity or shape-specific recognition of a specifically attractive surface feature. Catalytic recognition refers to the selective interactions between enzymes, catalyst and their substrates, inhibitors and cofactors.

Recognition refers to all forms of recognition disclosed in the instant application, including molecular recognition, structural shape recognition, catalytic recognition and specific attractivity. Probes are specific recognition elements, i.e., recognition partners capable of specifically recognizing a selected target wherein the target comprises a nucleotide or nonnucleotide molecule or a structural shape.

Templates are MOLECULAR MACHINES comprising at least one probe. Probes comprising MOLECULAR MACHINES of the instant invention are capable of specific recognition, i.e., specific binding, hybridization or shape-specific recognition. MOLECULAR MACHINES are also capable of catalytic recognition, e.g., via nucleotide catalyst, hybridized or specifically bound catalytic nucleotides and specifically attached selected molecules. Recognition, when used in reference to a MOLECULAR MACHINE, refers to specific recognition or, as the case may be, catalytic recognition (i.e., specific binding, hybridization, structural shape recognition or catalytic recognition). MOLECULAR MACHINES, templates, recognition partners and probes of the instant invention may be targeted, delivered, attracted and bound by specific recognition of surface features (i.e., structural shapes) as well as art-accepted specific binding and hybridization modalities). Conversely, surfaces may be recognized, probed, targeted, modified, bound and bonded by the structural shape recognition properties of the instant MOLECULAR MACHINES.

MOLECULAR MACHINE and MOLECULAR MACHINES include methods and devices of the instant invention, e.g., nucleotide-based and plastic segments and templates, paired selected molecules, templates, libraries, processes, devices and systems, functionally coupled selected molecules, templates, libraries, processes, devices and systems, paired specific recognition devices, designer drugs, smaRTdrugs, shape recognition probes, shape recognition libraries, bivalent and multivalent templates, shape recognition templates, specifically attractive surfaces, surface feature libraries, multimolecular devices, tethered specific recognition devices, molecular adhesives, molecular adherents, molecular adsorbents, molecular lubricants, promolecular delivery devices, any of these devices, libraries or surfaces in combination, and particularly a MOLECULAR MACHINE operatively attached to a surface and/or informational device, particularly a transducer surface and/or informational system, particularly operative attachment comprising functional coupling.

Paired specific recognition pairs and paired specific recognition devices are molecules, molecular scaffolds or multimolecular structures comprising at least two specific recognition pairs, each pair comprising two specific recognition partners. Specific recognition partners, i.e., members of a specific recognition pair, include nucleotide and nonnucleotide molecules and groups of molecules, including nucleotides, modified nucleotides, nucleotide analogs, nucleotide ligands, nucleotide receptors, defined sequence segments, nucleotide spacers, linker oligonucleotides, selected nucleic acid sequences, nonnucleotide linkers, selected molecules and molecular scaffolds. Specific recognition partners may be capable of specifically binding, hybridizing or shape-specific recognition. Paired specific recognition devices include nucleotide-based and nonnucleotide multimolecular devices, tethered specific recognition devices, multimolecular adhesives, multimolecular adherents, targeted promolecular delivery devices, aptameric devices and mapping libraries capable of either 1) detecting, isolating, identifying or transposing matter, energy, data or information or 2) exchanging matter, energy, data or information between two molecules or groups of molecules, between two systems or subsystems, or between a system or subsystem and its environment, including, but not limited to, informational devices, switches, sensors, transducers, actuators, molecular delivery systems, drug delivery systems, adhesive devices, adherent devices, soluble molecular complexes and assemblies, aptameric devices, structural shape recognition probes and mapping libraries.

In a preferred embodiment of the instant invention, template-directed assembly may be used to produce a promolecular delivery device comprising a payload molecule(s) specifically bound in inactive, quasireversible, releasable and/or activatable form to a designer receptor (as distinct from a target receptor, targeted receptor or disease target). The promolecular delivery device is capable of binding, storing, preserving, stabilizing, transporting, delivering, releasing and/or attaching the payload molecule in such manner that device binding to a selected target via a second recognition site (i.e., a targeting site) results in delivery, concentration, localization, release and/or activation of payload molecule(s) at a desired site of action (e.g., a selected molecule or selected nucleic acid sequence comprising a pollutant, contaminant, plant pathogen, biological weapon, toxic chemical, oil spill, microbe, virus, disease marker, or therapeutic receptor). The payload molecule is bound to a first molecular recognition or shape recognition site (i.e., a designer receptor) of the promolecular delivery device template in inactive and/or unavailable form. The resulting promolecule complex (i.e., payload-designer receptor complex) is analogous to a prodrug complex comprising a drug bound in inactive form to a designer receptor selected to bind and occupy the active site of the drug. The difference is that a promolecule complex may comprise as payload molecule not only a drug, but any nucleotide or nonnucleotide molecule or structural shape (e.g., a surface feature comprising a buckyball, nanotube or nanorod) which is capable of performing a useful function when delivered to a selected target. The payload is preferably a selected molecule (e.g., a ligand, structural molecule or effector molecule) or a selected nucleic acid sequence (e.g., an aptamer, ribozyme, antisense or triplex-forming nucleotide). The second, optionally allosteric, specific recognition site comprising a promolecular delivery device is responsible for delivering and/or releasing the payload molecule(s) to selected molecules or selected nucleic acid sequences comprising, attaching or neighboring a selected target.

In a preferred mode of operation, the designer receptor is a relatively low affinity or low avidity target-mimetic receptor that competes with a higher affinity target for binding of the payload molecule. When brought within close spatial proximity of the selected target, e.g., by allosteric targeting, the payload molecule preferentially dissociates from the lower affinity designer receptor and binds to the higher affinity target recognition site. In a particularly preferred embodiment, binding of the allosteric recognition site influences the binding or activity of the payload molecule at the designer receptor site by a second (i.e., allosteric) mechanism. In the allosteric mode, binding of the target recognition site to the selected target facilitates, enables or accelerates the dissociation of the payload molecule from the designer receptor. This preferred aspect of promolecular delivery comprises three distinct and additive, preferably synergistic, mechanisms. First, the payload molecule is advantageously partitioned or titrated between a high capacity-low affinity designer receptor and a high affinity target recognition site, the target optionally being present at very low concentration. Second, payload delivery is site-directed, i.e., specifically directed to the target by means of a target-specific recognition site. Third, local delivery of the payload to the target recognition site is accelerated or facilitated by the allosteric triggered release mechanism.

In another preferred mode of operation, the payload molecule is also tethered to a molecular scaffold comprising the designer receptor, providing a tethered molecular delivery device, i.e., a tethered device. In this aspect, the payload molecule is not only specifically attached, but also pseudoirreversibly or covalently attached (i.e., tethered) to the designer receptor.

In another preferred mode of operation, the reversible activation (i.e., repeat-action) potential of tethered specific recognition devices (vide infra) is used in a "detect-and-actuate" or "search-and-destroy" mode, e.g., for defense, detoxification, environmental remediation, and agriceutical (e.g., fertilizers, vaccines and pesticides), cosmeceutical, nutraceutical and pharmaceutical molecular delivery applications. For example, a tethered specific recognition device comprising a prodrug that is reversibly and repeatedly activated and inactivated in response to sequential target binding is configured as follows. A payload molecule comprising a therapeutic enzyme is tethered (via a linear and flexible molecular scaffold preferably less than about 100 nm in length) and specifically bound in inactivated form to a first molecular recognition site comprising a selected inhibitory ligand. A second molecular recognition site (i.e., a targeting ligand selected for high-affinity specific binding to the substrate (i.e., target) of the therapeutic enzyme) is positioned within the loop region between the inhibitory ligand and the therapeutic enzyme to which the inhibitory ligand is bound. The targeting ligand is located toward the inhibitory ligand end of the molecular scaffold in close proximity to the tethered, specifically bound inhibitory ligand-therapeutic enzyme complex, preferably within about 10 nm of the bound inhibitory ligand and more preferably within about one nanometer of the bound inhibitory ligand. Binding of the high-affinity targeting ligand to its receptor (i.e., the therapeutic target) dissociates the inhibitory ligand-therapeutic enzyme complex, resulting in activation of the therapeutic enzyme. The activated therapeutic enzyme catalyzes the cleavage, modification, digestion and/or degradation of its substrate (i.e., the receptor of the targeting ligand). Modification of the targeting ligand's receptor (i.e., the therapeutic enzyme substrate) causes, facilitates or accelerates ligand-receptor dissociation, freeing the targeting ligand. with the targeting ligand in the free state, the tethered recognition device switches back to the inhibited state (i.e., the tethered inhibitory ligand rebinds and inhibits the therapeutic enzyme), resetting the device for another search-and-destroy cycle. The choice of molecular scaffold for this type of reversible, autocatalytic device depends on the environment in which it is to be used. For in vivo, topical and extracorporeal applications (e.g., prodrug delivery, detoxification, dynamic imaging), the choice of molecular scaffold composition is limited to biological or biocompatible molecules, polymers, microstructures and nanostructures comprising, e.g., nucleotides, peptides, carbohydrates, lipids, dendrimers, surfactants, organic hydrocarbons and polyamines; implantable, injectable and bioerodible polymers, particularly imprint polymers, copolymers and heteropolymers; and bifunctional, trifunctional and multifunctional molecules, particularly heterofunctional, heterobifunctional and heterotrifunctional molecules and groups of molecules. For environmental, military, agricultural and industrial applications (e.g., ground, water and site remediation, chemical and biological defense) important attributes include durability and/or biodegradability, safety, scalability and cost. Flexible, durable, well-defined and inexpensive synthetic polymers, bifunctional and heterofunctional molecules are particularly suitable, particularly copolymers and heteropolymers, preferably flexible and/or looped, bent, hinged, branched. circular or polygonal polymers that can be designed and manufactured with controlled topology and/or precision joints, hinges, bends or branchpoints, and more preferably polymers amenable to imprinting and/or reproducible, site-directed attachment of selected molecules.

In another preferred mode of operation, the bond(s) used to tether the payload molecule to the designer receptor (i.e., scaffold) is both pseudoirreversible, optionally covalent, and willfully or environmentally reversible. The tethering bond (s) may be cleavable, for instance and without limitation, by chemical, photochemical, thermal, enzymatic or ionic means, including laser-driven and photodynamic and hyperthermic modalities. In a particularly preferred embodiment, cleavage is mediated by a selected condition or substance which is relatively specific for or localized to the selected target. Cleavage and triggered release may be catalyzed, for example, by a particular hazardous waste substance at a bioremediation site; or accumulation of a pesticide residue in an agricultural setting; or a particular excreted solute or analyte absorbed by a transdermal drug delivery system (e.g., a patch); or a biological or chemical warfare agent.

Where the payload molecule is a drug, the first specific recognition pair is referred to as a prodrug complex or drug-receptor complex. Promolecular effector complexes of the invention (i.e., a promolecule being analogous to a prodrug) include not only prodrug complexes, but also prosignal-generating species complexes comprising specifically bound tags, tracers, radioisotopes, labels, reporters, polymers, light-harvesting structures, antennae, photonic assemblies, photosynthetic molecules, macromolecules, microparticles, nanoparticles, colloids, metals, dyes, fluorophores, phosphors, photosensitive molecules, metabolic, signal transduction and photosystem molecules, reaction centers, enzymes, coenzymes, cofactors, catalytic antibodies, molecular mimics, biomimetics, luminescent, triboluminescent, sonoluminescent, chemiluminescent, bioluminescent and electroluminescent molecules, electron transfer donors and acceptors, oxidizing and reducing compounds, mediators, and the like.

In a particularly preferred designer drug embodiment (i.e., smaRTdrugs), the combination of drug-device tethering and prodrug complex-based partitioning provides a fourth and failsafe level of specificity for maximal safety and efficacy of the targeted, partitioned, triggered-release therapeutic device. Target specificity is achieved by the additive and preferably synergistic combination of 1) site-specific targeting, and 2) affinity partitioning between designer receptor and target, and 3) allosteric triggered-release mechanisms, and further 4) localized enzymatic, metabolic or cofactor-dependent cleavage of the prodrug tether. This fourth level of target selectivity is achieved by a molecular effector (e.g., an enzyme, metabolite, pathophysiologic event or willfully or endogenously supplied cofactor) which is relatively site-localized (e.g., infection, inflammation, cancer) or disease-dependent (e.g., cancer, diabetes, cirrhosis atherosclerosis).

Prodrug complex means a prodrug comprising at least two noncovalently bound molecules and includes, preferably a drug specifically bound to a designer receptor wherein the designer receptor mimics the specificity of a therapeutic target for a drug. Prodrug complexes may also comprise a pair or plurality of drugs specifically bound to a pair or plurality of designer receptors. Prodrug complexes may also be operatively attached to biological or biocompatible microstructures or nanostructures free to distribute in one or more physiological compartments. Alternatively, prodrug complexes may attach to solid tissues or anatomically confined biologic or biocompatible structures, or they may be willfully attached to cells, tissues or organs, optionally reversibly or by a willfully biodegradable, cleavable and/or metabolizable linkage. Prodrug complexes may be stored, confined or released in a selected physiological or anatomical compartments or, alternatively, transported, delivered and/or confined to a selected physiological or anatomical compartment, site or target. Designer receptor, selected receptor and synthetic receptor mean any naturally occurring, recombinant, biological, biologically produced or synthetic nucleotide or nonnucleotide molecule or group of molecules comprising a specific recognition partner selected from the group consisting of specific binding partners, hybridizable nucleic acid sequences, shape recognition partners, specifically attractive surfaces or a catalytic recognition partner selected from the group consisting of enzymes, catalysts, biological recognition sites, biomimetics, enzyme mimetics and molecules participating in catalytic recognition reactions. Advantageously, designer receptors comprising multimolecular drug delivery systems of the instant invention are selected for the ability specifically recognize a drug or therapeutic receptor, optionally to mimic the specificity of a therapeutic receptor for a drug.

Catalytic recognition partner means a natural or synthetic substance participating in a selective catalytic or enzymatic reaction and includes protein and nonprotein enzymes and catalysts; nucleotide and nonnucleotide enzymes and catalysts; organic and inorganic enzymes and catalysts; specific, selective, class-specific and class-selective enzymes and catalysts; and mimetics and imprints and conjugates of any of these molecules. Molecules participating in catalytic reactions include substrates, products, intermediates, coenzymes, cofactors, prosthetic groups, regulatory factors, steric and allosteric modulators, inhibitors, mediators, and the like.

Promolecular delivery devices are also paired recognition devices as will be apparent from the following general description. A first specific recognition pair comprises a designer receptor capable of specifically recognizing, storing or transporting a selected molecule, preferably an effector molecule in inactive or unavailable form. An attached second specific recognition pair comprises a targeting and/or release-triggering first member (i.e., a ligand, receptor, defined sequence segment or shape-specific probe) that specifically recognizes a second member (i.e., recognition partner) that comprises a site at, on or near an identified (i.e., selected) target. On binding of the targeting first member of the second specific recognition pair at the target site, the selected (preferably inactive effector) molecule releases and/or attaches to the selected target. The released and/or targeted selected molecule is thereby made actively available to the selected target, generating or causing to be generated a desired effect (e.g., modification of the selected target).

Informational device means a synthetic device, product, medium, machine, program, code, process, library, database or means for marking, displaying, conveying, representing, mapping, transposing, imprinting, embodying, storing, replicating, archiving, comparing, analyzing, searching, researching, or transmitting data, information or instructions, particularly including molecular modeling, biocomputing, multifactorial search engines and hardware and software designed for ultrafast, ultrapowerful mapping, transposing, comparing, integrating, interpreting, interrogating, modeling and simulating molecular sequence, structure, shape, docking, dynamics, quantitative structure-activity relationships (QSAR).

Informational system means a pair of functionally coupled informational devices. Functionally coupled informational devices of the invention are capable of iteratively expanding the domain of informational space comprehended by either device and/or the paired devices, i.e., evolving, if the informational system is functionally coupled to a second system, i.e., a source of information, preferably an evolving source of information. The source of information may be natural, biological or synthetic. For purposes of the instant invention, the source of information is preferably willful, i.e., provided or mediated by humans. Willful functional coupling between information source and sink (i.e., processor) advantageously includes human-directed and/or human-supervised direct functional coupling between an information source (e.g., nature) and an informational system (e.g., paired search engines). Evolution, when used in reference to paired informational devices of the instant invention, means learning. Machine learning, machine-directed and machine-intelligence refer to products and processes enabled, facilitated or accelerated by informational devices, particularly paired informational devices comprising informational systems, more preferably informational systems comprising, attaching to, or capable of attaching to learning machines, e.g., evolving expert systems and intelligent machines. Intelligent means capable of learning. When used in reference to learning for willful purpose(s), intelligence requires either a functionally coupled system comprising an informational device and a human and/or humanly introduced information source or a functionally coupled paired informational device comprising or connecting to an external information source. Learning, when used in reference to an informational device(s) or system(s), means that the domain of informational space (i.e., knowledge) comprehended by the device(s) or system(s) expands with time as a function of the expanding domain encompassed by that which is heretofore known at a given point in time (i.e., all present knowledge).

Functional coupling between the machine-comprehended domain (i.e., machine domain) and the informational source domain (i.e., information source) may be tight and efficient in time and space, or functional coupling may be loose and inefficient. In perfectly tight and efficient functional coupling between paired informational device(s) (i.e., an informational system) and an information source, the source information is instantly available (i.e., immediately known) to the informational system. Perfect functional coupling is unattainable, as incoming source information must be added to, integrated, compared with and combinatorially permuted against its(new)self, The process of achieving the new, higher order informational state (i.e., knowledge) comprising its(new)self requires finite processing time, i.e., the time required for added information to be adopted, archived and combinatorially internally permuted, thereby forming a higher order information state which must its(new)self be combinatorially internally permuted, and so forth. Even assuming instantaneous (i.e., timeless) communication between information source and informational device(s) (i.e., sink), functional coupling efficiency between source and sink is limited by the internal processing time of the informational device(s).

Molecular search engine and search engine, when used in reference to molecular diversity, diversity space, molecular space, shape space, structural space, surface space, chemical space, catalytic space, surface attractivity space, positional space, means at least one member of a set of networked, massively parallel informational systems comprising pairs of paired informational devices comprising paired processors comprising paired switches. Advantageously, the informational system architecture comprises paired pairs of devices comprising processors comprising switches, e.g., (pairs of paired informational devices)$^N$, each informational device comprising (pairs of paired processors)$^N$, each processor comprising (pairs of paired switches)$^N$, each switch being advantageously binary. Processing speed is a function of degree of parallelism, e.g., number of processors per system. A first-generation search engine comprising a one-dimensional linear systolic array with 364,000 on-board processors operating in parallel has been designed for this purpose. Alternative processor architectures comprising arrays with two-dimensional and three-dimensional connectivity are presently under consideration. The operative informational system advantageously comprises a first molecular search engine (i.e., molecular knowledge base) that encompasses, archives and provides access to information regarding the evolving set of heretofore known and emerging (i.e., knowable and discoverable) molecules as well as structural shapes and surface features comprising materials. A second application-specific and functionally coupled search engine encompasses, e.g., the relationship among chemical identity, structure, shape and function of newly discovered selected molecules and materials. A third application-specific and functionally coupled search engine encompasses, e.g., the evolving domain of useful applications for heretofore known and unknown materials and molecules. A fourth application-specific and functionally coupled search engine encompasses, e.g., the relationship between structurofunctional properties of newly discovered (as well as heretofore known) selected molecules/materials and the evolving domain of useful applications for such known and unknown materials/molecules. A fifth application-specific and functionally coupled search engine generates hypotheses regarding the intersection between commercially useful applications and properties/activities of material/molecules. A sixth application-specific and functionally coupled search engine tests the hypotheses generated by the fifth search engine, and so forth. Networked means functionally coupled machines capable of generating and testing hypotheses with timely and efficient access to an evolving collective knowledge base comprising application specific evolving knowledge bases.

Materials, selected materials and identified materials, when used in reference to a molecular knowledge base and/or search for new materials, refer to structures, structural shapes, surfaces and surface features comprising selected molecules, as distinct from the selected molecules themselves. This distinction is made for clarity to enable well-articulated searches for selected molecules capable of interacting with structures, structural shapes, surfaces and surface features and, conversely, intelligent searches for structures, structural shapes, surfaces and surface features capable of specifically interacting with selected molecules. In general, structures, structural shapes, surfaces and surface features may be viewed as solid structures and surfaces as a conceptual guide. Selected molecules, on the other hand, may be viewed as mobile for conceptual purposes, wherein mobility does not imply anything definitional regarding the size, solubility, dispersion, solute, solvent or colligative properties or characteristics, particulateness, autonomy, three-dimensional structure or architecture of a selected molecule. The distinction between selected molecules and selected materials is also made to elaborate and underscore a central premise and inventive step disclosed herein, that materials comprising structural shapes and surface features are capable of specifically recognizing selected molecules independent of the chemical composition of the molecules comprising the structural shapes and surfaces. This premise derives from the following seminal, albeit modest, insight: As technologies emerge to enable precision manufacturing at the submicron scale, preferably nanometer and subnanometer scale, heretofore unappreciated specific recognition and catalytic properties of matter will emerge within chemically bland materials as a consequence of newly selected and designed three dimensional shapes at molecular scale. In other words, heretofore chemically bland materials will become plastic and personable with respect to interactions with compositionally diverse molecules referred to herein as selected molecules. So the distinction between selected materials and selected molecules relates to the transposition of structures and surfaces heretofore used as chemically passive into materials with diverse and useful recognition properties. Nanofabrication, nanomanipulation and molecular-scale sculpting of inorganic (as well as organic) substrates enables the conversion or transformation of passive, bulk materials into usefully active (i.e., reactive) materials. The emerging activities of chemically bland (e.g., monolithic, elementally pure, homogeneous, structurally uniform, amorphous, or specifically unrecognizable) materials will resemble and complement the specific binding and catalytic recognition properties heretofore understood and applied only in respect of the chemical composition of selected molecules. Coupling inefficiencies arise from imperfect sensitivity or receptiveness to input data (i.e., inaccessible or unrecognizable data or information), temporal lags (i.e., delays in reception, sluggish processing), noise (i.e., nonsense) and contamination (i.e., distortion, misinformation), disadvantageously accompanied by destructive interactions (e.g., negative synergy, negative cooperativity, cooperativity in a negative direction, competition and/or unresolved conflict). Tight coupling and efficient coupling, when used in reference to the functional coupling of machine intelligence to a process, domain or system, means that data and/or information are effectively comprehended in a usefully timely manner.

Informational devices of the invention particularly include high-order paired search engines comprising massively parallel processors, switching and software capabilities for transposing molecular structure-activity space and surface attractivity space, i.e., structure-activity-surface space (SASS), into informational space. Contemplated herein are multiply networked arrays of parallel processors with adequate computing power to engage in a willfully automatable, self-sustaining, closed-loop feedback system comprising an informational search engine functionally coupled to a molecular diversity generator. The molecular diversity generator is designed to express and explore vast regions of structure-activity space by generating and evolving polydiverse libraries of libraries, preferably paired nucleotide and nonnucleotide libraries operating in a divergent, self-sustaining nucleotide-nonnucleotide cycle of imprinting imprints. In a preferred mode of operation, the molecular diversity generator and informational search engine are tightly coupled and fully automated, albeit willfully directed.

Instructions include written or nonwritten letters, words, numbers or numerals, recordings, replicas, representations or facsimiles, pictures, signs, symbols, digital or analog data or code, static or dynamic images, audio, visual, tactile, olfactory or other sensory, perceptible or interpretable messages, data or information. Detection, deciphering, decoding, deconvolution or interpretation of instructions may be accomplished by sensory means, or, alternatively, may require suitable instrumentation, e.g., a light source, laser, scanner, reader, detector, sensor, transducer, amplifier, magnifier, decoder, microphone, recorder, transmitter, imaging system or the like.

Aptamers and aptamer targets as used herein are distinguished from ligands and receptors. Although an aptamer and its target are specific binding partners and members of a specific binding pair, they are not referred to herein as ligands and receptors. The inventor's lexicography in this regard is intended to avoid confusion arising from overlapping prior art usage of the terms ligand and receptor with respect to aptamers. Nucleic acid ligands, nucleic acid receptors, nucleic acid antibodies and aptamers are commonly described in the art without definition.

The synthetic heteropolymers of the present invention allow for the production of ordered pairs, groups and arrays of selected nonoligonucleotide molecules, preferably receptors, ligands or effector molecules, whose cooperative interactions have utility in diagnostics, therapeutics, bioprocessing, microelectronics, energy transduction and, more generally, molecular manufacturing. Cooperating, cooperative interactions and cooperativity refer either to the ability of selected molecules to interact positively or negatively to produce a desired result or to an effect on one molecule created by the presence of a second molecule or to an action or effect brought about by the proximity of two or more molecules or to the combined actions of two or more molecules on a third molecule or to a chemical, electrical, optical, thermal, mechanical, energetic or informational transformation involving two or more molecules. This invention enables preparation of ordered pairs, groups or arrays of selected biological or nonbiological molecules that function in a concerted manner to transduce energy or perform useful work. Whereas biological systems rely on membranes, molecular chaperones and self-assembling systems to create ordered arrangements of proteins, lipids and glycoconjugates as ion channels, effector-coupled membrane receptors, biochemical amplifiers and metabolic pathways, the present invention teaches methods to create multimolecular machines using selected, designed or engineered nucleotides as molecular ordering devices, i.e., molecular scaffolds or multisite templates. Nucleotide-based templates may be heteropolymeric, aptameric or non-aptameric. They may be synthesized by biological, chemical and/or enzymatic methods known in the art, including manual and automated methods, cloning, transcription, replication and/or amplification, optionally including willful infidelity and/or directed evolution.

Cooperativity includes but is not limited to functional coupling between or among two or more molecules, reactions or processes. Functional coupling and functionally coupled mean that at least two processes are connected by a common reaction, event or intermediate or that at least two compositions, which may be molecules, species, substances, structures, devices, groups or combinations thereof, participate as donor and acceptor in the transfer of mass (e.g., molecules, atoms or subatomic particles) or energy (e.g., photons, electrons or chemical or mechanical or thermal energy), or that two processes or compositions act on a third process, composition, disease or condition in an additive, partially additive or subtractive, mutualistic, synergistic, combined or interdependent manner. Examples of such coupling are well known in the art, e.g., Gust et al. (1993) *Accounts of Chemical Research* 26:198–205; Sheeler, P. and Bianchi, D. E. (1983) *Cell Biology: Structure, Biochemistry, and Function*, p. 203, John Wiley & Sons, Inc., New York; Saier, H. S. Jr. (1987), *Enzymes in Metabolic Pathways: A comparative Study of Mechanism, Structure, Evolution, and Control*, pp. 48–59 and 132–136, Harper & Row Publishers, New York; Aidley D. J. (1989), *The Physiology of Excitable Cells*, Third Edition, p. 320, Cambridge University Press, Cambridge; Bray, H. G. and White, K. (1957), *Kinetics and Thermodynamics in Biochemistry*, p. 135, Academic Press, N.Y.; and Guyton, AC (1971) *Textbook of Medical Physiology*, Fourth Edition, p. 786, W. B. Saunders Company, Philadelphia). When used in reference to the interaction between two specific recognition pairs, functional coupling and functionally coupled mean that the binding or activity of a member of a first specific recognition pair influences the binding or activity of a member of a second specific recognition pair or that members of both specific recognition pairs bind to or act upon a common substance, disease, condition or process in an additive, partially additive, or cooperative manner. Members of both specific recognition pairs bind to or act upon a common disease or condition, for example, when two (or more) functionally coupled drugs and/or targeting agents act in a combined, additive or synergistic manner at a single disease target or at two or more localized receptors. Nucleotide-based multimolecular delivery devices of the instant invention comprise at least two specific recognition pairs functionally coupled in this manner to deliver, target and/or release selected molecules and/or selected nucleic acid sequences to selected targets (e.g., therapeutic receptors, environmental, agricultural or food contaminants, pests, or pathogens, chemical or biological weaponry, selected sites, receptors or features comprising molecular arrays, biochips or microminiaturized devices). When used in reference to single-molecule detection, functional coupling means to enable detection of an individual complex comprising a pair or group of molecules attached by nucleotides or, alternatively, to enable discrimination of an individual complex comprising a pair or group of molecules attached by nucleotides from an uncomplexed molecule or plurality of molecules.

Nucleotide-based templates and/or multimolecular devices of the instant invention can also serve as molecular delivery devices by positioning selected molecules without functional coupling between the selected molecules. Selected molecules comprising structural molecules can, for instance, be positioned to provide a useful function which results from a microscopic or macroscopic structural effect, e.g., adhesion between two surfaces, attachment of a selected molecule to a nanostructural shape (e.g., an edge, lip or corner) or strengthening, lengthening, thickening, protecting or coloring an eyelash, eyebrow, nail or hair.

In one embodiment, bivalent or multivalent nucleotide-based templates, preferably one or multiple defined sequence segments comprising at least two specific binding or shape recognition pairs, optionally at least one specific binding or shape recognition pair plus one pair of hybridizable nucleotide sequences, are designed for use as adhesives. Adhesives may be used, e.g., for assembling, attaching, packing and sealing parts, products, packages and packing materials, e.g., by bonding two amphibious surfaces together. They may also be used to specifically bind or hybridize a selected molecule to an amphibious surface. For example, cosmetic adhesives disclosed herein may be used to specifically bind or hybridize eyeliners, thickeners and lengtheners eyelashes and eyebrows or, alternatively, polishes and strengthening agents to fingernails and toenails.

When used in reference to multimolecular adhesive attachment, surface means an amphibious surface. Amphibious surfaces are either able to operate on land, in air, in vacuum, or in fluids including, but not limited to, gaseous, liquid, aqueous and organic solutions and suspensions or in some combination of these environments. They are not reagent-binding or analyte-binding separation matrices of specific binding assays or nucleic acid hybridization assays. A surface is a boundary in two-dimensional or three-dimensional space.

Adhesives of the instant invention are optionally user-responsive or environment-responsive, meaning that after application of adhesive(s) to amphibious surface(s), the surface-bonding (i.e., adhesive) function can be willfully or environmentally triggered (i.e., initiated) by a first selected associative stimulus (i.e., an adhesive or bonding stimulus). Selected bonding stimuli include, for instance and without limitation, changes in ambient temperature, pressure, humidity or light exposure; the willful input or exchange of energy (e.g., laser light, photons, darkness, sound, heat, cold, electromagnetic radiation); or application or removal of a selected nonoligonucleotide molecule (e.g., a solvent, solute, ligand, receptor or effector molecule) or oligonucleotide (e.g., a linker oligonucleotide, aptamer or hybridizable defined sequence segment). The adhesives are also optionally reversible, preferably willfully or environmentally reversible, meaning that bonding can be reversed in response to a first dissociative selected stimulus (i.e., an unbending or antiadhesive stimulus). Unbonding stimuli include, for instance and without limitation, changes in ambient temperature, pressure, humidity or light exposure and/or the willful input or exchange of energy, or application or removal of a selected nonoligonucleotide molecule or oligonucleotide. The unbending stimulus may be the removal, absence or disappearance of the bonding stimulus (e.g., cooling, darkness, wetness or dryness). Alternatively, the unbending stimulus may not be substantively different from the bonding stimulus (e.g., use of a solvent to unbond light-induced adhesion). Following unbonding, adhesion may optionally be restored, preferably by a second bonding stimulus and advantageously a repetition of the first bonding stimulus.

In bonded form, adhesives of the instant invention comprise at least a bivalent molecule or scaffold comprising at least two specific recognition pairs, at least one specific recognition pair being a specific binding or shape recognition pair. A first selected molecule, preferably a structural molecule and optionally a structural shape comprising a first amphibious surface, is specifically bound and optionally covalently crosslinked to a first specific recognition site of the molecule or scaffold, optionally a discrete structure comprising a synthetic heteropolymer. A second selected molecule, preferably a structural molecule and optionally a structural shape comprising a second amphibious surface, is specifically bound or hybridized (i.e., via a conjugated oligonucleotide) to the second specific recognition site of the molecule or scaffold, optionally covalently crosslinked in place following specific binding or hybridization to the molecule or scaffold. In unbonded form, adhesives comprise at least a bivalent molecule or scaffold comprising at least two specific recognition sites, at least one specific recognition site being a ligand, receptor or a defined sequence segment comprising an aptamer. An adhesive synthetic heteropolymer, for example, comprises, a first defined sequence segment capable of specifically binding a first structural molecule of a first amphibious surface, edge or part and a second defined sequence segment capable of either specifically binding a second structural molecule of a second amphibious surface or of hybridizing to an immobilized or linker oligonucleotide. A second adhesive synthetic heteropolymer and/or immobilized oligonucleotide may be applied to or attached to the second amphibious surface.

A diverse array of different molecular adhesive compositions is possible using nucleotide-based and nonnucleotide templates. Synthetic heteropolymers, multivalent heteropolymeric hybrid structures, aptameric compositions, and modified nucleotides comprising single or multiple defined sequence segments can bond surfaces by different permutations of specific binding, structural shape recognition and hybridization. Plastic templates can bond surfaces by specific binding or structural shape recognition. Different molecular adhesive formulations may be applied either to a first surface or to a second surface or to both surfaces to be bonded.

Multimolecular adhesives, i.e., molecular adhesives, are molecular bonding or attaching devices comprising at least a bivalent molecule or scaffold having at least two specific recognition sites, at least one being capable of specifically recognizing a selected molecule and at least one being capable of specifically binding or hybridizing to an amphibious surface. When used in reference to multimolecular adhesive attachment, surface means amphibious surface. At least one specific recognition site is capable of specifically binding to a first selected molecule, optionally a structural molecule and advantageously a first structural shape comprising a first surface. The other specific recognition site is capable of specifically binding to a second selected molecule, advantageously a second structural shape comprising a second surface, or of hybridizing to a selected nucleic acid sequence. The selected nucleic acid sequence is preferably immobilized or capable of attaching to a solid support, optionally an oligonucleotide, conjugated oligonucleotide, linker oligonucleotide, defined sequence segment or a synthetic heteropolymer. The selected nucleic acid sequence may be immobilized or capable of attaching to the second surface or to a third surface capable of attaching to the second surface, e.g., a microparticle or nanoparticle, matrix, layer, membrane, gel, foam, nanostructure or microstructure. The second selected molecule, which may be a ligand, receptor, effector or structural molecule, may advantageously be a structural shape on the second surface which does not occur on the first surface. In this way, a bivalent multimolecular adhesive comprising a first structural shape specifically bound to a first specific binding site and a second structural shape specifically bound to a second specific binding site of a molecule or scaffold can be used to specifically and reversibly bond two surfaces having the same chemical composition. Unlike conventional glues and adhesives, the multimolecular adhesive is specifically oriented, polarized or sided with respect to the two surfaces, enabling precise titration and control of adhesive force between the bonded surfaces. In addition, a bivalent multimolecular adhesive that specifically binds and attaches a first structural shape on a first surface and a second structural shape on a second surface provides an entirely novel and commercially valuable method for attaching nanometer-scale features on the two surfaces in register.

In a preferred embodiment, multimolecular adhesives are designed for use in industrial environments, e.g., for alignment and specific attachment of nanoscale features comprising micromachined surfaces, e.g., physical and chemical sensors, semiconductors, microelectromechanical systems (MEMS) and MEMS devices, nanoelectromechanical systems (NEMS) and NEMS devices and ultrafast molecular computers. Because industrial-use MEMS and NEMS devices and associated sensor, actuator and transducer surfaces represent extremely harsh and unforgiving environments, nucleotide ligands, nucleotide receptors, aptamers and hybridizable nucleotides are preferred, even required, over more readily available ligands and receptors (e.g., antigens, antibodies, avidin, streptavidin, lectins, drug and hormone receptors). and receptors and are preferred over specific recognition. Protein-based antibodies and receptors currently used in diagnostic and analytical specific binding assays are not sufficiently robust to function for protracted intervals under the extreme and volatile thermal, chemical and electromechanical conditions operative during MEMS manufacture and use.

A bivalent heteropolymeric multimolecular adhesive is prepared as follows for precise feature-to-feature bonding of silicon-etched first and second amphibious surfaces comprising a hybrid memory device. A first convex tip of the first surface and second concave pit of the second surface, each having specifically attractive surface features (i.e., a recognizable vertex and nadir, respectively) are referred to as male and female surfaces. The first (i.e., male) amphibious surface comprises a tip feature which is a nanometer-scale vertex (i.e., first feature) of a solid, convex, conical tip on a silicon semiconductor. The conical tip has a height of about two microns and a base diameter of about two microns. The second amphibious surface comprises a concave, conical pit about two microns in diameter at the base (i.e., surface) and about two microns deep at the nadir (i.e., second feature). For selection of template recognition elements, an array of corresponding tip vertex and pit nadir features is micromachined into a single silicon surface by a combination of lithographic and chemical etching techniques well known in the art. A diverse nucleic acid library comprising random-sequence single-stranded nucleotides (with fixed primer-annealing sequences) labeled to high specific activity with rhodamine is screened and selected for a first defined sequence segment capable of specifically recognizing the first surface feature (i.e., conical tip vertex) and a second defined sequence segment capable of specifically recognizing the second surface feature (i.e., concave pit nadir) in a selected solvent system. Counterselection is performed using unmachined and polished silicon wafers. Specific recognition of rhodamine-labeled nucleotides to first and second surface features is detected by continuous wave laser excitation with fluorescence detection (e.g., Soper et al. (1991) Anal. Chem. 63:432–437) coupled with AFM. Surface feature-bound nucleotides are then imaged, isolated, extracted, amplified and sequenced by single-molecule detection methods disclosed herein. Single-molecule imaging is achieved by AFM (Radmacher et al. (1992) Ultramicroscopy 42–44:968). A bivalent heteropolymeric template comprising the first and second defined sequence is synthesized on an automated DNA synthesizer, optionally including rhodamine-modified nucleotides to enable evaluation of template binding to first and second surface features. The adhesive properties of the template are evaluated by titration of templates onto the first or second surface followed by an aspiration and/or washing to remove excess. Following validation, the heteropolymeric template is advantageously converted into a nonnucleotide medium by two cycles of molecular imprinting (e.g., Ramström et al. (1993) J. Org. Chem. 58:7562–7564; Shea et al. (1993) J. Am. Chem. Soc. 115:3368–3369) or nucleotide-nonnucleotide transposition as disclosed elsewhere herein. Alternatively, two hybridizable templates are synthesized, each comprising a first defined sequence segment capable of specifically binding one surface feature. Each template is then specifically attached to its corresponding surface feature, and the surfaces are attached to one another by hybridization of complementary second defined sequence segments. Whether accomplished by a single heteropolymeric template, an imprinted plastic template or two hybridizable synthetic heteropolymers, specific recognition of two different structural shapes (i.e., surface features) by a single discrete structure or bivalent template enables attachment of corresponding surfaces in proper register.

Templates can also be designed to specifically recognize biological structural molecules, e.g., keratin comprising hair and nails, for precise and specific binding of safe, lasting, yet reversible cosmetic dyes, pigments and liners. The ability of shape recognition partners to specifically recognize structural shapes on biological surfaces e.g., teeth, skin, hair, bone, nails, scar tissue, provides unique opportunities for delivery of targeted pharmaceutical and cosmeceutical devices. Applications for surface-specific and shape-specific MOLECULAR MACHINES in agriculture, veterinary, environmental, military and industrial settings abound.

Specific recognition of surface features as described herein differs from specific binding as known in the art, and the distinction has important practical implications. Unlike specific binding, surface attractivity is not competitively inhibited by molecules having the same chemical identity as structural molecules comprising a selected surface feature. Nor is crossreactivity observed with congeners and/or solution phase molecules that are structural analogs of molecules comprising a selected surface feature. As emerging nanofabrication techniques enable progressively more precise machining of an expanding assortment of different structural shapes at the nanometer-scale, the diversity of specific surface attractivities described herein will evolve into a catalog of usefully distinct and targetable surface features. Highly diverse molecular shape libraries, advantageously paired nucleotide-nonnucleotide libraries of the instant invention, can be used to select recognition elements capable of targeting synthetic and/or nanofabricated surface features comprising chemically bland surfaces (e.g., silicon, gallium arsenide, synthetic metals, synthetic semiconductors, insulators) and nanostructures comprising or attaching to chemically bland surfaces (e.g., buckyballs, carbon nanotubes, carbon nanorods and molecular-scale devices, e.g., wires, gates, channels and switches). In other words, as current bulk material processing and microfabrication technologies evolve toward the molecular level (i.e., nanometer-scale precision), the ability to design, select, sculpt, shape, imprint, graft and template specifically recognizable surface features into chemically bland materials can evolve concurrently. Selection of molecular shape libraries for the ability to specifically recognize emerging surface features enables feature-specific integration of selected molecules and surface materials. Conversely, surface library selection techniques disclosed herein enable selection of specifically attractive surfaces for attachment of selected molecules, advantageously template-directed molecules comprising MOLECULAR MACHINES. Bridging the dimensional gap between molecules and substrate materials are the instant MOLECULAR MACHINES as well as nanostructures having discrete three-dimensional architectures, e.g., buckyballs, carbon nanotubes and carbon nanorods. Nucleotide-based and nonnucleotide segments, templates and MOLECULAR MACHINES of the instant invention enable the functional diversification of chemically bland materials and diamondoid nanostructures by specific recognition of heretofore undescribed surface features.

Multimolecular adherents, i.e., molecular adherents, are molecular bonding or attaching devices comprising a specific recognition element (i.e., probe) attached to a first selected molecule, wherein the specific recognition element is capable of attaching the first selected molecule to a second selected molecule comprising a surface. In a preferred mode of operation, the second selected molecule is a structural molecule comprising an amphibious surface. In a particularly preferred aspect, the second selected molecule is a surface feature comprising either an amphibious or nonamphibious surface and the specific recognition probe is a shape-specific probe.

A molecular adsorbent, i.e., mimetic adsorbent, is a solid phase, material, surface or structure comprising or attaching to a MOLECULAR MACHINE or having a recognition property introduced by grafting, templating, copying, imprinting or transposing a segment, template or MOLECULAR MACHINE, or having a recognition property identified by screening and/or selection of a surface library for a specifically attractive surface feature. Mimetic adsorbents of the invention, i.e., molecular adsorbents mimicking a heretofore known molecular recognition property, provide the art with materials and surfaces having solid phase recognition properties heretofore achieved only by immobilization of selected molecules or nucleic acid sequences, e.g., by covalent attachment of a recognition molecule (e.g., an enzyme, ligand, receptor or DNA probe) to a solid phase or by specific binding or hybridization of a selected molecule or selected nucleic acid sequence to an immobilized recognition molecule. The instant invention provides methods for surface grafting, surface templating, surface feature selection and template-guided surface feature fabrication (i.e., using immobilized selected molecules as recognition shape templates). These methods for fabricating, grafting and templating recognition properties into surfaces are broadly enabling for development of designer adsorbents useful as immunosorbents, affinity matrices, chromatography supports, and, more generally, separation media for analytical, diagnostic and preparative fractionation, purification and processing. Molecular adsorbents are also particularly useful for solid phase assembly of the instant MOLECULAR MACHINES, e.g., using specific recognition as a means for site-directed surface attachment of a selected molecule, segment or template comprising a MOLECULAR MACHINE.

In adsorbing a selected target molecule to an acceptor surface, a molecular adsorbent is also capable of removing the selected target molecule from a donor surface (i.e., the target surface). For example, molecular adsorbents comprising plaque-binding, microbe-binding, dust-binding, pollen-binding, toxin-binding, grease-binding, oil-binding, or even rust- or paint-binding recognition properties can be used to remove unwanted substances from target surfaces, e.g., dental enamel, dental appliances, microelectronic devices, consumer products, machine components and painted, coated, rusted, oiled or contaminated surfaces. The acceptor surface may comprise or attach a cleaning device, material or tool, e.g., a brush, sponge, pad, cloth, abrasive or porous surface, and may further comprise one or more catalytic recognition elements capable of facilitating the degradation, digestion or detoxification of adsorbed target molecules.

Multimolecular lubricants, i.e., molecular lubricants are MOLECULAR MACHINES capable of modulating the interaction between two surfaces by means of a segment-directed or template-directed selected molecule and/or selected nucleic acid sequence, preferably a structural molecule (e.g., a buckyball, carbon nanotube, carbon nanorod, polymer, surfactant or glass) or an effector molecule (e.g., a colloid, nanosphere, microsphere or molecular ball bearing), and more preferably a structural molecule or effector molecule comprising or attaching to a recognition molecule (e.g., an oligonucleotide, ligand or receptor) which is capable or binding at least one surface feature or surface-attached selected molecule, segment or template. In a preferred mode of operation, a multimolecular lubricant comprises a first selected molecule (e.g., a nanosphere) that serves as a rigid or pliable spacer between two surfaces and an attached second selected molecule (e.g., an oligonucleotide or ligand) that specifically recognizes, weakly binds, specifically binds, hybridizes, tethers, or ratchets the selected molecule to at least one of the two surfaces. In this way, the friction between the two surfaces can be controlled by coselection of the type and number of recognition molecules per multimolecular lubricant and the type and number of multimolecular lubricants between the surfaces. In a particularly preferred mode of operation, the recognition molecules comprise a plurality of oligonucleotides or imprinted segments ratcheted to variably complementary immobilized oligonucleotides or variably attractive surface features or surface-immobilized selected molecules, segments or templates, wherein the sequential association and dissociation of weakly attractive binding pairs results in net movement of one surface relative to another, i.e., directional motion.

Functional coupling includes electron transfer in and through nucleic acid molecules. Donor-acceptor coupling in DNA has been described (e.g., Risser et al. (1993) *J. Am. Chem. Soc* 115:2508–2510). Long-range photoinduced electron transfer through DNA has also been reported (e.g., Murphy et al. (1993) *Science* 262:1025–1029), although the conductive properties of DNA have not been definitively established. The electron tunneling reactions studied rely upon photoexcitation of a donor species and quenching by electron transfer to an acceptor. Electron tunneling mediated by the DNA double helix appeared to be relatively long-range, with separation distances up to 40 angstroms. Propagation of electronic coupling through DNA remains controversial, because reported tunneling rates as a function of distance conflict with theoretical expectations. Regardless of the still-unresolved question as to the insulating or conducting properties of DNA, electron transfer between selected molecules specifically bound to DNA has not heretofore been reported. Functional coupling as described herein between pairs or groups of selected molecules specifically bound to defined sequence segments, modified nucleotides or nucleotide analogs comprising multimolecular devices and tethered molecules includes but does not require electron transfer through nucleotides. Functional coupling as disclosed herein is achieved by specifically binding a selected molecule (e.g., a donor or acceptor species) to a defined sequence segment comprising a multimolecular device. The specifically bound selected molecule (e.g., a donor or acceptor) may subsequently be covalently attached to the defined sequence segment, but such covalent attachment is optional. The donor and acceptor species are selected from the group consisting of molecular effectors (i.e., effector molecules), advantageously signal-generating species. Some, but not all, signal-generating species are capable of useful electron transfer reactions. Others participate in functional coupling that does not involve electron transfer. For functional coupling of electron transferring effector molecules of the instant invention (e.g., electroactive compounds, redox proteins, redox enzymes, redox mediators, cytochromes), electron tunneling through DNA may be exploited if useful, but such tunneling is not required. Alternatively, the insulating properties of nucleic acids may be exploited, if useful, to maximize the efficiency of functional coupling between donor and acceptor species.

The functional coupling described herein relies on specific binding of at least one selected molecule (i.e., a donor or acceptor species) in close spatial proximity to a second selected molecule comprising or attached to a defined sequence segment. Electronic coupling between electroactive effectors of the instant invention is preferably achieved by intimate proximity between the nucleotide-positioned donor and acceptor species, preferably sustained intimate contact. Sustained intimate contact may be achieved by covalently attaching the nucleotide-positioned donor and acceptor species to one another or, optionally, covalently attaching donor or acceptor species to one or more nucleotides.

Functional coupling does not refer to specific binding between two molecules and/or nucleic acid sequences, nor does it refer to hybridization between complementary nucleic acid sequences, nor does it refer to the action of a catalyst or enzyme on its substrate or, similarly, the action of a cofactor, coenzyme, prosthetic group or product of an enzyme molecule on the same enzyme molecule, nor does it refer, more generally, to the interaction between any two members of a pair of molecules heretofore known to specifically bind, hybridize, recognize or spontaneously attract or attach one another, e.g. as a cation interacts with an anion or a chelator interacts with a metal. In other words, a ligand is not functionally coupled to its receptor, nor is a ligand-receptor complex functionally coupled, nor does the binding between a ligand and its receptor entail functional coupling as these terms are defined herein.

A first selected molecule or group of molecules or nucleic acid sequence is said to be functionally coupled to a second selected molecule or group of molecules or nucleic acid sequence or to a device (e.g., a sensor, transducer or actuator) when a photon, electron, property, activity, mass or energy of the first selected molecule or group of molecules or nucleic acid sequence is transferred to or from a second selected molecule or group of molecules or nucleic acid sequence or to a device. Such functional coupling includes, for example, the participation of selected molecules or nucleic acid sequences as effector molecules, signal-generating molecules, donors or acceptors of mass (e.g., precursors, cofactors or products) or energy (e.g., electrons, photons, or radiationless transfer), reactants, substrates, cofactors, coenzymes, prosthetic groups, catalysts or intermediates in chemical or enzymatic reactions, including, electrochemical, photochemical and mechanochemical processes.

Actuator means any device or process capable of providing or performing useful work (i.e., a desirable result) in response to a stimulus, e.g., an input from a user, operator, environment, sensor or transducer, particularly useful work resulting from or mediated by the binding or activity of a selected molecule or group of molecules or nucleic acid sequence comprising a multimolecular device.

Actuators of the invention further include devices which comprise, attach, are functionally couple to or are capable of functionally coupling to MOLECULAR MACHINES of the invention, particularly paired MOLECULAR MACHINES and advantageously systems comprising pairs or networks of paired MOLECULAR MACHINES.

Particularly useful nucleotide-based multimolecular devices of the instant invention that rely on functional coupling as described herein include soluble and immobilized multimolecular switches, multimolecular transducers, multimolecular sensors and multimolecular delivery systems comprising oligonucleotides, aptamers or synthetic heteropolymers attached to selected molecules, selected nucleic acid sequences or conjugates. Multimolecular devices include, e.g., multimolecular switches, multimolecular sensors, multimolecular transducers, multimolecular drug delivery systems, nucleotide-based molecular delivery systems and tethered specific recognition devices comprising synthetic nucleotide-based, aptamer-based or heteropolymer-based discrete structures, nonnucleotide scaffolds or multivalent molecular structures. Nucleotide-based means comprising at least one synthetic defined sequence segment. Aptamer-based and aptameric mean comprising at least one synthetic aptamer. Heteropolymer-based and heteropolymeric mean comprising at least one synthetic heteropolymer.

The positioning of selected molecules and selected nucleic acid sequences comprising multimolecular devices disclosed herein relies upon molecular recognition (i.e., specific binding of a selected molecule or hybridization of a selected nucleic acid sequence to a nucleotide or defined sequence segment comprising the multimolecular device) or structural shape recognition (i.e., specific recognition of a structural shape or surface feature). Once specifically attached (e.g., specifically bound or hybridized) to a nucleotide or defined sequence segment comprising a multimolecular device, selected molecules and/or selected nucleic acid sequences may further be covalently attached to one or more nucleotides (including modified nucleotides, nucleotide analogs, nucleotide ligands, nucleotide receptors and associated, conjugated or attached molecules and functional groups) comprising the nucleotide or defined sequence segment. Selected molecules or selected nucleic acid sequences specifically bound or hybridized to nucleotides comprising a multimolecular device may optionally be covalently attached to one another or to one or more nucleotides comprising a defined sequence segment of the multimolecular device (e.g., using crosslinking reagents, enzymes and/or irradiation) to stabilize the multimolecular device against dissociation or denaturation of specifically bound molecules or hybridized nucleic acid sequences. Covalent conjugation of nucleotide-ordered selected molecules can also be used to enhance functional coupling between the selected molecules, enabling efficient communication between donor and acceptor molecules, preferably radiationless and radiative energy transfer and including direct electronic coupling. Covalent attachment to a defined sequence segment comprising a multimolecular device is preferably directed to a particular functional group, optionally a pair or group of functional groups, comprising a single nucleotide, modified nucleotide, nucleotide position, nucleotide analog, type of nucleotide or group of nucleotides. Covalent attachment to a selected molecule, selected nucleic acid sequence or conjugate comprising multiple functional groups and/or multiple types of functional groups (e.g., a macromolecule, polymer or conjugate such as a protein or protein-ligand conjugate) may be advantageously directed to a single functional group, pair or group of functional groups that is uniquely represented or preferentially accessible or addressable (e.g., for steric, electrostatic, conformational or kinetic reasons) in the selected molecule, selected nucleic acid sequence or conjugate. Covalent attachment of nucleotides or selected molecules comprising a multimolecular device is preferably achieved by selectively modifying particular or unique functional groups on the nucleotides and/or selected molecules to be covalently conjugated, e.g., by site-directed modification as known in the art (e.g., Fisch et al. (1992) *Bioconjugate Chemistry* 3:147–153; Gaertner et al. (1992) *Bioconjugate Chemistry* 3:262–268; Offord (1990) In: *Protein Design and Development of New Therapeutics and Vaccines* (Eds. J. B. Hook and G. Paste), New York: Plenum, pp. 252–282). Alternatively, regiospecific covalent attachment of specifically bound or hybridized molecules may be achieved by exploiting the favored reaction kinetics between functional groups on closely approaching surfaces of the bound molecules. Reaction conditions can be adjusted to preferentially bond functional groups in nearest mutual proximity, e.g., by selecting a rapid-acting, zero-length or short-spacer, advantageously photoactivatable, heterobifunctional crosslinker and optimizing reaction conditions (e.g., crosslinker selection, incubation time, temperature, pH and buffer conditions, reagent concentrations, photoactivation protocol) to drive bonding between functional groups on docking surfaces in favor of more distant interactions.

The process of specifically binding a selected molecule to a defined sequence segment or nucleotide comprising a defined sequence segment (e.g., a modified nucleotide, nucleotide analog, nucleotide ligand or nucleotide receptor) followed by site-specific covalent attachment represents a generally useful method for site-directed covalent conjugation, particularly for complex macromolecules (e.g., particularly proteins and polymers) lacking a unique and accessible reactive group. A defined sequence segment, nucleotide ligand or nucleotide receptor selected for the ability to specifically bind a defined epitope of a first selected molecule (even one having no heretofore known specific binding partner, e.g., a novel macromolecular fluorescent donor signal-generating species comprising multiple chromophores) is first conjugated to a second selected molecule (e.g., a luminescent acceptor signal-generating species) by methods known in the art. High intensity fluorescent microspheres comprising multiple energy-transferring dyes with suitable spectral overlap to yield a single emission peak at a selected wavelength are commercially available, as are high molecular weight fluorescent proteins and dextrans (e.g., Molecular Probes, Eugene Oreg.). The conjugated product is a luminescent acceptor-fluorescent signal-generating species conjugate capable of specifically binding to a defined epitope of the novel donor signal-generating species. The defined sequence segment conjugated to the luminescent acceptor is capable of specifically binding the conjugated luminescent acceptor to the novel macromolecular fluorescent donor to produce a noncovalent donor-acceptor conjugate. Covalent site-specific attachment of the specifically bound fluorescent donor to functional groups on the luminescent acceptor conjugate yields a covalent donor-acceptor conjugate with defined composition (i.e., one defined sequence segment, one donor and one acceptor per covalent conjugate). The same approach may be practiced using nonaptameric nucleotides, e.g., modified nucleotides, nucleotide ligands or nucleotide receptors, to prepare covalent conjugates of selected molecules, preferably functionally coupled selected molecules comprising multimolecular devices. A particular preferred embodiment of site-directed covalent conjugation involves nucleotide-dependent positioning of at least two selected molecules specifically bound to defined positions of a heteropolymeric, aptameric or nonaptameric multimolecular device followed by covalent, site-directed attachment of the selected molecules to one another or to nucleotides comprising the multimolecular device. Covalent attachment of the selected molecules to one another is particularly useful for preparation of stable, reproducible conjugates with well-defined composition (i.e., specific activity), preferably heteroconjugates comprising at least one macromolecule, more preferably heteroconjugates comprising a first selected molecule regiospecifically conjugated to a second selected molecule. Covalent conjugation of nucleotide-positioned effector molecules also provides sustained intimate contact between the effector molecules, enabling maximally efficient functional coupling (e.g., radiative and nonradiative energy transfer), including resonance energy transfer and, advantageously, electronic coupling. Electronic coupling means single-electron transfer and coupling mediated by direct, through-space overlap of the relevant orbitals of the donor(s) and acceptor and by through-bond superexchange(s) and may occur by single-step or multistep processes within a molecule or between molecules positioned by noncovalent interaction(s) or, preferably, covalent bonding.

Nucleotide-dependent molecular positioning, nucleotide-dependent positioning and nucleotide-positioned mean positioning dependent on attachment to a nucleotide comprising a defined sequence segment or attachment to a defined sequence segment comprising a nucleotide of a discrete structure and dependent on the position of the nucleotide comprising the defined sequence segment or the position of the defined sequence segment comprising the nucleotide of the discrete structure. Nucleotide-dependent functional coupling means functional coupling dependent on or brought about by attachment to a nucleotide comprising a discrete structure. Nucleotide-directed, nucleotide-ordered, and nucleotide template-ordered mean nucleotide-dependent molecular positioning, nucleotide-dependant functional coupling and/or the preparation, properties or use of nucleotide-based multimolecular devices. Also included are nucleotide and nonnucleotide replicates, clones, mimetics, imprints and conjugates of nucleotide-ordered multimolecular devices, including nucleotide and nonnucleotide replicates, clones, mimetics, imprints and conjugates thereof. Replication, cloning and mimicking include, without limitation, copies, mimetics, analogs, variants and progeny prepared, selected and/or evolved with varying degrees of fidelity by rational, combinatorial and/or randomized design, screening and selection methods including but not limited to directed molecular evolution, advantageously including directed supramolecular evolution. Genetic, enzymatic and chemical methods for in vitro and in vivo evolution of nucleotides and products of nucleotide transcription and expression are known in the art and will themselves evolve to suit the purposes of the instant invention.

It will be apparent to the skilled artisan on reading this disclosure that the replicative properties of nucleotides are enabling for development of self-replicating templates. It is also the self-replicating properties of nucleotides that renders them uniquely useful in high-resolution screening and selection of vastly diverse nucleotide and nucleotide-encoded chemical libraries for aptamers, nucleotide ligands, nucleotide receptors, nucleotide shape probes and pairs of these useful recognition partners, advantageously including catalytic nucleotides and catalytic nonnucleotide recognition partners. The inventive step, however in capitalizing on these wonderfully ramifying properties of nucleotides is single-molecule detection and characterization, i.e., the ability to detect individual complexes comprising a selected nucleic acid molecule and its target. The selected nucleic acid molecule may be an aptamer, a nucleotide ligand, a nucleotide receptor, an aptameric or nonaptameric shape recognition partner, or even a nonnucleotide ligand or nucleotide receptor comprising a nucleotide-encoded chemical library. Single-molecule amplification of the selected probe and/or single-molecule sequencing followed by amplification provides a singularly unique tool for exploring diverse chemical, nucleotide sequence and shape recognition libraries in a manner untenable with nonamplifiable chemical or polymeric libraries.

The instant invention is therefore drawn in part to the useful method of applying single-molecule detection to the screening and selection of a mixture of nucleotide or nonnucleotide molecules, preferably a highly diverse mixture of molecules that can be characterized by single molecule detection. In a most referred mode of operation, the highly diverse mixture comprises molecules or nucleotides that can be replicated, enabling their precise chemical characterization. In a preferred embodiment, the library comprises a mixture of nucleic acids, preferably randomized or varied on an arbitrary, random or combinatorial fashion with respect 1) length 2) sequence, 3) backbone composition, 4) precursor nucleotide composition 5) chemical or functional groups added at a single nucleotide comprising 6) chemical or functional groups at a second nucleotide position, 7) distance or number of nucleotides between first and second positions. In a particularly preferred mode of operation, selection is achieved by incorporation into approximately each molecule of the mixture a preselected donor or acceptor species, enabling selection for a second molecule or sequence comprising selected molecules which is capable of functioning as an acceptor or donor (i.e., functionally coupling) to the preselected first molecule in a manner dependent on intimate spatial proximity, i.e., intramolecular or intraassembly coupling. The selected molecule or nucleic acid sequence segment may comprise a probe (e.g., a ligand, receptor, aptamer, shape recognition partner) or a catalytic recognition partner (e.g., a ribozyme, catalytic DNA, enzyme or catalyst) and may be a sequence of nucleotides (e.g., an aptamer, ribozyme or catalytic DNA molecule) or a nonnucleotide molecule (e.g., a selected molecule), preferably a heretofore unknown and selectable nucleotide or nonnucleotide molecule.

The invention is also drawn to a method for selecting a recognition element (e.g., an aptamer, ligand, receptor or catalytic species) from a diverse mixture of preferably amplifiable molecules (e.g., a nucleic acid library) comprising a preselected specific recognition partner or probe (i.e., an aptamer, nucleotide ligand, nucleotide receptor, shape recognition partner) or catalytic recognition partner (e.g., a ribozyme, a catalytic DNA sequence, catalyst or enzyme) attached to a fixed-position nucleotide or sequence, optionally by specific binding or hybridization. The preselected recognition partner is preferably an effector molecule, more preferably an effector molecule or conjugate comprising a donor or acceptor signal-generating species. The library is then selected for a second, heretofore undiscovered probe or catalyst comprising or binding to a selected donor or acceptor molecule or nucleic acid sequence. Selection is directed toward a detectable signal resulting from functional coupling brought about by the spatial proximity of preselected and selected recognition partners comprising a single discrete structure. Functional coupling is detected by single-molecule sequencing and amplification as disclosed herein. It will be apparent to the skilled artisan on reading this disclosure that high-resolution selection of a highly diverse library (e.g., greater than $10^{12}$ and preferably greater than about $10^{15}$ molecules) based upon functional coupling between first and second donor and acceptor species cannot be achieved sans single-molecule detection. Discrimination of functional coupling within a single multimolecular structure requires the ability to resolve with single-molecule sensitivity the interaction between donor and acceptor species comprising the single multimolecular structure.

Two or more selected recognition elements can be combined within a single multimolecular structure to provide a useful synthetic template of the instant invention, i.e., a bivalent or multivalent template capable of assembling nucleotide and nonnucleotide molecules, advantageously positioning the molecules for additive, combined, cooperative or synergistic interaction, i.e., template-directed molecular positioning and/or functional coupling.

Nucleotide templates are combinations of defined sequence segments capable of attaching at least two selected molecules to one another, wherein the template is capable of specifically recognizing at least one of the selected molecules. The other selected molecule may be specifically, covalently or pseudoirreversibly attached to the template. Nucleotide templates can be transcribed, amplified, replicated and imprinted to provide clones, replicates, mimetics, imprints, conjugates and progeny therefrom, including nucleotide or nonnucleotide molecular templates. Templates may be synthesized ab initio from nucleotide or nonnucleotide precursors, i.e., molecules, monomers or polymers, or they may prepared by chemical and/or enzymatic methods known in the art, or they may prepared by cloning, replication, transcription, imprinting, or in vitro amplification, optionally including iterative cycles of willful infidelity and/or directed evolution.

Selected recognition elements, templates, multimolecular structures and multimolecular devices may also be immobilized, insolubilized, attached to or operatively associated with an insoluble, partially insoluble, colloidal, particulate, dispersed or suspended substance, and/or a dehydrated or solid phase comprising a solid support. Solid supports include immobilization matrices, insolubilized substances, solid phases, surfaces, substrates, layers, coatings, transducers and transducer surfaces, woven or nonwoven fibers, matrices, crystals, membranes, liposomes, vesicles, gels, sols, colloids, insoluble polymers, plastics, glass, biological, biocompatible, bioerodible and biodegradable polymers and matrices, suspensions, precipitates, microparticles, nanoparticles, microstructures and nanostructures. Commonly used solid phases include monolayers, bilayers, vesicles, liposomes and cell membranes or fixed cells, commercial membranes, resins, beads, matrices, fibers, chromatography supports and other separation media, hydrogels, foams, polymers, plastics, microparticles, nanoparticles, glass, silicon and other semiconductor substrates. Microstructures and nanostructures include, without limitation, microminiaturized, nanometer-scale and supramolecular probes, tips, bars, pegs, plugs, rods, sleeves, wires, filaments, tubes, ropes, tentacles, tethers, chains, capillaries, vessels, walls, edges, corners, seals, pumps, channels, lips, sippers, lattices, trellises, grids, arrays, cantilevers, gears, rollers, knobs, steps, steppers, rotors, arms, teeth, ratchets, zippers, fasteners, clutches bearings, sprockets, pulleys, levers, inclined planes, cords, belts, cams, cranks, wheels, axles, rotating wheels, springs, nuts, screws, bolts, shafts, pistons, cylinders, bearings, motors, generators, gates, locks, keys, solenoids, coils, switches, sensors, transducers, actuators, insulators, capacitors, transistors, resistors, semiconductors, diodes, electrodes, cells, antennae, appendages, cages, hosts, capsules, sieves, coatings, knedels, ultrafine particles and powders and micromachined and nanofabricated substrates, surfaces, layers, films, polymers, membranes and parts including stationary, mobile, attached, tethered, ratcheted and robotic structures, devices, machines, components, elements and features. The attachment may be covalent or noncovalent, specific or nonspecific. The method of attachment may be optimized to achieve a preferred orientation of a synthetic heteropolymer, defined sequence segment, discrete structure, nucleotide-based multimolecular device or specifically bound or hybridized selected molecule or selected nucleic acid sequence. For some applications, it may be desirable that. a synthetic heteropolymer, defined sequence segment, multimolecular structure or a selected molecule or selected nucleic acid sequence capable of specifically binding or hybridizing a multimolecular structure be attached to a solid support in an array, preferably an ordered array such as a grid or other pattern, and optionally a three-dimensional array, e.g., an array comprising multiple layers of molecules, nucleotides, multimolecular structures or multimolecular devices. For other applications, it may be desirable that multimolecular structures immobilized to a solid support comprise an array of nucleotides, optionally arbitrary or randomized sequences or an arbitrarily or randomly arranged array or library of sequences, e.g., a cDNA array or a library of hybridizable or complementary sequences. Arrays, grids, supramolecular assemblies, three-dimensional lattices or other patterns of immobilized molecules or defined sequence segments comprising synthetic heteropolymers, multivalent heteropolymeric hybrid structures and nucleotide-based or nonnucleotide multimolecular structures can be achieved either by surface deposition of defined sequence segments, selected nucleic acid sequences or selected molecules (i.e., ligands, receptors, structural or effector molecules) or by in situ synthesis of selected molecules or polymers on solid supports.

Attachment surfaces may be modified by covalent and noncovalent techniques such as photochemical coupling, plasma treatment, chemical etching, chemical grafting and micromachining processes which are well known in the art such as lithography, thin film deposition, wet and dry substrate etching, plating, bonding, fusion, templating, injection molding, and the like. Defined sequence segments, selected molecules or selected nucleic acid sequences comprising synthetic heteropolymers, discrete structures and multimolecular structures of the instant invention may be localized at or near a transducer surface by methods including, but not limited to, covalent attachment, hybridization, specific binding, adsorption, encapsulation, controlled deposition and/or self-assembly. Alternatively, a defined sequence segment, selected nucleic acid sequence, or selected molecule (e.g., a peptide ligand or receptor) can be synthesized on a surface in situ (e.g., Fodor et al. (1991) Science, 251:767–772) followed by specific binding or hybridization of a selected molecule, selected nucleic acid sequence or defined sequence segment comprising a nucleotide-based discrete structure. In addition to surface attachment, synthetic heteropolymers, discrete structures and multimolecular devices may be incorporated or encapsulated within a transducer, e.g., a microvesicle, microparticle, liposome, monolayer, membrane, film, gel or polymer. Multimolecular devices embedded, entrapped or incorporated in this manner can be used to transfer mass, energy, electrons or photons or perform useful work across a membrane or within a segregated phase, environment or vessel. Methods for embedding, entrapping and attaching substances using lipids, micelles, liposomes, membranes and membrane mimetics are well known in the art (e.g., Betageri et al. (1993) Liposome Drug Delivery Systems, Technomic Publishing Company, Lancaster Pa.; Gregoriadis, G. (Ed.) (1993) Liposome Technology, volumes 1, 2 and 3, Boca Raton, Fla., CRC Press). A wide variety of established techniques may be used to prepare or modify attachment surfaces, including, but not limited to, addition of amino groups by fuming of nitrous acid, bromoacetylation, oxidation by use of plasma, ultraviolet light or an electron beam as energy source in the presence of oxygen and air, chemical grafting, coating with bifunctional reagents (e.g., glutaraldehyde) or polymers (e.g., latex), covalent attachment of linker or spacer molecules, and noncovalent attachment of affinity spacers. Methods for physically and chemically patterning surfaces (e.g., by lithography, etching, plasma deposition, plating, bonding and templating techniques) and for preparing biomolecular arrays on surfaces (e.g., by in situ synthesis, robotic dotting and spotting, lithographic methods such as photolithography, piezoelectric and inkjet technologies) are known in the art (e.g., Drmanac et al. (1989) Genomics 4:114–128; Fodor et al. (1991) Science, 251:767–772; Crkvenjakov et al. (1993) Human Genome Program, U.S. Department of Energy, Contractor-Grantee Workshop III, February 7–10, p. 77; Cubicciotti (1993) DNA chips. In: Medical & Healthcare Marketplace Guide, MLR Biomedical Information Services, 9th Edition, pp. 113–115; Pirrung et al. (1993) Human Genome Program, U.S. Department of Energy, Contractor-Grantee Workshop III, February 7–10, p. 173).

In a particular preferred embodiment of the instant invention, one or more multimolecular structures or multimolecular devices is immobilized to a solid support comprising a transducer, i.e., a device and/or process capable of converting the output (e.g., matter, energy and/or heat) of a molecule or group of molecules comprising a multimolecular complex or multimolecular device to a different form of matter, energy and/or heat, preferably useful work or a detectable signal. Functional coupling between a multimolecular device of the invention (e.g., a multimolecular transducer, a multimolecular switch or a multimolecular sensor) and a transducer surface can occur, e.g., by the transfer of mass, energy, electrons or photons or by coupled chemical or enzymatic reactions that share a common intermediate, mediator or shuttle species. Transducers capable of converting matter, energy, data or information from a first form or state to a second form or state, include, without limitation, electronic, electrical, optical, optoelectronic, electromagnetic, mechanical, electromechanical, electrochemical, photochemical, thermal and acoustical devices. Transducers include, without limitation, batteries, marking devices, memory devices, mechanical devices, parts, motors and machines, optical fibers and waveguides, evanescent waveguides, light-addressable potentiometric devices, photovoltaic devices, photoelectric and photochemical and photoelectrochemical cells, conducting and semiconducting substrates, molecular and nanoscale wires, gates and switches, charge-coupled devices, photodiodes, electrical and optoelectronic switches, imaging and storage and photosensitive media (e.g., films, polymers, tapes, slides, crystals and liquid crystals), photorefractive devices, displays, optical disks, digital versatile disks, amperometric and potentiometric electrodes, ion-selective electrodes, field effect transistors, interdigitated electrodes and other capacitance-based devices, piezoelectric and microgravimetric devices, surface acoustic wave and surface plasmon resonance devices, thermistors, transmitters, receivers, signaling devices and the like. These and other transducers, transduction principles and related devices are known to those of skill in the art (e.g., Taylor (1990) Biosensors: Technology, Applications, and Markets, Decision Resources, Inc., Burlington Mass.).

Transducers of the invention also include devices which comprise, attach, are functionally coupled to or are capable of functionally coupling to MOLECULAR MACHINES of the invention, particularly paired MOLECULAR MACHINES and advantageously systems comprising pairs or networks of paired MOLECULAR MACHINES. Also included are transmitters, receivers and remote sensing and signaling devices, including paired devices comprising sensors and/or transducers, advantageously paired MOLECULAR MACHINES. Particularly preferred are remote signaling and sensing systems comprising networked pairs of paired and functionally coupled MOLECULAR MACHINES. In a preferred aspect of the instant invention, two members comprising a pair of MOLECULAR MACHINES are functionally coupled to one another by transmission of matter, energy or information whose reception does not require direct physical contact (i.e., attachment) between the member MOLECULAR MACHINES, preferably by transmission of a chemical, electrical, electromagnetic or acoustical signal. Where a transducer comprises a remote signaling and/or remote sensing system, the signaling substance, energy or information is considered to be a component of the transducer system. A pheromone, for example, is considered to be a component of a remote signaling system comprising a pair of MOLECULAR MACHINES. A first MOLECULAR MACHINE, e.g., comprising a promolecular delivery system and a second MOLECULAR MACHINE, e.g., comprising a tethered specific recognition device is considered to be functionally coupled by a selected molecule (e.g., a pheromone) that is released by the first MOLECULAR MACHINE and sensed by the second MOLECULAR MACHINE. In this case, the chemical messenger is aptly referred to as a transducer interconnecting a transmitter and a receiver comprising paired and functionally coupled (i.e., donor and acceptor) MOLECULAR MACHINES. In this case, it is the intimate proximity and tight functional coupling of donor and acceptor molecules within each MOLECULAR MACHINE that ironically enables functional coupling between two remote MOLECULAR MACHINES. In other words, intimate proximity and tight functional coupling at the molecular level is necessary and enabling for functional coupling between paired MOLECULAR MACHINES that are separated in and by space (i.e., not physically unattached to one another). A paired MOLECULAR MACHINE may be a single pair of attached and/or functionally coupled MOLECULAR MACHINES or a pair of pairs, pair of pairs of pairs, or a dendrimeric network of paired pairs of MOLECULAR MACHINES capable of collectively performing a useful function that cannot be performed by one member sans the other. Two members of a paired MOLECULAR MACHINE may be directly attached, indirectly attached or unattached to one another. Advantageously, the two members of a pair are functionally coupled, regardless of whether or how they are attached.

Transducers referred to herein typically comprise an organic or inorganic solid support, which may be a substrate, particle, matrix, membrane or surface to which effector molecules comprising nucleotide-based or nonnucleotide multimolecular structures can be attached either directly or through conductive, reflective, transmissive or passive intermediate(s) (e.g., a wire, lead, fiber, connector, interface, layer, channel or conduit). Solid supports include, without limitation, inorganic substrates such as silicon, silica, silicates, plastics, polymers, graphite and metals used in microfabrication of integrated circuits; glasses, plastics, polymers and quartz as used in optical fibers, planar waveguides and optical disks; thin and thick films and organic and inorganic monolayers, bilayers, multilayer stacks, membranes, polymers and coatings as used in semiconductors, field effect transistors, photoelectric devices and sensors; and microparticles, microvesicles, lipid bilayers, dendrimers, nanostructures, and biocompatible polymers as used in diagnostics, drug delivery and medical devices.

Multimolecular switches are nucleotide-based or nonnucleotide devices comprising at least two defined sequence segments or specific recognition pairs capable of participating in stimulus-response coupling, i.e., functional coupling between or among molecules, wherein an input of matter or energy (i.e., a stimulus) to a first defined sequence segment, selected molecule or specific recognition pair results in a stimulus-specific, effector-mediated response at or by a second defined sequence segment, selected molecule or specific recognition pair. Stimulus-specific responses are definitive effector-mediated responses elicited only or approximately only by a specified type or group of molecular or environmental inputs and not, under conditions of use, by unspecified, unintended or interfering substances or energies. For example, two defined sequence segments and/or specific recognition pairs comprising a multimolecular switch responsive to a specified stimulus molecule (e.g., a clinical analyte or therapeutic target) may function in an either/or or mutually competitive fashion with respect to their ability to coexist in the bound state. In this case, the binding of the stimulus molecule at a first defined sequence segment, ligand or receptor may result in the release, binding or activation of a ligand, receptor or effector molecule (e.g., a drug or signal-generating molecule) at a second defined sequence segment or specific recognition site. Alternatively, binding of a stimulus molecule (e.g., an antigen, particle, virus, microbe, quenching species, dye or conjugate) to a recognition site (e.g., an aptamer, ligand or receptor) positioned between donor and acceptor molecules conjugated to defined nucleotide positions of a multimolecular switch can produce as response the activation or inhibition of a particular output (e.g., photon emission by donor or acceptor) by enabling or facilitating (e.g., by serving as an intermediate or cofactor) or interrupting (e.g., blocking, reflecting, or quenching) energy transfer between nucleotide-conjugated donor and acceptor molecules or by stimulating or inhibiting the conjugated donor or conjugated acceptor. In a preferred embodiment, specific binding of a selected molecule, preferably a selected molecule comprising or conjugated to effector molecule, more preferably a selected molecule comprising a signal-generating species (e.g., a ligand, receptor or effector molecule conjugated to a dye, nanoparticle, phosphor, fluorophore or luminescent compound) to an aptamer or modified nucleotide (e.g., a nucleotide comprising a ligand or a receptor) positioned between two labeled nucleotides (e.g., fluorophore-modified or quencher-modified nucleotides) can stimulate as response the activation or inhibition of photon emission by a multimolecular switch.

Multimolecular switches of the instant invention may be nonaptameric, aptameric or heteropolymeric. A nonaptameric molecular switch comprises at least two different specific binding or shape recognition pairs attached to a defined sequence segment which positions the two specific binding or shape recognition pairs for stimulus-response coupling. An aptamer-based multimolecular switch comprises at least two functionally coupled specific recognition pairs, at least one of which is an aptamer sequence. A heteropolymeric multimolecular switch comprises at least two defined sequence segments that participate in stimulus-response coupling, e.g., the influence of binding or activity at one defined sequence segment on binding or activity at another defined sequence segment.

A multimolecular switch can exist in either of at least two states: an active state (i.e., a triggered, stimulated or "on" state) or an inactive state (i.e., a basal, unstimulated, untriggered or "off" state). Multimolecular switches configured as tethered recognition devices of the instant invention can even exist in two (or more) states that generate different signals, e.g., a first signal in the "off" state and a second, different signal in the "on" state. The state of a multimolecular switch relies upon the relative positions or activities of at least three molecules, at least one of which is a single-stranded, double-stranded or partially double-stranded oligonucleotide, aptamer or synthetic heteropolymer. A heteropolymeric multimolecular switch must further comprise or contact at least two additional molecules or selected nucleic acid sequences, at least one of which is a selected molecule. The second molecule may be a selected molecule, a selected nucleic acid sequence or a conjugate thereof. An aptameric multimolecular switch that does not contain a synthetic heteropolymer further requires, to become operational, at least three additional molecules, including 1) a first selected molecule which is conjugated to or incorporated in the aptamer (e.g., by covalent attachment to the aptamer or by conjugation to or synthesis of a nucleotide or nucleotide derivative which is then incorporated as a modified nucleotide during aptamer synthesis), 2) a second selected molecule which is capable of specifically recognizing or being recognized by the first selected molecule (e.g., as a ligand specifically binds a receptor or an enzyme specifically recognizes a substrate), and 3) a third selected molecule (i.e., the aptamer target), preferably an effector molecule and more preferably a signal-generating molecule, which the aptamer specifically recognizes with an affinity dictated by the nucleotide sequence of the aptamer. A nonaptameric multimolecular switch comprises at least a single defined sequence segment that connects two specific binding or shape recognition pairs, each having a member conjugated to a nucleotide or comprising a modified nucleotide of the defined sequence segment.

In a preferred embodiment, referred to herein as a tethered specific recognition device, tethered recognition device or simply tethered device, nucleotide-based or nonnucleotide multimolecular devices, e.g., multimolecular switches, multimolecular sensors and molecular delivery systems, comprise tethered specific recognition partners, e.g., two members of the same specific binding or shape recognition pair covalently or pseudoirreversibly attached to different chemical groups, sites or nucleotides of a single molecule, polymer or multimolecular structure, i.e., a molecular scaffold. The molecular scaffold provides suitable spacing and/or flexibility between the two tethered members of a specific recognition pair to permit the members to specifically attach to one another under defined conditions, e.g., in the absence of a selected target that inhibits, displaces, reverses, precludes or dissociates specific recognition between the tethered members (e.g., a competitor or allosteric inhibitor).

Tethered recognition devices are stimulus-responsive devices comprising a molecular scaffold, optionally a nucleotide-based molecular scaffold, and at least two members of a specific binding or shape-specific pair or four members of two different specific recognition pairs, each member being covalently or pseudoirreversibly attached to the molecular scaffold. Each member of a recognition pair comprising a tethered recognition device is covalently or pseudoirreversibly tethered to its specific recognition partner, so the partners remain indirectly attached to one another even when they are not directly and specifically attached. Tethered members of a specific binding or shape recognition pair, for example, remain connected to one another by covalent or pseudoirreversible attachment to a common molecular scaffold (i.e., a molecule or group of molecules), whether the binding partners are specifically bound or unbound (i.e., dissociated). The molecular scaffold preferably comprises a nucleotide, multimolecular structure or individual molecule which is linear, branched, circular, polygonal, bent, folded, looped, jointed, hinged and/or flexible, allowing the permanently attached specific recognition partners to exist in either of two states, specifically and directly attached (i.e., attached specifically and directly in a quasireversible manner as well as directly and permanently by covalent or pseudoirreversible means) or indirectly and not specifically attached. At least one member of at least one specific recognition pair comprising a tethered recognition device preferably comprises or attaches to an effector molecule, e.g., a drug or signal-generating species, so that the two states of the device are functionally distinguishable, e.g., by activation or inhibition of the attached effector. The molecular scaffold, preferably comprising a bifunctional or multifunctional molecule, preferably a heterofunctional molecule, polymer, copolymer or defined sequence segment which optionally comprises or attaches to a solid support, is designed, selected or engineered to provide suitable spacing and/or flexibility between tethered members of a specific recognition pair to permit interaction between the two members of the pair under defined conditions, e.g., conditional upon the absence of a stimulus (e.g., a selected target, analyte, competitor or allosteric inhibitor) that inhibits, displaces, reverses or precludes specific binding or dissociates a quasireversible complex between specific recognition partners.

One example of a tethered specific recognition device is a heteropolymeric multimolecular switch comprising three defined sequence segments: a first effector-attachment segment, a second effector-inhibiting segment, and a third target-binding segment. An effector species, preferably one capable of existing in both active and inactive or inhibited forms (e.g., an enzyme such as glucose oxidase, horseradish peroxidase, alkaline phosphatase, β-galactosidase, malate dehydrogenase, glucose-6-phosphate dehydrogenase) is attached to the first defined sequence segment, preferably to the 3' or 5' end and more preferably to the 5' end, in such manner to retain effector activity. The method of attachment may be covalent or noncovalent, so long as the association between the effector species and the first defined sequence segment is irreversible or pseudoirreversible, i.e., sufficiently permanent and stable to remain intact throughout the operational lifespan of the device. Covalent attachment may be achieved, e.g., using well known enzymatic and crosslinking methods (cf. Wong (1991), *Chemistry of Protein Conjugation and Crosslinking*, CRC Press) to attach hapten or protein effectors to an amino-, carboxyl- or thiol-modified nucleotide (e.g., from Glen Research, Sterling Va. and Boehringer Mannheim corporation, Indianapolis Ind.), preferably a modified 3' or 5' terminus and more preferably a 5'-terminal primary amine. Pseudoirreversible attachment may be achieved by specifically binding an avidin-effector or streptavidin-effector conjugate to a biotinylated nucleotide or by hybridizing an oligonucleotide-effector conjugate to the first defined sequence segment. The effector-conjugated first defined sequence segment of the heteropolymer is of such length, preferably about two to 80 nucleotides and more preferably about 10 to 50 nucleotides, to tether the second (effector-inhibiting) defined sequence segment within suitable range and yet with adequate flexibility to effectively inhibit the conjugated effector. Nucleotide spacers or sequence(s) are included, as appropriate, to maximize effector inhibition by the second defined sequence segment. The third (i.e., target-binding) defined sequence segment may be a subset of the first defined sequence segment, or it may be contiguous with either the first or the second defined sequence segment. This target-binding defined sequence segment is selected to specifically bind or hybridize a selected target with higher relative affinity (as indicated by affinity constant or melting temperature, as the case may be) than that of the second defined sequence segment for the conjugated effector. Hence, in the presence of the selected target molecule or sequence, specific binding or hybridization of the third defined sequence segment to the target disrupts the interaction of the second defined sequence segment with the conjugated effector. On release of effector inhibition by the target (i.e., the stimulus), the activated effector generates a stimulus-dependent signal (i.e., the response). In this particular tethered device configuration, the effector species is tethered to its specific binding partner (i.e., the second defined sequence segment) by means of the first defined sequence segment (i.e., the tether sequence). In other words, two members of a specific binding or shape recognition pair are mutually tethered, one member being a defined sequence segment (i.e., the second defined sequence segment). Both members are attached to a defined sequence segment (i.e., the first defined sequence segment). A particularly preferred embodiment of this heteropolymeric tethered specific recognition device is the special case in which the third defined sequence segment is not just a subset of the first defined sequence segment, it is one and the same sequence, i.e., the device comprises only two defined sequence segments (cf. Example 11, vide infra). In this case, the first defined sequence segment fulfills the dual role of 1) tethering the second defined sequence segment to the effector species with suitable spacing and flexibility to allow specific binding between the effector and the second defined sequence segment, and 2) specific recognition and binding to a selected target with sufficient affinity to disrupt or preclude specific binding between the effector and the second defined sequence segment. Target binding therefore releases effector inhibition, yielding a stimulus-dependent response (i.e., effector activation). The specifically bound effector comprising a tethered recognition device need not be inhibited when specifically bound, e.g., by a second defined sequence segment. Specific binding between tethered binding partners may also result in activation of the specifically bound effector species, e.g., by proximity-dependent functional coupling between donor and acceptor species (e.g., Example 11). In this case, target recognition (i.e., by specific binding or hybridization) can inhibit the signal resulting from a functionally coupled effector and/or increase the signal generated by an uncoupled donor (cf. Examples 10 and 11, vide infra). The detectable output may therefore be a decrease in acceptor or coupled effector signal, an increase in donor signal, or some combination, quotient, product or derivative thereof.

In alternative modes of operation, a tethered specific recognition device may comprise, e.g., a ligand and its receptor conjugated to different sites or positions of a single defined sequence segment; multiple hybridized, contiguous or connected defined sequence segments comprising a discrete structure; a sequence of nonnucleotide monomers (e.g., amino acids, sugars, ethylenes, glycols, amidoamines) or a pair or group of connected polymers comprising a molecular scaffold; two or more ligands and their corresponding receptors, each conjugated to a different nucleotide position, site or functional group of one or more defined sequence segments or polymers comprising or attached to a molecular scaffold; and even two or more noncomplementary oligonucleotides, each conjugated to a selected molecule, preferably an effector species, which is tethered by a defined sequence segment or a sequence of nonnucleotide monomers comprising a molecular scaffold, each oligonucleotide preferably being complementary to a different defined sequence segment of the specific recognition device (e.g., Example 10, vide infra).

Tethered specific recognition devices have several distinct advantages over prior art diagnostic assays (e.g., immunoassays, DNA probe assays), chemical sensors (e.g., for blood gases and electrolytes), biosensors (e.g., for glucose and therapeutic drugs) and drug delivery systems (e.g., biodegradable polymers, gels and transdermal devices) which rely on freely diffusible and/or matrix-entrapped recognition reagents, signal-generating species and/or drugs. Tethered specific recognition devices are self-contained multimolecular assemblies, i.e., all necessary recognition and effector species comprise or attach a single multimolecular structure or molecular scaffold. Hence the only potentially diffusible species to hinder stimulus-response kinetics, efficiency or reliability is the stimulus molecule (e.g., a selected molecule or selected nucleic acid sequence). Also, tethered recognition devices can be designed and constructed with defined molecular composition, owing to scaffold-dependent positioning of recognition sites. Within-lot and between-lot reproducibility are therefore limited only by the stability of constituent molecules and not by the compositional heterogeneity and positional variability of alternative multimolecular reagent formulations. Additionally, tethered devices can be constructed with multiple effector molecules, preferably signal-generating species, in such manner that different device states generate different signals. The reportable or actionable output of the device may therefore be a product, sum, quotient, derivative, function, transformation or algorithm of two or more signals which is more reliable and/or more informative than either signal alone. For example, a tethered device configured as a binary switch having two distinct states, each generating a different fluorescent signal, produces an output which depends on which of two different fluorescence energy transfer acceptors is excited by a donor fluorophore capable of transferring energy to one or the other acceptor (cf. Example 10, vide infra).

In a preferred embodiment, tethered specific recognition devices described herein are immobilized to a solid support. Immobilized tethered devices are particularly useful for dry-reagent product configurations, because effector species pseudoirreversibly attached to a molecular scaffold attached to a solid support is not freely diffusible in a surrounding medium. Hence, on addition of a fluid sample to the dry-reagent device, the concentration of effector species at the liquid-solid interface (i.e., within the tethering distance of the scaffold) remains relatively constant. In conventional specific binding assay systems comprising a soluble or diffusible reporter or labeled species (e.g., for diagnostic, monitoring and drug discovery applications, including high-throughput screening) the final concentration of the labeled reagent is inversely proportional to the volume of sample added. Any variability in sample volume influences the concentration of the label and therefore the equilibrium binding result. Also, additional reagent additions, separation steps, washing procedures, evaporation and other handling and environmental factors compromise accuracy, precision, reproducibility and sensitivity of the assay. Tethered recognition devices of the instant invention are relatively unaffected by variability in sample and reagent volume additions and fluid manipulations, because labeled species (i.e., effectors) are pseudoirreversibly attached to the device. Effectors are not freely diffusible and are therefore not variably diluted with variable volume addition. Immobilized tethered recognition devices provide the benefits of homogeneous assay techniques (i.e., no need for physical separation of bound from free signal-generating species, because specific binding influences the activity of the signal-generating species), advantageously in a solid phase format that minimizes diffusion distances between participating specific binding partners and signal-generating species and also provides intimate contact and therefore rapid, efficient communication with a macroscopic device or a surface, preferably a transducer surface.

In another preferred embodiment, reversible activation, repeat-action, tethered specific recognition devices described herein are used in detect-and-actuate and search-and-destroy modes for military and defense applications, decontamination, detoxification, environmental remediation, and agriceutical (e.g., fertilizers, vaccines and pesticides), cosmeceutical, nutraceutical and pharmaceutical applications (i.e., smaRTdrugs, vide supra) and in multimolecular adhesives and molecular adherents.

In short, tethered specific recognition devices of the instant invention advantageously comprise two members of a specific binding pair or even two different specific recognition pairs tethered by covalent attachment or, optionally, pseudoirreversible attachment (e.g., using avidin/biotin or a hybridized oligonucleotide conjugate) to a scaffold comprising a multimolecular device in such manner that specific binding and unbinding between covalently connected molecules provides a useful and quasireversible (i.e., potentially repeatable) function, e.g., stimulus-responsive binary switching. Covalently or pseudoirreversibly tethering specific recognition pairs and effector molecules to the scaffold obviates dissociative or diffusional loss or dilution of participating binding partners and effectors, providing a reliable, efficient, reproducible and robust multimolecular switch composition. Tethered specific recognition devices are preferably nucleotide-based (i.e., a nucleotide scaffold is used for molecular positioning), but can also be constructed using a nonnucleotide scaffold, preferably a flexible polymer, more preferably a copolymer or heteropolymer and optionally a polymer comprising folds, bends, joints, branchpoints and/or hinges.

The closest prior art to the tethered specific recognition devices described herein are nucleic acid assays using a nucleotide-based molecular switch comprising mutually complementary switch sequences capable of existing either in the hybridized or unhybridized state, depending on whether a selected nucleic acid target is present (Lizardi, et al., U.S. Pat. No. 5,118,801). Specifically, Lizardi et al. describe a probe for the detection of a nucleic acid target sequence containing a olecular switch comprising three essential elements: a probe sequence of 20–60 nucleotides surrounded by switch sequences of 10–40 nucleotides which are complementary to each other, wherein the state of the switch is useful for selectively generating a detectable signal if the probe is hybridized to a target. Unlike the molecular switches described by Lizardi et al., tethered specific recognition devices described herein can respond to any type of molecular stimulus or surface feature (i.e., nucleotide or nonnucleotide molecules or structural shapes). Also, the instant invention does not rely on internal hybridization of switch sequences. Although nucleic acid detection can be achieved using tethered recognition devices described herein, e.g., using effector-conjugated oligonucleotides complementary to defined sequence segments of the molecular scaffold (cf. Example 11), the instant invention does not involve the allosteric switch process described by Lizardi et al. and requires entirely different compositions and methods. First, whereas the allosteric switches described by Lizardi et al. require at least three essential sequence elements (i.e., a probe sequence and two switch sequences), different embodiments of the instant invention can be practiced with as few as two defined sequence segments (e.g., Example 11, vide infra) and even a single defined sequence segment (e.g., Example 13, vide infra). Second, tethered recognition devices of the instant invention may be designed to exist in at least two different states (i.e., basal and stimulated or "on" and "off" states), each of which generates a distinctly different signal (e.g., Example 10, vide infra). Multimolecular switches generating a different signal in each state provide a more reliable and informative output than a "signal-when-on" or "signal-when-off" switch, because 1) signaling occurs regardless of the state of the switch, 2) one of two selected signals can serve as a control to ensure the functional integrity of the device, and 3) signal processing, calibration and data reduction algorithms can be used with a multi-signal device to provide a quantitative result that does not directly depend on the response of a single effector or amplitude of a single signal. Third, unlike the allosteric molecular switch described by Lizardi et al., multimolecular switches of the instant invention do not rely on internal hybridization of complementary nucleotide switch sequences. Fourth, multimolecular switches described herein do not require a nucleic acid probe sequence. Although multimolecular switches of the instant invention can incorporate defined sequence segments comprising nucleic acid probes for the detection of selected nucleic acid targets (e.g., Example 11, vide infra), these devices do not operate by means of an allosteric switch mechanism, i.e., hybridization of target and probe sequences precluding internal hybridization of complementary switch sequences. Fifth, tethered specific recognition devices of the instant invention can be distinguished from prior art molecular switches in comprising combinations of effector molecules and mutually specific ligands and receptors which are both covalently attached to one another, optionally via an intervening molecular scaffold or tether, and capable of existing in both specifically bound and unbound (i.e., dissociated) configurations. Finally, Lizardi et al. do not describe molecular switches capable of detecting selected nonoligonucleotide molecules, i.e., does not provide a general method for detecting different molecules of commercial importance, e.g., clinical, environmental, veterinary, military, agricultural, and industrial process monitoring analytes). Nor do the allosteric switches of Lizardi enable triggered release of an effector molecule in response to a specific binding event, e.g., drug delivery by a nucleotide-based prodrug. Unlike the hybridization-based switch described by Lizardi et al. the instant invention encompasses numerous embodiments unrelated to diagnostic switches, e.g., a multimolecular switch comprising a triggered-release multimolecular drug delivery system (e.g., a heteropolymeric prodrug) or a reversible tethered specific recognition device for search-and-destroy or detect-and-actuate applications (e.g., detoxification, environmental remediation, chemical and biological defense, agriceutical delivery, prodrug targeting and dynamic imaging).

Multimolecular devices of the invention which position two or more selected molecules, nucleic acid sequences or conjugates to provide additive or partially additive, combined, simultaneous, cooperative or synergistic functional coupling between or among molecules (instead of or in addition to stimulus-response coupling) are referred to as multimolecular transducers. Multimolecular transducers are multimolecular devices whose function depends on additive or partially additive, combined, simultaneous, cooperative or synergistic functional coupling between or among two or more selected molecules. Multimolecular transducers of the instant invention are capable of transforming a first form or state of matter, energy, order or information into a second form or state of matter, energy, order or information and include, without limitation, molecular channeling devices, enzyme channeling devices, molecular processing devices, electron transfer devices, energy transfer devices, and the like. A multimolecular transducer comprises at least two specific recognition pairs or defined sequence segments that function in a combined or concerted manner to perform a function different from or superior to that of any constituent molecule.

Aptamer-based multimolecular transducers of the instant invention comprise a single-stranded, double-stranded or partially double-stranded aptamer which is either 1) conjugated to a first selected molecule and specifically bound to a second selected molecule, wherein the second selected molecule is an effector molecule which is functionally coupled to the first selected molecule, or 2) a defined sequence segment of a synthetic heteropolymer. Nonaptameric multimolecular transducers comprise at least a single defined sequence segment connecting two specific binding or shape recognition pairs which are functionally coupled to one another, e.g., a member of the first specific binding or shape recognition pair, transfers mass or energy to a member of the second specific binding or shape recognition pair, wherein donor and acceptor members are either effector molecules or conjugates of effector molecules and ligands or receptors.

Multimolecular sensors are multimolecular devices, optionally comprising a multimolecular transducer and/or a multimolecular switch, which are capable of sensing, detecting, measuring, monitoring, determining or quantifying one or more substances or events. Sensor means any and all sensing means and devices known in the art, including, without limitation, mechanical sensors, force and mass sensors, velocity sensors, pressure sensors, acoustic sensors, temperature and thermal sensors, chemical sensors, biosensors, electrochemical sensors, optical sensors, electromagnetic sensors, electrical sensors, electronic sensors, optoelectronic sensors, motion sensors, photodetectors, gas sensors, liquid sensors, liquid and solid level sensors as well as multimolecular devices and tethered specific recognition devices of the instant invention. Sensors of the invention further include devices which comprise, attach, are functionally couple to or are capable of functionally coupling to MOLECULAR MACHINES of the invention, particularly paired MOLECULAR MACHINES and advantageously systems comprising pairs or networks of paired MOLECULAR MACHINES. Multimolecular devices include multimolecular switches, multimolecular transducers, multimolecular sensors, nucleotide-based molecular delivery systems and multimolecular drug delivery systems described herein as comprising at least two specific recognition pairs or two defined sequence segments. Functional coupling between or among selected molecules and selected nucleic acid sequences is brought about nucleotide-dependent molecular positioning. Tethered specific recognition devices comprise at least two members of one specific binding or shape recognition pair or four members of two specific recognition pairs. Each member is either covalently or pseudoirreversibly attached to a molecular scaffold. The scaffold may be a defined sequence segment, a nucleotide, or a nonnucleotide molecule.

Multimolecular delivery systems and molecular delivery systems are multimolecular structures capable of binding or storing and transporting, carrying, providing, presenting, delivering or releasing a selected molecule or nucleic acid sequence to a desired target, receptor, site, region, proximity or destination. Like multimolecular switches, transducers and sensors, multimolecular delivery systems comprise at least two specific recognition pairs or two defined sequence segments connected and functionally coupled by nucleotide-dependent positioning of the constituent specific recognition sites. Unlike multimolecular switches, transducers and sensors, however, a preferred embodiment of multimolecular delivery system construction produces additive, combined or synergistic functional coupling of a first and second selected molecule or nucleic acid sequence to a third object (i.e., a selected target) comprising a molecule, group of molecules, process, disease or condition. In other words, a preferred form of functional coupling for multimolecular delivery systems does not involve the exchange of matter or energy between two specific recognition pairs connected by nucleotides, but instead relies on the combined binding or activity of two specific recognition pairs positioned by nucleotides to modulate the binding or activity of a selected target.

Multimolecular drug delivery systems are molecular delivery systems capable of facilitating, enhancing, enabling or modulating the administration, delivery, dosing, safety, efficacy, release, activation, clearance, pharmacodynamics or pharmacokinetics of a drug or prodrug administered to or contacting an organism. When used in reference to a multimolecular drug delivery system, immobilized refers either to an insoluble multimolecular structure or to a multimolecular structure that is rendered insoluble by attachment to a biological or biocompatible solid support. Biocompatible means an exogenous substance that is relatively nonimmunogenic, nonallergenic and nontoxic when administered in vivo.

A drug is any molecule, group of molecules, complex or substance administered to an organism for a diagnostic, therapeutic, forensic or medicinal purpose, including medical imaging, diagnostic, therapeutic, prognostic or preventive screening, detection or monitoring, contraceptive, cosmetic, nutraceutical, pharmaceutical, prosthetic and prophylactic applications. Prodrugs are drugs, drug precursors or modified drugs which are not fully active or available until converted in vivo or in situ to their therapeutically active or available form. Prodrugs of the instant invention include drugs specifically bound in inactive form to a first ligand, receptor or defined sequence segment of a multimolecular drug delivery system, wherein the inactive drug is released or activated by binding of a ligand or receptor, preferably a therapeutic ligand or receptor, at a second defined sequence segment, ligand or receptor comprising the multimolecular drug delivery system.

Nonaptameric nucleotide-based multimolecular devices comprise at least two specific binding or shape recognition pairs attached in a site-directed manner to a defined sequence segment or plurality of attached defined sequence segments. At least one specific binding or shape recognition pair advantageously comprises an effector molecule. The defined sequence segment provides for ordered attachment of the two specific binding or shape recognition pairs in suitable spatial proximity that binding or activity of a member of a first specific binding or shape recognition pair influences the binding or activity of a member of the second specific binding or shape recognition pair.

A nucleotide-based nonaptameric multimolecular switch typically comprises two and optionally more than two specific binding or shape recognition pairs attached to nucleotides of a discrete structure and thereby attached to one another by nucleotides. The specific binding or shape recognition pairs are typically positioned within about one micron of one another, preferably within about 100 nm of one another and more preferably within about 10 nm of one another, by site-directed attachment to nucleotides comprising or hybridized to a defined sequence segment. In the simplest case, a first member of a first specific binding pair (e.g., biotin) is attached to (or incorporated as) a 3'-modified nucleotide of a defined sequence segment (e.g., using biotin phosphoramidite or a biotin-spacer-support). A first member of a second specific binding pair is attached to (or incorporated as a constituent of) a second nucleotide of the defined sequence segment (e.g., by incorporation of a fluorescein-labeled 5'-terminal nucleotide). The number of nucleotides between nucleotide-attached members of the first and second specific binding pairs is designed to preclude simultaneous binding of both specific binding pairs, i.e., the defined sequence segment provides inadequate docking space for second members of both specific binding pairs to remain bound within a single discrete structure. Hence, the mutual proximity of the two specific binding (and optionally shape recognition) pairs brought about by site-directed attachment to the defined sequence segment sets up a mutual competition between the two specific binding pairs. In the presence of both members of both specific binding pairs (at equimolar concentrations), only the higher affinity specific binding pair remains specifically bound. The lower affinity specific binding pair preferentially dissociates, and rebinding is sterically hindered by specific binding of the higher affinity pair. In a preferred embodiment of a nucleotide-based multimolecular switch, the lower affinity specific binding pair comprises donor and acceptor members which are specifically bound and functionally coupled, e.g., by fluorescence energy transfer. The second, higher affinity specific binding pair comprises a nucleotide-conjugated receptor directed against an analyte (e.g., a diagnostic marker, a pesticide, an environmental pollutant, an infectious contaminant), wherein specific binding does not occur unless and until the multimolecular switch comes in contact with the analyte. In the presence of the analyte, high-affinity binding between analyte and receptor induces dissociation of the lower affinity specific binding pair, interrupting fluorescence energy transfer. Activation of the switch by analyte is thus detectable by an increase in emission of the donor fluorophore, a decrease in emission of the acceptor fluorophore, or a change in the ratio of the two.

Single-stranded and double-stranded nucleic acids capable of specifically binding nonoligonucleotide molecules may be identified and produced using in vivo or in vitro methods known in the art. For example, recombinant DNA methods have been used to produce modified host cells comprising stochastic synthetic polynucleotides for screening and selection of DNA or RNA sequences showing a desired property (Ballivet et al., GB 2 183 661 A). A variety of in vitro selection methods have also been described for identifying nucleic acids that bind nonoligonucleotide molecules (e.g., Gold et al., U.S. Pat. No. 5,270,163), including single-stranded RNA (e.g., Ellington and Szostak (1990) *Nature* 346:818–822), single-stranded DNA (e.g., Bock et al. (1992) *Nature* 255:564–566, Wang et al. (1993) *Biochemistry* 32:1899–1904), and double-stranded DNA (e.g., Bielinska et al. (1990) *Science* 250:997–1000) aptamers. By way of example, single-stranded and double-stranded RNA and DNA aptamers can be selected in vitro by methods including, but not limited to, those of Ellington et al. (Ellington and Szostak, *Nature* 346:818–822) and Bielinska (Bielinska et al. (1990) *Science* 250:997–1000) which rely on enrichment cycles comprising alternating amplification and selection steps. Following is a brief summary of these methods, for illustrative purposes only. For DNA aptamers, a library of oligonucleotide sequences (sequence library) is synthesized comprising a randomized nucleotide region flanked by two defined polymerase chain reaction (PCR) primer binding sites. The sequence library is amplified to yield double-stranded PCR products. To select for double-stranded DNA aptamers, the resultant population of double-stranded PCR products is then incubated (sans primer biotinylation and strand separation) with an identified target molecule (e.g., a target protein). For preparation of single-stranded aptamers, the downstream PCR primer is biotinylated at the 5' end and PCR products are applied to an avidin-agarose column. Single-stranded DNA oligonucleotides are recovered by elution with a weakly basic buffer. Resultant DNA strands are incubated with a selected target molecule (e.g., a target protein) either in solution or bound to a filter, chromatography matrix or other solid support. Nonbinding sequences are separated from binding sequences, e.g., by selective elution, filtration, electrophoresis or alternative means of partitioning bound from free fractions. Typically, preselection and/or counterselection steps are included in the selection protocol to select against (i.e., remove or discard) nucleic acids that bind to nontarget substances (e.g., to a filter, gel, plastic surface or other partitioning matrix) and/or irrelevant epitopes (e.g., the membrane portion of a membrane-associated receptor). Target-bound DNA sequences are then dissociated from the target and subjected to another round of PCR amplification, binding and partitioning. After several rounds of enrichment and/or affinity maturation, the final amplification step may be performed with modified primers allowing subcloning into a plasmid restriction site and sequencing of target-binding positive clones. For RNA aptamers, the oligonucleotide sequence library is amplified to yield double-stranded PCR products containing a T7 bacteriophage polymerase promoter site. RNA molecules are then produced by in vitro transcription using T7 RNA polymerase. The resultant single-stranded RNA pool is then incubated with the selected target molecule, optionally immobilized. Target-bound RNA is separated from unbound RNA, e.g., by elution, filtration or alternative partitioning procedures, and reverse transcribed to DNA. The resultant population of DNA molecules is then amplified to produce a second round of double-stranded DNA products comprising the T7 RNA polymerase promoter. After repeated cycles of amplification and selection, modified PCR primers are used to allow subcloning into a plasmid and sequencing of selected clones.

Prior art methods for identifying nonnaturally occurring nucleic acid molecules capable of specifically binding nonoligonucleotide targets (i.e., for selecting aptamers or nucleic acid ligands) rely particularly on the steps of partitioning and amplification. For example, Gold et al., U.S. Pat. No. 5,270,163 describe a method referred to as SELEX (Systematic Evolution of Ligands by EXponential Enrichment) for the identification of nucleic acid ligands as follows. A candidate mixture of single-stranded nucleic acids having regions of randomized sequence is contacted with a target compound and those nucleic acids having an increased affinity to the target are partitioned from the remainder of the candidate mixture. The partitioned nucleic acids are amplified to yield a ligand enriched mixture. Bock et al. describe a method for identifying oligomer sequences that specifically bind target biomolecules involving complexation of the support-bound target molecule with a mixture of oligonucleotides containing random sequences and sequences that can serve as primers for PCR (Bock et al. (1992) *Nature* 255:564–566). The target-oligonucleotide complexes are then separated from the support and the uncomplexed oligonucleotides, and the complexed oligonucleotides are recovered and subsequently amplified using PCR. The recovered oligonucleotides may be sequenced and subjected to successive rounds of selection using complexation, separation, amplification and recovery.

Aptameric and heteropolymeric synthetic defined sequence segments of the instant invention can be selected for their ability to specifically bind nonoligonucleotide molecules using the above-referenced methods (e.g., Gold et al., U.S. Pat. No. 5,270,163), Ellington and Szostak (1990) *Nature* 346:818–822), Bock et al. (1992) *Nature*

255:564–566, Wang et al. (1993) *Biochemistry* 32:1899–1904, and Bielinska et al. (1990) *Science* 250:997–1000) that rely on repeated cycles of contacting an oligonucleotide mixture with a target nonoligonucleotide molecule, affinity-dependent partitioning of the oligonucleotide-target complexes from unbound oligonucleotides, and amplifying the target-bound oligonucleotides. Alternatively, aptameric defined sequences of the instant invention, particularly aptameric defined sequence segments comprising synthetic heteropolymers or multimolecular devices, can be selected by methods that do not rely on the combination of affinity-dependent partitioning and amplification.

For example, a synthetic aptamer may be selected from a mixture of nucleic acids, preferably a diverse mixture or nucleic acid library and more preferably a diverse mixture or library of nucleic acid molecules comprising at least one randomized sequence, based upon the ability to assemble two molecules or groups of molecules, preferably selected molecules and/or conjugated and/or immobilized selected molecules, more preferably selected molecules comprising effector molecules and most preferably selected molecules comprising signal-generating molecules, so as to render the assembled molecules or groups of molecules distinctly detectable, preferably as a single discrete structure.

In a preferred embodiment, selected molecules, preferably signal-generating molecules, are assembled in suitable proximity to produce a detectable image or signal whose detection enables the identification and isolation of a single discrete structure comprising an aptamer, preferably a single aptamer or a pair of aptamers, which attaches the selected molecules. In a related embodiment, selected molecules, preferably donor and acceptor signal-generating molecules, are assembled in suitable proximity to produce a detectable image or signal whose detection enables the identification and isolation of a single discrete structure comprising at least one aptamer, preferably a single aptamer or a pair of aptamers, which attaches the selected molecules within suitable spatial proximity for functional coupling between the donor and acceptor signal-generating species. The resultant assembly comprises donor and acceptor signal-generating species attached and functionally coupled by at least one aptamer, preferably a single aptamer or pair of aptamers.

The method for isolating and identifying (e.g., sequencing) the aptameric sequence capable of connecting and functionally coupling two selected molecules may involve amplifying the sequence using, e.g., PCR, LCR, Q-beta replicase, 3SR, TAS, RCR, CPR, ribonuclease H or reAMP methods, but amplification is not required. For example, a combination of optical microscopy (e.g., using bright-field, epi-fluorescence or confocal methods) and scanning probe microscopy (SPM; e.g., atomic force microscopy (AFM), scanning force microscopy (SFM) or scanning tunneling microscopy (STM)), including hybrid techniques such as scanning electrochemical microscopy (SECM), can be used to image, isolate and extract an aptamer-coupled effector complex from a mixture. Further, the aptamer may be isolated from the complex, e.g., by application of a current, voltage or piezoelectric force. A preferred method relies on the integration of fluorescence detection with AFM (e.g., Radmacher et al. (1992) *Ultramicroscopy* 42–44:968), enabling rapid fluorescence imaging of large fields followed by high-resolution AFM probing and extraction of selected aptamers. Alternatively, high-throughput screening and selection at high resolution can be achieved by multiplexing AFM probes, one or more probes optionally comprising separate detection, extraction and/or amplification tips, preferably a microrobotic array of multiplexed probes attached to cantilevers, each probe, set or bundle comprising application-specific tips (e.g., for topographical scanning, aptamer-target extraction, aptamer-target dissociation, amplification, and/or sequencing).

In a preferred mode of aptamer selection by proximity-dependent functional coupling, selection relies on the concerted activities of two or more amplification enzymes, e.g., a polymerase and a reverse transcriptase, assembled by aptamer-target binding. A first amplification enzyme is preferably conjugated to a target molecule, advantageously through a flexible spacer molecule, scaffold or tether that provides the enzyme with at least a moderate degree of diffusional and rotational freedom. A second amplification enzyme is conjugated and/or tethered to a fixed nucleotide of a nucleic acid molecule comprising a random-sequence mixture. In this way, aptamer-target binding results in assembly of amplification enzymes into a single discrete structure comprising a preferentially amplified nucleic acid molecule. Aptamer detection by target-dependent functional coupling of amplification enzymes advantageously represents a homogeneous assay method, as aptamer-target binding alters the activity of a signal-generating process, i.e., replication of the target-bound nucleic acid to yield a detectable number of copies.

Single-molecule sequencing of the selected aptameric sequence can be achieved, e.g., by discriminating the differing fluorescent signals of individual nucleotides in response to laser excitation, preferably laser-induced multicolor fluorescence of fluorophore-tagged nucleotides. Alternatively, rapid sequencing of DNA may be achieved with AFM (e.g., Hansma et al. (1991b) *J. Vac. Sci. Techn. B* 9:1282–1284), obviating the need to extract aptamers from the AFM substrate for amplification and/or sequencing.

Single-molecule aptamer selection and characterization can also be achieved without single-molecule sequencing. A variety of signal-generating species can be detected with single-molecule sensitivity (e.g., enzymes, dyed microspheres, fluorescent liposomes, tanned red cells). Detection of individual molecules of low molecular weight fluorophores (e.g., rhodamine) and high molecular weight phycobiliproteins (e.g., phycoerythrin) has been reported (e.g., Shera et al. (1990) *Chem. Phys. Lett.* 174:553–557; Soper et al. (1991) *Anal. Chem.* 63:432–437; Peck et al. (1989) *Proc. Natl. Acad. Sci. USA* 86:4087–4091). Single-molecule isolation methods such as optical trapping (e.g., optical force, laser scanning or optical tweezer methods) or SPM-based extraction (e.g., AFM, STM) can be used to deliver a single nucleic acid molecule to an amplification vessel, thereby enabling replicative production of a sufficient number of copies of a single, isolated nucleic acid molecule for routine sequencing (e.g., using a sequencing gel or automated DNA sequencer). Optical trapping methods are known in the art (e.g., Ashkin et al. (1987) *Nature* 330:769–771; Frej et al. (1993) *J. Chem. Phys.* 98:7552–7564; Sasaki et al. (1991) *Opt. Lett.* 16:1463–1465; Sasaki et al. (1992) *Appl. Phys. Lett.* 60:807–809), as are SPM-based detection and extraction methods (e.g., Henderson (1992) *Nucleic Acids Research* 20:445–447, Hansma et al. (1992) *Science* 256:1180–1184; Weisenhorn et al. (1990) *Scan. Microsc.* 4:511–516). Nanometer-scale measurements on individual DNA and protein molecules have been demonstrated, e.g., using AFM, enabling resolution of interactions between individual DNA and protein molecules (e.g., Allen et al. (1993) *Biochemistry* 32:9390). Linker DNA of chromatin fibers was shown to comprise 3780 base pairs with 18 tandem repeats of 208-base pair positioning sequences. Measured changes in fiber length were consistent with 146-base pair DNA wrapped 1.75 times around a nucleosome core. Protein-induced DNA bending in response to binding of RNA polymerase and Cro protein molecules has also been resolved (Rees et al. (1993) *Science* 260:1646). Direct imaging of DNA-protein complexes enabled discrimination between specific and nonspecific binding.

Single-molecule detection methods of the instant invention include optical force fields (e.g., optical tweezers, laser scanning), scanning probe microscopy (e.g., SPM, AFM, SFM, STM and-hybrid techniques, e.g., SECM) and emerging but heretofore unproved techniques. Methods and devices capable of single-molecule detection which have not heretofore demonstrated adequate sensitivity are included within the scope of the instant invention. Emerging methods and devices for single-molecule detection include, without limitation, mass spectrometry; capillary electrophoresis and microminiaturized electrophoretic detectors, including on-chip electrophoretic elements, channels and arrays; microminaturized and nanofabricated optical, spectroscopic, spectrometric, electrochemical, optoelectronic and electronic detectors; microsensors, nanosensors, integrated on-chip sensors, transducers and arrays; and molecular sensors and transducers, including multimolecular sensors, multimolecular transducers and tethered specific recognition devices of the instant invention.

Preferred single-molecule detection and manipulation methods of the instant invention include optical trapping (e.g., optical tweezers, force fields, laser scanning and manipulation) and scanning probe microscopy (e.g., SPM, AFM, SFM, STM and hybrid techniques, e.g., SECM). SPM, for example, can be used to detect and isolate a single, target-bound aptamer from a mixture or library of nucleic acid molecules. The isolated aptamer can then be either 1) sequenced in situ by SPM, optionally with localized amplification 2) transferred to a single-molecule sequencing apparatus (e.g., a laser-driven nucleotide fluorescence detector) followed by large-scale synthesis of the selected sequence, 3) transferred to an amplification reaction followed by, e.g., gel-based or automated sequencing., or 4) optionally amplified in situ either on the target-modified SPM substrate or on the target-modified probe tip, e.g., by in situ hybridization (e.g., Patterson et al. (1993) *Science* 260:976–979) and optionally by primer extension. Amplification may be achieved via thermal cycling (e.g.,. using PCR or LCR) or, advantageously, by isothermal methods (e.g., 3SR or CPR).

Methods disclosed herein for selecting synthetic defined sequence segments capable of specifically binding selected nonoligonucleotide molecules using single-molecule detection of an individual aptamer-target complex and/or single-molecule isolation of an individual aptamer-target complex and/or single-molecule amplification of an aptamer comprising an individual aptamer-target complex and/or single-molecule sequencing of an aptamer comprising an individual aptamer-target provide the art with the ability to select and unambiguously characterize a single aptamer molecule, i.e., to determine the chemical identity of an individual target-binding nucleic acid molecule without artifacts or contamination from nontarget-binding or target-nonbinding nucleic acids (e.g., matrix-binding nucleic acids and/or contaminating nucleic acids retained due to uncontrolled selection pressure or ineffective or inefficient preselection or counterselection methods, or imperfect specificity, selectivity, effectiveness or efficiency of the partitioning method or composition).

A combination of single-molecule detection, isolation, amplification and/or sequencing as disclosed herein enables the selection, characterization and identification of an individual nucleic acid molecule capable of specifically binding a selected nonoligonucleotide molecule from a mixture of synthetic nucleic acids, optionally a highly diverse mixture and preferably a highly diverse library comprising synthetic nucleic acids. Unlike prior art methods, the single-molecule selection methods described herein enable the unambiguous identification of an individual aptamer molecule without iterative cycles of partitioning and amplification heretofore required to eliminate, remove, separate, reject or discard contaminating nontarget-binding and target-nonbinding nucleic acids. In other words, unlike prior art aptamer selection methods, the instant single-molecule selection methods do not rely on affinity-based partitioning of one population, pool or fraction of nucleic acid molecules (i.e., target-binding nucleic acids) from another population, pool or fraction of nucleic acid molecules (i.e., nontarget-binding or target-nonbinding nucleic acids). In fact, the instant single-molecule selection methods do not rely on any form of partitioning, separating or discriminating two or more populations, pools or fractions of nucleic acids based on any selection criterion (e.g., affinity, activity, structure or function). Rather, the instant single-molecule synthetic aptamer selection methods rely on the detection and isolation, and preferably the sequencing and/or amplification, of an individual synthetic aptamer molecule or a synthetic aptamer molecule comprising an individual discrete structure, which methods are heretofore unknown in the art.

Proximity-based methods for single-molecule detection disclosed herein include proximal probe methods (e.g., AFM, STM) with reporter molecules (e.g., macromolecules, polymers or preferably nanoparticles or microparticles) to select and isolate one or more aptamers based upon a user-defined selection criterion or setpoint (e.g., target-binding affinity). For example, by varying the size, density, surface charge and/or solubility of a reporters conjugated to the target molecule, on the one hand, and random-sequence nucleic acids, on the other, an individual aptamer or group of aptamers can be selected with desired binding strength. The affinity or binding strength required for aptamer-dependent assembly and maintenance of paired reporter particle complexes increases with the cube of the diameter of each associated particle. Increasing reporter particle size can therefore be used to establish an affinity threshold favoring selection of individual aptamers capable of passing an operator-defined fitness test.

Alternatively, single-molecule affinity selection can be achieved by immobilizing a target molecule to an SPM tip (i.e., negatively charged silicon nitride) used to probe a random-sequence, nanosphere-conjugated nucleic acid library. Scanning is performed in fluid mode to detect aptamer binding to the tip-immobilized target following application of the nucleic acid library sample to a freshly cleaved mica substrate. The force of aptamer binding to the target-immobilized probe tip is quantified by varying loading and discharge forces associated with aptamer-nanoparticle binding and unbinding to target-probe tip. Individual, high-affinity aptamers are selected on quantitative grounds against an operator-defined binding force specification.

In another preferred aspect of the instant invention, the critical selection criterion for identifying an aptamer capable of specifically binding an identified nonoligonucleotide molecule is not affinity (i.e., partitioning as described by Gold et al., U.S. Pat. No. 5,270,163), but the specific site of interaction on the identified molecule and/or the specific epitope or region recognized and/or the degree of surface interaction between the aptamer and the identified molecule and/or the degree of selectivity for the identified molecule, i.e., the specificity of interaction. For example, an aptamer may be selected from a mixture of nucleic acids, preferably a diverse mixture or library of nucleic acid molecules comprising at least one randomized sequence, based upon the ability of the aptamer to displace (i.e., dissociate) a ligand-receptor complex by binding to either the ligand or the receptor at or near the epitope recognized by its specific binding partner (i.e., the receptor or ligand, as the case may be). In this embodiment, both the ligand and the receptor of the ligand-receptor complex are preferably labeled with effector species (or, optionally, either the ligand or the receptor is labeled with an effector) in such manner that a single ligand-effector conjugate and/or a single receptor-effector conjugate can be distinguished from a single (ligand-receptor)-effector complex, optionally from a plurality of (ligand-receptor)-effector complexes.

In another preferred aspect of the instant invention, defined sequence segments are selected for the ability to bind neither a ligand nor a receptor, but to recognize an epitope, site or topographical region formed by a selected molecule (i.e., a pair or group of molecules) comprising a ligand specifically bound to its receptor. In this case, the selection process does not involve affinity-based partitioning of ligand-bound or receptor-bound nucleic acids from the unbound fraction of a diverse mixture of nucleic acids. Rather, nucleic acids capable of binding ligand alone or receptor alone are discarded (i.e., selected out for undesirable specificity). Unbound nucleic acids are screened or selected for the ability to specifically bind the ligand-receptor complex and to unbind (i.e., dissociate) concomitantly with disruption of the ligand-receptor complex (e.g., by addition of a competing ligand or receptor or by addition of salts, acids, bases, detergents, or mild chaotropes). Some of the highest affinity nucleic acids (i.e., those binding the ligand-receptor complex with the highest affinity) may be deselected (i.e., discarded) by this procedure, because the selection criterion is not affinity, but specificity. In this way, aptamers are selected for the ability to specifically recognize an event or interaction, i.e., the specific binding between a ligand and its receptor. Aptamers capable of specifically binding a pair or group of molecules in this manner, i.e., with specificity for an epitope or site or topological region unique to the specifically bound pair or group, are particularly useful as defined sequence segments comprising multimolecular drug delivery systems (e.g., for targeting drugs based upon a pathophysiological interactions between ligands and receptors) and in multimolecular transducers and multimolecular switches, particularly multimolecular sensors (e.g., for sensing specific interactions between ligands and receptors, particularly a specific binding reaction between a probe and an analyte).

In another preferred embodiment, selection of a defined sequence segment capable of specifically binding an identified nonoligonucleotide is based not upon the partitioning of target-bound from free nucleic acid molecules, but on the ability to protect a selected nonoligonucleotide molecule from structural modification, e.g., thermal denaturation enzymatic digestion or chemical modification. For example, an aptamer may be selected from a mixture of nucleic acids, preferably a diverse mixture or library of nucleic acid molecules, based upon the ability of the aptamer to bind and protect a selected target molecule from covalent modification, e.g., by shielding a peptide hormone from cleavage by an endopeptidase or insulating all or part of a glycoprotein antigen from proteolytic degradation by a protease or protecting an Fab or MRU or hinge region of an antibody from enzymatic digestion or chemical modification.

In another preferred embodiment providing advantages over single-molecule affinity selection, a selected target (e.g., alkaline phosphatase; AP) is immobilized to the silicon nitride AFM probe tip and used to probe a random-sequence, nanosphere-conjugated RNA library applied in solution (i.e., freely diffusible) to a freshly cleaved mica substrate. On detection of aptamer binding to the probe tip, varying unloading (i.e., discharge) forces is applied to dissociate aptamer-nanosphere conjugates from tip-immobilized AP. Individual, high-affinity aptamers are selected on quantitative grounds based on the empirical binding and unbinding forces accompanying aptamer-target association and dissociation from tip-immobilized target. Selected aptameric nucleotides, i.e., those displaying a binding force exceeding an operator-established set point (in micronewtons, relative force or loading and unloading force(s) or force curves relative to a reference ligand-receptor pair such as peroxidase-antiperoxidase, fluorescein-antifluorescein or DNP-antiDNP). In a particularly preferred mode of operation, a panel of reference ligand-receptor pairs having predetermined apparent affinities (e.g., by Scatchard analysis using labeled ligand(s) and a family(ies) of unlabeled competitors) are used to establish a (force x apparent affinity) calibration curve against which the apparent affinity of individual identified aptamer-target pairs can be interpolated from loading and unloading AFM force data. In this way, an individual aptamer having the highest measured binding force can be selected against reference apparent affinities determined for nonaptameric ligand receptor pairs. For example, a family of biotin congeners (e.g., biotin, imidobiotin, diimidobiotin, iminobiotin) can be selected to represent a broad dynamic range of affinities for avidin, streptavidin and/or recombinant or otherwise modified streptavidin and/or avidin mutants. A panel of biotin derivatives or an array of mutant and/or modified streptavidins permuted against biotin derivatives can be used to calibrate the binding force of an aptamer-target complex over a range spanning many decades of apparent affinity (i.e., as related to inverse concentration on log scale).

Alternatively, selection criteria and stringencies can be quantitatively titrated against the empirically determined behavior of a selected population of individually probed aptamer-target complexes. For example, the binding force of a selected population of fluorescence proximity-imaged aptameric complexes can be determined either in terms of absolute force (i.e., binding force in newtons) or as apparent affinity against a calibration curve (vide supra). The population distribution of measured binding forces can then be plotted as a histogram and/or analyzed statistically to enable willful articulation of a use-appropriate set-point for harvesting an individual aptamer or a selected plurality or population of aptamers meeting said willful and quantitative set point. The quantitative selection process is advantageously automated and supported by a functionally coupled informational system.

Quantitative selection may alternatively be based not upon the magnitude of empirically determined binding force (s) of an individual aptamer or selected population of aptamers, but upon aptamer specificity for target epitope, an epitope formed by a ligand receptor pair or by conformational changes in a target or ligand receptor pair (optionally AFM tip-induced). Quantitative and discrete (i.e., single complex) discrimination may also be based on multimolecular size of the aptamer-target complex (e.g., dimensions in nm). Alternatively, selection may be based on the apparent shape of the complex, tip-induced shape changes and/or resistance to shape changes (i.e., rigidity, resilience, compactness), all of which data are useful in selecting aptameric defined sequence segments of the instant invention, and all of which methods and capabilities are heretofore unknown in the art. Quantitative selection may alternatively be based upon aptamer-conferred stabilization of the target against AFM tip-induced damage, or against stability of the target and/or aptamer to changes in solution or solid phase environment. For example, the stability of the target, the aptamer and/or the aptamer-target complex to organic solvents, as useful, e.g., in microelectronics, industrial, environmental, chemical and polymer processing, adhesive, adherent and adsorbent development (and so forth, as described elsewhere, vide supra) can be used as a selection criterion. Or stability to salts, acids, bases, polyamines, detergents, chaotropes, chelators, intercalators, coordinators, crosslinkers, hydrophobic polymers, photoactivatable reagents, secondary ligands and receptors (i.e., competitors), enzymes indigenous to a particular environment, e.g., nucleases, proteases, peroxidases, phosphatases, lipids, proteins and other matrix-active agents, crossreactants, interfering substances, and so forth. All of these interactions between an aptamer, target or aptamer-target complex and its microenvironment, covalent and noncovalent, specific and nonspecific, ionic and nonionic, reversible and pseudoirreversible and irreversible, can be explored and quantitatively reported at the single-molecule level using methods disclosed herein. Understanding these interactions is important to the selection, design, assembly, stabilization, replication and/or scale-up of well-defined, stable, uniform, precise, reliable, efficiently coupled and robust MOLECULAR MACHINES of the instant invention. None of these interactions can be resolved at the single molecule level by selection methods known in the art (e.g., Gold et al., U.S. Pat. No. 5,270,163), Ellington and Szostak (1990) *Nature* 346:818–822), Bock et al. (1992) *Nature* 255:564–566, Wang et al. (1993) *Biochemistry* 32:1899–1904, and Bielinska et al. (1990) *Science* 250:997–1000).

Selection of nucleotides for template-directed assembly by methods described herein unleashes a paradigm shift in the utility of oligonucleotides. Nucleotide-based templating to produce spatially ordered arrangements of molecular effectors expands the scope of nucleotide applications from therapeutics and diagnostics to nonmedical applications (e.g. industrial processes, microelectronics) that do not require physiological conditions. The more conventional use of nucleic acid libraries for drug discovery revolves around the achievable diversity of nucleotides under relatively physiologic conditions. The potential shape-charge diversity of nucleotides can be expanded by screening libraries under alternative, nonphysiologic solvent conditions, yielding different shape-charge profiles. Since the fitness landscape of a nucleotide library is influenced by hydration state (e.g., bound water, hydrophilic effects), the properties of a nucleic acid library may be dramatically altered when screened and selected in nonaqueous or polar-nonpolar solvent systems. Nucleotides, unlike proteins and peptides, are relatively stable to organic solvents. Oligonucleotides directed against selected targets that are both soluble and stable in nonphysiologic, optionally organic solvents (e.g. fluorophores, redox mediators, certain enzymes, supermolecules, etc.) can therefore be selected for industrial applications in which nucleotide recognition properties promise to be quite useful. Representative uses for nucleotide selection in nonaqueous and organic solvents include, e.g., biochips and biomolecular circuitry; multienzyme catalysis and synthesis in organic media; production of sided (i.e., directional or rightside out) liposome-nucleotide assemblies for use in industrial environments; and sensors, transducers and actuators for nonaqueous applications (e.g., detection of contaminants in petroleum products, bioremediation, QA/QC of organic syntheses). Use of nucleotides derivatized with lipophilic and nonpolar groups also provides a convenient means to orient the instant MOLECULAR MACHINES in monolayers, films, vesicles and coatings that can be reproducibly layered on transducer surfaces by well known thin film and thick film deposition methods.

In another nucleotide selection method of the instant invention, single-stranded target-binding nucleotides are selected from a diverse mixture of random-sequence DNA or RNA duplexes or heteroduplexes, preferably duplexes comprising fixed primer annealing sequence(s), by the relative propensity of denatured single-stranded nucleotides to bind a selected target molecule rather that reannealing to form the parent duplex. Alternatively, the selection is performed as a competition between a selected target molecule and a selected nucleic acid sequence (i.e., a complementary or partially complementary strand) for recognition by a single-stranded nucleotide comprising a random-sequence single-stranded nucleic acid library. In either case, the length and degree of complementarity of duplex regions is used to establish a target-binding affinity set point (i.e., threshold denaturation energy or melting energy) against which aptameric nucleotides are selected. Single-stranded nucleotides or duplexes are preferably labeled (e.g., with fluorophore-tagged nucleotides or fluorescent nanospheres) and are optionally immobilized to a working electrode or a solid phase comprising, e.g., an electrophoretic gel or chromatography support. For selection based on denaturation and target-competitive renaturation of duplexes, a denaturing stimulus is applied, e.g., a voltage (e.g., about −0.5 to about −2.0 volts) or heat (e.g., to above about 60° C., preferably above about 80° C.) or a chemical denaturant (e.g., high salt, a chaotrope, or a nonpolar solvent). Following thermal, chemical, photochemical or electrochemical denaturation of duplexes, a selected target is added to the resulting single-stranded nucleotide mixture which is returned toward its initial, renaturing state (e.g., by cooling, desalting or depolarization). A single-stranded nucleotide whose affinity for the selected target is advantageously greater than the reannealing hybridization energy of its corresponding duplex can then be detected, characterized, isolated and amplified and/or sequenced by optical imaging and SPM methods, as described elsewhere herein. Alternatively, iterative cycles of partitioning and amplification of uncharacterized pools comprising target-bound single-stranded nucleotides may be used to select a relatively high-affinity aptamer by methods known in the art (e.g., Gold et al., U.S. Pat. No. 5,270,163), Ellington and Szostak (1990) *Nature* 346:818–822) Bock et al. (1992) *Nature* 255:564–566, Wang et al. (1993) *Biochemistry* 32:1899–1904, and Bielinska et al. (1990) *Science* 250:997–1000).

Screening and selection of a nucleotide library by methods of the instant invention can be also be used to identify a defined sequence segment capable of specifically binding not only a single target molecule, but also a complex comprising two molecules specifically bound to one another.

In one preferred embodiment, a nucleic acid library can be counterselected against a selected ligand and receptor and then selected for defined sequence segments capable of specifically binding the bound ligand-receptor complex. This method is particularly useful for selecting a donor-labeled or acceptor-labeled defined sequence segment for use in homogeneous detection of ligand-receptor binding, wherein either the ligand or the receptor is labeled with an acceptor or donor species capable of functional coupling with the aptamer label. For example, an anti-(ligand-receptor complex) aptamer synthesized with modified and/or biotinylated nucleotides comprising or attaching a donor fluorophore (e.g., fluorescein, a cyanine dye, a phycobiliprotein) can be used with an acceptor-labeled receptor (e.g., cyanine dye-labeled or phycobiliprotein-labeled anti-PSA antibody) for detection of an analyte comprising a ligand (e.g., PSA). In this case, the aptamer is specific for an epitope formed by the PSA/anti-PSA complex. In the presence of PSA, acceptor-labeled antibody is functionally coupled to donor-labeled aptamer specific for the PSA/anti-PSA complex. Using a similar approach, an effector-labeled defined sequence segment (e.g., enzyme-labeled, fluorophore-labeled or luminescent) can be selected for specific binding to a (labeled aptamer)-target complex in such manner that the selected defined sequence segment binds neither the labeled aptamer nor the free target. Independent counterselection against the free (i.e., uncomplexed) target and the uncomplexed, labeled aptamer, optionally immobilized, allows subsequent selection of a nucleic acid library for a labeled defined sequence segment capable of specifically recognizing an epitope comprising the (labeled aptamer)-target complex, which epitope is formed by labeled aptamer-target binding. Not only can the labeled defined sequence segment be selected by functional coupling, but it can also be used in homogeneous specific binding assays relying on functional coupling for detection of aptamer-target binding. Selection of defined sequence segments capable of specifically binding complexes formed by aptamer-hapten binding provides a means to perform pseudoimmunometric (i.e., sandwich) assays for low molecular weight analytes. Homogeneous, pseudoimmunometric assays using donor-labeled and acceptor-labeled nucleotide-based specific binding reagents (i.e., in excess) enables more sensitive detection of low molecular weight analytes than possible with a conventional competitive assay architecture. Even greater sensitivity can be achieved in a heterogeneous mode by amplifying a defined sequence segment comprising specifically bound nucleotide-target complex(es).

These detection, selection, isolation, sequencing and/or amplification methods provide the art with the ability to identify novel defined sequence segments comprising multivalent templates for assembly of useful multimolecular devices. Combined with paired nucleotide library transposition and imprinting capabilities described herein, identification of synthetic nucleotide recognition elements is enabling for many heretofore unimagined processes and devices. For example, single-molecule(s) selection methods disclosed herein enable quantitative resolution of aptamer-surface interactions, e.g., the influence of surface materials and structural shapes on aptamer-target binding and/on the structure and stability of immobilized aptamers, targets and aptamer-target complexes. In addition, and particularly important to microelectronic and industrial, environmental and biomedical sensors, transducers, switches and actuators embodied herein, the influence of hydration state on aptamer, target and aptamer-target interactions and conformations can be quantitatively assessed at the individual molecule and complex level by the instant methods.

The ability to characterize recognition reactions, e.g., binding and catalysis, at the interface between solid and liquid, particularly the structural and functional integrity of ligands, receptors and catalysts, particularly enzymes, proteins, nucleic acids, glycoproteins, glycolipids and other macromolecules at the boundary between wet and dry is seminal and enabling toward the development of fully integrated and functionally coupled molecular electronic, optoelectronic, photonic, mechanochemical, multicatalytic and multienzymatic devices comprising ordered assemblies of molecules cooperating with one another and with inorganic or synthetic materials, preferably electronically active devices functionally coupled to the macroscopic world.

Similarly important is stable, fast, efficient, reliable collaboration between hard surfaces and soft biological molecules and groups of molecules comprising complexes and supramolecular assemblies.

Equally important is the adaptation of biomolecular machines to nonaqueous environments, particularly organic solvent systems and harsh chemicals, acids, bases and salts ingrained in the world of micromachining, photolithographic and semiconductor technologies. Transposing Mother Nature's bounteous secrets in respect of molecular cooperativity to hard and dry surfaces is a challenging and evolutionary process that has yet to be fulfilled. Surface-induced conformational perturbations are substantially nontrivial, as amply evident in the art (e.g., Volkin et al. (1991) Int'l. Symp. on Biological Product Freeze-Drying and Formulation, Bethesda, Md. *Develop. Biol. Standard* 74:73–81; Volkin et al. (1991) *Biotechnol. Bioeng.* 37:843–853; Hsu et al. (1991) *Develop. Biol. Standard* 74:255–271; Prestelski et al. (1993) *Biophys. J.* 65:661–671).

Methods disclosed herein for selecting and assembling nucleotide-based and plastic templates comprising MOLECULAR MACHINES address these technical obstacles through a number of innovations, including: 1) selection of specifically attractive surface features and reactivities from surface libraries, obviating the need for biomolecule immobilization, 2) mapping recognition properties selected from molecular shape libraries into surfaces, e.g., by template-guided nanofabrication, 3) surface templating, wherein a nucleotide-based or plastic template comprising a recognition element specific for a surface feature attaches by specific recognition, 4) use of nucleotide-based and plastic templates comprising molecular adhesives and adherents to bond and bind selected structural and functional molecules and groups of molecules to surfaces, 5) coselection of surface libraries and molecular shape libraries to identify mutually attractive molecular and structural shapes, and 6) imprinting selected molecular shapes into selected materials, e.g., for preparation of designer adsorbents (e.g., for affinity separations, industrial purification, catalysis and downstream processing).

The combination of nucleotide-directed diversification and templating provides a novel, practical and general approach to integration of molecular recognition, shape recognition and catalytic properties with industrial materials. Parent and progeny templates can be used to select and assemble nucleotide-based and nonnucleotide materials, polymers, adhesives, adherents, adsorbents and lubricants, e.g., as well as complex MOLECULAR MACHINES (e.g., multimolecular devices, tethered specific recognition devices, smaRTdrugs). For example, template-guided, attractive lubricants (e.g., surface-feature targeted nanospheres, buckyballs, polymers) can be used to assemble moving parts on surfaces. Specific attachment of MOLECULAR MACHINES can be used to cushion the denaturing and destabilizing impact on biological molecules by dehydration and surface forces (e.g., Prestelski et al. (1993) *Biophys. J.* 65:661–671). These are but two of the many ways in which MOLECULAR MACHINES can improve compatibility between molecular shapes, structural shapes and surfaces. Another is to endow chemically bland materials, structures, substrates and surfaces with specific recognition and catalytic recognition properties heretofore known only to molecules in free space (i.e., unencumbered by bondage to like molecules, e.g., structure and surface neighbors. Another is enhance specific attractivity and catalytic recognition properties of surfaces by mapping surface features against free space effector molecule shapes and introducing the properties into surfaces either by grafting (e.g., using surface templates) or by template-guided nanofabrication. Another is to seamlessly integrate specific recognition, catalytic, and, particularly multimolecular and supramolecular functionalities into surfaces heretofore confined to the realm of chemically bland inorganic materials. Another is to bridge the dimensional gap between the molecular and macroscopic worlds, between electronics devices and electroactive molecules, between photonic devices and photoactive molecules, between attractive surfaces and molecular attractors, between drugs and devices, and more generally, between molecules and machines, and more generally, between man and machine and nature. Another is to bridge the solvent gap by using paired libraries to select templates and selectable molecules in organic solvents or solvent systems not conventionally applied to library screening an selection.

Another is the ability to characterize the interaction between an aptamer and its target at molecular scale in functional as well as structural terms. Another is the ability to select cooperative molecular pairs using a first selected molecule tethered to a nucleotide comprising a randomized sequence selectable on the basis of affinity for a cooperative second selected molecule. Another is to identify competing and interfering molecular, particularly biomolecular, interactions. Another is to determine and respect solvent and solute effects at the level of individual aptameric and intermolecular activities. Another is to individually select, preferably by automated and massively parallel machine-directed scanning, probing, characterization and isolation techniques, a single aptamer capable of best performing a particular function, e.g., stabilizing a target or partitioning a drug to a receptor. Another is to identify a pair or group of defined sequence segments, at least one being an aptamer, wherein the sequence segments consort to assemble selected molecules or nucleotides which are, in turn, capable of consorting to perform a useful function that cannot be performed by any constituent aptamer-target pair. Another is to identify and respect the significance of wet versus dry at the molecule-transducer interface, as well as molecular and structural factors influencing device integration.

Additional objectives of the instant nucleotide library screening and selection methods include: 1) to provide a method of resolving molecular diversity at single-molecule resolution by combining emerging single-molecule and detection technologies with replicatable nucleotide libraries, 2) to provide a paired nucleotide-nonnucleotide library-based diversity generator for exploring molecular shape space and structural surface space, 3) to provide a paired nucleotide-nonnucleotide library-based diversity generator functionally coupled to an informational system comprising paired informational devices comprising at least a massively parallel search engine, 4) to provide a single-molecule detection method capable of identifying an individual synthetic aptamer, synthetic nucleotide or pair or group of synthetic nucleotides having a selected recognition property, 5) to provide a single-molecule detection method capable of identifying an individual ribozyme, catalytic nucleotide, or pair or group of nucleotides having a selected catalytic activity, 6) to provide a multiplexed single-molecule detection method for a) selecting a selected population or library of individual aptamers based on functional or structural criteria, or b) characterizing the activity of a single (i.e., cloned) aptamer species against a diverse array of selected molecules, optionally structurally related, or c) coselecting a selected population of selected aptamers (i.e., an aptamer library) against a selected population of selected molecules (i.e., a molecular shape library) to identify the relationship or fitness profile of interactions between the libraries, 7) to provide a method for selecting from a library of nucleotide libraries, preferably paired nucleotide-nonnucleotide libraries, a diverse library of aptamers comprising a defined set, preferably digitally represented and archived, of members selected to recognize (i.e., map) the recognition space of a selected population of selected molecules, wherein the identities and behavior of the collective selected population provide information that cannot be obtained from a single selected molecule or pair or subthreshold group, 8) to transpose any selected target molecule or selected population of selected target molecules into a corresponding anti-idiotypic or anti-antiidiotypic or idiotypic nucleotide library, wherein the nucleotide mapping library can be used to further transform the recognition profile of the target molecule(s) into a new and more preferable molecular medium, e.g., a nonnucleotide imprint medium, i.e., a plastic segment, 9) to provide a method for transforming a defined sequence segment comprising an aptamer, catalytic nucleotide, hybridizable nucleotide, encoding nucleotide, conjugated or otherwise derivatized nucleotide, nucleotide ligand, nucleotide receptor or nucleotide catalyst into a nonnucleotide plastic segment by molecular imprinting or, preferably, transposition between paired, functionally coupled, nucleotide and nonnucleotide libraries, i.e., a nucleotide-nonnucleotide library pair, 10) to provide a method for transforming a template comprising at least two defined sequence segments comprising, e.g., aptamers, catalytic nucleotides, hybridizable nucleotides, encoding nucleotides, conjugated or otherwise derivatized nucleotides, nucleotide ligands, nucleotide receptors or nucleotide catalysts, into a nonnucleotide plastic template by molecular imprinting or transposition between paired nucleotide and nonnucleotide libraries, i.e., a nucleotide-nonnucleotide library pair, 11) to use a nucleotide-based template to assemble selected molecules, thereby creating a useful MOLECULAR MACHINE, 12) to use a plastic template to assemble selected molecules, thereby creating a semiplastic MOLECULAR MACHINE, 13) to use a nucleotide template to assemble plastic imprints of imprinted selected molecules, thereby creating semiplastic MOLECULAR MACHINES, 14) to use a plastic template to assemble selected plastic molecules, thereby creating a fully plastic MOLECULAR MACHINE, 15) to provide a synthetic process that exploits the replicative and distortional potential of nucleotide amplifiers for the projection and evolution of said MOLECULAR MACHINES in diversity space and retrieval (reentry) in nucleotide space, and 16) to thereby create for industrial use self-replicating MOLECULAR MACHINES selected and evolved for application-specific purposes (e.g., search-and-destroy, triggered release environmental remediants and agricultural therapeutics), 17) to use said nucleotide-based and plastic MOLECULAR MACHINES as smart materials, polymers, adhesives, adherents, adsorbents, molecular counting devices, molecular sorting devices, smaRTdrug delivery devices, 18) to provide a methods for endowing chemically bland materials, structures, substrates and surfaces with specific recognition and catalytic recognition properties heretofore known only to molecules in free space, 19) to provide a method for improving the specific attractivity and catalytic recognition properties of surfaces by mapping surface features against free space effector molecule shapes and introducing the properties into surfaces either by grafting (e.g., using surface templates) or by template-guided nanofabrication, 20) to provide surface modification methods (e.g., grafting, templating, mapping, surface feature selection) that introduce surface recognition and catalytic functions heretofore confined to the realm of inorganic materials, 21) to provide a functionally coupled MOLECULAR MACHINE production system comprising varying combinations of a molecular diversity generator, an informational system, a molecular selection (sorting) station, a template selection (consorting) station, a proximity selection (functional coupling) station, a transposition (casting and molding) station, an assembly (templating) station, a conjugation (pairing and stabilization) station and a recycling (salvage) station, wherein each station is functionally coupled to a distortable amplifier (e.g., a modulatable replicator), 22) to provide a method for characterizing the interaction between a synthetic nucleotide (e.g., aptamer or ribozyme) and its target at molecular scale in functional as well as structural terms, 23) to provide a method for selecting cooperative molecular pairs using a first selected molecule tethered to a nucleotide comprising a randomized sequence selectable on the basis of affinity for a cooperative second selected molecule, 24) to provide single-molecule detection methods for identifying factors and interactions that compete or interfere with the activity of a nucleotide recognition element (e.g., an aptamer or ribozyme), 25) to provide single-molecule detection methods for determining solvent and solute effects at the level of individual intermolecular activities of synthetic nucleotide recognition elements, 26) to provide single-molecule detection methods enabling individual selection, preferably by automated and massively parallel machine-directed scanning, probing, characterization and isolation techniques, of a single aptamer capable of best performing a particular function, e.g., stabilizing a target or partitioning a drug to a receptor, 27) to provide a method for identifying a pair or group of defined sequence segments, at least one being an aptamer, wherein the sequence segments consort to assemble selected molecules or nucleotides which, in turn, are capable of consorting to perform a useful function that cannot be performed by any constituent aptamer-target pair, 28) to provide single-molecule detection methods for identifying and overcoming structurally and functionally stressful interface effects between macromolecules and surfaces, e.g., wet versus dry, hard versus soft, macroscopic versus microscopic, organic versus inorganic and aqueous versus nonaqueous, 29) to provide paired nucleotide-nonnucleotide templates capable of directing the selection, assembly and conjugation of paired and functionally coupled selected molecules comprising MOLECULAR MACHINES, including transposition into novel molecular media, replication with varying fidelity, to wit, evolution of multimolecular structure and function, 30) to provide methods for bridging the dimensional gap between molecular and macroscopic worlds, between electronic devices and electroactive molecules, between photonic devices and photoactive molecules, between attractive surfaces and molecular attractors, between drugs and devices, and more generally, between molecules and machines, and more generally, between man and machine and nature.

In another preferred embodiment of synthetic aptamer selection methods disclosed herein, chemical and enzymatic structure probing methods are used to select aptamers with desired target-binding properties and/or to characterize the interaction between a selected aptamer and its target and/or to identify and/or sequence one or more nucleotides comprising an aptamer, particularly nucleotides comprising a target-binding region or cognate or consensus sequence of an aptamer. A wide variety of structure probing reagents and associated detection methods can be used to characterize the structure of nucleic acids with atomic resolution (e.g., Shouche et al. (1990) *Nucleic Acids Res.* 18:267–275; Bach et al. (1990) *Nucleic Acids Res.* 18:449–458).

Structure probing typically relies on enzymes or chemicals selective for and therefore capable of identifying single-stranded or double-stranded regions comprising nucleic acids. Selectivities widely used in ribosomal RNA structure mapping, for instance, include S1 nuclease, cobra venom nuclease and DMS. S1 nuclease is selective for single-stranded regions of substrate RNA, while cobra venom nuclease is specific for double-stranded regions. Although the selectivity of enzymes for double-stranded versus single-stranded regions is useful, steric hindrance due to the large molecular size of enzymes limits the resolution that can be achieved with these probes. DMS (a methylating agent) is a chemical probe that reacts with guanine and single-stranded adenine and cytosine. Base-paired adenine and cytosine do not react well, because their reactive residues are involved in base-pairing. Commonly used RNA structure probing reagents and associated specificities and detection methods include: RNAse VI, which is specific for double-stranded RNA and can be detected using end-labeled RNA or primer extension; RNAse T1, which is specific for single-stranded guanine and can be detected using end-labeled RNA or primer extension; RNAse T2, which is specific for single-stranded RNA and can be detected using end-labeled RNA or primer extension; RNAse A, which is specific for single-stranded cytosine and single-stranded uracil and can be detected using end-labeled RNA or primer extension; DEPC, which is specific for the N7 position of adenine (and to a lesser extent the N7 position of guanine) and can be detected using end-labeled RNA or □ by primer extension after chemical strand scission; DMS, which is specific for the N1, N3 and N7 positions, respectively, of adenine, cytosine and guanine and can be detected variously using primer extension, primer extension after chemical strand scission, and/or end-labeled RNA after chemical strand scission; CMCT, which is specific for the N3 position of uracil and the N1 position of guanine and can be detected by primer extension; and Fe(II)EDTA, which is specific for ribose and can be detected using end-labeled RNA or primer extension.

Because of their small molecular size and minimal steric hindrance compared to enzymes, chemical probes provide more detailed information on secondary structure. They do so by modifying bases at Watson-Crick base pairing positions. The three fundamental elements in RNA secondary structure include 1) stems, which are runs of base-paired bases, 2) loops, which are adjacent nonpaired bases, and 3) bulges, which are interruptions of pairing within otherwise base-paired stems. If a base is involved in a Watson-Crick base pair (i.e., in double-stranded RNA), modification by the probe does not occur. If a base is not involved in a Watson-Crick base pair (i.e., in single-stranded RNA), chemical modification occurs. The site of modification can be detected, e.g., by primer extension, because modification prevents incorporation of the next base by reverse transcriptase. Information regarding tertiary structure can be obtained from the availability of N7 atoms (only present in A and G). If N7 atoms are involved in tertiary interactions, they will not be modified. Detection requires strand scission at the site of modification.

The use of structure probing to select and characterize defined sequence segments comprising multimolecular devices, particularly aptameric and heteropolymeric multimolecular devices, enables atomic-scale resolution of the nucleotide recognition sites for selected molecules. By identifying within a defined sequence segment the specific nucleotide atoms in intimate contact with a specifically bound selected molecule and by providing precise secondary and tertiary structural information regarding the aptameric docking region of the defined sequence segment, structure probing can be used to complement synthetic aptamer selection methods disclosed herein (e.g., single-molecule selection, dissociation, stabilization and aptamer-dependent effector assembly methods) and/or prior art aptamer selection methods (e.g., Gold et al., U.S. Pat. No. 5,270,163), Ellington and Szostak (1990) Nature 346:818–822), Bock et al. (1992) Nature 255:564–566, Wang et al. (1993) Biochemistry 32:1899–1904, and Bielinska et al. (1990) Science 250:997–1000) with detailed structural information. In combination with functional (e.g., binding and activity) information from specific binding assays and functional coupling assays, nucleotide sequence and structure probing information enables determination of quantitative structure-activity relationships for nucleotide-based multimolecular devices of the instant invention. Quantitative structure-activity relationships enable nucleotide template-ordered multimolecular devices to be developed with maximal control over the relative positions of specific recognition sites. Optimal nucleotide-dependent positioning of specific recognition sites means specifically bound selected molecules are properly positioned to perform useful work with maximally efficiency, e.g., by the additive, mutualistic, synergistic, combined or interdependent activity of molecules functionally coupled within a nucleotide-based multimolecular device.

Defined sequences segments of the instant invention are selected to specifically recognize identified nonoligonucleotide molecules, particularly ligands, receptors, structural and effector molecules, particularly for use in aptameric and heteropolymeric multimolecular devices, e.g., multimolecular drug delivery systems, multimolecular transducers, multimolecular switches and multimolecular sensors. In a preferred aspect of the invention, selected defined sequence segments provide newly discovered specificities for detecting and characterizing heretofore unknown receptors and ligands, particularly plant, animal, viral and microbial receptors and ligands discovered through genomic and proteomic research and corresponding newly discovered ligands. Defined sequence segments selected for the ability to specifically recognize newly discovered ligands, e.g., drugs, drug candidates or receptor probes, for plant, animal, viral and microbial receptors can serve as receptor mimics or mimetics, e.g., soluble surrogate receptors or antiidiotypic ligands useful in multimolecular drug delivery systems and multimolecular devices disclosed herein. In another preferred aspect of the invention, defined sequence segments are selected for incorporation into multimolecular devices capable of specifically recognizing and assembling or processing selected molecules, e.g., ligands, receptors, structural or effector molecules, for which suitably specific or avid ligands or, as the case may be, receptors are either rare or nonexistent. In addition to multimolecular drug delivery systems (e.g., for heretofore undiscovered drugs and/or heretofore undiscovered therapeutic receptors), multimolecular devices comprising such rare or heretofore nonexistent specificities include multimolecular transducers, multimolecular switches and, particularly multimolecular sensors capable of detecting, quantifying and monitoring selected molecules comprising hazardous wastes, environmental pollutants, chemical and biological weaponry, agricultural diseases, pests and pesticides, foods, food additives and food contaminants, chemical and biological products and contaminants, industrial, chemical and food production and processing streams, microbial, viral and botanical proteomes, antigens, membranes, cells, cell walls and surface markers, and particularly hormones, transmitters, receptors, lipids, proteins and carbohydrates of edible plants and animals.

A multimolecular device comprising an aptamer, modified nucleotide, nucleotide ligand or nucleotide receptor capable of specifically recognizing a selected target, e.g., a therapeutic receptor, may be used to evaluate and quantify the target-binding properties of the operative recognition element, e.g., by an allosteric mechanism relying on binding or hybridization of a second recognition element to a calibrator comprising a selected molecule or selected nucleic acid sequence. For example, a labeled synthetic heteropolymer comprising an anti-target aptameric first defined sequence segment may be used to quantify the affinity or binding strength of the aptamer sequence for its target (e.g., a drug or therapeutic receptor) by the propensity of the aptamer-target complex to dissociate on hybridization of a second defined sequence segment to a complementary and variable-length selected nucleic acid sequence (i.e., a melting temperature calibrator). The binding strength of the aptameric first defined sequence segment for its target can be expressed in terms of the melting temperature or length of hybridized calibrator required to allosterically prevent or disrupt aptamer-target binding. Similarly, the binding strength of a receptor-specific nucleotide ligand for its target receptor can be determined using a labeled bivalent nonaptameric multimolecular device comprising the nucleotide ligand as a first recognition site and a hybridizable defined sequence segment as a second, allosteric recognition site. In each case, hybridization of an allosteric recognition site of a multimolecular device to a selected nucleic acid sequence influences binding of a primary target-specific recognition site in a quantifiable manner, i.e., aptamer-target or ligand-receptor dissociation can be correlated with the melting temperature of a hybridized allosteric defined sequence segment. Alternatively, the allosteric recognition site may be a second aptameric sequence or nucleotide ligand, for example, in which case binding strength of the primary recognition site is determined against calibrated, variable-affinity specific binding partners of the second recognition site (i.e., an affinity or crossreactivity panel).

Defined sequence segments of the instant invention capable of specifically recognizing nonoligonucleotide molecules may be single-stranded or double-stranded nucleotides comprising DNA, RNA or even heteroduplexes thereof. They may be selected by in vitro or in vivo methods, and they may be naturally occurring or synthetic defined sequence segments. Aptameric multimolecular devices of the instant invention rely on the specific recognition properties of synthetic aptamers, i.e., at least one defined sequence segment comprising the aptameric device is an aptamer sequence not heretofore known to occur in nature and function as a biological recognition site. Synthetic heteropolymers and heteropolymeric devices also comprise at least one synthetic aptamer sequence, but may also include one or more naturally occurring aptamer sequences (e.g., a biological recognition site or a defined sequence segment selected from a biological library or genomic sequence database). A synthetic heteropolymer comprising a heteropolymeric multimolecular device may also be hybridized or specifically bound to synthetic or naturally occurring selected nucleic acid sequences having useful recognition properties and/or functions other than the specific binding and hybridization capabilities of defined sequence segments making up the synthetic heteropolymer, particularly substrate recognition, catalysis, and/or generation of a reaction product or detectable signal. For example, a heteropolymeric device capable of enzyme channeling, enzyme cycling, or enzymatic synthesis, preferably biosynthesis and more preferably chiral synthesis, can be constructed from a synthetic heteropolymer having a first synthetic defined sequence segment specifically bound to a donor or acceptor enzyme, e.g., a dehydrogenase, esterase, lipase, aminotransferase, glycosidase, phosphatase or protease, and a second defined sequence segment specifically bound or hybridized to a selected nucleic acid sequence comprising a ribozyme or catalytic DNA sequence. The ribozyme or catalytic DNA sequence preferably comprises at least two elements, a selected nucleic acid sequence capable of hybridizing or specifically binding to the second defined sequence segment of the synthetic heteropolymer and a catalytic element, preferably a synthetic sequence designed or selected for functional coupling to the synthetic heteropolymer-bound enzyme (i.e., designed or selected to donate or accept a substrate or product of the synthetic heteropolymer-bound enzyme or to modulate the binding or activity of the enzyme or to act in an additive, synergistic, cooperative or sequential manner with respect to a common target, intermediate or substrate). Optionally, a molecular effector which is specifically bound to a defined sequence segment of a synthetic heteropolymer and functionally coupled to a hybridized ribozyme or catalytic DNA sequence may also be covalently conjugated to the defined sequence segment. Alternatively, a molecular effector covalently conjugated to a synthetic heteropolymer may be functionally coupled to a ribozyme or catalytic DNA molecule by hybridizing or specifically binding a defined sequence segment of the synthetic heteropolymer to a nucleic acid sequence comprising the ribozyme or catalytic DNA molecule. In an alternative embodiment, the enzymatic activity of a ribozyme or catalytic DNA sequence may be functionally coupled to a nonenzymatic acceptor hybridized to a synthetic heteropolymer, e.g., by selecting and hybridizing to the synthetic heteropolymer a catalytic DNA molecule or ribozyme capable either of donating a product to a synthetic heteropolymer-bound effector which is a drug or signal-generating species (e.g., a chromogenic or fluorogenic or electroactive or luminescent acceptor). Alternatively, a ribozyme or catalytic DNA molecule may be selected for the ability to hybridize and functionally couple to a synthetic heteropolymer-bound effector species by catalytically activating, modifying or releasing the heteropolymer-bound effector species.

Bifunctional synthetic heteropolymers of the present invention are prepared in the following manner. Two molecules or groups of molecules capable of performing a useful function when brought into close spatial proximity are identified. At least one of the identified molecules is a nonoligonucleotide molecule, preferably a receptor, ligand, structural molecule or molecular effector. A first defined sequence segment capable of specifically binding to an identified nonoligonucleotide molecule is selected, preferably by repeated selection and amplification of oligonucleotide pools, more preferably by combinatorial selection and amplification of an oligonucleotide library. A second defined sequence segment capable of specifically binding to the second identified molecule, which may be a nonoligonucleotide molecule or a selected nucleic acid sequence, is also selected. A synthetic heteropolymer comprising the first and second defined sequence segments, optionally separated by a spacer sequence of variable length, secondary and tertiary structure (e.g., including stems, loops, bulges, stem-loop structures, pseudoknots and internally hybridized, branched and hyperbranched sequences) and composition, preferably a single-stranded or double-stranded sequence comprising 1 to 200 nucleotides and more preferably about 1 to 40 nucleotides, is then synthesized ab initio by methods well known in the art. The length and composition of the spacer sequence is such that the spatial relationship between the first and second defined sequence segments is optimal to provide for specific binding of the two identified molecules in close intermolecular proximity. Spacer sequences are single-stranded or double-stranded nucleotides which increase the topological distance between defined sequence segments (i.e., the number of intervening nucleotides or base pairs) and also influence the spatial distance between them (i.e., the average or approximate distance in three-dimensional space between two defined sequence segments or between specified nucleotides, regions, positions, structures or functional groups comprising the two defined sequence segments). Spacer sequences can be used to increase the distance between two defined sequence segments of a synthetic heteropolymer, typically to maintain independent operability, i.e., the ability of a defined sequence segment to retain its selected recognition properties when incorporated into a multisegment synthetic heteropolymer. Nonlinear spacer sequences, preferably branched, looped, bulged and/or internally hybridized sequences, e.g., dendritic, stem-loop or pseudoknot structures, can also be used to decrease the spatial distance between defined sequence segments or specified regions of a synthetic heteropolymer and therefore to decrease the spatial distance between attached selected molecules or selected nucleic acid sequences. The efficiency of functional coupling between selected molecules within multimolecular complexes can therefore be enhanced by including synthetic heteropolymer spacer sequences that reduce the spatial distance between the functionally coupled molecules.

The spacing between defined sequence segments of a synthetic heteropolymer may also be adjusted using one or more spacer modifiers, modified nucleotides or nucleotide analogs comprising a spacer arm, e.g., SPACER 9, SPACER 18, SPACER C3 OR DSPACER (Glen Research, Sterling Va.). Spacing between nucleotides within a defined sequence segment may also be varied using such spacer modifiers, e.g., to maximize the affinity or specificity with which a defined sequence segment specifically binds a selected molecule or nucleic acid sequence. Spacer modifiers include, without limitation, nucleotides, spacer arms and groups designed to adjust the distance between nucleotides, defined sequence segments and nonnucleotide molecules, e.g., individual nucleotides, nucleotide analogs, spacer modifiers, spacer sequences, linker oligonucleotides and mutually hybridizable defined sequence segments comprising multivalent heteropolymeric hybrid structures and nucleotide-based multimolecular devices, and contiguous or punctuated groups or combinations thereof.

Alternatively, it may be preferable to synthesize a synthetic heteropolymer lacking any spacer modifiers between selected defined sequence segments so that specific binding or hybridization of a first selected molecule or nucleic acid sequence at one defined sequence segment precludes specific binding or hybridization of a second selected molecule or nucleic acid sequence at another defined sequence segment or displaces a previously bound molecule or nucleic acid sequence. It may even be preferable to produce the synthetic heteropolymer with contiguous defined sequence segments sharing a single nucleotide or even a few nucleotides, e.g., with a small number of nucleotides of one defined sequence segment overlapping another defined sequence segment (i.e., common to both), so long as one or the other defined sequence segment is capable at any given time of specifically binding or hybridizing to a selected molecule or nucleic acid sequence.

The three-dimensional shape of the synthetic heteropolymer and rigidity of the spacer sequence may be further modified by hybridizing or specifically binding one or more nucleotide sequences to the spacer sequence. In the instant application, multimolecular complex refers to a synthetic heteropolymer or multivalent heteropolymeric hybrid structure having at least one identified molecule specifically bound or at least two different aptamer molecules bound to the same target molecule or to a linker molecule. When used in reference to a complex comprising a synthetic heteropolymer, multimolecular heteropolymeric complex is the preferred term. A complex comprising at least two aptamers may also be referred to as an aptameric multimolecular complex or synthetic heteropolymer. Two different aptamer molecules joined to one another either directly or via a linker molecule (i.e., a nucleotide spacer, spacer molecule, oligonucleotide linker or nonnucleotide linker) to comprise a discrete structure capable of specifically recognizing two different nonoligonucleotide molecules is a synthetic heteropolymer. Similarly, an aptamer molecule and a second defined sequence segment may be referred to as a synthetic heteropolymer, if they comprise a discrete structure capable of specifically recognizing a nonoligonucleotide molecule and of hybridizing a selected nucleic acid sequence.

Multivalent heteropolymeric hybrid structure refers to two or more synthetic heteropolymers hybridizably linked. Each heteropolymer comprises nucleotides, preferably oligonucleotides, having at least two defined sequence segments. A first defined sequence segment of at least one heteropolymer is capable of specifically binding to a nonoligonucleotide molecule or group of molecules, preferably a receptor, ligand, structural molecule or molecular effector. The first defined sequence segments of other synthetic heteropolymers comprising the multivalent heteropolymeric hybrid structure are capable either of specifically recognizing a selected molecule or of specifically binding or hybridizing to a selected nucleic acid sequence or of positioning a conjugated selected molecule within functional coupling distance of a nonoligonucleotide molecule specifically bound to the first defined sequence segment of the first synthetic heteropolymer, thereby enabling functional coupling between the conjugated selected molecule and the specifically bound nonoligonucleotide molecule. Where the first defined sequence segment of the second synthetic heteropolymer is designed or selected to position a conjugated selected molecule for functional coupling to a specifically bound nonoligonucleotide molecule, the nonoligonucleotide molecule is preferably an effector molecule and more preferably a signal-generating species or a drug. The specifically bound nonoligonucleotide molecule is not a ligand or a receptor covalently attached to the conjugated selected molecule. Second defined sequence segments of the synthetic heteropolymers are capable of hybridizing to each other or to a linker oligonucleotide, optionally forming a double-stranded recognition site (e.g., an aptamer, immunoreactive epitope or biological recognition site) or intercalation site (e.g., for a drug or a dye) between the first defined sequence segment of a first synthetic heteropolymer and the first defined sequence segment of a second synthetic heteropolymer. Linker oligonucleotide, also referred to herein as a linker oligonucleotide, refers to an oligonucleotide sequence, plurality of oligonucleotide sequences, monomers or polymers, or a linker molecule capable of specifically binding or hybridizing to two or more conjugated defined sequence segments or to second defined sequence segments of two or more synthetic heteropolymers, thus joining the conjugated defined sequence segments or synthetic heteropolymers into a discrete structure. An oligonucleotide linker may also join two nucleotides by covalent attachment. Alternatively, an oligonucleotide linker may attach a first nucleotide covalently and a second nucleotide noncovalently. Oligonucleotide linkers conjugated to selected molecules may also join pairs of nucleotides by specific binding or by combinations of specific binding, hybridization and covalent attachment. A nucleotide may also first bind a linker oligonucleotide noncovalently and subsequently be attached covalently. Examples of the linker oligonucleotide include, but are not limited to: an oligonucleotide; a stem-loop, bulged or pseudoknot structure having single-stranded ends capable of hybridizing to the second defined sequence segments; a duplex, triplex or quadruplex structure having single-stranded ends capable of hybridizing to the second defined sequence segments; a branched-chain or branched-comb structure having defined sequence segments capable of hybridizing to the second defined sequence segments; a nucleic acid dendron or dendrimer (e.g., Tomalia et al. (1993) In: *Topics in Current Chemistry*, pp. 193–245 Springer, Berlin) or a dendron, dendrimer or other branched or hyperbranched structure attached to nucleotides comprising defined sequence segments capable of hybridizing to the second defined sequence segments; a nonoligonucleotide dimer, multimer or polymer comprising monomeric subunits attached to defined sequence segments of nucleotides capable of hybridizing to the second defined sequence segments; a heteroconjugate comprising a nonoligonucleotide molecule or group of molecules attached to defined sequence segments of nucleotides capable of hybridizing to the second defined sequence segments; a single-stranded or partially single-stranded nucleic acid molecule or group of molecules having a defined topology comprising defined sequence segments capable of specifically binding or hybridizing to the second defined sequence segments; a double-stranded or partially double-stranded nucleic acid molecule or group of molecules having a defined topology comprising defined sequence segments capable of specifically binding or hybridizing to the second defined sequence segments; and a cyclic oligonucleotide or circular structure having defined sequences capable of hybridizing to the second defined sequence segments.

Second defined sequence segments, linker oligonucleotides and hybridizable spacer sequences may be selected so as to introduce, via hybridization of first and second synthetic heteropolymers, duplex regions that can be selectively targeted or modified, e.g., by intercalating agents or anti-double-stranded oligonucleotide antibodies, or that comprise specific recognition properties, e.g., a double-stranded aptamer, triplex-forming sequence or biological recognition site. In addition, duplex regions formed by hybridized defined sequence segments and/or linker oligonucleotides can be stabilized, e.g., using crosslinking agents, disulfide bonds, photoactivatable reagents, irradiation, covalently linked intercalators, hydrophobic interactions, triplex-forming oligonucleotides, or conjugates or combinations thereof.

Linkers, linker molecules, and nonnucleotide linkers, when used in reference to nonnucleotide molecules that link nucleotides, include molecules capable of joining two nucleotides either covalently or noncovalently. Nonnucleotide linkers include, for instance and without limitation, selected molecules capable of binding two aptamers (i.e., joining two aptamers to form a multimolecular complex), dendrons, nonDNA dendrimers, peptides, proteins, nonnucleotide linkages and bridges, nonnucleotide monomers, dimers and polymers, ligands and receptors (e.g., biotin, digoxigenin, avidin, streptavidin, antibodies), lipids, sugars, polyethylene glycols, cholesterol, fusion proteins, bispecific antibodies, chelating agents, intercalating agents, crosslinking agents, and nonnucleotides comprising bifunctional, heterofunctional multifunctional molecules and nonnucleotide oligonucleotide linkers.

Two or more defined sequence segments comprising a synthetic heteropolymer may be attached to one another by internucleotidic linkages, e.g., by automated nucleic acid synthesis, recombinant methods or in vitro replication, transcription, amplification, ligation or strand extension procedures well known in the art. Alternatively, defined sequence segments comprising a synthetic heteropolymer may be attached by covalent methods, preferably using a bifunctional crosslinker and optionally a carrier, bridge or spacer molecule or a dendritic or polymeric linker species (e.g., a monomer such as glycine, glucose, monoglyceride or ethylene diamine, a dendron such as a poly(amidoalcohol), poly(arylester) or poly(siloxysilane) monodendron, a dimer such as glycylglycine, or a linear or branched polymer, copolymer or multimer such as an oligopeptide, protein, polysaccharide, fatty acid, fatty alcohol or fatty alcohol methyl ester, a branched or hyperbranched polymer such as a poly(amidoamine) dendrimer, or a water insoluble polymer such as polystyrene (i.e., latex), nylon or polypropylene) and more preferably using 3' and 5' terminal linkers with 5' to 5', 3' to 3', or 3' to 5' crosslinkers, particularly heterobifunctional crosslinkers, optionally including a carrier, bridge or spacer molecule, monomer, dendron or polymer. Defined sequence segments comprising a synthetic heteropolymer may also be attached to one another noncovalently, preferably pseudoirreversibly, e.g., using conjugated members of a high-affinity specific binding pair (e.g., avidin/biotin or streptavidin/biotin), conjugated chelating or intercalating agents, or conjugated molecules or groups of molecules capable of attaching the defined sequence segments by hydrophobic or ionic association. Methods for preparing a synthetic heteropolymer by non-covalent attachment of a biotinylated defined sequence segment and a streptavidin-conjugated defined sequence segment are described in Example 12 (vide infra).

Two or more synthetic heteropolymers may be attached to one another by hybridization (i.e., to form a multivalent heteropolymeric hybrid structure) or by specific binding (e.g., between defined sequence segments or between a defined sequence segment and a conjugated molecule). Synthetic heteropolymers may also be attached to one another either directly or via one or more intervening carrier, bridge or spacer molecules or dendritic or polymeric linkers by covalent or pseudoirreversible methods, as described for attachment of defined sequence segments in the preceding paragraph (vide supra).

Bifunctional or multifunctional hybrids of synthetic heteropolymers, referred to as multivalent heteropolymeric hybrid structures, may also be formed in accordance with the methods of the invention, having the ability to specifically bind two or more selected molecules or nucleic acid sequences. A multivalent heteropolymeric hybrid structure comprises at least two synthetic heteropolymers, at least one of which comprises a defined sequence segment capable of specifically binding a nonoligonucleotide molecule. Multivalent heteropolymeric hybrid structures capable of assembling molecules within a multimolecular transducer is prepared as follows. Two molecules or groups of molecules capable of performing a useful function when brought into close spatial proximity are identified, at least one of which is a nonoligonucleotide molecule, preferably a receptor, ligand or molecular effector. A first defined sequence segment capable of specifically binding to an identified nonoligonucleotide molecule is selected, preferably by repeated selection and amplification of oligonucleotide pools, more preferably by combinatorial selection and amplification of an oligonucleotide library. A first synthetic heteropolymer comprising the first defined sequence segment and a second defined sequence segment capable of hybridizing to a selected nucleic acid sequence is synthesized by methods well known in the art. A second synthetic heteropolymer comprising a first defined sequence segment selected to bind the second identified molecule and a second defined sequence segment capable of hybridizing with the second defined sequence segment of the first synthetic heteropolymer is synthesized by methods well known in the art. The first and second synthetic heteropolymers are then hybridized through their complementary second defined sequence segments to produce a multivalent heteropolymeric hybrid structure. The hybridized second defined sequence segments, which may comprise from as few as five to as many as several hundred nucleotides, are of such length, preferably about 5 to 40 nucleotides and more preferably about 8 to 20 nucleotides, to provide for controlled spacing between the two defined sequence segments of the multivalent heteropolymeric hybrid structure that are capable of specifically binding to the identified molecules. Accordingly, these two defined sequence segments are separated by such distance, preferably 1 to 10 microns and more preferably 2 to 15 nm, to accommodate specific binding of the two identified molecules in close intermolecular proximity. The molecules can then be bound to their respective defined sequence segments of the multivalent heteropolymeric hybrid structure to form a multimolecular heteropolymeric complex with specifically bound molecules suitably positioned for optimal cooperative function. Multivalent heteropolymeric hybrid structures useful in assembly of multimolecular switches are prepared in a similar manner, but the distance between first defined sequence segments is kept to a minimum, preferably less than 1 micron and more preferably less than 10 nm, so that binding or activity of a selected molecule or nucleic acid sequence at the first defined sequence segment of a first synthetic heteropolymer influences the binding or activity of a selected molecule or nucleic acid sequence at the first defined sequence segment of a second synthetic heteropolymer. The appropriate distance between first defined sequence segments to enable such functional coupling is achieved, for example, by 1) adjusting the length of the hybridizable second defined sequence segments, preferably to less than 20 nucleotides and optionally less than 12 nucleotides (preferably crosslinked in place to produce stable, covalent hybrids), 2) including a nucleotide spacer, spacer sequence or linker oligonucleotide (e.g., a branched, internally hybridized, dendritic, stem-loop or pseudoknot structure) to create a bend, loop, bulge or branchpoint which increases the topological distance but reduces the spatial distance between first defined sequence segments, and/or 3) including in the synthetic heteropolymers mutually complementary third defined sequence segments whose hybridization within the heteropolymeric hybrid structure forms a bent, looped, bulged, hairpin, knotted or closed-loop structure that reduces the spatial distance between first defined sequence segments to less than that of control structures lacking third defined sequence segments (e.g., a closed-loop heteropolymeric hybrid structure having single-stranded first defined sequence segments bracketed between hybridized second defined sequence segments at one end and hybridized third defined sequence segments at the other end).

In accordance with a preferred embodiment of the present invention, two or more nonoligonucleotide molecules or groups of molecules capable of cooperating to carry out a desired function or functions, preferably receptors, ligands, structural molecules or molecular effectors, are assembled in a multimolecular heteropolymeric complex in the following manner. Nonoligonucleotide molecules or groups of molecules capable of cooperating to carry out a desired function or functions are identified. A first defined sequence segment capable of specifically binding an identified molecule is selected for each molecule, preferably by repeated selection and amplification of oligonucleotide pools, more preferably by combinatorial selection of an oligonucleotide library. A synthetic heteropolymer or multivalent heteropolymeric hybrid structure comprising each of the first defined sequence segments is then prepared such that the arrangement and spacing of these defined sequence segments provides for specific binding of the identified molecules in close, spatially ordered intermolecular proximity. The identified molecules can then be specifically bound to their respective defined sequence segments to form a multimolecular heteropolymeric complex capable of performing the desired cooperative function or functions of the constituent nonoligonucleotide molecules.

In addition, a synthetic heteropolymer, multivalent heteropolymeric hybrid structure or multimolecular heteropolymeric complex capable of specifically binding to a selected nucleic acid sequence may be prepared by a modification of the above method, wherein a particular defined sequence segment is selected for its ability to hybridize to a selected nucleic acid sequence. A synthetic heteropolymer capable of specifically binding to a selected nucleic acid sequence may be prepared by selecting a second defined sequence segment capable of hybridization, preferably a nucleic acid probe sequence. A multivalent heteropolymeric hybrid structure capable of specifically binding to a selected nucleic acid sequence may be prepared by selecting a first defined sequence segment of a constituent synthetic heteropolymer capable of hybridization, preferably a nucleic acid probe sequence. A multimolecular heteropolymeric complex capable of specifically binding to a selected nucleic acid sequence may be prepared by specifically binding selected molecules to either a synthetic heteropolymer or a multivalent heteropolymeric hybrid structure comprising a suitable defined sequence segment capable of hybridization.

The synthetic heteropolymers, multivalent heteropolymeric hybrid structures and multimolecular heteropolymeric complexes of the present invention can be added to a reaction mixture directly, incorporated into a device, or they may be capable of attaching to solid supports and matrices including, but not limited to, thin and thick films, lipid bilayers, microvesicles, membranes, organic polymers, microparticles, and inorganic substrates such as silicon, silicates, plastics, polymers, graphite and metals. They may be immobilized by covalent attachment, adsorption, controlled deposition or affinity-based methods such as hybridization. Immobilization may also be achieved by in situ synthesis of constituent synthetic heteropolymers or linker oligonucleotides on suitable substrates followed by in situ self-assembly of multivalent heteropolymeric hybrid structures or multimolecular heteropolymeric complexes.

The proximity of the selected defined sequence segments to one another within the synthetic heteropolymer or multivalent heteropolymeric hybrid structure, which is controlled by the length, composition and three-dimensional structure of the spacer nucleotide and linker oligonucleotide sequences, is such that the binding of a molecule at one defined sequence segment can modulate the affinity of another defined sequence segment for a second nonoligonucleotide molecule. Modulating the affinity refers to any increase or decrease in the association or dissociation rate constants that characterize the binding between a defined sequence segment and its specific binding partner. The binding of a molecule at one defined sequence segment can also modulate the activity of a molecule bound to another defined sequence segment. Modulating the activity refers to restoration, transduction or elimination in part or in full of the biological, chemical, optical, catalytic, mechanical, electrical or electrochemical activity of a selected molecule or nucleic acid sequence. For example, in a diagnostic assay, specific binding of a nonoligonucleotide molecule such as a receptor or ligand to a second defined sequence segment of a synthetic heteropolymer may decrease the binding affinity of a first defined sequence segment for a bound, inactive or partially inactive molecular effector. This results in displacement of the molecular effector and restoration of its activity. Thus, the presence of the selected receptor or ligand may be monitored by measuring activity of the molecular effector. In the case of a selected nucleic acid sequence, activity refers either to catalytic properties (e.g., ribozyme or catalytic DNA activity) or to information content (e.g., coding or regulatory properties). Modulation includes effects on catalytic activity, replication, transcription, translation and enzyme-dependent processes such as strand extension, ligation, amplification, and the like.

The activity of a molecule specifically bound at one defined sequence segment can also modulate the affinity of a second defined sequence segment for a second nonoligonucleotide molecule. Local production of hydrogen ions by an enzyme specifically bound to one defined sequence segment, for example, can modulate the affinity of a second defined sequence segment for a second molecule by decreasing the microenvironmental pH surrounding the second defined sequence segment. Similarly, the activity of a nonoligonucleotide molecule specifically bound at one defined sequence segment can modulate the activity of a second molecule bound to a second defined sequence segment. A specifically bound enzyme, for example, may generate any number of products, including hydrogen ions, electrons, photons, heat, substrates, prosthetic groups, cofactors or inhibitors, that can influence the activity of a second bound effector either directly or through effects on the microenvironment. The occupation state of a ligand or receptor bound at one defined sequence segment can also modulate the affinity of a second defined sequence segment for a second nonoligonucleotide molecule or the activity of the second nonoligonucleotide molecule. Specific binding of a ligand bound at one defined sequence segment to its receptor, for example, can increase the dissociation rate of a selected second molecule bound to a second defined sequence segment through steric or conformational effects. The activity of the second molecule can increase or decrease with dissociation, depending on its relative activity in the bound and free states.

By positioning molecules so that binding or activity at a first defined sequence segment modulates binding or activity at a second defined sequence segment, synthetic heteropolymers of the present invention can be used to functionally couple a first selected molecule or nucleic acid sequence to a second selected molecule or nucleic acid sequence. For example, a first signal-generating molecule such as a fluorophore can be functionally coupled to a second signal-generating molecule such as a second fluorophore (e.g., a donor or acceptor), a light-driven or bioluminescent enzyme (e.g., an ATPase or luciferase) or an artificial reaction center (i.e., a molecule capable of photoinduced charge separation).

Alternatively, a synthetic heteropolymer of the instant invention can be designed to specifically attach and properly orient a signal-generating molecule to an electronic or optoelectronic transducer (e.g., an amperometric electrode or photovoltaic cell) so that the signal-generating molecule, preferably a particular region of the signal-generating molecule (e.g., a photon-emitting chromophore or electron-donating redox center), communicates intimately with the device (e.g., by energy transfer or direct electronic coupling). A first defined sequence segment is selected to specifically bind the selected signal-generating molecule. A second defined sequence segment is selected to specifically bind or hybridize a selected molecule or nucleic acid sequence comprising or immobilized to the device. A synthetic heteropolymer comprising the two defined sequence segments, optionally separated by a spacer sequence, is then synthesized and used as a molecular template to specifically bind the signal-generating molecule within functional coupling distance of the transducer.

In addition, synthetic heteropolymers of the instant invention can be used as molecular positioning devices to enable functional coupling between different molecules conjugated to selected molecules, nucleic acid sequences or defined sequence segments. For example, a first signal-generating molecule (e.g., a donor fluorophore or donor enzyme) conjugated to a first selected molecule (e.g., a peptide) can be functionally coupled to a second signal-generating molecule (e.g., an acceptor fluorophore or acceptor enzyme) conjugated to a second selected molecule, (e.g., dextran) wherein the first and second selected molecules are specifically bound within functional coupling distance to first and second defined sequence segments of a synthetic heteropolymer or multivalent heteropolymeric hybrid structure designed to position said first and second selected molecules within close spatial proximity. Alternatively, one or more signal-generating species (e.g., donor or acceptor fluorophores or enzymes) may be conjugated to a selected nucleic acid sequence which is capable of hybridizing to a second defined sequence segment of a synthetic heteropolymer, enabling energy transfer or enzyme channeling between the conjugated selected nucleic acid sequence and one or more signal-generating molecules (e.g., donor or acceptor fluorophores or enzymes) conjugated to either 1) a first or second defined sequence segment of the synthetic heteropolymer, or 2) a selected molecule or nucleic acid sequence capable of specifically binding or hybridizing to a defined sequence segment of the synthetic heteropolymer. In a related mode of operation, a first signal-generating molecule which is conjugated to a selected molecule or nucleic acid sequence may be functionally coupled to a second signal-generating molecule which is specifically bound to a defined sequence segment of the synthetic heteropolymer or multivalent heteropolymeric hybrid structure. It will be apparent to one of skill in the art that synthetic heteropolymers of the instant invention can be used to provide functional coupling between selected molecules and nucleic acid sequences which are attached to the synthetic heteropolymer either covalently or noncovalently and either directly or indirectly, so long as at least one defined sequence segment of the synthetic heteropolymer is capable of specifically recognizing a nonoligonucleotide molecule or conjugate.

Heteropolymeric functional coupling of the instant invention does not include the interaction between a ribozyme and its biological recognition site, i.e., the catalytic activity resulting from ribozyme-based recognition and cleavage of a biological nucleic acid sequence. Also outside the scope of the instant invention are ribozymes comprising synthetic defined sequence segments that bring the ribozyme catalytic element under allosteric control, i.e., by specific recognition of a selected molecule or selected nucleic acid sequence that regulates ribozyme catalytic activity.

The synthetic heteropolymers, multivalent heteropolymeric hybrid structures and multimolecular heteropolymeric complexes of the present invention may be used in a variety of applications which will become apparent to those skilled in the art upon reading this disclosure. For example, the present invention may serve as a homogeneous nucleic acid probe diagnostic used to report hybridization reactions. Nucleic acid probes are single-stranded sequences of DNA or RNA that specifically hybridize to defined target sequences of nucleic acids in a test sample. DNA probes labeled with detectable markers such as enzymes, isotopes, fluorophores or chemiluminescent compounds, provide a useful means for detecting and quantifying selected nucleic acid sequences in biological samples. DNA probe diagnostics have yet to realize substantial commercial success, however, largely because the complexity of test protocols have precluded routine implementation in clinical laboratory settings. In addition, current DNA probe assays are substantially more time-, labor-, skill- and cost-intensive than the two dominant in vitro diagnostic modalities, clinical chemistry and immunodiagnostics.

In general, present technologies for heterogeneous DNA probe diagnostics involve the following steps. Genomic, cellular or plasmid DNA is extracted from test samples. The DNA is denatured to yield single-stranded targets. Target sequences are then amplified by successive replication using methods such as the polymerase chain reaction (PCR) or ligase chain reaction (LCR). Amplified target sequences are immobilized, and labeled probes are hybridized to the immobilized targets. The immobilized probe-target hybrids then require separation from unbound probes and successive washing before the bound probes can be detected by addition of a signal generator.

In accordance with the present invention, a variety of homogeneous DNA probe reagents can be prepared utilizing synthetic heteropolymers which simplify this process. In the present invention, the term homogeneous, as contrasted with heterogeneous, refers to properties of assay reagents that eliminate the need for tedious separation and washing steps. In homogeneous assays, the activity of a signal-generating species, process, or detectable label is altered when a probe specifically binds its target. Specific binding can then be quantified without physically separating bound complexes from unbound reagents. In one embodiment, a multimolecular heteropolymeric complex comprises a synthetic heteropolymer having an effector molecule specifically bound to one of the defined sequence segments. Examples of preferred molecular effectors include, but are not limited to, such detectable species as chromogenic, fluorescent, chemiluminescent, bioluminescent and electroactive substances and enzymes, more preferred enzymes being glucose-6-phosphate dehydrogenase (G6PDH), acetyl cholinesterase, glucose oxidase, β-galactosidase, lysozyme and malate dehydrogenase. The second defined sequence segment of the multimolecular heteropolymeric complex is capable of hybridizing with a selected nucleic acid sequence. This defined sequence segment serves as a nucleic acid probe. The multimolecular heteropolymeric complex may be incorporated into a dry-reagent test device, attached to a solid support to create an immobilized reagent or added to a liquid reaction mixture. In this embodiment, the activity of the molecular effector is modulated by target hybridization at the second defined sequence segment. It will be appreciated by those skilled in the art that many permutations of a single-reagent homogeneous format can be developed by selecting different combinations of molecular effectors and defined sequence segments. The state of activity of a particular molecular effector depends on the binding locus, length and affinity of the selected defined sequence segment, which can be optimized for maximal target-dependent modulation.

In another embodiment, the multimolecular heteropolymeric complexes of the present invention comprise a synthetic heteropolymer having a ligand specifically bound to a first defined sequence segment and a second defined sequence segment capable of hybridization. The multimolecular heteropolymeric complex may be attached to a solid support to create an immobilized reagent, incorporated into a dry reagent test device, or added to a liquid reaction mixture. In this embodiment, hybridization at the second defined sequence segment can modulate either the affinity of the first defined sequence segment for the ligand or the activity of the ligand, resulting in activation or inhibition of a molecular effector that is not a constituent of the multimolecular heteropolymeric complex.

This same basic reagent composition described for homogeneous DNA probe diagnostics can be used for pseudoimmunodiagnostic applications through modular substitution of the defined sequence segments. Homogeneous diagnostic assays employing molecular effector-oligonucleotide complexes to detect nonoligonucleotide molecules represent a replacement technology for immunodiagnostics. The utility of this approach resides in its simplicity, ease of use, modular design and versatility. By selecting defined sequence segments that specifically bind the nonoligonucleotide molecules to be analyzed, hereinafter analytes, diagnostic reagents can be developed which function much like labeled antibodies but with a number of important advantages. Activation of a molecular effector, preferably an enzyme, bound at a first defined sequence segment by analyte binding at the second defined sequence segment provides for a homogeneous, single-step, single-reagent diagnostic test. In addition, labeling of the synthetic heteropolymer with the molecular effector is accomplished by self-assembly of specific binding partners, thereby precluding tedious and imprecise covalent conjugations.

Development of new diagnostic products using the modular design approach requires only selection and optimization of one defined sequence segment of the synthetic heteropolymer. The defined sequence segment that binds the molecular effector, the molecular effector itself, and any linker oligonucleotides are conserved from product to product. This modular approach to product development is both efficient and economical. Unlike homogeneous immunoassays, which tend to be best suited for either large molecules or small molecules, the present approach provides a common reagent configuration and assay protocol for any class of analytes. These pseudoimmunodiagnostic compositions can be incorporated into any reagent delivery system including, but not limited to, slides, cartridges, sensors, test tubes, microtiter plates and autoanalyzer reagent channels.

In one embodiment of homogeneous pseudoimmunodiagnostics, low molecular weight analytes are detected with high sensitivity in the following manner. A multimolecular heteropolymeric complex is prepared comprising a synthetic heteropolymer or multivalent heteropolymeric hybrid structure with a reporter molecule, preferably a molecular effector, more preferably an enzyme such as G6PDH, specifically bound to one defined sequence segment and the ligand moiety of a ligand-carrier conjugate specifically bound to a second defined sequence segment. Examples of analytes for which such a complex is useful include, but are not limited to, hormones such as thyroxine ($T_4$) and triiodothyronine ($T_3$), prolactin, cortisol, estriol, estradiol, progesterone and testosterone; therapeutic drugs such as theophylline, digoxin, phenytoin, valproic acid, phenobarbital, antibiotics and immunosuppressants; and drugs of abuse such as THC, cocaine, PCP, opiates and amphetamines. Due to their low molecular weights, some of these analytes may not be as effective in modulating the activity of a molecular effector specifically bound to a synthetic heteropolymer as high molecular weight analytes such as proteins, immunoglobulins and cell surface antigens. The impact of specific binding of such low molecular weight analytes to a first defined sequence segment of a multimolecular heteropolymeric complex on the activity or affinity of an effector molecule specifically bound to a second defined sequence segment can be amplified through analyte-dependant displacement of a large ligand-carrier conjugate from the first defined sequence segment.

The homogeneous configurations of the present invention can be adapted for use with a wide range of reporter molecules. Examples of molecular effectors that can serve as effective reporters in a multimolecular heteropolymeric complex include, but are not limited to, fluorophores, phosphors, bioluminescent and chemiluminescent reagents, quenchable dyes, activatable dyes and enzyme-enhanced luminescent and fluorescent reagent systems. Homogeneous pseudoimmunodiagnostic configurations are therefore compatible with all existing and anticipated nonisotopic detection systems, including, but not limited to, spectrophotometers, reflectance photometers, luminometers, fluorimeters, potentiostats, potentiometers, and confocal and fluorescent microscopes.

Classes of analytes for which multimolecular pseudoimmunodiagnostic heteropolymeric complexes may be most useful include, but are not limited to: infectious diseases, including viral, bacterial and fungal antigens and antibodies against these antigens; endocrinology and metabolism, including thyroid and reproductive hormones, $B_{12}$, folate, ferritin, glycosylated hemoglobin, parathyroid hormone, calcitonin and cortisol; therapeutic drugs, including theophylline, digoxin, phenytoin, valproic acid, phenobarbital, antibiotics and immunosuppressants; allergy and immunology, including allergen-specific IgE and autoantibodies; drugs of abuse, including cocaine, cannabinoids, phencyclidine and amphetamines; cancer, including CEA, AFP, CA 125, CA 50, CA 19-9, CA 15-3, PAP and PSA; and cardiovascular disease, including apolipoproteins, fibrinogen, cardiac enzymes and isoforms, troponin, myosin light chains and myoglobin.

Clinical chemistry tests relying on coupled enzyme reactions can also be performed efficiently and with high sensitivity through use of multimolecular heteropolymeric complexes. The benefits of using multimolecular heteropolymeric complexes over conventional reaction mixtures include increased sensitivity, reagent stability and reaction rates; decreased sample volume and reagent mass/test; and suitability for direct signal transduction using immobilized multimolecular heteropolymeric complexes.

The combination of homogeneous DNA probes, homogeneous pseudoimmunodiagnostic assays and coupled enzyme clinical chemistries provides a unified approach to the three major classes of in vitro diagnostics, thereby enabling development of a universal clinical analyzer through use of multimolecular heteropolymeric complexes. Synthetic heteropolymers are particularly attractive for development of integrated diagnostic platforms, e.g., multianalyte biosensors and biochip arrays, because multimolecular complexes comprising each required type of effector or target specificity (i.e., for DNA probing, pseudoimmunodiagnostics and clinical chemistry) can be attached to a transducer surface using a single, common process, e.g., immobilization of oligonucleotides and/or hybridization of defined sequence segments. In this way, nucleotide-directed molecular assembly can be used to produce useful arrays, e.g., ordered arrays of multimolecular complexes for diagnostics, drug discovery and/or high-throughput screening, e.g., by patterning on a chip or transducer surface (e.g., a slide, cartridge, semiconductor or optoelectronic device) oligonucleotide sequences comprising or complementary to defined sequence segments of nucleotide-based discrete structures, preferably synthetic heteropolymers or multimolecular devices.

An in vitro diagnostic tool is just one of the many applications for synthetic heteropolymers, multivalent heteropolymeric hybrid structures and multimolecular heteropolymeric complexes. Molecular complexes comprising multiple coupled effector molecules, such as enzymes, represent molecular processing compositions that can be applied to cost-effective biosynthesis, including the production of chiral drugs and intermediates, industrial production and processing, computer-aided metabolic simulation and development of artificial organs. The multimolecular heteropolymeric complexes described for homogeneous diagnostic assays are special examples of stimulus-sensitive molecular effectors or molecular switches that can be applied to in vivo diagnostic imaging, implantable devices, biosensors and biochips, pharmaceuticals and drug delivery.

Using a therapeutic enzyme as the molecular effector component of a multimolecular heteropolymeric complex, delivery of the active therapeutic can be triggered by a specific binding event between an unoccupied defined sequence segment of the complex and a physiological receptor or pathological target. Examples of therapeutic enzymes include, but are not limited to, tissue plasminogen activase and streptokinase (for acute myocardial infarction and pulmonary embolism), superoxide dismutase (for oxygen toxicity in premature infants), DNAse (for cystic fibrosis and chronic bronchitis) and cerebrosidase (for Gaucher's disease). It will be appreciated by those skilled in the art that in addition to enzymes, a virtually limitless array of therapeutic effectors can be specifically bound in inactive or inaccessible form to one defined sequence segment of a synthetic heteropolymer or multivalent heteropolymeric hybrid structure such that activation occurs upon specific binding of a second defined sequence segment to a physiological receptor or pathological target.

Many diseases, syndromes and pathological processes are multifactorial, suggesting the potential clinical value of combination therapies. However, combination therapies present significant risks in the form of combined toxicities and drug interactions. Major therapeutic development strategies aimed at increasing drug efficacy without concomitant increases in toxicity revolve around novel drug delivery and targeting approaches. Therapeutic immunoconjugates for site-specific delivery of radioisotopes or cytotoxins have received a great deal of attention over the past decade. Fusion proteins comprising a targeting moiety and a toxic moiety are also being developed for infectious diseases and cancer.

Synthetic heteropolymers, multivalent heteropolymeric hybrid structures and multimolecular heteropolymeric complexes enable novel approaches to combination therapies and targeted drug delivery that cannot be achieved using therapeutic immunoconjugates or fusion proteins. In simplest form, synthetic heteropolymers or multivalent heteropolymeric hybrid structures can be designed to specifically bind two or more neighboring sites on a single pathophysiological target. Bifunctional heteropolymers, for example, can act upon: two sites on a single molecule, such as an enzyme or a receptor; two molecules in a single structure, such as two proteins in a multimolecular receptor-effector system or a viral nucleic acid sequence and an associated coat protein; or two molecules on different structures, such as cell adhesion molecules or receptors located on different cells. Although most of these approaches are technically plausible with immunoconjugates, bispecific antibodies or fusion proteins, synthetic heteropolymers and multivalent heteropolymeric hybrid structures provide a number of advantages that render them substantially more useful. First, nucleotide sequences that make up the synthetic heteropolymers can be selected and synthesized with desired specificity and affinity for either specific nucleic acid sequences or nonoligonucleotide molecules. Second, unlike bispecific antibodies and therapeutic immunoconjugates, multivalent heteropolymeric hybrid structures can be conveniently engineered with three or more specific binding sequences. Third, synthetic heteropolymers and multivalent heteropolymeric hybrid structures can be synthesized by established chemical methods, obviating the technical challenges and uncertain outcomes of designer antibody and fusion protein production. Fourth, the spacing of multiple specific binding sequences in synthetic heteropolymeric and multivalent heteropolymeric hybrid structures can be rationally designed and controlled through systematic production and evaluation of structures composed of variable-length and variable composition spacer sequences and linker oligonucleotides. In addition to two-site therapeutic actions, a number of other drug development approaches can be pursued through nucleotide-directed molecular assembly.

In a first embodiment, multimolecular heteropolymeric complexes are synthesized comprising two or more specific binding sequences, wherein a therapeutic drug is specifically bound to a first defined sequence segment and the second defined sequence segment is capable of specifically binding to a therapeutic target. This embodiment enables use of the specifically bound drug as a targeting agent for site-specific delivery of the unoccupied specific binding sequence or, alternatively, use of the unoccupied defined sequence segment for site-specific delivery of the bound drug. In either case, the combination of drug action and specific binding of the unoccupied defined sequence segment to a pathophysiologic target can produce therapeutic effects through two distinct mechanisms of action. For example, a therapeutic for HIV could comprise a multimolecular heteropolymeric complex having a protease or reverse transcriptase inhibitor specifically bound to one site of a synthetic heteropolymer with an HIV-specific DNA probe or antisense sequence as the second site.

In a second embodiment, combination therapies relying on multimolecular heteropolymeric complexes comprising a ligand, preferably a therapeutic drug, specifically bound to one defined sequence segment and a molecular effector, preferably an enzyme, specifically bound to a second defined sequence segment are synthesized. In this embodiment, a high-affinity ligand may be used to deliver the complex to a particular site where simultaneous actions of the ligand and the molecular effector yield an additive or synergistic therapeutic effect. An example of such a multimolecular heteropolymeric complex is an adenosine regulating agent such as Arasine™ (Gensia Pharmaceuticals, San Diego, Calif.) specifically bound to a first defined sequence segment with the enzyme tissue plasminogen activase or Activase™ (Genentech, San Francisco, Calif.) bound to a second defined sequence segment to yield localized thrombolytic and cardioprotective effects in perimyocardial infarction, coronary artery bypass surgery and angioplasty procedures.

In a third embodiment, combination therapies relying on multimolecular heteropolymeric complexes comprising different ligands, preferably drugs, specifically bound to different defined sequence segments of a synthetic heteropolymer or multivalent heteropolymeric hybrid structure are synthesized. Examples of pairs of ligands which can be bound to selected defined sequence segments of synthetic heteropolymers or multivalent heteropolymeric hybrid structures include, but are not limited to: a histamine $H_2$ receptor antagonist such as Tagamet™ (SmithKline Beecham Pharmaceuticals, King of Prussia, Pa.) and a proton pump inhibitor such as Losec™ (Astra AB Pharmaceuticals, Sodertalje, Sweden) for the treatment of gastric ulcers; a histamine $H_1$ receptor antagonist such as terfenadine and a mast cell release inhibitor such as cromolyn sodium for the treatment of histamine-mediated diseases such as bronchial asthma; an interleukin such as IL-3 and a colony stimulating factor such as GM-CSF for treatment of leukemias, cerebral malaria, leishmaniasis and allergic disorders such as bronchial asthma; and a P-glycoprotein inhibitor such as verapamil or cyclosporin and one or more chemotherapeutic agents such as 5-FU and levamisole to eliminate the risks of multi-drug resistance while treating malignancies.

It is preferred that the combination therapies discussed be administered in a triggered release configuration, i.e., as a prodrug, wherein binding of a first defined sequence segment, as in the first embodiment, or specifically bound ligand, as in the second and third embodiments, to its therapeutic receptor releases or activates the ligand or effector specifically bound to a second defined sequence segment of a multimolecular heteropolymeric complex. For example, binding of the $H_2$ antagonist Tagamet™ to a gastric histamine receptor would result in release of Losec™ to the gastric proton pump through a conformational shift in the multivalent heteropolymeric hybrid structure used to deliver the two drugs.

In addition to the diagnostic and therapeutic utilities discussed, the present invention can also be utilized in a variety of applications including, but not limited to: sequential, multistep enzymatic synthesis of a particular product or degradation or a toxic metabolite; coupling proteins to selectively or actively transport ions and metabolites; coupling cytochromes to transduce chemical energy by means of electron transfer-dependent oxidation-reduction reactions; coupling redox mediators such as ubiquinones, ferricinium salts, rubidium, viologens, tetrathiofulvalene, tetracyanoquinidodimethane, N-methylphenazinium, benzoquinone or conducting polymers or organic conducting salts to transfer electrons between electroactive molecules such as redox enzymes and electrodes in bioelectronic and optoelectronic devices such as biosensors and biochips; coupling photoactive compounds such as fluorophores with other photoactive compounds or with redox proteins or enzymes for energy transfer devices and artificial photosynthetic systems; and coupling pro-drugs for staged-delivery or triggered activation. Medical applications that rely on ordered arrangements of one or more exogenously administered molecules with an endogenous pathophysiological target include, but are not limited to: targeting radioconjugates or radiochelates of gamma-emitting isotopes such as iodine-131, iodine 123, indium-111, technetium-99m and copper-67 to pathophysiological markers such as cancer antigens CEA, TAG-72, CA 125 and CA 19-9 for in vivo diagnostic imaging; targeting radioconjugates, cytotoxins or cytotoxic cells to disease markers for localized cell kill; and targeting drugs to pathophysiologic receptors to achieve receptor-, cell- or tissue-selective therapeutic action.

Nucleotide-directed enzyme assembly using multimolecular heteropolymeric complexes provides a general method for production of spatially ordered, cooperative multienzyme systems. Applications include, but are not limited to, production of chiral intermediates and chiral drugs, industrial biosynthesis and bioprocessing, diagnostics, detoxification and computer-aided metabolic simulation. Advantages over soluble multienzyme systems include control over the spatial arrangement of individual enzymes within complexes; control over protein-protein interactions, diffusion distances and diffusion times; direct channeling of the product of one enzyme to a proximate enzyme; increased efficiencies through preferential reaction within the Nernst layer; protection of unstable intermediates; regulation of microenvironmental factors; control over the direction of thermodynamically unfavorable reactions; and enhanced enzyme stability. Of particular commercial value, nucleotide-directed enzymatic cycling can be used to drive NAD(P)H- and ATP-driven biosynthetic reactions using catalytic amounts of expensive pyridine nucleotides. In addition, multistep sequential reactions involving unstable intermediates can be efficiently coordinated through nucleotide-directed juxtaposition of participating enzymes.

Sequential, multistep enzymatic synthesis refers to the conversion of an initial substrate into a final product through a series of enzyme reactions, wherein each proximal enzyme generates a product that is a substrate for a subsequent enzyme reaction. Practical application of multistep enzyme systems to industrial scale production requires enzymatic cycling. This technique has been developed for soluble enzymes and has stimulated intense efforts in the area of immobilized enzyme systems. For purposes of this invention, enzymatic cycling refers to the shuttling of oxidized and reduced forms of a coenzyme between two linked enzymes. This type of reaction scheme is useful for a variety of applications. There are over 250 NADH-dependent dehydrogenases alone, not including NAD(P)H-dependent enzymes. Representative NADH-dependent dehydrogenases currently used in clinical, fermentation, food and environmental applications include, but are not limited to, alcohol dehydrogenase, 3α-hydroxysteroid dehydrogenase, lactate dehydrogenase, malate dehydrogenase, glutamate dehydrogenase, glucose dehydrogenase, amino acid dehydrogenase, tartrate dehydrogenase, 12α-hydroxysteroid dehydrogenase, estradiol 17α-dehydrogenase, aryl-alcohol dehydrogenase and testosterone β-dehydrogenase.

Extremely sensitive determination of either NAD(P)H or analytes can be achieved through enzymatic cycling. Concentrations of NAD(P)H as low as $10^{-15}$M can be determined by measuring formation of an NAD(P)H-driven product, because the number of cycles per unit time depends on the initial concentration of pyridine nucleotide. Since NAD(P) can be supplied to the cycling reaction by a wide variety of pyridine nucleotide-requiring enzymes, highly sensitive detection can also be achieved for any analyte that is a substrate of an enzyme that can be coupled to a cycling reaction.

Enzymatic cycling reactions can also be used for removal of a toxic substance or unwanted inhibitor from a reaction mixture or biological system. They can be coupled to a wide range of discrete enzymes or multienzyme reaction sequences to catalytically degrade a particular undesirable substance. Multienzyme systems simulating hepatic detoxification processes and renal denitrification reactions, for example, represent enabling tools for valuable biomedical devices. Possible applications include extracorporeal devices for patients with severe hepatic disease; enhanced renal dialysis through enzymatic removal of urea and other toxic metabolites; and in vivo detoxification through multienzyme drugs, implantable devices and artificial organs.

The same principles applicable to nucleotide-directed multienzyme assemblies can also be applied to development of labeling reagents for specific binding assays. Such labeling reagents can amplify a signal to improve the detection limit of a diagnostic assay or transduce a detectable signal into a different type of signal that can be measured using an alternative detection system. Examples of this transduction capability include conversion of: a product that absorbs ultraviolet light into a product that absorbs in the visible range; an electrochemically detectable product into a spectrophotometrically detectable product and vice versa; a spectrophotometrically detectable product into a luminescent or fluorescent product; light of one wavelength into longer wavelength light, thereby effectively increasing the Stoke's shift; and a product with a high detection limit into a product with a low detection limit.

Nucleotide-directed molecular assembly provides a practical approach for the juxtaposition of different fluorophores with overlapping emission and absorption spectra. Applications include diagnostics, artificial photosynthesis and optical signal processing. Conjugation of fluorescein, Texas red, rhodamine, phycobiliproteins and other fluorophores to ligands and receptors provides a useful means to quantify specific binding reactions either directly or through fluorescence energy transfer. Application of fluorescence energy transfer to the development of self-organizing molecular photonic structures (Heller et al. (1993) *Clinical Chemistry*, 39:742) and artificial photosynthesis have also been proposed.

Those skilled in the art will recognize that the general principles of nucleotide-directed enzyme channeling and fluorescence energy transfer can be applied to the interconversion of chemical, electromagnetic, mechanical and thermal energy. Contractile, secretory and transport proteins, for example, represent suitable mechanical acceptors for chemical energy in the same way that cytochromes and chlorophyll serve as acceptors of electrons and photons, respectively, in oxidative metabolism and photosynthesis.

The potential utility of synthetic heteropolymers, multivalent heteropolymeric hybrid structures and multimolecular heteropolymeric complexes encompasses all applications for which the ordered arrangement of molecules enables or improves reactions and processes that do not proceed efficiently when such molecules are either randomly distributed or ordered in bulk. Other utilities for the present invention will become obvious to those skilled in the art from this disclosure.

The following examples illustrate certain aspects of the present invention and are not intended to limit the same.

EXAMPLES

Example 1

Homogeneous Nucleic Acid Probe Diagnostics using Multimolecular Heteropolymeric Complexes with Bound G6PDH to Monitor Hybridization Reactions A first defined sequence segment, approximately 5 to 40 nucleotides, capable of specifically binding the enzyme glucose-6-phosphate dehydrogenase (G6PDH) so that its enzymatic activity is inhibited, is selected. A second defined sequence segment, a nucleic acid probe sequence comprising at least approximately 10 to 20 nucleotides complementary to a defined sequence of an infectious agent, an oncogene or a known genetic defect, is also selected. Examples of infectious agents include, but are not limited to, the viruses HIV, HBV, HCV, CMV, HPV, EBV, RSV, rotavirus, adenovirus, influenza virus and rubella; the bacteria *Escherichia coli* (*E. coli*), Shigella, Klebsiella, Staphylococcus, Streptococcus, Salmonella, Helicobacter, Chlamydia, Gonococcus, and *M. tuberculosis*; and the fungi Candida, Aspergillus, Histoplasma, Blastomyces and Coccidioides. Examples of oncogenes include, but are not limited to, p53 and DCC genes, c-neu, c-myc, N-myc and activated ras oncogenes. Examples of known genetic defects include, but are not limited to, those associated with cystic fibrosis, sickle cell disease, β-thalassemia, Fragile X, Down's syndrome, muscular dystrophy, familial hypercholesterolemia, phenylketonuria, galactosemia, biotinidase deficiency and markers of polygenic disorders. A third nucleotide sequence capable of linking the first defined sequence which binds G6PDH and the second defined sequence capable of hybridization at a distance sufficient to maintain independent operation of each defined sequence segment is then selected, if required or if sterically or kinetically preferred, e.g., to improve the efficiency or rate of G6PDH binding to the first defined sequence segment. The term "independent operation" means that the synthetic heteropolymer is capable of specifically binding a selected molecule or hybridizing a selected nucleic acid sequence with the same specificity as the isolated selected defined sequence segments, i.e., incorporation of the two defined sequence segments into a single discrete structure (e.g., a synthetic heteropolymer) does not impair the function of either defined sequence segment. A synthetic heteropolymer is synthesized comprising the first selected defined sequence segment and the second selected defined sequence segment, optionally connected by the third nucleotide sequence. G6PDH is then bound to the first defined sequence segment to form a multimolecular heteropolymeric complex. About 1 to 50 µl of a sample containing extracted, denatured genomic, cellular or plasmid DNA or RNA is added to a reaction mixture containing this multimolecular heteropolymeric complex, glucose-6-phosphate, nicotinamide adenine dinucleotide phosphate (NAD(P)), sodium azide and phosphate buffered saline (pH 7.4; PBS). Hybridization of the DNA or RNA in the sample to the second defined sequence segment results in a decrease in the affinity of the first defined sequence segment for the G6PDH so that it is no longer bound. The unbound G6PDH, now active, produces reduced NAD(P) (i.e., NAD(P)H) from the NAD(P) in the reaction mixture. This production can be monitored spectrophotometrically at 340 nm or calorimetrically using an indicator such as asiodonitrotetrazolium.

Example 2

High Sensitivity Homogeneous Binding Assays for Low Molecular Weight Analytes

Determination of the low molecular weight analyte thyroxine ($T_4$) can be accomplished through use of a synthetic heteropolymer whose first defined sequence segment is specific for G6PDH and whose second defined sequence segment is specific for $T_4$. A multimolecular heteropolymeric complex is formed by specifically binding G6PDH to the first defined sequence segment and a ligand-carrier conjugate to the second defined sequence segment. Suitable ligands include analogs of $T_4$, particularly iodothyronines such as $T_3$. Suitable carriers include nonphysiological macromolecules such as nonhuman proteins and high molecular weight dextrans. In general, the ligand-carrier conjugate is selected on the basis of: its ability to bind the second defined sequence segment of the multimolecular heteropolymeric complex with adequate affinity to maintain a stable, quasireversible complex; its affinity for the second defined sequence segment being lower than that of native analyte, such that analyte will competitively displace the conjugate; and the degree of inhibition, upon binding, of the signal-generating enzyme specifically bound to the first defined sequence segment of the multimolecular heteropolymeric complex. Inhibition may result either from steric hindrance by the bulky carrier group or modulation of the affinity of the first defined sequence segment for the enzyme. Examples of carriers include, but are not limited to, large proteins such as ferritin, Keyhole limpet hemocyanin (KLH), or thyroglobulin, or insoluble particles such as latex microspheres to which ligands are covalently attached through an appropriate spacer such as 5-aminocaproic acid, diaminohexane or various N-hydroxysuccinimide, hydrazide or maleimide derivatives. In this manner, the specifically bound signal-generating enzyme is inactivated when the carrier-ligand conjugate is specifically bound to the analyte recognition sequence of the bifunctional oligonucleotide. When the multimolecular heteropolymeric complex is exposed to sample analyte ($T_4$), the ligand-carrier conjugate is displaced by higher affinity analyte and the signal generating enzyme is activated with release of the conjugate.

For detection of $T_4$, a synthetic heteropolymer is synthesized which has a first defined sequence segment capable of specifically binding G6PDH and a second defined sequence segment capable of specifically binding $T_4$. G6PDH is bound to the first defined sequence. A ligand-carrier comprising $T_3$ and KLH is bound to the second defined sequence segment. This multimolecular heteropolymeric complex is then used to detect $T_4$ concentrations. About 1 to 50 µl of blood, serum or plasma is added to a reaction mixture or dry-reagent device such as a slide, cartridge or sensor containing the multimolecular heteropolymeric complex, glucose-6-phosphate, NAD(P) and buffer ingredients. $T_4$ in the sample, which has a higher affinity for the second defined sequence segment than the conjugate, binds to the multimolecular heteropolymeric complex and displaces $T_3$-KLH conjugate. This displacement results in activation of G6PDH which reduces NAD(P) to NAD(P)H. Thus, concentrations of $T_4$ can be determined by monitoring production of NAD(P)H spectrophotometrically at 340 nm or colorimetrically using an indicator such as asiodonitrotetrazolium.

Example 3

Homogeneous Nucleic Acid Probe Diagnostics Using Synthetic Heteropolymers with Bound Flavin Adenine Dinucleotide to Monitor Hybridization Reactions A defined sequence segment of nucleotides, at least approximately 5 to 20 nucleotides and optionally 20 to 60 nucleotides or even up to 200 nucleotides, is selected which is capable of specifically binding flavin adenine dinucleotide (FAD), the prosthetic group for apoglucose oxidase, in such a manner that the FAD is inaccessible to apoglucose oxidase. Apoglucose oxidase is inactive until reconstituted to the holoenzyme glucose oxidase with FAD. A second defined sequence segment of at least approximately 10 to 20 nucleotides that is complementary to a defined sequence of an infectious agent, an oncogene or a known genetic defect is selected as a probe. Examples of infectious agents include, but are not limited to, HIV, HBV, HCV, CMV, HPV, EBV, RSV, Chlamydia, Gonococci, and TB. Examples of oncogenes include, but are not limited to, p53 and DCC genes, c-neu, c-myc, N-myc and activated ras oncogenes. Examples of known genetic defects include, but are not limited, to those associated with cystic fibrosis, sickle cell disease, β-thalassemia, Fragile X, Down's syndrome, muscular dystrophy, familial hypercholesterolemia, phenylketonuria, galactosemia, biotinidase deficiency and markers of polygenic disorders. A third nucleotide sequence is optionally selected which is capable of linking the first selected sequence and the second selected sequence in such a manner that each sequence remains independently operative. The term "independently operative" means the first defined sequence segment and the second defined sequence segment do not interact with one another in such manner as to preclude the first defined sequence segment from being capable of specifically binding a selected molecule (e.g., FAD) or the second defined sequence segment from being capable of hybridizing or specifically binding a selected nucleic acid sequence (e.g., a nucleic acid target). In other words, the ability of each defined sequence segment to specifically bind a selected molecule or hybridize to a selected nucleic acid sequence is maintained when the defined sequence segments are incorporated into a synthetic heteropolymer having two or more independently operative defined sequence segments. A heteropolymer is synthesized which contains the first and second selected defined sequence segments optionally linked by the third nucleotide sequence. FAD is then bound to the first defined sequence segment of the heteropolymer to form a multimolecular heteropolymeric complex. About 1 to 50 µl of a sample containing extracted, denatured genomic, cellular or plasmid DNA or RNA is added to a reaction mixture containing this multimolecular heteropolymeric complex, apoglucose oxidase, glucose, horseradish peroxidase, and buffer. Hybridization of DNA or RNA in the sample to the second defined sequence segment alters the affinity of the first defined sequence segment for FAD such that bound FAD is displaced or rendered sterically accessible to apoglucose oxidase. Glucose oxidase is thereby reconstituted in proportion to the number of hybridization events, so the concentration of target sequences can be quantified either photometrically through coupling of glucose oxidase to a chromogenic peroxidase reaction or electrochemically through coupling to an amperometric enzyme electrode. For photometric detection, enzymatic oxidation of 2,2'-azino-bis (3-ethylbenzthiazoline-6-sulfonic acid (ABTS) by peroxidase is monitored spectrophotometrically at 405 nm and the concentration of target nucleic acid is determined as the rate of change of absorbance compared with rates for calibrator solutions. Alternatively, reactions can be stopped at a fixed time point, approximately 10 to 60 minutes, by addition of 1% sodium dodecyl sulfate for endpoint measurements.

Example 4

Enzyme Channeling Reagents for Coupled Enzyme Clinical Chemistry Assays

Clinical chemistry analytes can be measured with high efficiency and sensitivity using enzyme channeling complexes assembled from selected enzymes specifically bound to synthetic heteropolymers or multivalent heteropolymeric hybrid structures. In this embodiment, the analyte of interest must be a substrate of a first selected enzyme. One or more additional enzyme reactions are coupled to the first enzyme reaction to yield a detectable signal, preferably an amplified detectable signal. The selection of coupling enzymes is based on the preferred detection method. For example, different enzymes or enzyme combinations are preferred for electrochemical versus optical measurements, ultraviolet versus visible absorbance measurements, and rate versus endpoint measurements.

All of the examples that follow can be practiced with multimolecular heteropolymeric complexes comprising two or more enzymes specifically bound to either a synthetic heteropolymer or a multivalent heteropolymeric hybrid structure. Multivalent heteropolymeric hybrid structures are preferred, because they allow convenient evaluation and optimization of different specifically bound enzyme combinations using a library of defined sequence segments that specifically bind different enzymes.

Multimolecular heteropolymeric complexes for each combination of enzymes are prepared from multivalent heteropolymeric hybrid structures as follows. For two-enzyme complexes, two synthetic heteropolymers are synthesized, each having a selected first defined sequence segment capable of specifically binding a selected enzyme and a second defined sequence segment capable of hybridizing. The first defined sequence segments are selected for maximal enzyme-binding affinity and minimal inhibition of enzyme activity. The second defined sequence segments are complementary, capable of hybridizing the two synthetic heteropolymers into a multivalent heteropolymeric hybrid structure. The selected enzymes are then specifically bound to their respective defined sequence segments to form multimolecular heteropolymeric complexes. For three-enzyme complexes, two sequence segments capable of hybridizing are selected for the third synthetic heteropolymer, each capable of hybridizing to a second defined sequence segment of another synthetic heteropolymer of the multivalent heteropolymeric hybrid structure. The synthetic heteropolymers are then hybridized, and the selected enzymes are specifically bound to their respective sequence segments to form a multimolecular heteropolymeric complex. A four-enzyme system may be assembled in a similar manner by preparing two synthetic heteropolymers, each having one hybridizing sequence segment, and two synthetic heteropolymers, each having two hybridizing sequence segments. Alternatively, a four-enzyme system may be developed using a pair of two-enzyme complexes, as exemplified by triglyceride detection in the instant example.

Examples of coupled enzyme reactions for detection of clinical chemistry analytes using multimolecular heteropolymeric complexes are provided below.

Detection of Cholesterol

Cholesterol is a serum lipid and a constituent of lipoproteins. Increased serum levels may occur in atherosclerosis, nephrosis, diabetes mellitus, myxedema and obstructive jaundice. Decreased levels have been observed in hyperthyroidism, certain anemias, malabsorption and wasting syndromes.

The coupled enzymatic reactions are as follows: cholesterol ester plus water in the presence of cholesterol esterase yields cholesterol plus fatty acids; cholesterol plus oxygen in the presence of cholesterol oxidase yields cholest-4-en-3-one plus hydrogen peroxide; hydrogen peroxide plus 4-aminoantipyrine plus p-sulfonate hydroxybenzene in the presence of peroxidase yields quinoneimine dye plus water.

A multimolecular heteropolymeric complex comprising cholesterol esterase and cholesterol oxidase specifically bound to a multivalent heteropolymeric hybrid structure is assembled. Cholesterol levels in a sample can then be measured through amperometric detection of the consumption of oxygen or the production of peroxide. Alternatively, cholesterol can be measured photometrically by using all three enzymes coupled through a trifunctional multivalent heteropolymeric hybrid structure and detecting the oxidized quinoneimine dye at 500 nm.

Detection of Triglycerides

Triglycerides represent the predominant form of fatty acids in blood. Serum levels are used to classify various types of hyperlipoproteinemia. Serum triglyceride levels may be elevated in nephrotic syndrome, coronary artery disease, hypothyroidism, diabetes mellitus and liver disease. Decreased levels may be observed in protein malnutrition, hyperthyroidism, cachectic states and abetalipoproteinemia.

The coupled enzymatic reactions are as follows: triglycerides in the presence of lipoprotein lipase yield glycerol plus fatty acids; glycerol plus ATP in the presence of glycerol kinase yields glycerol-1-phosphate plus ADP; glycerol-1-phosphate plus oxygen in the presence of glycerol phosphate oxidase yields dihydroacetone phosphate plus peroxide; peroxide plus 4-aminoantipyrine plus N-ethyl-N-(3-sulfopropyl)m-anisidine in the presence of peroxidase yields quinoneimine dye plus water.

Using a three-enzyme multimolecular heteropolymeric complex, triglycerides are measured through amperometric determination of glycerol phosphate oxidase activity either as oxygen consumption or peroxide production. using all four of the above enzymes in paired, two-enzyme multimolecular heteropolymeric complexes, triglycerides are measured photometrically through detection of quinoneimine dye absorbance at 540 nm.

Detection of Creatine Kinase

Creatine kinase is a cardiac, brain and muscle enzyme whose serum levels increase four to six hours following myocardial infarction and peak after 18–30 hours. Elevated levels are also associated with muscular dystrophy, hypothyroidism, pulmonary infarction and acute cerebrovascular disease.

The coupled enzymatic reactions are as follows: ADP plus creatine phosphate in the presence of creatine kinase yields creatine plus ATP; ATP plus glucose in the presence of hexokinase yields ADP plus glucose-6-phosphate; glucose-6-phosphate plus NAD in the presence of glucose-6-phosphate dehydrogenase yields 6-phosphogluconate plus NADH.

Using a three-enzyme multimolecular heteropolymeric complex, creatine kinase activity is detected spectrophotometrically as the increase in NADH absorbance at 340 nm or electrochemically through amperometric determination of NAD reduction using a modified G6PDH electrode.

Detection of Alanine Aminotransferase

Alanine aminotransferase (ALT) is a liver enzyme routinely included in clinical chemistry profiles. Increased serum levels are associated with hepatitis and other liver diseases.

The coupled enzymatic reactions are as follows: L-alanine plus 2-oxoglutarate in the presence of alanine aminotransferase yields pyruvate plus L-glutamate; pyruvate plus NADH in the presence of lactate dehydrogenase yields L-lactate and NAD.

Oxidation of NADH can be detected spectrophotometrically at 340 nm or amperometrically using a modified lactate dehydrogenase electrode.

Detection of Amylase

Amylase is a pancreatic enzyme whose serum levels increase in acute pancreatitis, pancreatic duct obstruction, intraabdominal diseases, mumps and bacterial parotitis.

The coupled enzymatic reactions are as follows: p-nitrophenyl-α-D-maltoheptaside (PNPG7) in the presence of α-amylase yields p-nitrophenylmaltotriose (PNPG3) plus maltotetraose; PNPG3 in the presence of glucoamylase yields p-nitrophenylglycoside (PNPG1) plus glucose; PNPG1 in the presence of α-glucosidase yields p-nitrophenol plus glucose.

Amylase is detected through photometric detection of p-nitrophenyl at 405 nm.

Detection of Aspartate Aminotransferase

Aspartate aminotransferase is a muscle and liver enzyme whose serum levels increase with myocardial infarction, liver cell damage, muscular dystrophy and dermatomyositis.

The coupled enzymatic reactions are as follows: L-aspartate plus 2-oxoglutarate in the presence of aspartate aminotransferase yields oxalacetate plus L-glutamate; oxalacetate plus NADH in the presence of malate dehydrogenase yields L-malate and NAD.

Aspartate aminotransferase activity is measured kinetically through photometric detection of NADH at 340 nm or amperometric detection of NADH oxidation using a modified malate dehydrogenase electrode.

Detection of Urea

Urea nitrogen levels in blood are used as an index of protein catabolism. Increased levels are observed in renal disease, dehydration, diabetic coma, hypoadrenal crisis, gastrointestinal hemorrhage and circulatory collapse. Decreased levels are sometimes seen in severe liver disease.

The coupled enzymatic reactions are as follows: urea plus water in the presence of urease yields carbon dioxide and ammonia; ammonia plus 2-oxoglutarate plus NADH in the presence of glutamate dehydrogenase yields glutamate plus NAD plus water.

Urea levels are quantified photometrically by measuring the decrease in NADH absorbance at 340 nm or amperometrically by measuring oxidation of NADH using a modified glutamate dehydrogenase electrode.

Detection of Uric Acid

Uric acid is an end-product of nitrogen metabolism. Increased serum levels occur in gout, leukemia, toxemia of pregnancy and severe renal impairment.

The coupled enzyme reactions are as follows: uric acid plus water plus oxygen in the presence of uricase yields allantoin plus carbon dioxide plus hydrogen peroxide; hydrogen peroxide plus 3,5-dichloro-2-hydroxybenzenesulfonate plus 4-aminoantipyrine in the presence of peroxidase yields quinoneimine dye plus water.

Uric acid is measured through photometric detection of oxidized quinoneimine dye at 520 nm.

Detection of Phosphohexose Isomerase

Phosphohexose isomerase is a cellular enzyme that plays an important role in carbohydrate metabolism. Increased serum levels are associated with various types of carcinoma, and levels appear to correlate with the stage of the neoplastic process.

The coupled enzyme reactions are as follows: fructose-6-phosphate in the presence of phosphohexose isomerase yields glucose-6-phosphate; and glucose-6-phosphate plus NAD(P) in the presence of glucose-6-phosphate dehydrogenase yields 6-phosphogluconate plus NAD(P)H.

Phosphohexose isomerase is measured through photometric detection of NAD(P)H at 340 nm or through amperometric detection of the reduction of NAD(P) using a modified G6PDH electrode.

Detection of Carbon Dioxide

Carbon dioxide is a blood gas whose measurement is useful in the assessment of acid-base imbalances. Increases are associated with metabolic alkalosis and respiratory acidosis. Decreases occur in metabolic acidosis and respiratory alkalosis.

The coupled enzymatic reactions are as follows: phosphoenol pyruvate plus carbonate in the presence of phosphoenol pyruvate carboxylase yields oxalacetate plus hydrogen phosphate; oxalacetate plus NADH in the presence of maleate dehydrogenase yields L-malate plus NAD.

Carbon dioxide can be measured through photometric detection of NADH at 340 nm or amperometric detection of NADH oxidation using a suitable electron transfer mediator.

Detection of Glucose

Glucose is a blood sugar whose levels are elevated in diabetes mellitus and hyperactivity of the thyroid, pituitary or adrenal glands. Decreased blood glucose levels occur with insulin overdose, insulin-secreting tumors, myxedema, hypopituitarism, hypoadrenalism and glucose malabsorption.

The coupled enzymatic reactions are as follows: glucose plus water plus oxygen in the presence of glucose oxidase yields gluconic acid plus hydrogen peroxide; hydrogen peroxide plus 4-aminoantipyrine plus p-hydroxybenzene sulfonate in the presence of peroxidase yields quinoneimine dye plus water.

Glucose is detected colorimetrically through detection of the oxidized quinoneimine dye at 505 nm.

Example 5

Donor-acceptor Complex

The term "donor-acceptor complex" means an association between two species, wherein a first "donor" species contributes a unit of matter or energy that can be converted to a different form by a second "acceptor" species in close spatial proximity. Enzyme channeling occurs when a donor enzyme contributes a product that serves as a substrate or cofactor for an acceptor enzyme. Fluorescence energy transfer occurs when photons emitted by a donor fluorophore are absorbed by an acceptor fluorophore.

Enzyme channeling complexes can be applied to any specific binding assay, including pseudoimmunodiagnostics, DNA probe assays, receptor-based assays and bioaffinity sensors, and to biosynthesis, bioprocessing, computer-aided metabolic simulation and detoxification. Similar multimolecular heteropolymeric complexes are also useful in energy transfer reactions including, but not limited to, transfer between fluorescent, phosphorescent, chemiluminescent and bioluminescent donors and acceptors.

A simple channeling complex in which a product ($P_1$) of donor enzyme ($E_1$) is a substrate, coenzyme or prosthetic group for an acceptor enzyme ($E_2$) is prepared from a synthetic heteropolymer comprising a nucleotide sequence having a first defined sequence segment capable of specifically binding $E_1$ and a second defined sequence segment capable of specifically binding $E_2$. It is preferred that the product channeled from donor to acceptor enzyme is a coenzyme or prosthetic group of the acceptor enzyme, rather than a substrate, so that each channeled product catalytically activates the acceptor enzyme. The length and composition of the spacer sequence of the synthetic heteropolymer are optimized to ensure intimate proximity between the donor enzyme and the acceptor enzyme. Examples of preferred effector combinations and their corresponding substrates are provided in the following table.

ing sequences within a given multivalent heteropolymeric hybrid structure must be optimized for a given pair or group of molecular effectors to achieve the desired efficiency of channeling or energy transfer.

Alternatively, enzymes that interact through allosteric inhibition can be coupled in an inhibited state in multimolecular heteropolymeric complexes such that inhibition is disrupted by analyte binding to a defined sequence segment, yielding homogeneous enzyme activation. Aspartate aminotransferase and phosphoenol pyruvate carboxylase, for example, can be used in homogeneous specific binding assays relying on analyte-dependent disruption of negative cooperativity.

Spatial optimization is accomplished through systematic production and evaluation of synthetic heteropolymers with varying spacer sequences and of multivalent heteropolymeric hybrid structures with varying hybridizable sequence segments and linker oligonucleotides.

Preparation of Multimolecular Fluorescence Energy Transfer Complexes Comprising Synthetic Heteropolymers The phycobiliprotein B-phycoerythrin, isolated from red algae, is an excellent energy acceptor when fluorescein is used as donor. The efficiency of Forster energy transfer from fluorescein to B-phycoerythrin approaches 100% as the distance between fluorescein and the surface of the phycoerythrin protein decreases to approximately 2 nm. 50% efficiency occurs at about 8.7 nm and significant energy transfer (>20% efficiency) occurs at distances up to about 11 nm.

| Coupled effectors (E1, E2) | Substrates | Products (P1, P2) |
|---|---|---|
| Enzyme channeling | | |
| E1: glucose oxidase<br>E2: peroxidase | glucose<br>reduced indicator | P1: peroxide<br>P2: oxidized indicator (color) |
| Enzyme channeling | | |
| E1: hexokinase<br>E2: G-6-P dehydrogenase | ATP, glucose<br>NAD | P1: glucose-6-P<br>P2: gluconolactone-6-P, NADH<br>(ultraviolet absorbance) |
| Allosteric activation | | |
| E1: phosphofructokinase<br>E2: phosphoenol pyruvate carboxylase | fructose-6-phosphate<br>NADH<br>(malate<br>dehydrogenase) | P1: phosphoenol pyruvate<br>P2: $NAD^+$ (enhanced signal via allosteric activation) |
| Enzyme-driven bioluminescence | | |
| E1: NAD oxidoreductase<br>E2: luciferase | NADH<br>FMN | P1: $FMNH_2$<br>P2: photons (bioluminescence) |
| Enzyme-driven chemiluminescence | | |
| E1: peroxidase<br>E2: luminol | peroxide | P1: $H_2O$<br>P2: photons (chemiluminescence) |
| Fluorescent energy transfer | | |
| E1: fluorescein<br>E2: B-phycoerythrin | absorption at 488 nm<br>absorption at 525 nm | P1: emission at 525 nm<br>P2: emission at 576 nm |
| Fluorescent energy transfer | | |
| E1: B-phycoerythrin<br>E2: R-phycocyanin | absorption at 495 nm<br>absorption at 576 nm | P1: emission at 576 nm<br>P2: emission at 642 nm |
| Fluorescent energy transfer | | |
| E1: R-phycocyanin<br>E2: allophycocyanin | absorption at 555 nm<br>absorption at 642 nm | P1: emission at 642 nm<br>P2: emission at 660 nm |

Any of the above-listed combinations of molecular effectors can be brought into close spatial proximity for use as signal-generating diagnostic reagents through nucleotide-directed assembly. The spatial arrangement of specific bind- Double-stranded DNA has a periodicity of approximately 0.34 nm (3.4 Å), equivalent to 10 nucleotide base pairs per 3.4 nm. When fluorescein and phycoerythrin are specifically bound at defined sequence segments separated by hybridized sequences in a multimolecular heteropolymeric complex, the efficiency of energy transfer from fluorescein to phycoerythrin depends on the length of defined sequence segments separating the bound fluorophores. Since the diameter of phycoerythrin is approximately 3 nm to 6 nm, a multivalent heteropolymeric hybrid comprising a fluorescein-binding heteropolymer hybridized to a phycoerythrin-binding heteropolymer will position fluorescein and phycoerythrin for efficient energy transfer provided they are separated by less than about 40 base pairs. Maximally efficient energy transfer occurs if binding sequences are separated by linker sequences less than or equal to about 10 base pairs in length. Preparation of Fluorescence Energy Transfer Complexes using Multivalent Heteropolymeric Hybrid Structures to Assemble Selected Fluorophores The following reagents were used: Fluorescein conjugate: fluorescein ($C_{20}H_{12}O_5$; FW=332.3; available as free acid, sodium salt and derivatives) may be conjugated to a wide range of carriers, including proteins, peptides, oligosaccharides, oligonucleotides and low molecular weight haptens. Preferred derivatives for conjugation include fluorescein isothiocyanate (FITC) and fluorescein succinimidyl esters. For convenience, commercially available FITC-dextran (average MW=40,000; specific activity= 0.003–0.020 mole FITC per mole glucose) was selected for this example.

B-phycoerythrin (MW=240,000; isolated from red alga *Porphyridium cruentum*)

B-phycocyanin (MW=110,000; isolated from red alga *Porphyridium cruentum*)

Allophycocyanin (MW=104,000; isolated from filamentous cyanobacterium *Anabaena variabilis*)

Multivalent heteropolymeric hybrid structures are prepared by self-assembly of two or more fluorophore-binding synthetic heteropolymers, each having three defined sequence segments as follows:

| Fluorophore Specificity | Defined sequence segments |
| --- | --- |
| FITC-dextran | internal segment specifically binds FITC-dextran; 5' and 3' sequence segments specifically hybridize to complementary sequence segments of other synthetic heteropolymers |
| B-phycoerythrin | internal segment specifically binds B-phycoerythrin; 5' and 3' sequence segments specifically hybridize to complementary sequence segments of other synthetic heteropolymers |
| R-phycocyanin | internal segment specifically binds R-phycocyanin; 5' and 3' sequence segments specifically hybridize to complementary sequence segments of other synthetic heteropolymers |
| Allophycocyanin | internal segment specifically binds allophycocyanin; 5' and 3' sequence segments specifically hybridize to complementary sequence segments of other synthetic heteropolymers |

Different combinations of the above-listed synthetic heteropolymers are mixed in equimolar amounts to yield the following structures useful in assembling energy transfer complexes: three permutations of bivalent heteropolymeric hybrid structures; two permutations of trivalent heteropolymeric hybrid structures; or a single tetravalent heteropolymeric hybrid structure.

Sequential incubation of each preparation with equimolar or greater concentrations of each targeted fluorophore yields the following energy transfer complexes:

| Nucleotide-ordered fluorophores | Idealized Stoke's shift (nm) | | |
| --- | --- | --- | --- |
| | Abs | Emax | Δ(E-A) |
| FITC-dextran + phycoerythrin | 490 | 575 | 85 |
| phycoerythrin + phycocyanin | 543 | 642 | 99 |
| phycocyanin + allophycocyanin | 555 | 660 | 105 |
| FITC-dextran + phycoerythrin + phycocyanin | 490 | 642 | 152 |
| phycoerythrin + phycocyanin + allophycocyanin | 543 | 660 | 117 |
| FITC-dextran + phycoerythrin + phycocyanin + allophycocyanin | 490 | 660 | 170 |

Preparation of Fluorescence Energy Transfer Complexes with Specific Binding Capabilities Nucleotide-ordered fluorescence energy transfer complexes such as those described above can be hybridized with synthetic heteropolymers comprising a suitable complementary defined sequence segment plus a defined sequence segment selected for specific binding to a ligand or receptor. The resulting multimolecular heteropolymeric energy transfer-probe complexes, having both specific binding and fluorescence energy transfer capabilities, can be used as labeled probes in a number of diagnostic applications, such as fluorescence activated cell sorting, immunohistochemical studies and immunodiagnostics. In addition, self-assembling complexes of fluorophores and ligand- or receptor-binding synthetic heteropolymers can be designed to provide for modulation of energy transfer efficiency upon exposure to a particular ligand or receptor. A number nucleotide-directed complexes for ligand- or receptor-modulated energy transfer can be developed, depending on the size and properties of the ligand or receptor, the range of concentrations to be detected and the preferred frequencies of excitation and detection.

In one embodiment, ligand-sensitive energy transfer complexes for high molecular weight and low molecular weight ligands and receptors, hereinafter analytes, are assembled as follows. For high molecular weight analytes, a multivalent heteropolymeric hybrid structure is prepared comprising three defined sequence segments capable of specifically binding nonoligonucleotide molecules. The defined sequence segments at the 5' and 3' ends of the nucleotide structure are selected for high-affinity binding to FITC-dextran and B-phycoerythrin, respectively. The internal defined sequence segment is selected for high-affinity binding to a high molecular weight analyte, such as TSH, hCG, FSH, LH, TBG, CEA, AFP, PSA, CK-MB, an infectious disease antigen, an apolipoprotein, a cancer antigen, a cell surface marker or an immunoglobulin. This hybrid structure is then incubated with FITC-dextran and B-phycoerythrin to yield a multimolecular heteropolymeric fluorescence energy transfer complex comprising FITC-dextran and B-phycoerythrin specifically bound to the 5' and 3' ends of the multivalent heteropolymeric hybrid structure, separated by an internal analyte-binding sequence. Within this multimolecular heteropolymeric complex, FITC-dextran and B-phycoerythrin are separated by a distance of 2–10 nm, spanning the analyte-binding sequence and hybridized defined sequence segments, such that upon exposure to a 488 nm argon-ion laser, fluorescence energy is efficiently transferred from fluorescein to B-phycoerythrin. With subsequent addition of sample containing analyte, specific binding to the analyte-binding sequence between the two fluorophores occludes energy transfer from FITC-dextran to B-phycoerythrin. Specific binding is detected either as a decrease in B-phycoerythrin emission at 575 nm or as an increase in fluorescein emission at 515 nm.

For low molecular weight analytes, an analogous multimolecular heteropolymeric complex is prepared comprising 5' and 3' defined sequence segments selected for high-affinity binding to FITC-dextran and R-phycocyanin. The internal defined sequence segment is selected for high-affinity binding to a hapten, such as $T_4$, $T_3$ estriol, estradiol, progesterone, cortisol, a therapeutic drug or a drug of abuse. A conjugate comprising a structural analog of the selected analyte covalently attached to B-phycoerythrin is specifically bound to the internal defined sequence segment of the multimolecular heteropolymeric complex through the analog moiety. This defined sequence segment is selected to provide for stable, quasireversible binding to the conjugate, but of lower affinity than for the native analyte. For this example, the internal defined sequence segment was selected for high-affinity binding to $T_4$ with lesser affinity for $T_3$-phycoerythrin. In the absence of free ligand, illumination of the multimolecular heteropolymeric complex with a 488 nm argon-ion laser results in efficient fluorescence energy transfer from fluorescein ($E_{max}$=515 nm) to B-phycoerythrin ($E_{max}$=575 nm) to R-phycocyanin ($E_{max}$=642 nm). Upon addition of sample containing $T_4$, the $T_3$-phycoerythrin conjugate is displaced from the complex, interrupting the transfer of energy from fluorescein to the $T_3$-phycoerythrin conjugate and from the conjugate to R-phycocyanin. Specific binding of $T_4$ is measured either as a decrease in B-phycoerythrin emission at 575 nm, a decrease in R-phycocyanin emission at 642 nm, an increase in fluorescein emission at 525 nm, or some combination of the three measurements.

Example 6

Enzymatic Cycling Complex

An enzymatic cycling complex can also be assembled by the multivalent heteropolymeric hybrid structures described in Example 4, vide supra. In an enzymatic cycling complex, the product of the acceptor enzyme $E_2$ is also a substrate, coenzyme or prosthetic group for donor enzyme $E_1$. There are many enzyme pairs suitable for this type of cycling reaction, the most prominent being dehydrogenases and oxidoreductases relying on nicotinamide and flavin dinucleotide coenzymes to shuttle electrons. An example of enzymatic cycling using two pyridine nucleotide-dependent enzymes is described below.

In this example, conversion of a first substrate to product by a first enzyme ($E_1$) is linked to reduction of a second substrate by a second enzyme ($E_2$) through the pyridine nucleotide NAD(P). The oxidized coenzyme NAD(P) is reduced by $E_1$ to NAD(P)H which is required as a coenzyme for the reduction of the second substrate by $E_2$.

Such complexes may be amplified by having the donor enzyme $E_1$ channel two or more molecules of product per cycle to the acceptor enzyme $E_2$ which, in turn, channels two or more product molecules to donor enzyme $E_1$. This complex provides a means to achieve exponential increases in the rate of product formation, enabling development of high sensitivity detection systems for diagnostic tests. An example of suitable paired enzymes for such a complex is the combination of myokinase and pyruvate kinase to convert one molecule each of ATP and AMP to four molecules of ATP per cycle.

Example 7

Multivalent Heteropolymeric Hybrid Structures with Synthetic Heteropolymers Attached to DNA Dendrimers A first 30-nucleotide defined sequence segment capable of specifically binding to prostate-specific antigen (PSA), a diagnostic marker for prostate cancer, is selected by repeated cycles of partitioning and amplification of progressively higher affinity nucleic acid ligands from a candidate mixture as described by Gold et al., U.S. Pat. No. 5,270,16. A second defined segment is designed to hybridize to a region of the first of two types of single-stranded arms (i.e., nucleotide sequences) of the outermost layer of a four-layer DNA dendrimer (Polyprobe™, Inc., Philadelphia, Pa.). A synthetic heteropolymer comprising the first and second defined sequence segments separated by a 15-nucleotide spacer sequence is synthesized using an automated DNA synthesizer (Applied Biosystems, Inc., Foster City, Calif.). This synthetic heteropolymer is then hybridized to the four-layer DNA dendrimer at a molar ratio of approximately 3–10 moles of synthetic heteropolymer per mole of dendrimer to form a multivalent heteropolymeric hybrid structure (i.e., a PSA-binding synthetic heteropolymer-DNA dendrimer hybrid, wherein the DNA dendrimer is a second synthetic heteropolymer having first and second defined sequence segments capable of hybridizing to selected nucleic acid sequences). The resulting PSA-binding multivalent heteropolymeric hybrid structure can then be used without further preparation in PSA assays relying on secondary labeling reagents (e.g., labeled, biotinylated or digoxigenin-modified oligonucleotides), or signal-generating species can be directly incorporated into the structure to create a labeled primary detection reagent (cf. Example 8, vide infra).

In an alternative mode of preparation, the first defined sequence segment of the PSA-binding synthetic heteropolymer described above is incorporated during the final stage of dendrimer polymerization rather than by hybridization of the synthetic heteropolymer to the completed dendrimer. The selected PSA-binding defined sequence segment is added to the dendrimer synthetic process during the final polymerization step either as a single-stranded defined sequence segment (i.e., "end") of an arm or as a double-stranded region (i.e., hybridized "middle") of two arms making up the partially double-stranded "monomer" used to assemble the outermost layer of the DNA dendrimer. Incorporation of this PSA-binding monomer yields a multivalent heteropolymeric hybrid structure having the specific binding capabilities of a first synthetic heteropolymer polymerized into a hyperbranched discrete heteropolymeric structure by means of a dendrimeric linker oligonucleotide. In a further modification of this approach, the PSA-binding synthetic heteropolymer is covalently attached to the 5' end of the outermost arm of the DNA dendrimer, rather than being attached by hybridization. Covalent attachment is accomplished either by enzymatic ligation or by heterobifunctional crosslinking to a 5'-terminal amine linker.

R-Phycoerythrin (R-PE; Sigma Chemical Company, St. Louis, Mo.) (or one or more alternative signal-generating species) is attached to either of the above PSA-binding multivalent heteropolymeric hybrid structures either by covalent crosslinking using bifunctional conjugation reagents (cf. Wong (1991), *Chemistry of Protein Conjugation and Crosslinking*, CRC Press) or by hybridization or specific binding of a second defined sequence segment of another, different synthetic heteropolymer having a first defined sequence segment capable of specifically binding R-PE (Example 8, vide infra).

Example 8

Fluorescent Multivalent Heteropolymeric Hybrid Structures using Dendrimers

A biotinylated oligonucleotide complementary to a 20 nucleotide sequence segment of the second of two types of single-stranded arms of the outermost layer of the four-layer DNA dendrimer is synthesized using biotin-16-dUTP (Boehringer Mannheim Corporation, Indianapolis, Ind.) in place of dTTP. This biotinylated oligonucleotide is then hybridized to the PSA-binding multivalent heteropolymeric hybrid structure of Example 7 at a molar ratio of approximately 50–150 moles of oligonucleotide per mole of dendrimer. An excess of streptavidin-phycoerythrin conjugate (Pierce Chemical Company, Rockford, Ill.) is then specifically bound to the biotin moieties of the multivalent heteropolymeric hybrid structure, and the fluorescent product is purified by denaturing sucrose gradient centrifugation. The product is used as a high-intensity, high-sensitivity fluorescent labeled reagent for PSA screening or diagnostic testing, preferably in solid phase, immunochromatographic or homogeneous energy transfer assay formats.

A functionally equivalent fluorescent PSA detection reagent that does not rely on avidin-biotin chemistry is produced in the following manner. A first defined sequence segment is selected (e.g., by methods described by Ellington et al. (1990), *Nature* 346:818–822) for the ability to specifically bind R-PE with relatively high affinity ($K_d$<100 nM). A second sequence segment is designed to hybridize to a region of the second of two types of single-stranded arms of the PSA-binding synthetic heteropolymer-DNA dendrimer hybrid of Example 7 (vide supra). A synthetic heteropolymer comprising the first and second defined sequence segments separated by a 15-nucleotide spacer sequence is then produced using an automated DNA synthesizer. This synthetic heteropolymer is then hybridized at a molar ratio of 100/1 to the synthetic heteropolymer-DNA dendrimer hybrid of Example 7 to yield a multivalent heteropolymeric hybrid structure comprising a first (PSA-binding) synthetic heteropolymer and a second (R-PE-binding) synthetic heteropolymer connected by a dendrimeric linker oligonucleotide. In a modification of this example, the second defined sequence segment of the second, R-PE-binding synthetic heteropolymer is not designed to hybridize to the linker oligonucleotide, but is instead selected for the ability to specifically bind to the outermost monomer strands of the PSA-binding synthetic heteropolymer-DNA dendrimer hybrid by non-Watson-Crick mechanisms, e.g., through triplex or quadruplex formation. In this manner, the R-PE-binding synthetic heteropolymer can be specifically bound to the PSA-binding synthetic heteropolymer-DNA dendrimer hybrid structure and subsequently dissociated from the remainder of the heteropolymer-dendrimer structure without denaturing hybridized defined sequence segments).

Alternatively, a multivalent heteropolymeric hybrid structure is constructed from a first synthetic heteropolymer having a first defined sequence segment capable of specifically binding R-PE and a second synthetic heteropolymer having a first defined sequence segment capable of hybridizing to a nucleic acid target (e.g., a nucleic acid probe specific for a target RNA or DNA sequence of an infectious organism or genetic marker). The second defined sequence segment of each synthetic heteropolymer is hybridized to a complementary single-stranded arm of the DNA dendrimer. The resulting product is a multivalent heteropolymeric hybrid structure having an available defined sequence segment capable of specifically binding R-PE which is attached via a DNA-dendrimer (i.e., a linker oligonucleotide) to an available defined sequence segment capable of hybridizing to a nucleic acid target (i.e., a selected nucleic acid sequence).

Alternatively, a multivalent heteropolymeric hybrid structure having R-PE-binding and PSA-binding defined sequence segments hybridized to a DNA dendrimer linker oligonucleotide is prepared as follows. A first synthetic heteropolymer is synthesized with a first defined sequence segment selected to specifically bind R-PE, a 10-nucleotide spacer sequence, and a second defined sequence segment selected to hybridize to a segment of one of two outermost single-stranded arms of the DNA dendrimer. A second synthetic heteropolymer is synthesized with a first defined sequence segment selected to specifically bind PSA, a 10-nucleotide spacer sequence, and a second defined sequence segment selected to hybridize to a segment of the other outermost single-stranded arm of the DNA dendrimer. The PSA-binding synthetic heteropolymer is then hybridized to the DNA dendrimer at a molar ratio of three, and the R-PE-binding synthetic heteropolymer is added at a molar ratio of 50 per dendrimer. R-PE may then be specifically bound prior to, during, or after addition of the multivalent heteropolymeric hybrid structure to an assay system.

Nonnucleic acid dendrimers can also be used as linker oligonucleotides and/or assembly scaffolds by first attaching one or more selected nucleic acid sequences as follows. Generation seven poly(amidoamine) dendrimers having a molecular weight around 234 kilodaltons and approximately 1024 terminal amine groups are synthesized by the divergent controlled method of Tomalia and Durst (Tomalia et al. (1993) In: *Topics in Current Chemistry*, pp. 193–245 Springer, Berlin). The polyamido dendrimers are then complexed by charge neutralization with a four-fold molar excess of a single-stranded 80 mer oligonucleotide comprising an 18-nucleotide synthetic heteropolymer hybridization sequence. A synthetic heteropolymer comprising a first 30-nucleotide R-PE-binding defined sequence segment, a 10-nucleotide spacer sequence, and a second 18 mer defined sequence segment complementary to the hybridization sequence of the dendrimer-complexed oligonucleotide is then added at 10% molar excess over the 80 mer oligonucleotide. The solution is mixed thoroughly and left standing for two hours at room temperature. R-PE is then added stoichiometrically with vortexing, the mixture is left standing for two hours at room temperature, and the resultant R-PE-synthetic heteropolymer-oligonucleotide-dendrimer complex is purified over SEPHAROSE™ (beaded agarose; Pharmacia LKB, Piscataway, N.J.).

Example 9

Multimolecular Transducer Comprising a Fluorescent Synthetic Heteropolymier Conjugate A 36-nucleotide synthetic heteropolymer is synthesized having a first 3'-end 30-nucleotide R-PE-binding defined sequence segment (cf. Example 8, vide infra) and a second, noncomplementary 5'-end six-nucleotide defined sequence segment (ATTTGC) terminating in the 13-carbon, 5'-terminal primary amine-generating reagent [N-trifluoroacetamido-(3-oxa)-pentyl-N,N-diisopropyl-methyl]phosphoramidite (Boehringer Mannheim Corporation, Indianapolis, Ind.). R-Phycocyanin (R-PC; absorption/emission maximum ($A_{max}/E_{max}$)=617/640 nm; Sigma Chemical Company, St. Louis, Mo.) is covalently attached to the 5'-terminal amine of the synthetic heteropolymer using the NHS-ester-maleimide heterobifunctional crosslinking reagent SULFO-MBS (Pierce Chemical Company, Rockford, Ill.). The R-PC-synthetic heteropolymer conjugate is purified by gel filtration using a P-100 column (Bio-Rad Laboratories, Hercules Calif.) and the molar concentration is determined by absorbance at 617 nm using a Shimadzu Model UV-160 recording spectrophotometer. An equimolar amount of R-PE ($A_{max}/E_{max}$=565/578 nm) is then added, and formation of the R-PC-synthetic heteropolymer-R-PE multimolecular transducer is monitored by kinetic readings of 640 nm fluorescence following excitation through a 550/30 nm band pass filter using a FLUOSTAR microplate fluorimeter (SLT Labinstruments, Research Triangle Park, N.C.) and black FluoroNunc™ plates (Nunc, Inc. Naperville, Ill.). Wells containing equivalent amounts of R-PE, R-PC and a random 36 mer oligonucleotide are used as negative controls. Only wells containing R-PE specifically bound to the R-PC-synthetic heteropolymer conjugate demonstrate time-dependent increases in fluorescence emission at 640 nm, indicating the presence of functionally coupled effector molecules.

Functionally coupled R-PE molecules can be covalently attached to the R-PC-synthetic heteropolymer conjugate using the homobifunctional crosslinking reagent, glutaraldehyde (Sigma Chemical Company, St. Louis, Mo.). Glutaraldehyde is added dropwise with vortexing (0.025–0.10% final concentration) to the R-PC-synthetic heteropolymer-R-PE mixture containing R-PE at a final concentration of 0.10–1.0 mg/ml. After a 1–4 hour incubation at room temperature, the reaction is quenched with glycine, reduced with sodium cyanoborohydride and purified by gel chromatography.

The Stokes shift of the resulting multimolecular transducer is approximately 75 nm ($A_{max}/E_{max}$=565/640 nm). For use as a signal-generating system in fluorescent affinity-based sensors, specific recognition reagents can be hybridized or covalently attached in a site-directed manner to nucleotides of the synthetic heteropolymer portion of the covalent R-PC-synthetic heteropolymer-R-PE transducer.

Example 10

Binary Switch Using a Tethered Specific Recognition Device with Two Different Fluorescent States The general case of the instant example is a tethered recognition device for use in diagnostics and drug discovery, particularly as a single pixel of a multi-element array for high-throughput screening. Parenthetical details in the instant example relate to a specific device designed for serotonergic drug discovery. The tethered multimolecular device described in this example is a multimolecular switch, more precisely a heteropolymeric multimolecular sensor, that happens to be attached and functionally coupled to a macroscopic device, e.g., an optoelectronic transducer. Although detecting, reporting or actuating the output of the heteropolymeric multimolecular device can be achieved using a variety of different macroscopic transducers or actuators, e.g., a planar waveguide, charge-coupled device, photodiode or photosensitive transistor, the instant example describes generation of an electronic signal through immobilization and functional coupling of the heteropolymeric multimolecular device to a fiberoptic waveguide that is, in turn, functionally coupled to photodiodes of a portable fluorimeter (ORD Inc., North Salem, N.H.). The fluorimeter is equipped with removable, variable-wavelength excitation and emission filters. Fibers are mounted vertically in a flow cell having and perfused with buffer. Fluorescent light is collected and guided by the fiber and detected by photodiodes arranged so as to distinguish between surface-bound fluorescence (from smaller angles) and background light (from larger angles). Evanescent detection principles for both planar waveguides (e.g., Badley, et al. (1987) *Phil. Trans. R. Soc. Lond.*, B316:143–160) and optical fibers (e.g., Rogers, et al. (1992) In: Biosensor Design and Application (Eds. P. R. Mathewson and J. W. Finley), *Am. Chem. Soc. Symp. Ser.*, 511, Chapter 13, pp. 165–172) are well known in the art. The transducer in this example is the optical fiber operatively coupled through its evanescent field to photodiode(s) capable of generating an electronic signal (voltage).

A branched molecular scaffold comprising a flexible polymer shaped like an inverted "T" (e.g., a synthetic heteropolymer comprising three 30-nucleotide defined sequence segments, each having nucleotide spacers and a terminal linker group) is immobilized to an optoelectronic transducer (e.g., a silanized optical fiber capable of evanescent coupling to a photodiode) with the crossbar of the "T" affixed to the fiber (e.g., having 3' and 5' ends attached to silane amines). The immobilized crossbar of the "T" comprises two defined sequence segments: a first defined sequence segment between its 3' end and the branchpoint and a second defined sequence segment between the branchpoint and its 5' end. The trunk of the "T," comprising a third defined sequence segment (i.e., the tethering sequence) is attached at its 3' end to the crossbar branchpoint, i.e., the midpoint between the first and second defined sequence segments. The 5' end of the third defined sequence segment is covalently attached to a "tethered" fluorescent donor (e.g., a 0.04 micron diameter 488/560 nm ($A_{max}/E_{max}$) fluorescent latex microsphere (Molecular Probes, Eugene Oreg.)). Covalently conjugated to the fluorescent donor via long-chain heterobifunctional crosslinkers are two ligands, a serotonin analog (L1) and a DNP analog (L2). The first (e.g., 40-nucleotide) defined sequence segment of the tethered device comprises modified nucleotides labeled with a first acceptor fluorophore (e.g., Cy3 ($A_{max}/E_{max}$=550/570 nm); Biological Detection Systems, Pittsburgh, Pa.) and is selected to specifically bind L1 (as well as serotonin) with relatively high affinity (i.e., K>$10^7$ M$^{-1}$). The second defined sequence segment comprises modified nucleotides labeled with a second acceptor fluorophore (e.g., Cy3.5 ($A_{max}/E_{max}$=581/596 nm); Biological Detection Systems, Pittsburgh, Pa.) and specifically binds L2 (as well as DNP) with relatively low affinity (i.e., K<$10^7$ M$^{-1}$). In the basal or unstimulated state (i.e., in the absence of a serotonergic drug candidate capable of binding the first defined sequence segment with high affinity), the tethered donor fluorophore conjugate of the multimolecular device is specifically bound through its first ligand (L1) to the (Cy3-labeled) first defined sequence segment. On excitation at 488 nm by an argon-ion laser, the donor fluorophore transfers energy to the first (Cy3) acceptor-labeled nucleotides of the first defined sequence segment which, in turn, emit photons detectable at 570 nm by evanescent tunneling to a photodiode comprising a portable fluorimeter (ORD Inc., North Salem, N.H.) equipped with removable excitation and emission filters. In the stimulated state (i.e., in the presence of a serotonergic drug candidate that specifically binds the first defined sequence segment with high affinity), the tethered donor fluorophore conjugate of the multimolecular device is specifically displaced from the (Cy3-labeled) first defined sequence segment by the higher affinity serotonergic candidate and specifically binds the (Cy3.5-labeled) second defined sequence segment. With 488 nm excitation, the donor fluorophore of the tethered recognition device now transfers energy to the second (Cy3.5) acceptor-labeled nucleotides of the second defined sequence segment which, in turn, emit photons detectable at 596 nm. The presence and/or concentration of selected target(s) (e.g., serotonergic drug candidates) is determined as a function of first acceptor and second acceptor emission intensities by measuring fluorescence responses to 488 nm excitation with selected emission filters and signal processing algorithms. The resulting output of the tethered recognition device is essentially that of a simple logic gate. If "target is absent," then signal=$hv_1$ (i.e., 570 nm). If "target is present," then signal=$hv_2$ (i.e., 596 nm).

A tethered recognition device for nucleic acid detection is similarly constructed by tethering to the bivalent crossbar of the polymeric molecular scaffold an effector species, preferably a donor signal-generating species (e.g., a 488/560 nm fluorosphere), which is conjugated to two different oligonucleotides. The first donor fluorosphere-conjugated oligonucleotide (oligo-1) comprises a 28 mer DNA probe complementary to a selected target sequence, e.g., a relatively conserved sequence of the infectious organism, *Chlamydia trachomatis*. The DNA probe segment of oligo-1 further comprises a 15-nucleotide sequence capable of hybridizing to a first defined sequence segment between the 3' terminus and the branchpoint of the polymeric scaffold crossbar (i.e., conversely, this first defined sequence segment comprises a 15-nucleotide segment selected to hybridize to a region of the DNA probe sequence of oligo-1). The second fluorosphere-conjugated oligonucleotide (oligo-2) comprises a 12-nucleotide sequence capable of hybridizing (optionally with one or more nucleotide mismatches) to a second defined sequence segment between the branchpoint and the 3' terminus of the polymeric scaffold crossbar (i.e., the second defined sequence segment and oligo-2 are selected to hybridize with a lesser degree of complementarity than the first defined sequence segment and oligo-1). As in the tethered specific binding device of the preceding paragraph, each specific recognition site (i.e., defined sequence segment) of the polymeric scaffold crossbar comprises nucleotides labeled with a different acceptor signal generating species. The first defined sequence segment is labeled with the fluorescence acceptor Cy3, and the second defined sequence segment is labeled with the fluorescence acceptor Cy3.5. In the absence of the Chlamydia target sequence, the tethered donor fluorosphere of the multimolecular device remains hybridized via oligo-1 to the Cy3-labeled first defined sequence segment of the crossbar. On excitation at 488 nm by an argon-ion laser, the donor fluorosphere transfers energy to the Cy3 acceptor fluorophores of the first defined sequence segment. The excited Cy3 acceptors emit photons detectable at 570 nm. In the stimulated state (i.e., in the presence of the Chlamydia target sequence), the tethered fluorosphere-conjugated oligo-1 is specifically displaced from the Cy3-labeled first defined sequence segment by more complementary hybridization between the 28mer DNA probe and Chlamydia target sequence. With oligo-1 hybridized to exogenous Chlamydia, the Cy3.5-labeled second defined sequence segment of the tethered recognition device becomes accessible to fluorosphere-conjugated oligo-2. Hybridization of oligo-2 to the second defined sequence segment results in fluorescence energy transfer from donor fluorosphere to Cy3.5-labeled nucleotides, resulting in laser-induced 596 nm emission. The presence and/or concentration of selected target sequences is thus determined by analyzing fluorimeter signals at 570 and 596 nm using selected optical filters, signal processing and data reduction routines.

One potentially attractive commercial application of tethered specific recognition principles exemplified in the preceding paragraphs is a molecular counting device, i.e. an array of multimolecular sensors capable of detecting and quantifying very few molecules in very small sample volumes, preferably even an individual molecule in a nanoliter or subnanoliter volume. Conventional affinity-based assays and sensors measure the concentration of an analyte by specific binding of some fraction of analyte molecules within a sample (i.e., a percentage of analyte molecules determined by reagent and analyte concentrations, equilibrium binding constants and the reagent and analyte masses per test). Quantification relies on factory or operator calibration of the assay response (i.e., signal) using reference standards (i.e., calibrators) comprising known concentrations of analyte. The molecular counting device, by contrast, is designed to bind essentially every analyte molecule in a nanoscale sample volume. The number of analyte molecules is counted by detecting a first signal corresponding to the number of multimolecular sensors (i.e., tethered recognition devices) in the stimulated state and a second signal corresponding to the number of multimolecular sensors in the basal state.

The advantages of counting molecules rather than simply interpolating analyte concentration from a calibration curve will become progressively more apparent as microminiaturization (e.g., of combinatorial synthesis and high-throughput assays) creates new testing requirements (e.g., the need for analytical and QA/QC capabilities beyond the limits of conventional methods). Evolving analytical requirements include the ability to 1) reproducibly measure ultralow analyte concentrations in ultralow volumes (i.e., as few as one molecule per unit volume), 2) precisely measure ultralow delivered volumes (i.e., nanoliter and even picoliter volumes) for quality control purposes, and 3) test and control cell-to-cell variability in on-chip arrays.

Tethered molecular recognition methods described in the instant example can be applied to the development of molecular counting devices capable of quantifying very small numbers of molecules (i.e., 1–100) in very small samples (i.e., picoliter to nanoliter volumes). In a quality control mode, use of a calibrator solution comprising a known concentration of a selected signal-generating species can be used to precisely measure the delivered sample volume. Measured signal is a function of the product of the delivered volume times the concentration of signal-generating species. Therefore, the delivered volume can be measured as a function of the measured signal divided by the known concentration of signal-generating species. The dynamic range of molecular counting devices can be further expanded through fabrication of transducers comprising massively parallel arrays of multimolecular sensors (e.g., to create a "molecular abacus").

Tethered recognition devices illustrated in the instant example are advantageously suited, e.g., for use in microminiaturized diagnostic assays and sensors, molecular sorting devices, high-throughput assays for screening libraries, (particularly highly diverse combinatorial libraries having only one or few copies of each chemical entity), biosensor and biochip arrays, e.g., DNA chips for genomics, sequencing and drug discovery.

In an alternative embodiment from those described in the preceding paragraphs, a paired catalytic recognition pair is used as effector. Device construction is similar to the DNA probe and serotonergic drug screening systems (vide supra) with the following exceptions. First, pair enzymes are used as the dual signal-generating modality in place of two competing fluorescent energy transfer pairs. The signaling state of the paired enzyme system does not require either energy transfer or functional coupling between two effector molecules. Rather, a pair of enzymes (e.g., oxidase/peroxidase, phosphatase/dehydrogenase) is conjugated and used a single effector pair tethered to the polymeric crossbar of the inverted "T" as above. Conjugated to at least the first enzyme is a ligand (e.g., a serotonin agonist or antagonist), advantageously attached to the enzyme in a site-directed manner (e.g., Offord, R. E. (1990) In: *Protein Design and Development of New Therapeutics and Vaccines* (Eds. J. B. Hook and G. Paste), New York: Plenum, pp. 252–282; Fisch et al. (1992) *Bioconjugate Chemistry* 3:147–153). This ligand conjugated, tethered enzyme is specifically bound in the basal state of the switch to a heteropolymeric defined sequence segment that occludes the catalytic surface of the enzyme, rendering it reversibly inhibited. In this basal state, signal can be generated only by the second (paired) enzyme. On binding of a high affinity serotonergic drug candidate, displacement of the serotonin-enzyme conjugate trips the switch into its stimulated state, wherein the second enzyme is specifically bound in an inhibited state to a second, lower affinity (anti-enzyme) heteropolymeric defined sequence segment. Signal from the stimulated state can be generated only by the first enzyme, In this example, signal discrimination is based on the different, e.g., spectral or electrochemical properties of the two paired enzymes. The polymeric wings of the immobilized crossbar need not be labeled or otherwise modified. Tethered devices comprising enzymatic effectors are particularly well suited for solution phase applications. Tethered and triggered release drug delivery systems comprising unpaired therapeutic enzymes are described elsewhere in the instant specification.

Example 11

Soluble Tethered Specific Recognition Device

Tethered recognition devices rely upon specific recognition between at least two binding partners pseudoirreversibly attached to one another within a single discrete structure, molecule or complex. The molecular scaffold comprising the discrete structure, molecule or complex may be insolubilized or immobilized, e.g., by attachment to a solid support. Alternatively, tethered recognition devices may be dispersed, dispersible or soluble in a particular fluid or solvent. An important property of soluble tethered recognition devices (e.g., soluble multimolecular sensors) is homogeneous signal generation and therefore homogeneous detection. Homogeneous detection or stimulus-response coupling means that a specific recognition event (i.e., stimulus) influences the activity of a signal-generating species, providing a detectable signal (i.e., response) without need for physical separation of bound from free fractions.

Soluble tethered recognition devices enabling homogeneous detection of selected molecules or selected nucleic acid sequences may be configured as follows. For detecting a selected molecule (e.g., a drug candidate, clinical analyte, or a ligand or receptor of agricultural, environmental or military interest) or a selected nucleic acid sequence (e.g., an infectious agent or a genomic, cellular or plasmid nucleotide sequence) a heteropolymeric sensor is constructed with (a minimum of) two defined sequence segments. The first defined sequence segment is covalently attached to an effector species, and the second defined sequence segment is capable of specifically binding the effector species. For example, a first defined sequence segment capable of specifically binding HIV-1 reverse transcriptase (HIV-RT) with nanomolar affinity ($K>10^8$ $M^{-1}$) is selected from an RNA library. A second defined sequence segment capable of specifically binding and inhibiting the effector enzyme AP ($K_i>10^6$ $M^{-1}$) is selected from a second RNA library. A 5'-biotinylated synthetic heteropolymer comprising the first defined sequence segment at the 5' end and the second defined sequence segment at the 3' end, optionally separated by one or more nucleotide spacers, is prepared on an Applied Biosystems (Foster City Calif.) synthesizer using 5'-biotin phosphoramidite from Glen Research (Sterling Va.). Streptavidin-AP is then specifically (and pseudoirreversibly) bound to the biotinylated synthetic heteropolymer, and the product is purified by gel filtration using a Bio-Rad P-100 column (Bio-Rad Laboratories, Hercules Calif.). Effector AP activity is assayed kinetically in 96-well plates using 4-nitrophenyl phosphate for photometric detection at 405 nm or ATTOPHOS™ (substrate set; Boehringer Mannheim Corporation, Indianapolis Ind.) for 420/560 nm fluorescence detection. The AP-tethered, HIV-RT-binding synthetic heteropolymer is titrated by photometric assay to undetectable levels and then assayed in the presence and absence of isolated HIV-RT. An HIV-RT-dependent signal can be detected both photometrically and fluorimetrically against buffer controls and normalized reagent controls (comprising AP plus AP-binding oligonucleotide). In an alternative embodiment of this approach, the second defined sequence segment capable of specifically binding and inhibiting the effector enzyme AP is not an aptameric sequence, but a defined sequence segment comprising a nucleotide ligand capable of inhibiting the enzyme, i.e., a nucleotide analog or modified nucleotide comprising an AP-inhibitory moiety with $K_i>10^6$ $M^{-1}$.

An HIV-responsive DNA probe version of the two-segment tethered recognition device for detection of a selected nucleic acid sequence comprising HIV-1 is prepared as described in the previous paragraph with the following modifications. An unbiotinylated, 5'-amino-modified, 28-nucleotide HIV-1 DNA probe sequence is substituted for the HIV-RT-binding first defined sequence segment. The bivalent synthetic heteropolymer is covalently attached via its 5'-amino group (i.e., the first defined sequence segment) to AP using the bifunctional crosslinking agent SULFO-SMCC (Pierce Chemical Company, Rockford Ill.) according to the manufacturer's instructions. The AP-conjugated synthetic heteropolymer is purified by gel filtration and assayed photometrically and fluorimetrically for enzyme activity (i.e., inhibited state) and responsiveness to target (i.e., isolated, heat-treated HIV) as described in the preceding paragraph.

In an alternative embodiment of the homogeneous tethered recognition device, functional coupling between attached donor and acceptor effectors (i.e., in the basal state) is used in place of effector (e.g., AP) inhibition. For example, a fluorescence energy transfer-based multimolecular sensor for detecting HIV-RT is configured with a fluorescein-labeled HIV-RT-binding second defined sequence segment (e.g., using fluorescein phosphoramidite (Glen Research, Sterling Va.) at a specific activity of six) capable of specifically binding and transferring energy to the acceptor fluorophore, R-PE (Sigma Chemical Company, St. Louis Mo.). A first, 5'-amino-modified HIV-RT-binding defined sequence segment is covalently attached via its 5'-amino group to R-PE using the bifunctional crosslinker SULFO-SMCC (Pierce Chemical Company, Rockford Ill.).

A second, fluorescein-labeled R-PE-binding (K<10$^7$ M$^{-1}$) defined sequence segment connected to the first defined sequence, optionally separated by a nucleotide spacer, specifically binds R-PE so as to position attached fluorescein moieties within energy transferring distance of the R-PE. In the absence of HIV-RT, argon-ion laser excitation (i.e., 488 nm) of the multimolecular sensor results in efficient energy transfer from fluorescein to R-PE with minimal detectable fluorescein emission. In the presence of HIV-RT, high-affinity specific binding of the first defined sequence segment to HIV-RT disrupts the interaction between the fluorescein-labeled second defined sequence segment and R-PE. HIV-RT recognition is detectable either by an increase in fluorescein emission, a decrease in R-PE emission or some combination or algorithm of the two signals.

For detecting hybridization of a selected nucleic acid sequence, a fluorescence energy transfer-based multimolecular sensor like the one described in the preceding paragraph is prepared with a first defined sequence segment comprising a DNA probe rather than an aptamer sequence. For example, R-PE is covalently conjugated to the 5' terminus of a 28-nucleotide 5'-amino-modified first defined sequence segment capable of hybridizing to a relatively conserved HIV-1 nucleotide sequence. A second, fluorescein-labeled R-PE-binding defined sequence segment is connected to the first defined sequence, optionally separated by nucleotide spacers to facilitate specific binding to the conjugated R-PE. In the absence of HIV-1, intraheteropolymer specific binding results in efficient energy transfer from fluorescein to R-PE. In the presence of HIV-1, hybridization of the probe sequence to its target is favored over intraheteropolymer specific binding, and energy transfer from fluorescein to R-PE is interrupted.

Homogeneous multimolecular devices comprising only two defined sequence segments are the simplest possible heteropolymeric tethered recognition devices. In each configuration described in the instant example, a first defined sequence segment plays the dual role of tethering an effector to a second defined sequence segment and specifically recognizing a selected target molecule or nucleic acid sequence. In alternative configurations, different defined sequence segments may be preferred or required for the different functions of a tethered recognition device, e.g., 1) pseudoirreversible attachment of an effector, 2) tethering (i.e., positioning) the effector with respect to an effector-binding (e.g., aptameric) sequence, 3) intradevice specific binding to a conjugated effector, 4) specific recognition of a selected target molecule or nucleic acid sequence.

Example 12

Heteropolymeric Multimolecular Device with Two Defined Sequence Segments Connected by Nonnucleotide Linker For most applications, preferred methods for producing synthetic heteropolymers include automated synthesis and biological methods, e.g., using recombinant DNA procedures. However, in some cases it is advantageous to simulate the function or evaluate the potential utility of a synthetic heteropolymer using two or more defined sequence segments which are either readily available or can be conveniently modified for a particular molecular assembly task. In such instances, it may be preferable to prepare a synthetic heteropolymer by less than ideal methods, e.g., by conjugating two defined sequence segments using covalent or pseudoirreversible means. Also, synthetic heteropolymers comprising defined sequence segments joined by non-nucleotidic linkages and/or linkers (e.g., nonnucleotide spacer groups, molecules, or polymers) have utility in screening and analytical applications, e.g., to identify compounds or fractions having a desired catalytic activity and/or selectivity. For example, a population, generation or library of enzymes created by site-directed mutagenesis or directed in vitro evolution (e.g., random mutagenesis plus recombination) can be screened for activity in cleaving a bond connecting two defined sequence segments to which functionally coupled effectors are attached.

A bifunctional synthetic heteropolymer capable of assembling R-PE and R-PC (Sigma Chemical Company, St. Louis, Mo.) into a functionally coupled multimolecular device is prepared by specific binding of two conjugated defined sequence segments as follows. A first defined sequence segment specific for R-PE (cf. example 8, vide supra) and further comprising a the 5'-terminal primary amine-generating reagent [N-trifluoroacetamido-(3-oxa)-pentyl-N, N-diisopropylmethyl]phosphoramidite (Boehringer Mannheim Corporation, Indianapolis, Ind.) is synthesized using an automated DNA synthesizer (Applied Biosystems, Inc., Foster City, Calif.) and conjugated to streptavidin using the heterobifunctional crosslinker MBS (Pierce Chemical Company, Rockford Ill.) according to the manufacturer's instructions. A second 3'-biotinylated, R-PC-conjugated six-nucleotide defined sequence segment (5'-R-PC-ATTTGC-3'-biotin) is prepared as per Example 9 with biotin phosphoramidite (Glen Research, Sterling Va.) at the 3' terminus. Equimolar amounts of the two conjugated defined sequence segments (streptavidin-conjugated R-PE-binding and R-PC-conjugated biotinylated sequence segments) and R-PE are mixed, incubated for four hours at room temperature and purified by SEPHAROSE™ (Pharmacia LKB, Piscataway, N.J.) gel exclusion chromatography.

An endopeptidase-cleavable synthetic heteropolymer comprising R-PE-binding and R-PC-binding defined sequence segments attached by the tripeptide glycyl-glycine (gly-gly-gly or triglycine) is prepared as follows. A defined sequence segment capable of specifically binding to R-PC is selected by iterative cycles of partitioning and amplification of a library of oligonucleotide sequences comprising a randomized 30-nucleotide region flanked by PCR primer sequences. The selected defined sequence segment with 5'-phosphomonoester end is then synthesized on an Applied Biosystems (Foster City Calif.) automated synthesizer. The C-terminal carboxyl group of triglycine is conjugated to the 5'-amino group of the amine-modified R-PE-binding defined sequence segment described in the preceding paragraph (vide supra) using the heterobifunctional crosslinker 1-ethyl-3-(3-dimethylaminopropyl)-carbodiimide (EDC; Pierce Chemical Company, Rockford, Ill.) according to the manufacturer's instructions. Following removal of excess reagent by elution of the triglycine-conjugated R-PE-binding oligonucleotide over a desalting column, the N-terminal glycine amine is reacted with the 5'-phosphate group of the R-PC-binding defined sequence segment using EDC in a pH 6.0 imidazole buffer to form the stable phosphoramidate conjugate. The R-PE-binding-triglycine-R-PC-binding synthetic heteropolymer is then dialyzed against phosphate-buffered saline and purified by gel chromatography. Equimolar amounts of R-PE and R-PC are specifically bound to the synthetic heteropolymer to produce a multimolecular fluorescence energy transfer device with a Stokes shift of approximately 75 nm ($A_{max}/E_{max}$=565/640 nm). This energy transfer transducer may be used as a cleavable reporter to screen enzyme libraries for endopeptidase or amidase activity. Alternatively, a covalent transducer assembly may be prepared with R-PC and R-PE crosslinked to their respective defined sequence segments of the synthetic heteropolymer, e.g., by ultraviolet irradiation (1.8 J, GS Gene Linker® UV Chamber; Bio-Rad Laboratories, Hercules Calif.) or by chemical crosslinking to thiol-modified nucleotides using a bifunctional crosslinking reagent (e.g., the pyridyl disulfide reagent SPDP; Pierce Chemical Company, Rockford Ill.).

Example 13

Nucleotide-based Multimolecular Devices Using Two Specific Binding Pairs for Enzyme Attachment Nucleotide-based molecular scaffolds can be used to build multimolecular switches, transducers and drug delivery systems by positioning selected molecules in suitable proximity to allow functional coupling between the molecules. In a preferred mode of operation, each of two specific binding pairs is positioned along a defined sequence segment by site-directed attachment or positionally defined incorporation of a ligand or receptor (or sequence-directed hybridization of an oligonucleotide-conjugated ligand or receptor). Specific binding partners of the conjugated ligand(s) and/or receptor(s), typically effector molecules and more typically signal-generating molecules and/or drugs, are then attached (either simultaneously or sequentially) to assemble and operate the nucleotide-based multimolecular device. The instant example illustrates the preparation of multimolecular transducers and switches relying on nucleotide-dependent positioning of effector molecules. Positioning is achieved by specifically binding a first effector-receptor conjugate to a first ligand-modified nucleotide of a defined sequence segment and a second effector-receptor conjugate to a second ligand-modified nucleotide of the defined sequence segment, wherein the number of nucleotides between first and second ligands is selected to maximize the degree of cooperativity or competition between effector-receptor conjugates. In the first example, a multimolecular transducer producing enzyme-driven luminescence is prepared by nucleotide-dependent positioning and functional coupling of the enzymes horseradish peroxidase (HRP) and alkaline phosphatase (AP). In a second example, an immobilized multimolecular switch produces two different fluorescent responses to laser excitation depending on whether a stimulus molecule (e.g., an effector-receptor conjugate or a selected target molecule) is present.

For preparation of an enzyme-based chemiluminescent multimolecular transducer, the enzymes HRP and AP are used to transduce chemical energy into photons through the following coupled reactions. HRP catalyzes the cleavage of the 1,2-dioxetane substrate 4-[3-(4-hydroxy-2-methylnaphthalene-1-phosphoryl)phenyl]-4-methoxyspiro (1,2-dioxetane-3,2-adamantane (HMPPD) to liberate the product 2-methylnaphthylquinone and 3-(2'-spiroadamantanane)-4-methoxy-4-(3"phosphoryloxy) phenyl-1,2-dioxetane (AMPPD; Urdea et al., EPO 401 001). AP catalyzes the chemiluminescent decomposition of AMPPD, generating photons.

A defined sequence segment comprising a 20 base pair synthetic DNA duplex is prepared by hybridizing a 5'-biotinylated 20 mer deoxyoligonucleotide (A-strand) to a 5'-digoxigenin-labeled complementary 20 mer deoxyoligonucleotide (A'-strand). The A-strand is biotinylated using 5'-biotin phosphoramidite (Glen Research, Sterling Va.). Digoxigenin labeling of the A'-strand is performed using the GENIUS™ oligonucleotide 5'-end labeling set (a digoxigenin-NHS-ester and 5'-AMINOLINKER; Boe- hringer Mannheim Corporation, Indianapolis Ind.) according to the manufacturer's instructions. AP conjugated to sheep anti-digoxigenin (Boehringer Mannheim Corporation, Indianapolis Ind.) and HRP conjugated to streptavidin (Pierce Chemical Company, Rockford Ill.) are specifically bound to their respective synthetic DNA-conjugated ligands (i.e., digoxigenin and biotin) by combining equimolar amounts of the effector-receptor conjugates with the ligand-modified defined sequence segment to produce a coupled effector nucleotide-based transducer. An uncoupled reagent control mixture is prepared by combining equimolar amounts of the two conjugated effectors with an unlabeled 20 base pair DNA duplex. Luminescence is determined in a Tropix luminometer with dioxetane indicator reagents, detection buffer and instrument settings (e.g., photon integration time) as recommended by the manufacturer (Tropix, Inc., Bedford Mass.). The uncoupled reagent control mixture (i.e., negative control) is titrated by doubling dilutions in indicator reagent-containing detection buffer to determine the threshold effector/duplex concentration below which the photon count rate is within two standard deviations of the mean count rate obtained with detection buffer alone (i.e., reagentless buffer control). The count rate of the nucleotide-based transducer preparation (i.e., anti-digoxigenin-AP, streptavidin-HRP plus digoxigenin-modified and biotin-modified defined sequence segment) is then determined in quadruplicate over a three-log dilution series spanning the detection threshold of the negative control. Subtracting count rates of buffer control replicates from transducer dilutions, significant transducer luminescence is apparent over the entire range tested. At all points along the dilution curve, count rates of transducer dilutions significantly exceed negative controls, demonstrating nucleotide-dependent functional coupling of donor (HRP) and acceptor (AP) effector molecules.

An aptameric multimolecular transducer yielding enzyme-driven luminescence by nucleotide-dependent functional coupling between HRP and AP is produced as follows. Double-stranded DNA aptamer sequences with relatively high affinity for HRP are identified by iterative rounds of in vitro selection and amplification of a DNA oligonucleotide library comprising a 28-nucleotide randomized region. Selected HRP-binding aptamers are further selected for the ability to bind HRP in the presence of dioxetane indicator reagents (cf. preceding paragraph) with minimal enzyme inhibition (i.e., without reducing apparent Vmax or increasing apparent Km). A digoxigenin end-labeled 35-base pair DNA oligonucleotide comprising the selected aptamer sequence is then prepared enzymatically using terminal transferase to incorporate digoxigenin-11-dUTP (Boehringer Mannheim Corporation, Indianapolis Ind.). HRP and anti-digoxigenin-AP are specifically bound to the digoxigenin-modified aptamer by mixing equimolar amounts of the aptameric digoxigenin-oligonucleotide, HRP and anti-digoxigenin-AP in assembly buffer to form an aptameric multimolecular transducer. Activity of the aptameric transducer is determined by measuring photon count rates at doubling dilutions of the aptamer-effector assembly in detection buffer against negative controls (unmodified DNA oligonucleotide plus effector dilutions) and buffer controls using a Tropix luminometer and dioxetane indicator reagents.

For preparation of an immobilized multimolecular switch using fluorescent effector-receptor conjugates, APC and R-PE are used as signal-generating species capable of evanescent coupling through an optical waveguide to a photodetector. A 3'-carboxyl 24 mer deoxyoligonucleotide prepared using a 3'-carboxylate photolabile support (Glen Research, Sterling Va.) is covalently immobilized through its 3'-carboxyl and 5'-phosphate groups using a bifunctional carbodiimide crosslinker (EDAC; Pierce Chemical Company, Rockford Ill.) to amine groups of silanized 1×60 mm cylindrical quartz fibers with polished ends. The immobilization is performed at room temperature in the dark with gentle shaking using carboxylated oligonucleotide at 500 pmol/ml in a reaction mixture comprising EDAC and p-nitrophenol each at 0.5 mg/ml. After two hours, oligonucleotide-treated fibers are washed four times with PBS-Tween® 20, blocked for one hour in PBS containing 0.5% BSA, and washed twice more with PBS-Tween® 20 containing 0.1% BSA (assembly buffer). A nucleotide-based multimolecular switch is prepared and hybridized to the immobilized oligonucleotide as follows. A 24 mer deoxyoligonucleotide is biotinylated at the 5'-penultimate nucleotide position using biotin-dT (at nucleotide position 23 from the 3' end) and 5'-digoxigenin-labeled using the GENIUS™ oligonucleotide 5'-end labeling set (digoxigenin-NHS-ester and 5'-AMINOLINKER; Boehringer Mannheim Corporation, Indianapolis Ind.) in accordance with manufacturer instructions. The biotinylated, digoxigenin-labeled 24 mer diluted in assembly buffer is hybridized to oligonucleotide-modified fibers. Fibers are then rinsed repeatedly in assembly buffer and transferred to a sterile, screw-capped 50 cc polypropylene centrifuge tube containing assembly buffer. An individual oligonucleotide-modified fiber is then removed, rinsed in buffer and dipped sequentially at 15 minute intervals into buffered solutions containing stepwise increasing concentrations of an anti-digoxin-fluorescein conjugate (anti-digoxin-FITC; Sigma Chemical Company, St. Louis Mo.) showing relatively high affinity for digoxigenin. Dose-dependent binding of the anti-digoxin-FITC conjugate to the fiber-immobilized, digoxigenin-labeled oligonucleotide is demonstrated using a previously described fiber-optic evanescent fluorosensor apparatus (Rogers et al. (1989) *Analytical Biochemistry* 182:353–359) with excitation at 485 nm and detection at 510 nm (i.e., near the FITC emission peak). For example, using a portable fiberoptic fluorimeter equipped with variable-wavelength excitation and emission band-pass filters (ORD Inc., North Salem N.H.), fibers are mounted vertically in a flow cell having a capacity of 46 µl and perfused with PBS-BSA at a rate of 184 µl/minute. Fluorescent light collected and guided by the fiber is detected by photodiodes arranged so as to distinguish surface-bound fluorescence from background light. Evanescent detection methods exploiting total internal reflection properties of optical waveguides are well known in the art (e.g., Badley, et al. (1987) *Phil. Trans. R. Soc. Lond.*, B316:143–160). The nucleotide-based multimolecular switch in this instance is attached and functionally coupled to a transducer, i.e., the optical fiber operatively coupled through its evanescent field to photodiode(s) capable of generating an electronic signal (voltage). Between FITC conjugate dilutions, the flow cell is washed with assembly buffer containing 1% SDS for two minutes followed by assembly buffer alone for 10 minutes. Initial binding rates are determined graphically from strip chart recordings of the fluorescence response (millivolts vs. time). Having established a maximal fluorescent signal of approximately 8.5 V/fiber at 10 micromolar FITC conjugate, the fluorescence signal with binding of 10 micromolar FITC conjugate is then re-determined with excitation through a 550/30 nm band pass filter and detection at 575 nm (i.e., the emission peak of R-PE). The FITC conjugate-saturated fiber is rinsed thoroughly in SDS-free assembly buffer and dipped in a buffered solution containing 10 micromolar streptavidin-R-PE conjugate (Pierce Chemical Company, Rockford Ill.). Binding of the R-PE conjugate is demonstrated by a rapid rate response (millivolts vs. time) at 575 nm, reaching maximal voltage within about two minutes. On re-measuring the FITC response of this fiber using 485 nm excitation and 510 nm emission filters (i.e., to detect bound FITC conjugate), the fluorescence signal is below 1 V/fiber, indicating that most of the FITC conjugate has dissociated from the fiber. Concomitant binding of the R-PE-streptavidin conjugate and dissociation of the anti-digoxin-FITC conjugate demonstrates the streptavidin-responsive switching property of the nucleotide-based multimolecular device.

Nucleotide-dependent positioning of biotin and digoxigenin as described in the above paragraph demonstrates the principle of a nucleotide-based multimolecular switch relying on mutually exclusive binding of anti-digoxin-FITC and streptavidin-R-PE. This mutually exclusive specific binding principle can be reconfigured for a variety of applications, including, without limitation, high-throughput screening of chemical and biological libraries (e.g., for drug discovery or directed evolution of enzymes for industrial use); clinical, forensic, veterinary, agricultural and environmental diagnostics; or detection and/or monitoring of pests, pesticides, foodborne or bloodborne pathogens, hazardous wastes or chemical and/or biological weaponry. For example, a nucleotide-based multimolecular switch for drug discovery (e.g., to identify potent receptor antagonists) can be configured much like the biotin- and digoxigenin-modified nucleotide-based switch described in the preceding paragraph. An agonist- and digoxigenin-modified nucleotide with neighboring agonist and digoxigenin moieties is first prepared as above. Anti-agonist antibody (or purified receptor or receptor mimetic) is conjugated to a first effector (e.g., R-PE) and prebound to the agonist-modified nucleotide. A second effector conjugate (e.g., anti-digoxin-FITC) is included in the screening buffer. In the presence of a pharmacophore with an affinity for the oligonucleotide-bound receptor conjugate which is higher than the anti-digoxin conjugate's affinity for its ligand (i.e., the crossreactant, digoxigenin), the detectable signal (e.g., fluorescence emission) is switched from emission by first effector (e.g., anti-agonist-R-PE) to emission by second effector (e.g., anti-digoxin-FITC) concomitant with anti-agonist conjugate dissociation and anti-digoxin conjugate binding. Aptameric multimolecular switches for drug discovery can be prepared in a similar manner, wherein an oligonucleotide is prepared with one or more ligand-modified nucleotides (e.g., agonist-modified or antagonist-modified nucleotides) within or attached to a reporter-binding aptamer sequence (i.e., an aptamer sequence selected to specifically bind a signal-generating species such as a reporter enzyme (e.g., HRP) or fluorophore (e.g., R-PE). In this case, the switch is prepared with a first effector conjugate (e.g., labeled anti-ligand antibody or anti-ligand receptor) prebound to a ligand-modified nucleotide of the aptameric oligonucleotide, which may in turn be immobilized to a transducer (e.g., hybridized to an optical waveguide). The ligand-modified nucleotide is positioned within the aptameric oligonucleotide in such manner that the prebound, labeled anti-ligand conjugate sterically precludes specific binding between the aptamer and its target, which signal-generating species is included in the pharmacophore screening buffer. In the presence of a high-affinity pharmacophore, dissociation of prebound anti-ligand conjugate enables the second effector (aptamer target) to specifically bind the aptamer sequence, switching the transducer output from a first effector signal to a second effector signal.

Example 14

Synthetic Heteropolymers with Hybridizable Second Defined Sequence Segments for Conjugation and Immobilization Nucleotide-directed molecular assembly provides a unifying approach for combining hybridization, specific binding and effector functions within a single discrete structure, e.g., a synthetic heteropolymer, multivalent heteropolymeric hybrid structure or multimolecular complex. A synthetic heteropolymer, for example, can be used to combine the specific binding properties of an aptameric first defined sequence segment with the hybridization properties of a second defined sequence segment. A selected nonoligonucleotide molecule (e.g., an effector) specifically bound to the first defined sequence segment (and optionally covalently crosslinked in place) can thus be endowed with the hybridization properties of a nucleic acid (i.e., the second defined sequence segment) in a reproducible and positionally controlled manner. Alternatively, a hybridizable sequence can be endowed with specific binding and/or effector capabilities by incorporation within a synthetic heteropolymer comprising an aptameric defined sequence segment capable of specifically binding an effector (i.e., an aptamer target) which is optionally crosslinked in place. Similarly, a defined sequence segment capable of molecular recognition (i.e., hybridization or specific binding) can be adorned with effector functions by incorporation of said defined sequence segment within a heteropolymeric discrete structure comprising a specifically bound or hybridized selected molecule (e.g., a drug or signal-generating species) or selected nucleic acid sequence (e.g., a ribozyme or catalytic DNA molecule).

In a preferred aspect of the instant invention, the ability of a synthetic heteropolymer to hybridize to a selected nucleic acid sequence is used as a means of attaching the synthetic heteropolymer to a selected nonoligonucleotide molecule (e.g., an effector molecule) by hybridizing the synthetic heteropolymer to an effector-oligonucleotide conjugate. In another and related preferred aspect of the invention, the ability of a synthetic heteropolymer to hybridize to a selected nucleic acid sequence is used as a means of attaching the synthetic heteropolymer to a solid support, e.g., by hybridizing the synthetic heteropolymer to an immobilized oligonucleotide. Preparation of a synthetic heteropolymer having a first defined sequence segment selected for the ability to specifically recognize a selected target molecule (i.e., the cancer marker PSA) and a second defined sequence segment selected for the ability to hybridize the synthetic heteropolymer to an oligonucleotide-conjugated effector molecule (i.e., the signal-generating species, HRP) or to an immobilized oligonucleotide is described below.

A synthetic heteropolymer is prepared and hybridized to a nonoligonucleotide molecule-oligonucleotide conjugate in the following manner. A 24 mer oligonucleotide is synthesized on an Applied Biosystems, Inc. (ABI; Foster City Calif.) nucleic acid synthesizer using 5'-THIOL-MODIFIER-C6 (Glen Research, Sterling Va.) to introduce a 5'-thiol terminus. The enzyme HRP (Sigma Chemical Company, St. Louis Mo.) is conjugated to the 5'-thiol group of the oligonucleotide using the water soluble NHS-ester-maleimide crosslinker, SULFO-SMCC (Pierce Chemical Company, Rockford Ill.). The oligonucleotide-HRP conjugate is purified by gel filtration using a BIO-RAD P-100 column 11.5×65 cm; Bio-Rad Laboratories, Hercules Calif.). A bifunctional synthetic heteropolymer having a 30-nucleotide first defined sequence segment capable of specifically binding PSA and a second 20-nucleotide defined sequence segment capable of hybridizing to the HRP-conjugated oligonucleotide is prepared using the ABI synthesizer. The purified HRP-oligonucleotide conjugate is then hybridized to the second defined sequence segment of the PSA-binding synthetic heteropolymer, and the HRP-labeled hybrid is purified by gel filtration using a P-100 column. Alternatively, the PSA-binding synthetic heteropolymer is added to a PSA assay reagent mixture, and the HRP-oligonucleotide conjugate is added either during or after the synthetic heteropolymer-PSA incubation step. Specific binding of the PSA-binding synthetic heteropolymer is determined by measuring HRP activity of either the bound or free fraction using colorimetric, fluorimetric, or luminescent detection reagents (e.g., a chromogen, substrate, and/or enhancer system).

In a preferred aspect of synthetic heteropolymer-directed conjugation, a first effector molecule specifically bound to a first defined sequence segment is functionally coupled to a second effector molecule-oligonucleotide conjugate which is hybridized to a second defined sequence segment of the synthetic heteropolymer. For example, using AP and HRP as donor and acceptor enzymes of a coupled enzyme-driven chemiluminescent pair (cf. Example 13, vide supra), the following multimolecular heteropolymeric complex is prepared using a synthetic heteropolymer that specifically binds a first effector (HRP) and hybridizes an oligonucleotide-second effector (AP) conjugate. A first 30-nucleotide defined sequence segment amino-modified using AMINO-MODIFIER C2 dT (Glen Research, Sterling Va.) at nucleotide positions 2, 6, 10, 20, 24 and 28 (from the 3' end) and 5'-amino modified using AMINOLINKER (Boehringer Mannheim Corporation, Indianapolis Ind.) is selected for the ability to specifically bind HRP without inhibiting the enzyme (cf. Example 15, vide infra). A second 24-nucleotide defined sequence segment is selected for the ability to hybridize a 5'-biotinylated 28 mer oligonucleotide specifically bound via its 5'-biotin to a streptavidin-AP conjugate (Boehringer Mannheim Corporation, Indianapolis Ind.). A synthetic heteropolymer comprising the first and second defined sequence segments separated by nucleotide spacers is prepared using an ABI (Foster City Calif.) synthesizer. HRP is specifically bound in excess and the AP-streptavidin/biotin-oligonucleotide conjugate is then hybridized during sequential two-hour incubations at room temperature in PBS-BSA buffer. Functional coupling of the synthetic heteropolymer-conjugated effector molecules (i.e., HRP and AP) is demonstrated by luminescent assay using dioxetane indicator reagents (Tropix, Inc., Bedford Mass.) as described in Example 13 (vide supra). For stable, long-term storage, the coupled enzymes may be covalently attached to the synthetic heteropolymer (e.g., using the heterobifunctional crosslinker EDC; Pierce Chemical Company, Rockford Ill.) or to one another (e.g., using the homobifunctional crosslinker glutaraldehyde (Sigma Chemical Company, St. Louis Mo.) followed by gel filtration and storage in PBS-BSA buffer.

In an alternative method of preparing functionally coupled HRP and AP effector molecules, a synthetic heteropolymer is prepared comprising a first defined sequence segment capable of specifically binding HRP, as in the preceding paragraph, and a second defined sequence segment of such length, preferably about two to 20 nucleotides and more preferably about five to 10 nucleotides, to enable conjugation of AP or, preferably, a streptavidin-AP conjugate, within functional coupling distance of specifically bound HRP. The synthetic heteropolymer is synthesized with either a 5'-amino group using AMINOLINKER (Boehringer Mannheim Corporation, Indianapolis Ind.) for covalent AP conjugation or a 5'-biotin phosphoramidite (Glen Research, Sterling Va.) for specific binding of a streptavidin-AP conjugate (Boehringer Mannheim Corporation, Indianapolis Ind.).

Alternatively, a synthetic heteropolymer capable of specifically binding both HRP and AP may be prepared without amino-modified nucleotides. A multimolecular complex is then formed by incubating the synthetic heteropolymer with equimolar concentrations of AP and HRP in assembly buffer (PBS-BSA). The specifically bound enzymes may then be covalently attached to one another by rapid conjugation, e.g., using a bifunctional crosslinking reagent such as glutaraldehyde or, more preferably, a photoactivatable crosslinker with pulsed irradiation. In this manner, homogeneous preparations of coupled enzyme conjugates can be prepared using the synthetic heteropolymer as a bifunctional template to position precursor molecules for selective conjugation, i.e., selectively favoring formation of one-to-one heteroconjugates. Templated conjugation provides a general method for reproducible, high-yield production of well-defined conjugates with a specific activity of one (i.e., each conjugate comprises a single donor molecule covalently attached to a single acceptor molecule).

Template-directed conjugation, i.e., using synthetic heteropolymers to assemble selected precursor molecules for proximity-directed covalent conjugation of selected molecular pairs (rather than relying on random molecular collisions in bulk solution), does not require use of an activating or crosslinking reagent. Templated conjugation can be used, for example, to accelerate the rate of product formation from spontaneously reactive species or transition states with relatively high energies of activation. By minimizing preferred intermolecular diffusion distances and maximizing the probability of an energetically favorable collision between two selected molecules, a heteropolymeric template can catalyze intermolecular reactions by effectively reducing the energy of activation for bond formation. A heteropolymeric template can therefore function much like a multisite enzyme in juxtaposing substrates and/or reactive intermediates and/or cofactors, coenzymes or prosthetic groups in facilitating covalent modification of reactants, optionally aided by input of exogenous energy, e.g., heat or photoactivation or sonic energy. For example, enzyme-like oxidase or dehydrogenase activity can be simulated by a synthetic heteropolymer having a first defined sequence segment capable of specifically binding a flavin or nicotinamide coenzyme (e.g., FMN, FAD, NAD, or corresponding reduced coenzymes) and a second defined sequence segment capable of specifically binding a substrate (e.g., a sugar, amino acid, redox indicator or dye molecule). Similarly, a heteropolymeric template can be used to deliver a preferred substrate and cofactor combination in suitable relative proximity to favor activation of a particular enzyme with selected specificity within a complex mixture comprising multiple related enzyme specificities, e.g., for selective assay of a specific a dehydrogenase, esterase, lipase, transferase, glycosidase, phosphatase or protease activity within a biological sample.

A relatively rigid heteropolymeric scaffold for assembly of functionally coupled enzymes is produced by selecting a first double-stranded HRP-binding defined sequence segment and a second 28-nucleotide defined sequence segment which is fully complementary to the 28 mer oligonucleotide moiety of an AP-oligonucleotide conjugate. On specifically binding HRP to the double-stranded first defined sequence segment and hybridizing the AP-oligonucleotide conjugate to the second defined sequence segment, the resulting multimolecular complex comprises a fully double-stranded scaffold. An even more rigid and globular tertiary structure can be achieved, if desired, e.g., by including self-complementary, single-stranded defined sequence segments at either end of the synthetic heteropolymer, causing the nucleotide scaffold to fold and self-hybridize.

For hybridization of a synthetic heteropolymer to a solid support, an oligonucleotide or plurality of oligonucleotides (e.g., an ordered set or random pool, a library, a cDNA array) is first immobilized to the solid support by covalent attachment, streptavidin/biotin chemistry or passive adsorption, optionally followed by irradiation or chemical crosslinking. Oligonucleotides may be attached to wells of microtiter plates, for example, by passive adsorption, using coating methods well known in the art. To maximize hybridization efficiency and solid phase capacity, it is preferable to immobilize oligonucleotides in a nonrandom fashion and more preferable to link a particular nucleotide or functional group to the solid support, e.g., by specific binding of a 5'-biotinylated oligonucleotide to a streptavidin-coated plate as follows. A synthetic 28 mer 5'-amino-oligonucleotide with 5'-amino group introduced using AMINOLINKER (Boehringer Mannheim Corporation, Indianapolis Ind.) is produced using an Applied Biosystems (Foster City Calif.) nucleic acid synthesizer. The oligonucleotide is biotinylated at the 5' end using the long chain NHS ester of biotin, NHS-LC-biotin (Pierce Chemical Company, Rockford Ill.). The 5'-biotinylated oligonucleotide is dialyzed extensively against PBS followed by gel filtration using a SEPHADEX G-25 column (crosslinked dextran; Pharmacia LKB, Piscataway, N.J.). Purified biotinylated oligonucleotide is specifically bound at 50 ng/well to black FluoroNunc™ 96-well plates (Nunc, Inc. Naperville, Ill.) passively coated at 500 ng/well with streptavidin (Pierce Chemical Company, Rockford Ill.). Oligonucleotide-treated plates are then washed extensively using a PBS-Tween® 20-BSA buffer.

For membrane immobilization, unmodified oligonucleotide is diluted serially in PBS buffer and spotted on a nitrocellulose transfer membrane (Schleicher & Schuell, Keene N H) using a dot blotting apparatus (Hoefer Scientific Instruments, San Francisco Calif.). Covalent attachment to the solid phase is then achieved by UV irradiation or vacuum drying at 85° C. The membrane is then blocked with a PBS-based blocking buffer containing 0.5–1.0% BSA and/or nonfat dry milk and washed by repeated immersion in fresh PBS containing 0.1% BSA.

Immobilization to quartz optical fibers, polymer-coated indium phosphide photodiodes, latex microspheres and polystyrene beads is achieved by variations of antibody coating methods (cf. Example 15, vide infra), optionally including protein coimmobilization (e.g., using BSA) and covalent fixation (e.g., using glutaraldehyde). Alternatively, end-modified (e.g., 3' or 5' amino-, thiol- or carboxyl-modified) oligonucleotides are covalently attached via the 5'-phosphate group or via added 3' or 5' amino, thiol or carboxyl groups using a suitable bifunctional reagent, e.g., a carbodiimide or NHS-ester-maleimide crosslinker.

For hybridization to an oligonucleotide-modified solid support, a synthetic heteropolymer is designed with at least one defined sequence segment capable of specifically binding to a selected molecule (e.g., the effector molecule, HRP; the ligand PSA; or the receptor, anti-human IgG antibody) and at least one defined sequence segment complementary to an immobilized oligonucleotide. To prepare a heteropolymeric solid phase for serotonergic drug discovery, for example, the synthetic heteropolymer comprises a first 40-nucleotide defined sequence capable of specifically binding serotonin with relatively high affinity, optionally including fluorophore-modified nucleotides, i.e., for detecting competition with labeled ligand binding by inhibition of fluorescence energy transfer. A second defined sequence segment of the synthetic heteropolymer is selected for the ability to hybridize to the FluoroNunc™ plate-immobilized 28 mer oligonucleotide described above. The serotonin-binding synthetic heteropolymer (10–50 ng in 100 μl PBS-Tween®-BSA) is then hybridized via its second defined sequence segment to the immobilized 28 mer oligonucleotide in a two-hour, room temperature incubation with shaking. After hybridization, wells are decanted and washed twice with PBS-Tween®-BSA. The amount of hybridized synthetic heteropolymer per well may be determined by measuring acceptor fluorophore emission in a fluorescence plate reader (SLT Labinstruments, Research Triangle Park, N.C.). Alternatively, the amount of hybridized synthetic heteropolymer may be determined by titration with fluorophore-labeled serotonin analog (e.g., L1; cf. Example 10, vide supra) and unlabeled serotonin.

Hybridization of synthetic heteropolymers to solid supports provides a convenient method to functionalize surfaces with specific binding properties, e.g., for screening, selection, detection, monitoring, separation, isolation, purification and characterization of selected molecules, samples, mixtures and libraries, e.g., clinical specimens, biological samples or combinatorial libraries comprising useful or informative ligands, receptors or effector molecules. For extremely sensitive detection of selected nonoligonucleotide targets, synthetic heteropolymers may be used not only for the capture phase, but also as solution phase specific binding partners. Amplification of a sequence comprising a target-bound synthetic heteropolymer (e.g., PCR, LCR or isothermal amplification of a target-specific defined sequence segment) can then be used to detect trace amounts, even a single copy, of an identified nonoligonucleotide molecule. Solid phase synthetic heteropolymers further comprising defined sequence segments selected as probes for selected nucleic acid sequences, preferably arrays of heteropolymeric probe sequences, can be used for screening, selection, detection, monitoring, separation, isolation, purification and characterization of selected nucleic acid sequences and samples, mixtures and libraries, e.g., clinical specimens, biological samples or combinatorial libraries comprising useful or informative nucleic acid sequences. In a particularly preferred embodiment, detection is accomplished by means of one or more effector molecules (e.g., fluorophore(s), enzyme(s), luminescent and/or electroactive species) specifically bound to heteropolymeric defined sequence segments.

Example 15

Bispecific Nucleic Acid Antibodies for Drug Delivery, Specific Binding and DNA Probe Assays Diagnostic and therapeutic applications of bispecific antibodies, fusion proteins (e.g., immunoadhesins) and immunoconjugates (e.g., immunotoxins) are being developed to capitalize on the potential advantages of peptide-based reagents and drugs with dual specificities and/or effector functions. Bispecific antibodies are immunoglobulins or immunoglobulin fragments designed, selected, rearranged or engineered to provide two different binding specificities within a single antibody molecule. Bispecific antibodies may exhibit greater target cell specificity than two monospecific antibodies. For some therapeutic applications, the Fc effector function of the bispecific antibody is required for clinical efficacy, e.g., to trigger an immune response by killer cells bound via the bispecific antibody to a therapeutic target such as a tumor. Specific receptors for immunoglobulins are present on the surfaces of diverse cell types, including phagocytes, eosinophils, natural killer cells and macrophages. Binding of immunoglobulins to these specialized receptors is an integral part of the immune system response, directing such activities as phagocytosis, clearance of immune complexes and antibody-dependent, cell-mediated cytotoxicity. Immunoadhesins, also referred to a antigen fusion proteins, are fusion proteins combining the hinge and Fc portions of an antibody with the binding domains of a receptor. Immunoadhesins exploit both the natural affinity of a receptor for its ligand and the effector functions of the immunoglobulin Fc region. Other fusion proteins, e.g., single-chain antibody fusion proteins, For other applications (e.g., specific binding assays) only the dual specificities achieved by combining two different antibody combining sites is functionally important. Fab fragment-effector fusion proteins and therapeutic immunotoxins, for example, combine two different binding specificities or a selected binding specificity with a selected effector function (e.g., cytotoxicity) which is different from the parental antibody Fc function.

The clinical potential of the bispecific antibody approach has yet to be convincingly demonstrated. One reason for early failures has been the inability of bispecific antibodies, e.g., of murine monoclonal origin, to interact with human Fc receptors, which act as trigger molecules on killer macrophages. Also, bispecific antibody technology has suffered from lack of efficient preparation methods. Coexpression of two antibodies tends to result in low yields of the desired bispecific product, likely due to unwanted heavy and light chain pairings.

Nucleotide-directed molecular assembly provides an efficient alternative to the design of bispecific drugs, imaging agents, reagents and devices (referred to herein as "bispecific nucleic acid antibodies") with greater flexibility and positional control in combining different specific recognition properties and/or effector functions than possible with bispecific antibodies. Synthetic heteropolymers useful as diagnostic imaging and therapeutic agents, for example, can be designed with a first defined sequence segment selected to specifically bind a therapeutic target (e.g., a tumor marker, cell surface antigen, enzyme, receptor, viral coat protein or bacterial cell wall) and a second defined sequence segment selected to bind an endogenous effector (e.g., a complement receptor, killer macrophage or cytotoxic lymphocyte) or a drug or imaging agent (e.g., a radioconjugate, cytotoxin, or cytokine). In vitro diagnostic assays can also be improved using bispecific nucleic acid antibodies, e.g., synthetic heteropolymers comprising a first defined sequence segment specific for a clinical analyte and a second defined sequence segment specific for a signal-generating species.

A bispecific nucleic acid antibody designed to improve the sensitivity and reaction kinetics of a PSA tumor marker assay compared to a conventional enzyme-linked immunosorbent assay (ELISA) is prepared in the following manner. A first defined sequence segment is selected for the ability to specifically bind PSA (cf. Example 7, vide supra). A second 30-nucleotide defined sequence segment comprising an amino modifier (AMINO-MODIFIER C2 dT; Glen Research, Sterling Va.) at nucleotide positions (from the 3' end) 2, 6, 10, 20, 24 and 28 and a 5'-amino modifier at position 30 is selected for the ability to specifically bind HRP without inhibiting the enzyme (i.e., without significantly reducing Vmax or increasing Km). A synthetic heteropolymer (i.e., the bispecific nucleic acid antibody) is synthesized on an automated ABI (Foster City Calif.) nucleic acid synthesizer comprising the first and second synthetic heteropolymers separated by a 10-nucleotide spacer sequence with AMINO-MODIFIER C2 dT at nucleotide positions 8 and 10.

To prepare a labeled PSA-binding assay reagent, HRP may be specifically bound at this point to the second defined sequence segment of the (PSA- and HRP-) bispecific nucleic acid antibody and crosslinked in place using the heterobifunctional crosslinker EDC (Pierce Chemical Company, Rockford Ill.). The resulting HRP-bispecific nucleic acid antibody conjugate is purified by gel filtration using a P-100 column (Bio-Rad Laboratories, Hercules Calif.).

Alternatively, the bispecific reagent can be used in a single-step, simultaneous PSA specific binding assay using a purified anti-PSA monoclonal anti-human PSA capture antibody (Accurate Chemical & Scientific Corporation, Westbury N.Y.) passively adsorbed to wells of IMMULON™-4 (Dynatech Laboratories, Chantilly Va.) 96-well microtiter plates. Briefly, the anti-PSA antibody is diluted to 10 ug/ml in 50 mM carbonate buffer (pH 9.6) and coated at 100 µl per well for four hours at room temperature. Plates are decanted, washed once by filling wells with assay buffer (PBS (pH 7.4) containing BSA at 1 mg/ml and TWEEN® 20 (Sigma Chemical Company, St. Louis Mo.)), blocked for 1 hour with 200 µl of assay buffer containing 5 mg/ml BSA, and washed five additional times with assay buffer. Bispecific nucleic acid antibody and HRP are then added in a total volume of 50 µl, and the assay is initiated with addition of 50 µl samples containing varying concentrations of PSA (0.01–100 ng/ml). The assay mixture is incubated for 1 hour at room temperature with shaking. Wells are decanted and washed twice with PBS. Bound HRP is detected kinetically after a five minute substrate and enhancer incubation using a microtiter plate fluorimeter (SLT Labinstruments, Research Triangle Park, N.C.) and black FluoroNunc™ plates (Nunc, Inc. Naperville, Ill.).

A similar bispecific nucleic antibody approach is applied to DNA detection in the following manner. A first 5'-aminated 24 mer oligonucleotide comprising a four-nucleotide 3'-end spacer sequence and a 20-nucleotide 5'-end DNA probe to a 46-nucleotide target sequence of a bacterial (E. coli) DNA is immobilized at 50 pmol per well to IMMULON™ polystyrene 96-well microtiter plates (Dynatech, Chantilly Va.) using EDAC (Pierce Chemical Company, Rockford Ill.) followed by washing and blocking as per the anti-PSA immobilization protocol. A synthetic heteropolymer is synthesized comprising the following sequence segments separated by a 10 mer spacer sequence: 1) as first defined sequence segment and spacer sequence, the 30–35 nucleotide HRP-binding, aminated defined sequence segment and the 10-nucleotide aminated spacer sequence described above, and 2) as second defined sequence segment, a second 24-nucleotide DNA probe to the 46-nucleotide E. coli target sequence nonredundant (i.e., nonoverlapping) with the first DNA probe sequence. This DNA probe-spacer-HRP-binding synthetic heteropolymer is mixed with HRP and samples containing varying amounts of denatured E. coli DNA. The E. coli DNA assay is then performed using incubation, wash and detection steps as per the bispecific nucleic acid antibody-PSA assay protocol (vide supra). Alternatively HRP may be specifically bound and, optionally, covalently crosslinked to the first defined sequence segment of the synthetic heteropolymer (e.g., using EDC) prior to assay, enabling use of a single conjugated detection reagent in place of two separate reagents. Although addition of a single, conjugated HRP-synthetic heteropolymer reagent may be more convenient, simultaneous incubation of self-assembling synthetic heteropolymer and signal-generating components may provide more rapid reaction kinetics and superior sensitivity.

In vivo applications such as diagnostic imaging, therapeutics and drug delivery are also possible using bispecific antibodies, fusion proteins and related antibody conjugates, e.g., as anticancer drugs, antimicrobial and antiviral compounds, fibrinolytic agents and immune modulators. Antibodies and antibody fragments have been chemically conjugated to a number of therapeutic effectors, including plant-derived, animal-derived and bacterial toxins (e.g., lectins, selectins, venom toxins, enterotoxins), enzymes, radionuclides and cytotoxic drugs. Through chemical conjugation, otherwise ineffective antibodies, fragments or MRUs may be equipped with potent effector mechanisms. Fragments conjugated to radioisotopes may be used for in vivo imaging or cancer therapy. However, chemical conjugation methods have drawbacks. They may be inefficient or give rise to unstable or inactive products, or they may alter binding specificities or effector functions of constituent molecules. Repeated cycles of antibody purification, modification, and repurification are time-consuming and expensive. Also, regardless of the degree of purification and repurification, immunoconjugates are not precisely defined chemical entities, but are typically heterogeneous at the molecular level.

An alternative to chemical coupling is creation of novel recombinant proteins with antibody specificities (i.e., fusion proteins) by genetically linking antibody genes to sequences coding for nonimmunoglobulin molecules, e.g., enzymes, cytokines or toxins. In Fc fusion proteins (i.e., immunoligands), the genes encoding a ligand (i.e., a peptide or protein) are genetically linked to sequences encoding an Fc region. (Fc-mediated effector functions may be avoided, e.g., by site-directed mutagenesis or by linking the ligand gene to a sequence coding for the constant region of an immunoglobulin isotype, such as IgG2). Antigen-binding fusion proteins (i.e., immunoadhesins) represent the converse of Fc fusion proteins, comprising recombinant proteins formed by genetically linking the antigen-binding portion of an antibody to a receptor-binding ligand.

Bispecific antibodies, also known as bifunctional antibodies, represent another alternative for combining two functions within a single therapeutic structure. Bispecific antibodies are capable of recognizing and complexing with epitopes of two different antigens, e.g., a tumor cell surface antigen and an immune cell receptor as a means of targeting effector cells against the tumor. To circumvent drawbacks of chemical conjugation, most efforts to produce bispecific antibodies rely upon hybrid hybridoma approaches. Once the hybrid hybridoma cell line has been developed, the secreted bispecific antibody is purified from other possible combinations of heavy and light chains, e.g., by isoelectric focusing, ion-exchange chromatography or double-affinity chromatography. Bispecific antibodies can be developed with a first specificity against a therapeutic target (e.g., a cancer antigen, viral coat protein, fibrinogen, platelet or endothelial receptor) and a second specificity against an endogenous or exogenous effector (e.g., an immune cell, cytotoxic, antineoplastic or antiinfective drug, radionuclide, chelating or photodynamic or hyperthermic agent).

However, hybrid hybridoma methods are time-consuming, labor-intensive and prone to low yields of the desired combination of heavy and light chains (e.g., <10%).

For imaging and therapeutic applications, bispecific nucleic acid antibodies represent an attractive alternative to bispecific immunoglobulin antibodies. Bispecific nucleic acid antibodies (i.e., synthetic heteropolymers) can be developed with any combination of desired specificities toward selected targets and/or effector species. Unlike immunoglobulin-based bispecific antibodies, synthetic heteropolymers can not only specifically bind, but also hybridize to selected targets (e.g., viral, bacterial, genomic or cellular nucleic acid sequences). Bispecific nucleic acid antibodies for in vivo use typically comprise at least a first target-binding defined sequence segment that specifically binds or hybridizes a pathological target (e.g., a cancer antigen, vascular lesion, microbial sequence, coat protein, surface marker or membrane receptor) combined with at least a second defined sequence segment capable of specifically binding an exogenous or endogenous effector (e.g., a T cell, macrophage, cell surface antigen or complement receptor; a fibrinolytic, antineoplastic or antiinfective drug; a cytotoxin, cytokine, photodynamic or hyperthermic agent; or a contrast or imaging agent, radionuclide or chelator). For example, a bifunctional therapeutic for mounting an endogenous defense against HIV can be developed using a synthetic heteropolymer comprising a first defined sequence segment capable of specifically binding the gp41 antigen of HIV-1 and a second defined sequence segment capable of specifically binding the Fc-gamma RI receptor site (primarily found on monocytes and macrophages). Alternatively, HIV replication can be inhibited using a synthetic heteropolymer comprising a first defined sequence segment capable of hybridizing to a selected nucleic acid sequence comprising the HIV-1 virion and a second defined sequence segment capable of specifically binding HIV-RT (and optionally a third defined sequence segment capable of specifically binding, e.g., the HIV-1 rev protein). For cancer imaging and therapy, a single-step, bifunctional, mix-and-use radionuclide preparation (i.e., prepare as needed, minimizing waste from isotopic decay) can be developed using a synthetic heteropolymer comprising a first defined sequence segment capable of specifically binding CEA and a second defined sequence segment capable of specifically binding an indium-111 chelate (for imaging) or, alternatively, a yttrium-90 chelate (for therapy). In a particularly preferred therapeutic embodiment (e.g., for anticancer or antiviral therapy), a first defined sequence segment of a synthetic heteropolymer specifically binds a selected target (e.g., Lewis-Y antigen for breast cancer), a second defined sequence segment specifically binds an exogenous effector (e.g., a hydrolyzable doxorubicin-peptide conjugate), and a third defined sequence segment specifically binds and activates an endogenous effector (e.g., the human Fc receptor of a killer macrophage). Optionally, this multimolecular drug delivery system may be designed as a triggered-release multimolecular switch, i.e., a prodrug, wherein binding of the first defined sequence segment to a tumor cell or the third defined sequence segment to a macrophage stimulates local release of the doxorubicin-peptide conjugate. Provided released doxorubicin-peptide conjugate is internalized by lysosomes more rapidly than synthetic heteropolymer-bound doxorubicin conjugate, this triggered-release composition enables more effective cellular delivery of doxorubicin.

In an alternative prodrug embodiment relying on a bispecific nucleic acid antibody, a targeted therapeutic enzyme is administered in inactive form and released and activated at the site of therapeutic action. A heteropolymeric multimolecular drug delivery system comprising a bispecific nucleic acid antibody prodrug is designed as follows to transport carboxipeptidase G2 in inactive form to tumors of colon carcinoma patients and release the enzyme in active form on specifically binding CEA. First and second defined sequence segments are selected for the ability to specifically bind first and second nonoverlapping epitopes on CEA, each with very high affinity (e.g., $>10^9$ $M^{-1}$). In other words, the two defined sequence segments specifically and tightly bind different regions on CEA in a noncompetitive manner. A third defined sequence segment is selected for the ability to specifically bind and inhibit the enzyme carboxipeptidase G2. A synthetic heteropolymer is prepared comprising the carboxypeptidase G2-binding defined sequence segment flanked by the two CEA-binding defined sequence segments in such manner that binding of the two flanking defined sequence segments to tumor-associated CEA results in release and activation of carboxypeptidase G2.

Example 16

Use of Synthetic Heteropolymers to Detect Membrane-immobilized Oligonucleotides and Proteins Synthetic heteropolymers can be used in a wide variety of immobilized reagent formats, e.g., to detect and quantify oligonucleotides or nonnucleic acid analytes, to immobilize a first defined sequence segment (e.g., an aptamer sequence) by hybridization of a second defined sequence segment to a solid phase oligonucleotide, to immobilize a multimolecular complex or to immobilize a multimolecular device comprising effector molecules functionally coupled to one another or to a transducer. Among the simplest embodiments of synthetic heteropolymer use in immobilized reagent formats are membrane detection applications, including DNA hybridization (Southern blots), RNA hybridization (Northern blots) and protein detection (western blots). Following are examples of the use of synthetic heteropolymers and multimolecular complexes to detect membrane-bound nucleic acids and proteins.

To demonstrate direct detection of an oligonucleotide attached to a membrane, the oligonucleotide is first serially diluted in PBS. Replicates of each dilution are applied to nitrocellulose membrane either manually or, preferably, using a dot blot or slot blot apparatus designed for quantitative transfer (Hoefer Scientific Instruments, San Francisco Calif.). Oligonucleotides are then covalently affixed to the membrane either by UV irradiation or drying in a vacuum oven (85° C.). Membranes are blocked with a PBS blocking buffer containing BSA, nonfat dry milk and Tween® 20 and rinsed extensively in a PBS-BSA-casein-Tween® 20 blotting buffer. A multimolecular complex is prepared comprising a synthetic heteropolymer with HRP specifically bound and covalently crosslinked to the first defined sequence segment (cf. Example 15, vide supra), a 10-nucleotide spacer sequence, and a second (DNA probe) defined sequence segment capable of hybridizing to the nitrocellulose-immobilized synthetic oligonucleotide. Blocked, washed membranes are immersed in a solution containing the HRP-synthetic heteropolymer complex in blotting buffer and incubated with gentle shaking to allow hybridization. Blots are then washed extensively in a modified blotting buffer and developed using a reagent mixture containing peroxide and a precipitating chromogen (e.g., insoluble 3,3',5,5'-tetramethylbenzidine or 4-chloro-1- napthol). Binding of the multimolecular complex is detected by visual inspection. For quantitative determinations, blots may be scanned photometrically. For maximal sensitivity, blots may be developed with fluorescent or chemiluminescent HRP substrates, enhancers or coupled enzyme reactions instead of a colorimetric indicator and scanned, e.g., using a FLUOROIMAGER (Molecular Dynamics, Sunnyvale Calif.) or MULTIIMAGER (Bio-Rad Laboratories, Hercules Calif.).

Alternatively, membrane-bound oligonucleotides are probed in a sequential, "forward sandwich" protocol using a first incubation with (oligonucleotide and HRP)-binding synthetic heteropolymer and a second incubation with HRP followed by washing, enzyme development and scanning. In this protocol, blocked, washed, oligonucleotide-spotted membranes are immersed and gently shaken in blotting buffer containing a DNA probe synthetic heteropolymer comprising a first defined sequence segment capable of specifically binding HRP and a second defined sequence segment capable of hybridizing to the nitrocellulose-immobilized synthetic oligonucleotide (i.e., a DNA probe sequence segment) separated by a 10-nucleotide spacer sequence. The immobilized oligonucleotide-synthetic heteropolymer hybrid complex is rinsed in modified blotting buffer to remove unbound and nonspecifically bound synthetic heteropolymer. The resulting composition (a synthetic heteropolymer attached to a solid support by hybridization of one defined sequence segment to an immobilized oligonucleotide and capable of specifically binding at another defined sequence segment to a nonoligonucleotide molecule) is a generally useful construct for endowing a surface with recognition properties, e.g., for use in solid phase assays, biosensors, biochips and molecular arrays for high-throughput screening and diagnostics. In the instant example, the recognition property introduced to the surface (nitrocellulose membrane) is specific binding of HRP, i.e. for detection of membrane-bound oligonucleotides. After rinsing to remove unbound material, the membrane with HRP-binding synthetic heteropolymer hybridized to membrane-bound bound oligonucleotide is incubated with HRP in blotting buffer, rinsed extensively in blotting buffer and developed according to procedures described in the preceding paragraph.

Detection of nucleic acid hybridization to an immobilized oligonucleotide is accomplished as follows. PCR is used to synthesize a single-stranded DNA probe oligonucleotide having a first 24-nucleotide sequence (A') complementary to a target oligonucleotide (A) and a second 24-nucleotide sequence (B') capable of hybridizing a second, different nucleic acid sequence (B). The target oligonucleotide A is serially diluted in PBS and immobilized to a nitrocellulose membrane by quantitative transfer followed by covalent attachment, blocking and washing as described in the preceding paragraph. A synthetic heteropolymer is prepared with a first defined sequence segment capable of specifically binding HRP and a second defined sequence segment (comprising nucleic acid sequence B) which is capable of hybridizing the probe oligonucleotide sequence B'. The DNA probe oligonucleotide is then hybridized via sequence A' with the immobilized target sequence A, and the membrane is washed in modified blotting buffer. The HRP-binding synthetic heteropolymer and HRP are then added, either sequentially or simultaneously. Alternatively, the synthetic heteropolymer and HRP are prebound prior to assay, optionally followed by crosslinking HRP in place to produce a stable heteropolymer-HRP conjugate. Blots are then washed extensively in a modified blotting buffer and developed using a reagent mixture containing peroxide and a precipitating chromogen (e.g., insoluble 3,3',5,5'-tetramethylbenzidine or 4-chloro-1-napthol). Results are determined visually, by instrumented scanning.

Synthetic heteropolymers and multivalent heteropolymeric hybrid structures may be used in DNA blotting (i.e., Southern blots), RNA blotting (i.e., Northern blots) and protein blotting (i.e., Western blots) by modification of methods described in the preceding paragraphs. For Western blots, proteins are transferred after electrophoresis to a blotting membrane (e.g., nitrocellulose) using an electric current. A selected protein is then detected using a synthetic heteropolymer or multivalent heteropolymeric hybrid structure having one defined sequence segment that specifically binds the selected target and another defined sequence segment that specifically binds or hybridizes the detection reagent (e.g., HRP or and HRP-oligonucleotide conjugate). Extremely high sensitivity detection of protein targets can be achieved (e.g., <10 molecules) by extensively washing blots after the synthetic heteropolymer binding step and then amplifying a defined sequence segment comprising the synthetic heteropolymer.

Example 17

Use of Synthetic Heteropolymers in Purifying Selected Molecules from Complex Mixtures Bifunctional synthetic heteropolymers capable of specifically binding a selected molecule and recognizing a surface or surface-immobilized molecule, e.g., a structural shape or solid phase ligand, receptor, polymer or biopolymer, provide a useful and efficient means of isolating and purifying valuable molecules from complex mixtures. For example, a bifunctional synthetic heteropolymer comprising a first defined sequence segment capable of specifically binding a high-value biopharmaceutical product, e.g., α-interferon, salmon calcitonin, taxol, human growth hormone or follicle stimulating hormone, and a second defined sequence segment capable of specifically binding an inexpensive polymer, preferably an insoluble or immobilized polymer such as dextran, agarose, or polyethylene glycol, can be used as a cost-effective and reusable purification reagent. Alternatively, isolation of related molecules from a complex mixture, e.g., a library, pool, biological sample or homogenate, can be achieved using a bifunctional synthetic heteropolymer comprising a first defined sequence segment selected for the ability to specifically recognize a class of molecules (e.g., taxoids, sex steroids, opiates, interferons, α-subunit-comprising glycoprotein hormones, homologous proteins, a family of ligands interacting with a particular receptor (e.g., congeners or receptor agonists, antagonists and/or mixed or partial agonists or antagonists) or a family of substrates, cofactors or coenzymes recognized by a particular enzyme or family of enzymes). The synthetic heteropolymer is first added to a biological mixture or process stream comprising the selected molecule or group or molecules of interest (e.g., the biopharmaceutical peptide hormone, calcitonin). After bulk-phase mixing for two to 24 hours at controlled room temperature, the synthetic heteropolymer-bound calcitonin is separated from the mixture using a polymer matrix, e.g., beaded agarose, in either batch or column mode. The calcitonin is then dissociated from the matrix-bound multimolecular complex under nondenaturing conditions (e.g., salt or pH elution). and the separation support is regenerated by thermal or ionic dissociation of the synthetic heteropolymer. Alternatively, processing conditions may be adjusted so that after unwanted constituents are removed (e.g., eluted, decanted and/or washed) from the purification vessel, the synthetic heteropolymer-calcitonin complex is eluted as an intact multimolecular complex. The calcitonin-synthetic heteropolymer complex is optionally covalently stabilized (i.e., chemically crosslinked), e.g., to prepare a specific binding assay reagent or an affinity support for calcitonin receptor. Alternatively, the multimolecular complex is subsequently dissociated, and the synthetic heteropolymer is recycled in downstream processing.

A particularly preferred batch process is developed to capitalize on use of a synthetic heteropolymer as an affinity reagent capable of specifically binding the target biopharmaceutical molecule (e.g., calcitonin) in solution followed by hybridization of the resulting multimolecular complex to an immobilized oligonucleotide. The first defined sequence segment of the synthetic heteropolymer is selected to specifically bind calcitonin with high affinity. The second defined sequence segment of the synthetic heteropolymer is selected for the ability to hybridize to an oligonucleotide immobilized to crosslinked dextran in such manner that the column can be regenerated and the synthetic heteropolymer recycled, e.g., by heating and/or buffer washes. Alternatively, a column procedure can be used, wherein the synthetic heteropolymer remains hybridized to the column support and the column is regenerated by variable salt, buffer and pH washes.

Any number of popular separation media (e.g., membranes, hollow fibers, filtration media, electrophoretic gels, and microparticles) to efficiently isolate and purify different classes of molecules and groups of molecules, e.g., industrial enzymes, dyes, monomers and polymers as well as pharmaceuticals, nutraceuticals, proteins, lipids, peptides, enzymes, hormones and other biologicals, including viruses, bacteria and even plant and animal cells.

In a particularly preferred type of separation process, synthetic heteropolymers are used to copurify multiple selected molecules, preferably multiple effector molecules, and more preferably multiple functionally coupled effector molecules, e.g., multiple enzymes, transport proteins, cytochromes or photosynthetic molecules comprising a pathway, shuttle or supramolecular assembly, particularly a pathway or process involving interaction between soluble and membrane-bound effectors (e.g., cytosolic and/or extracellular effectors as well as membrane-associated proteins, lipids and/or complexes).

Particular time, labor, equipment and cost savings can be achieved in processes requiring isolation of multiple selected molecules from a single source or mixture (e.g., a biological pool, a tissue homogenate or a bacterial, fungal or algal culture), especially if the multiple selected molecules are to be reconstituted or assembled into a functionally coupled multimolecular structure or process, e.g., a multienzyme pathway or photosynthetic apparatus. Multifunctional synthetic heteropolymers, multivalent heteropolymeric hybrid structures and discrete structures comprising multiple nucleotide ligands and/or nucleotide receptors of the instant invention enable copurification of multiple nucleotide-bound effectors, preferably in a functionally coupled form. In a particularly preferred mode of operation, copurified effectors are characterized and quantified in nucleotide-bound form by an assay that measures an output of the functionally coupled effectors.

Example 18

Selection of a Synthetic Defined Sequence Segment for the Ability to Stabilize a Peptide Drug The commercial potential of biological molecules is often limited by instability in a particular environment, i.e., unacceptable or suboptimal half-life or shelf-life. Biopharmaceuticals for human, veterinary and agricultural use, for example, and selected, engineered or evolved biomolecules for use in sensor and semiconductor devices (i.e., biosensors and biochips) tend to be less stable under conditions of use than synthetic or inorganic counterparts. To capitalize on the functional diversity and efficiency of biological molecules as drugs, devices and machine components, there is a need to stabilize. insulate, protect or shield vulnerable groups from enzymatic, chemical and environmental degradation. Aptameric and heteropolymeric multimolecular devices of the instant invention provide a means to stabilize specifically bound, fragile molecular effectors from attack by protecting vulnerable groups, sites or topological regions. Preparation of a protective aptameric or heteropolymeric composition requires selection of a defined sequence segment capable of binding a selected effector molecule and shielding susceptible group(s) from chemical and/or conformational modification under conditions of use.

For example, a defined sequence segment can be selected to bind a therapeutic peptide and attenuate peptide degradation under physiological conditions, thereby increasing the in vivo half-life and therapeutic efficacy of the nucleotide-bound peptide. The instant example describes selection of defined sequence segments capable of binding to and enhancing the stability of antiplatelet and antithrombotic peptides, e.g., the RGDS peptide SK&F 106760 (SmithKline Beecham, Philadelphia Pa.) or the Gp IIb/IIIa receptor-specific chimeric Fab fragment anti-7E3 (CENTORX; Centocor, Malvern Pa.).

Vascular thrombotic events associated with myocardial infarction, percutaneous transluminal coronary angioplasty (PTCA), stroke, peripheral arterial occlusion and venous thromboembolism, among other conditions, cause significant morbidity and mortality. Intense antithrombin and antiplatelet drug development efforts are underway to reduce the incidence of thrombotic events. Because rethrombosis occurs in 15% to 35% of treated patients, a major drug development focus for the treatment of acute myocardial infarction is maintaining vessel patency following thrombolytic therapy. Another major focus is reducing the incidence of restenosis following PTCA procedures from the historical rate of about 30%. Other important applications for antithrombin and antiplatelet agents include hronic maintenance of vessel patency following coronary artery bypass surgery and post-thromboembolitic stroke. Pharmacological approaches to thrombosis include prostaglandins, calcium channel blockers and antifibrinogen agents; antagonists of platelet activating factor and glycoprotein (Gp) Ib, IIb and IIIa receptors; ticlopidine, which alters GP IIb/IIIa receptor expression; and inhibitors of cyclooxygenase, thrombin, phosphodiesterase and thromboxane synthetase. Significant evidence indicates that fibrinogen binding to the platelet Gp IIb/IIIa (adhesion) receptor is the final common pathway of platelet aggregation, suggesting the utility of effective Gp IIb/IIa receptor antagonists. CENTORX (Centocor; Malvern, Pa.) is a chimeric anti-7E3 Fab fragment with Gp IIb/IIIa receptor specificity. RGD and RGDS peptides bind the active site of the Gp IIb/IIIa receptor through the adhesive protein recognition sequences Arg-Gly-Asp and Arg-Gly-Asp-Ser, respectively, which are essential for fibrinogen-receptor interaction. However, the clinical and commercial potential of such antibodies and peptides as antithrombotics is limited by their unacceptably short half-lives. Platelet Gp Ib receptors interact with von Willebrand factor associated with damaged vascular endothelium to initiate platelet adhesion. Adhesion is followed by platelet aggregation which, in turn, leads to thrombus formation. Gp Ib receptor antagonists may therefore interrupt thrombus formation at an earlier point in the pathologic cascade than Gp IIb/IIIa receptor antagonists.

Administration of a drug specifically bound to an aptameric or heteropolymeric defined sequence segment of the present invention can increase the circulating half-life and therapeutic efficacy of the drug, as exhibited by enhanced antithrombotic performance of a platelet receptor antagonist. For example, a therapeutic composition comprising a platelet Gp IIb/IIIa receptor antagonist (e.g., RGDS peptide SK&F 106760 (SmithKline Beecham; Philadelphia, Pa.), Britistatin or Echistatin (both of Merck; Rahway, N.J.)) specifically bound to selected defined sequence segments are administered perioperatively by intravenous infusion.

A library of fluorescein-labeled RNA molecules comprising a 35-nucleotide randomized sequence flanked by PCR primer sequences is produced by transcription of a corresponding cDNA array. The receptor-specific chimeric Fab fragment anti-7E3 (CENTORX; Centocor, Malvern Pa.) is incubated with the library for two hours at room temperature, and the mixture is transferred to a screw-capped flask comprising cultured fibroblasts in human serum protein-supplemented growth medium. After 24-hours in a 37° C., controlled $CO_2$ incubator, the medium is transferred to microfuge tubes and centrifuged at 8,000×g for one minute to remove cells, aggregates and debris. The supernatant is transferred to fresh microfuge tubes and fluorescein-labeled anti-7E3/nucleotide complexes are separated from the remainder of the mixture by agarose-RGDS affinity chromatography (and/or ion-exchange chromatography) with fluorescence monitored in black FluoroNunc™ plates (Nunc, Inc. Naperville, Ill.) using a FLUOSTAR microplate fluorimeter (SLT Labinstruments, Research Triangle Park, N.C.). Only aptamers that specifically bind the anti-7E3 Fab fragment and protect from enzymatic degradation in enzyme-supplemented medium are isolated by the selection procedure. Unbound fluorescein-labeled RNA sequences, fluorescent nucleotide fragments, and anti-7E3-binding nucleotides that fail to protect against anti-7E3 epitope modification in enzyme-supplemented culture are retained by the chromatography medium.

In alternative selection procedures, mixtures comprising anti-7E3 Fab fragment and cDNA-generated RNA libraries are subjected to heat-stress (85° C. overnight) and/or enzymatic treatment by panels of proteases, endopeptidases and exopeptidases. Complexes comprising stabilizing fluorescent aptamers are then identified by ion exchange chromatography or affinity chromatography using RGDS agarose as described in the preceding paragraph.

Selected aptamers are amplified by PCR and sequenced. Anti-7E3-binding epitopes are assessed by structure probing. Relative affinity is determined in competitive binding assays (e.g., fluorescence polarization, fluorescence energy transfer) using labeled anti-7E3. The relative protective utility of selected aptamers is determined by real-time and accelerated stability studies (i.e., in vitro, in culture and subsequently in animals). The selected aptamer(s) maximally effective in protecting anti-7E3 from degradation in animal studies is scaled up for controlled safety and efficacy comparisons using anti-7E3 administered alone versus anti-7E3 administered as an aptamer-anti-7E3 complex.

Example 19

Selection of Defined Sequence Segments Capable of Mimicking the Specificity of a Known Receptor The advent of hybridoma technology in the mid-1970s catalyzed the evolution of an entire industry dedicated to screening, selection, characterization, scale-up, purification, labeling and formatting of monoclonal antibodies for applications ranging from clinical, academic and industrial research to in vitro diagnostics, in vivo imaging, immunoconjugate therapy and environmental, agricultural, military, workplace and even home testing. Hybridoma technology offers the potential to create a highly diverse variety of reagents with differing binding specificities. Antibodies with useful specificities toward most haptens and antigens heretofore known to be important diagnostically (i.e., those detected by FDA-approved in vitro diagnostic assays) are readily available as catalog items from a large number of commercial suppliers. However, the structural attributes and potential constraints, limitations and/or conditions of use for immunoglobulin reagents are nonideal for certain applications and preclusive for others. Potentially undesirable attributes of antibodies include, for example, their relatively large size (160 kilodaltons), instability with prolonged storage at ambient or elevated temperatures, structural variability (i.e., carbohydrate composition and microheterogeneity), potential for structural (i.e., genetic, conformational) drift, and highly complex and unpredictable tertiary structure as a function of primary amino acid sequence.

As detection, amplification and signal transduction technologies improve and trends toward miniaturization continue to push formats toward the micron and even submicron scale, the performance of diagnostic technologies (e.g., sensitivity, specificity, precision, reproducibility, shelf-life) are becoming progressively more dependent on the molecular features and properties of recognition and transduction reagents. For applications requiring truly well-characterized reagents, e.g., pure preparations of chemically defined specific binding reagents whose function (e.g., binding assay performance, stability) correlates predictably with chemical composition and structure, antibodies are less than perfect. Achieving sensitive, specific, reliable and robust performance from antibody reagents of is particularly challenging in harsh, volatile and/or variable environments or processes (e.g., biological fluids, organic solvents, thermal cycling, freeze-drying, operating conditions within a machine or system and/or ambient indoor or outdoor conditions). Disadvantages of antibodies as reagents, drugs and device components include not only reliability, stability and shelf-life limitations. Antibodies are disadvantageously of relatively high molecular weight (e.g., 50–160 kilodaltons; 50–105 kilodaltons for Fab and $F(ab')_2$ fragments) and size (i.e., about 14×10×4 $nm^3$, for IgG and 7×5×4 $nm^3$ for Fab'), susceptible to proteolytic digestion, aggregation, microbial contamination, and are difficult to modify and/or conjugate at uniquely defined sites, except, e.g., at N-terminal and C-terminal amino acids, poly-his regions, strategically located thiols and/or sites introduced by genetic modification. Also, because of potential genetic drift of hybridoma cell lines and/or storage instability of frozen antibody stocks, guaranteed sourcing and the security of rare clones and secreted antibodies are nontrivial issues.

Nucleotides provide a number of significant advantages as feedstock molecules for the production of well-defined molecular recognition devices, particularly multisite nucleotides comprising multimolecular devices. Not only do nucleotides provide a convenient approach to self-assembly based upon predictable rules of base-pairing, effectors can also be readily attached by noncovalent, reversible or quasireversible means (e.g., specific binding to defined sequence segments). Unlike antibodies, oligonucleotides can be readily synthesized by automated methods (e.g., a DNA synthesizer) and strategically modified at defined positions by incorporating or attaching different functional groups at defined positions. Oligonucleotides can also be conveniently and reproducibly conjugated or immobilized via defined groups, e.g., functional groups of modified and/or 5' and/or 3' terminal nucleotides. Also, the geometry of the DNA duplex is well defined, the nucleotide backbone may be extensively modified and sequences comprising nucleotide reagents and devices can carry information useful in directing self-assembly, specific binding and enzymatic processes. This last informational role of nucleotides is particularly important in practicing nucleotide-directed assembly processes of the instant invention, particularly template-directed assembly of useful multimolecular devices and drug delivery systems.

Antibodies, particularly bispecific antibodies, can in certain instances usefully assemble two different molecules, e.g., an effector cell and a therapeutic target or a surface-bound analyte and a detectable reported molecule. However, antibodies cannot be built to suit, conveniently modified at defined positions, assembled by predictable rules of association, produced by automated synthesis, subjected to extreme temperatures, stored as benchtop reagents, or, perhaps most important, archived simply as sequence code that can be communicated by phone, fax or modem from one laboratory to another, enabling turnkey synthesis of the chemically defined product anywhere in the world within a matter of hours.

Nucleotides comprising synthetic heteropolymers of the instant invention, in contrast to antibodies, provide a general class of structures useful as bimolecular and multimolecular assembly templates. Templating (i.e., template-directed assembly) in turn, is an effective technique for mimicking the structural organization and efficiencies of biological systems, as apparent, e.g., in electron transport systems, light-harvesting antenna systems, biochemical amplification and feedback systems, e.g., metabolic and regulatory cascades, multistep enzyme and signal transduction pathways, immune and inflammatory responses, and the like. Commercial applications of template-directed multimolecular assemblies include, without limitation, advanced materials, devices and processes, e.g., smart polymers and polymer-device hybrids; microelectronic, photonic and optoelectronic devices; industrial process control systems, enzyme reactors, chiral processes, and detoxification systems; diagnostic reagents, devices, biosensors and biochips; and multimolecular drugs, prodrugs and drug delivery systems.

Templating offers a number of advantages for reproducibly constructing molecular-scale devices. For example, template-directed assembly eliminates the need for covalent attachment of effectors (or other selected molecules), a common source of heterogeneity in macromolecular conjugate preparations. Noncovalent effector attachment enables reversible or quasireversible stimulus-response coupling, an important feature of multimolecular devices, e.g., switches and sensors designed for repetitive activation and/or continuous monitoring. Effector molecules, complexes, supramolecular assemblies and even particles and devices of virtually any size, composition and structure can be reproducibly attached to templates by specific binding interactions, regardless of the number and diversity of functional groups. Specifically bound effector molecules remain chemically unmodified, obviating the risk of irreversible functional damage. Also, effector molecules need not be purified prior to assembly, reducing processing time, labor, and materials costs and improving device yields. Template-based multimolecular assemblies prepared by site-directed attachment of selected molecules have uniform and reproducible supramolecular composition. They can be therefore be used (and documented) as chemically defined (e.g., well-characterized) components for manufacture of higher order devices and systems. Templating can also be combined with chemical, electromechanical, and optical assembly and modification tools, including, e.g., crosslinking, use of derivatized nucleotides, nucleotide analogs, nucleotide ligands and nucleotide receptors; use of scanning probe techniques such as AFM and scanning tunneling microscopy; and use of lasers, e.g., for optical trapping, optical tweezers and the like.

Nucleotides are particularly advantageous building blocks for template construction. Efficient, reliable and programmable synthetic oligonucleotide production is routinely achieved on automated synthesizers amenable to large-scale, cost-effective production. With current efforts to scale up oligonucleotide manufacture (e.g., for antisense therapeutics) production costs are dropping at an accelerating rate. Also, nucleotide monomers and backbone-modified oligonucleotides have the potential to be stored and used more like benchtop chemicals than fragile biologicals. The combinatorial (i.e., sequence-related) and chemical (i.e., relating to backbone, nucleoside modifications and nucleotide analogs) diversity of nucleotides provides broad recognition potential for specific binding and assembly of virtually limitless combinations of molecules. Hybridization of complementary nucleotide sequences enables modular device construction, i.e., efficient design and production by synthesizing and assembling hybridizable components. Essentially, nucleotides are uniquely qualified for self-assembly processes relying on both complementary base pairing and ligand-receptor docking. Also, nucleotides comprising assembly templates can be recycled (i.e., salvaged and reused with or without modification) by dissociation from specifically bound effectors. Further, the replicative properties of nucleotides enables development of multimolecular devices that not only self-assemble, but also self-replicate. Finally, manufacturing technologies for nucleotide template-based assembly already exist, e.g., methods for preparing large arrays of (e.g., immobilized) nucleic acids for sequencing and diagnostic use. there is substantial and growing interest within the semiconductor industry in fabrication and commercialization of oligonucleotide chips, e.g., to capitalize on the potential synergies between biotechnology and microelectronics.

For these and other reasons, it may be desirable for a number of applications to "transpose" the useful binding specificity of an identified ("reference" or "parent") receptor or ligand, e.g., an antibody, membrane receptor or therapeutic target (e.g., a coat protein, disease marker and/or cell surface antigen) into a nucleotide sequence, preferably a efined sequence segment comprising a synthetic heteropolymer ran aptameric or heteropolymeric multimolecular device, which displays the same useful specificity, optionally a similar, related, antiidiotypic, idiotypic and/or more useful specificity, as the identified receptor or ligand. In other words, it may be useful to select an oligonucleotide, e.g., from a diverse mixture or library of nucleic acids, based upon the ability of the oligonucleotide to mimic the idiotypic or antiidiotypic binding specificity of an identified ligand or receptor. An oligonucleotide that mimics the binding specificity of a selected ligand or receptor is also referred to herein as a ligand or receptor mimetic or a mimetic nucleic acid sequence. Once characterized (e.g., for binding specificity and affinity, preferably following amplification) and sequenced, sequences with desirable binding specificities may be incorporated as defined sequence segments into synthetic heteropolymers, aptameric and heteropolymeric multimolecular devices disclosed herein.

A particularly preferred technique for identifying a defined sequence segment with specificity that mimics a selected ligand or receptor is the ligand-receptor dissociation method, also referred to as ligand dissociation, receptor dissociation, or simply a dissociation or displacement method or assay. Oligonucleotides comprising a diverse nucleic acid mixture are selected based upon their ability to dissociate a ligand-receptor complex. Heterogeneous selection assays are preferred, wherein either the ligand or the receptor is immobilized to a solid support. The specific binding partner of the immobilized reagent (e.g., the receptor or ligand, as the case may be) is specifically bound to the immobilized reagent, and mimetic nucleic acid sequences are selected (i.e., by subsequent characterization) from those capable of competitively displacing said specific binding partner. Homogeneous (i.e., solution phase) selection methods can also be used, wherein members of a nucleic acid library competitively dissociate a soluble ligand-receptor complex. In a typical protocol for selecting ligand or receptor mimetics, variations in specificity and/or affinity of selected ucleotide sequences are evolved by iterative or stepwise transitions in selection pressure, e.g., by substituting congeners or crossreactants for one or both members of the dissociable ligand-receptor pair, by changing the selection assay architecture (e.g., from immobilized ligand to an immobilized receptor or homogeneous format) or by changing the selection assay protocol, buffer composition or incubation conditions. The performance in a chosen assay of a defined sequence segment selected to precisely mimic the binding specificity of the model ligand or receptor is then used as a standard against which to compare the performance of variant sequences selected with overlapping, non-identical specificities. Through iterative selection for evolving specificities, it is even possible to identify defined sequence segments that specifically bind a selected target of the parent ligand or receptor in a manner that is noncompetitive with the parent. In other words, specificity migration enables the identification of pairs or groups of defined sequence segments that bind a selected target at fully redundant, concentric, partially overlapping or even non-overlapping target recognition sites. Refinement or migration of binding specificity (i.e., epitopic evolution and/or drift) may be rationally influenced or directed, e.g., by chemically modifying a selected target in a site-directed manner. Alternatively, selection pressure may be applied in an arbitrary or exploratory manner, e.g., by changing the buffer conditions, temperature, timing or protocol of the selection process.

A defined sequence segment with binding specificity mimicking that of an antibody for its antigen is identified using a selection method relying on competitive dissociation of the antigen-antibody complex (i.e., a ligand-receptor dissociation method), as described below for a monoclonal IgG antibody against the chemokine, human interleukin-8 (IL-8).

IL-8, also known as monocyte-derived neutrophil chemotactic factor, is a member of the chemokine alpha or C-X-C family. The mature form of human IL-8 consists of 72 amino acids, has a molecular weight of about 8,000 daltons and, like other chemokines, has four cysteine residues. IL-8 is a chemotactic factor that exhibits activity in vitro toward T cells, neutrophils and basophils, as measured, e.g., by the enzymes myeloperoxidase, α-mannosidase and β-glucuronidase. Recombinant IL-8 is expressed in $E.$ $coli$, purified (>97% purity by SDS-PAGE), diluted in PBS-BSA, sterile filtered and lypohilized. Murine monoclonal antibody specific for IL-8 (anti-IL-8) was produced from mice immunized with recombinant IL-8 and shown to neutralize the biological activity of recombinant IL-8 (Sigma Chemical Company, St. Louis Mo.). The IgG fraction of the ascites fluid was purified by protein A affinity chromatography. Specificity for IL-8 was demonstrated by indirect ELISA and western blot assays using a crossreactivity panel including, e.g., recombinant human RANTES, recombinant human GRO-α, recombinant human MIP-α, recombinant human MIP-β, recombinant mouse MIB-1α and recombinant mouse MIB-1-β. When immobilized on a microtiter plate, the antibody is capable of capturing recombinant as well as natural IL-8.

Proteins (e.g., IL-8 or anti-IL-8 antibody) are immobilized at room temperature to either paramagnetic particles or 96-well polystyrene microtiter plates according to the following protocols. In each case, control solid phases without immobilized antigen or antibody are prepared in parallel for use as counterselection matrices (e.g., to select against nucleic acids that bind supports and/or support-bound blocking agents such as BSA). For paramagnetic particles (amine-modified BIOMAG; Advanced Magnetics, Cambridge Mass.) is washed five times with vigorous vortexing and magnetic separation in 10 mM sodium phosphate (NaPi; pH 7.4) at a particle concentration of 5–10 mg/ml. After the final wash, the wet cake is resuspended to 25 mg/ml in 6.25% glutaraldehyde (GA; Sigma Chemical Company, St. Louis Mo.) and rotated at room temperature for three hours. GA-treated particles are washed six times in NaPi. Washed, GA-activated particles are resuspended with PBS (pH 7.2–7.4) containing the protein to be immobilized at a final concentration of 3–10 mg/ml. An aliquot of the protein solution is retained for determination of immobilization efficiency. The protein-particle slurry is rotated at room temperature for 16–24 hours. Particles are magnetically separated. The supernatant is decanted and retained for estimation of residual protein. Unreacted GA groups are quenched by resuspension of particles to about 10 mg/ml in 1 M glycine (pH 8.0) followed by rotation for one hour. Quenched particles are washed twice in PBS (pH 7.4) and blocked by rotation for two to four hours in PBS containing 2 mg/ml BSA. Blocked particles are washed three times in PBS containing 1 mg/ml BSA, resuspended to a particle concentration of 10 mg/ml and stored at 2–8° C. Working aliquots are washed three times in assay buffer with thorough vortexing at a particle concentration of about 1 mg/ml prior to use to protect against artifacts from leaching of immobilized reagents with prolonged storage.

Alternatively, IL-8 or anti-IL-8 antibody is noncovalently adsorbed to surface-modified polystyrene microtiter plates by passive adsorption according to the following protocol. Proteins are diluted to 2–20 ug/ml in 50 mM carbonate buffer (pH 9.6) or 10 mM sodium phosphate (pH 7.4) in borosilicate glass tubes or 50 ml polypropylene centrifuge tubes immediately before use. Clear polystyrene IMMU-LON™ 4 or white MICROLITE™ 2 flat-bottomed microtiter plates (Dynatech Corporation, Chantilly Va.) are coated at 100 μl per well for 2 hours at 37° C., 4 hours at room temperature (20–23° C.) or 15-24 hours at 2–8° C. Plates are decanted and washed once by filling wells with wash buffer (PBS (pH 7.4) containing BSA at 1 mg/ml) and decanting. Wells are blocked for 1 hour with 200 μl PBS containing 2 mg/ml BSA and washed five additional times with wash buffer. In modifications of this coating procedure, plates are pretreated or post-treated with 0.2–2.5% GA followed by quenching (i.e., with an excess of amines, e.g., using 1 M lysine) and reduction (e.g., using sodium cyanoborohydride) to covalently attach antibodies, particularly for selection methods relying on harsh selection pressures and/or thermal cycling.

IL-8 is specifically bound to washed BIOMAG-anti-IL-8 particle preparations by gently rotating a mixture of antigen (2–10 ug/ml) and particles (1–3 mg/ml) for two hours at room temperature. Immobilized antibody-antigen complexes (BIOMAG-antibody-IL-8) are washed five times at a particle concentration of 300 ug/ml and resuspended to a particle concentration of 5 mg/ml. The specifically bound IL-8 solid phase is stored at 2–8° C. and washed three times immediately before use.

A diverse mixture comprising approximately $10^{13}$ single-stranded RNA molecules consisting of a 30-nucleotide randomized sequence flanked by PCR primer-annealing sequences is prepared by methods known in the art (e.g., Ellington and Szostak (1990) *Nature* 346:818–822). Nonspecific, solid phase-binding nucleic acids are removed from the mixture by preabsorption with freshly washed BIOMAG-anti-IL-8 and control BIOMAG (200 µl each). Two hundred microliters of freshly washed BIOMAG-antibody-IL-8 is then added to the counterselected nucleic acid mixture. The nucleic acid-plus-BIOMAG reaction mixture is incubated with gentle rotation for 10 minutes at room temperature and magnetically separated. The resulting supernatant (comprising unbound nucleic acids and nucleic acid-IL-8 complexes formed by dissociation of IL-8 from the anti-IL-8 solid phase) is transferred to a clean 12×75 mm test tube, leaving behind the separated solid phase (comprising immobilized antibody-antigen complexes, immobilized complexes with nucleic acids bound noncompetitively to antibody-bound IL-8, and immobilized antibody lacking bound IL-8 (due to nucleic acid-dependent competitive dissociation)). The supernatant comprises free nucleic acids, free IL-8 (dissociated from solid ZO phase immune complexes either spontaneously and/or by immobilized antibody-binding RNA molecules) and nucleic acid-IL-8 complexes formed by competitive displacement of IL-8 from immobilized antibody. Nucleic acid-IL-8 complexes are separated from the supernatant mixture by gel chromatography using a SEPHADEX G-25 column (crosslinked dextran; Pharmacia LKB, Piscataway, N.J.). Nucleic acids comprising separated complexes are then amplified by PCR under thermal cycling conditions that dissociate bound IL-8.

Characterization of each IL-8-binding RNA sequence is preferably accomplished by 1) sequencing the IL-8-binding RNA molecule, 2) preparing a synthetic heteropolymer that includes a first defined sequence segment comprising the IL-8-binding sequence and a second defined sequence segment selected to hybridize an HRP-oligonucleotide conjugate (cf. Example 14) separated by nucleotide spacers, and 3) determining percent binding, affinity and specificity of PCR-amplified selected nucleic acids for IL-8 by modified ELISA using IL-8-coated microtiter plates as solid support and HRP-oligonucleotide conjugate as reporter. Synthetic heteropolymers are first titrated in a PBS-TWEEN™-BSA assay buffer against plates coated with 500 ng/well of recombinant IL-8. Plates are decanted and washed once in assay buffer. The HRP-oligonucleotide conjugate is then hybridized to bound synthetic heteropolymers, plates are decanted and washed twice in assay buffer, and HRP is developed by addition of a liquid substrate system comprising 3,3',5,5'-tetramethylbenzidine (TMB; Sigma Chemical Company, St. Louis Mo.). Color development is determined either kinetically at 655 nm (blue) or by first stopping reactions with 0.5 M sulfuric acid and reading the endpoint at 450 nm (yellow). The specificity of selected RNA sequences for IL-8 is determined by competition assay at half-maximally effective synthetic heteropolymer concentrations (i.e., $EC_{50}$) using a crossreactivity panel comprising recombinant mouse and human interleukins (i.e., interleukins 1 through 15) and selected recombinant interleukin receptors.

Defined sequence segments shown to specifically bind IL-8 in competition assays using interleukins and interleukin receptors as competing crossreactants are subsequently evaluated in competition assays with reference antibody (i.e., the parent anti-IL-8 antibody) and optionally by structure probing. In a first set of experiments, the ability of synthetic heteropolymers and corresponding RNAs (e.g., first defined sequences) to inhibit the binding of anti-IL-8 antibody to IL-8-coated plates is tested in ELISA format using a goat anti-mouse IgG-HRP conjugate as labeled second antibody. Selected RNA sequences that potently inhibit anti-IL-8 binding (i.e., as determined by both RNA and corresponding synthetic heteropolymer inhibition) are then evaluated in a reciprocal assay system, i.e., using anti-IL-8 antibody as a competitive inhibitor of synthetic heteropolymer binding to IL-8-coated plates. HRP-oligonucleotide conjugate is used as secondary label. Synthetic heteropolymers shown to be mutually competitive with parent anti-IL-8 antibody in reciprocal ELISA configurations (i.e., RNA sequence inhibits antibody binding and antibody inhibits synthetic heteropolymer binding) are selected as IL-8 antibody mimics.

To further resolve the specificity of a selected defined sequence as compared with parent antibody, epitope mapping may be achieved by structure probing or by modified ELISA using a synthetic heteropolymer assay protocol. A panel of monoclonal (mouse anti-human) anti-interleukin Fab fragments having specificities against human IL-1 through IL-15 is used to identify competitive inhibitors of synthetic heteropolymer binding to IL-8-coated plates. HRP conjugated to affinity purified, light chain-specific goat anti-mouse antibody (OEM Concepts, Toms River NJ) is used as labeled secondary antibody.

Defined sequence segments mimicking the specificity of ligands (e.g., interleukins) for their receptors (e.g., soluble, cloned interleukin receptors) can also be selected by ligand-receptor dissociation methods like those described in the preceding paragraphs for selecting antibody mimics. In this case, however, the ligand (e.g., recombinant human interleukin-4; IL-4) rather than an antibody or receptor is immobilized (e.g., on paramagnetic particles). IL-4 receptor (e.g., recombinant soluble receptor fragment) is specifically bound to immobilized IL-4 to form an IL-4 mimic-displaceable immobilized receptor-ligand complex. When incubated with a suitably counterselected (i.e., using control solid phases) library of nucleic acids, e.g., an RNA or transcribed cDNA library with randomized nucleotides flanked by primer annealing sequences, binding of IL-4 mimetic nucleic acids to solid phase-IL-4-bound IL-4 receptor fragments results in dissociation of IL-4 receptors into the supernatant in the form of nucleic acid-IL-4 receptor complexes. Nucleic acid-IL-4 receptor complexes are purified by gel chromatography. Nucleic acids of purified complexes are dissociated and amplified by PCR, sequenced and characterized by ELISA methods substantially as described in the preceding paragraphs. Competition assays are performed using interleukins, interleukin receptors and anti-IL-4 receptor antibodies to determine the specificity of selected nucleic acid IL-4 mimetics compared with the parent ligand.

Defined sequence segments (i.e., aptamers) that mimic the binding specificity of low molecular weight drugs can also be selected by receptor dissociation methods disclosed herein, as can aptamers that mimic drug receptors. For example, $H_2$ receptor-mimetic aptamers (i.e., synthetic histamine receptors) are selected using a cimetidine solid phase prepared, e.g., by immobilizing cimetidine-BSA conjugate to GA-activated BIOMAG particles and specifically binding cloned histamine $H_2$ receptors. A nucleic acid library is counterselected against BIOMAG and BIOMAG-BSA, BIOMAG-$H_2$ receptor and a mixture comprising cloned $H_2$ receptor and BSA in PBS. Nucleic acids remaining following counterselection are selected against the BIOMAG-BSA-cimetidine-$H_2$ receptor solid phase for sequences capable of binding cimetidine by competitively displacing specifically bound $H_2$ receptors. Bound nucleic acids are separated by magnetic separation and washing, amplified by PCR and sequenced. Binding of selected defined sequence segments (e.g., specificity and affinity of defined sequence segments comprising bifunctional synthetic heteropolymers) is compared with the parent drug, cimetidine, by competitive assay using HRP-oligonucleotide conjugate for detection in cimetidine-BSA-coated microtiter plates with and without varying dilutions of histamine agonists and antagonists.

Mimetic defined sequence segments selected to mimic the binding specificity of ligands and receptors (e.g., drugs, hormones, receptors, antibodies and antigens) as illustrated in the instant example are advantageously incorporated into synthetic heteropolymers and aptameric and heteropolymeric multimolecular devices of the invention. IL-8 antibody mimetics and IL-4 and cimetidine ligand mimetics, for example, may be used as defined sequence segments comprising aptameric and heteropolymeric multimolecular sensors, particularly for drug discovery and more particularly high-throughput screening assays. Alternatively, mimetic sequences may be used as targeting or drug-binding defined sequence segments comprising multimolecular drug delivery systems.

Example 20

Selection of Aptamers Using Single-molecule Detection and Sequencing of Target-bound Nucleic Acids Single-molecule sequencing techniques currently under development enable the sequence of bases in kilobase fragments of DNA to be determined at rates up to several bases per second. Modifications of these techniques can be used to detect and sequence nucleic acid molecules (e.g., from synthetic oligonucleotide libraries) capable of binding nonoligonucleotide target molecules, e.g., following library selection for target-binding nucleic acids. Direct detection and identification of specifically bound nucleic acids without amplification is accomplished using modifications of single-molecule DNA sequencing methods (e.g., Jett J. H. et al. (1992) In: *Human Genome* 1991–92 *Program Report*, DOE/ER-0544P, pp. 129–130; Harding et al. (1992) *Trends in Biotechnology* 10:55–57).

Nucleic acids capable of binding a selected target molecule are identified by incubation of the target molecule with a diverse mixture of nucleic acids, preferably a nucleic acid library, and separation of target-bound nucleic acids. For relatively large targets (e.g., soluble proteins, membrane receptors, cell surface antigens, membrane fragments, particles or cells), separation is achieved, e.g., by size exclusion, centrifugation, membrane or gel filtration or filter binding. For low molecular weight targets (e.g., haptens or small drug molecules, hormones, dyes or fluorophores), separation is preferably achieved by solid phase absorption using a ligand-modified membrane, bead, microparticle or affinity support. Diverse mixtures of nucleic acid libraries are preferably prepared by automated synthesis of nucleic acids comprising at least one randomized region, preferably comprising about 20 to 50 randomized nucleotides. Nucleotide-identifying fluorescent tags (i.e., selected fluorophores that uniquely identify each type of nucleotide in the sequence) are advantageously used to facilitate laser-induced fluorescence detection of individual nucleotides for single-molecule sequencing.

A selected nonoligonucleotide target (e.g., an omega-3-unsaturated fatty acid, a pesticide, enzyme, coenzyme, redox mediator, bacterial lipopolysaccharide, viral envelope protein or lectin) is incubated with a mixture of nucleic acids, preferably a diverse nucleic acid library. Bound nucleic acid-target complexes are separated from the remainder of the mixture, e.g., by gel filtration or affinity chromatography. Purified complexes are optionally dissociated by heating and rechromatographed to isolate target-binding nucleic acids. Alternatively, sequencing is performed using target-bound nucleic acids by selecting exonucleases capable of cleaving nucleotides without prior dissociation.

In a first method for identifying aptameric sequences, laser-induced fluorescence is used to identify and sequence fluorescently tagged, target-bound nucleic acid molecules. Aptamer-target complexes are suspended at 37° C. in the flow stream of a flow cytometer capable of single-fluorophore detection. Tagged nucleotides are cleaved sequentially from bound nucleic acid molecules by exonuclease (e.g., *E. coli* exonuclease III) and identified by laser-induced fluorescence as they pass through the excitation laser beam.

Alternatively, single-molecule sequencing may be achieved using laser-induced detection of endogenous nucleotide fluorescence, i.e., without using fluorophore-tagged nucleotides for nucleic acid library preparation. Target-bound sequences are isolated in an optical trap, and nucleotides are successively cleaved using exonuclease. Cleaved nucleotides are separated from the parent nucleic acid and irradiated by a laser to excite their native fluorescence. The identity of cleaved nucleotides is determined by spectral analysis and comparison with the stored spectra of each nucleotide used for library synthesis (e.g., A, G, U and C for an RNA library).

Sequences determined by single-molecule sequencing of target-bound nucleic acids are used to program an automated DNA synthesizer for production of synthetic heteropolymers (or optionally aptamers) comprising selected defined sequence segments. Synthetic heteropolymers are produced at sufficient scale (e.g., typically about ten nanomoles) to enable determination of affinity (e.g., binding constant by Scatchard analysis) and specificity (e.g., percent binding to selected target versus potential crossreactants) by modified ELISA methods (cf. Example 19, vide supra). Typically, synthetic heteropolymers prepared for binding studies comprise a first defined sequence segment identified by single-molecule sequencing as a target-binding sequence and a second defined sequence segment capable of hybridizing an HRP-oligonucleotide conjugate, optionally separated by nucleotide spacers. Alternatively, second defined sequence segments are selected to hybridize a biotinylated or digoxigenin-modified oligonucleotide, enabling detection with a selected streptavidin-effector conjugate (e.g., streptavidin conjugated to R-PE, AP, GO, or a fluorescent microsphere) or effector-labeled anti-digoxigenin antibodies. For characterizing aptamers selected for the ability to bind effector molecules (e.g., R-PE), synthetic heteropolymers are preferably prepared with a first defined sequence segment comprising the selected effector-binding sequence (e.g., R-PE-binding aptamer) and a second defined sequence segment conjugated to a corresponding donor or acceptor molecule (e.g., APC). Characterization can then be achieved by homogeneous assay, wherein binding of target effector to the selected (i.e., first) defined sequence segment results in functional coupling with APC conjugated to the second defined sequence segment.

Example 21

Aptamer Selection by Single-molecule Transfer of Target-bound Nucleic Acid

Recent advances in proximal probe techniques, particularly, scanning probe microscopes (SPM) and more particularly scanning tunneling microscopes (STM) and atomic force microscopes (AFM) provide the ability to image molecules and groups of molecules with unprecedented resolution (e.g., nanometer and even subnanometer detail). It is now possible to perform biomechanical studies on individual proteins, to physically manipulate individual protein and DNA molecules and to detect interactions between macromolecules. Prototype instruments now provide the capability of simultaneously acquiring nanometer-scale SPM images simultaneously with relatively large-field optical microscopy images (e.g., by bright-field or trans-illumination or epi-fluorescence). It is therefore possible to first scan an entire field or slide in search of a particular site, structure, image or signal (e.g., with micron-scale resolution) and then zoom in with an SPM probe to interrogate the image at far greater resolution (e.g., nanometer-scale).

On demonstrating molecular-resolution images of immunoglobulins and lipids by AFM Hansma et al. (*Clinical Chemistry* 37:1497–1501 (1991a)) suggested that a dedicated AFM could be used as a versatile, albeit expensive, biosensor by scanning a surface having an affinity for a particular type of molecule until detecting an individual molecule of this type. High-throughput sequencing of DNA has also been proposed (e.g., Hansma et al. (1991b) *J. Vac. Sci. Techn. B* 9:1282–1284), potentially at rates several orders of magnitude faster than conventional sequencing techniques. Imaging of single-stranded DNA and antigen-antibody complexes has been reported (e.g., Weisenhorn et al. (1990) *Scan. Microsc.* 4:511–516). AFM has also been used to determine and/or measure, e.g., DNA length, morphology and degree of coiling (including changes in length with drug binding), protein binding to DNA and protein-induced DNA bending, effects of ionic strength on the supercoiling structure of double-stranded DNA, and the pitch of the DNA helix in fluid. AFM can be used to directly map specific sites on plasmid and cosmid DNA molecules, e.g., by visualizing DNA restriction sites labeled with mutant restriction enzymes. Reproducible imaging and even dissection of plasmid DNA has also been reported (e.g., Henderson (1992) *Nucleic Acids Research* 20:445–447, Hansma et al. (1992) *Science* 256:1180–1184). It is therefore apparent that SPM, particularly AFM, can be used to study the interaction of drugs and DNA-binding proteins with DNA, ligands with receptors (e.g., antigen-antibody binding), and can even be used to dissect and extract biological DNA (e.g., from plasmids and supercoiled DNA).

Disclosed in this example are novel methods relying on SPM, preferably AFM, to isolate and sequence individual synthetic nucleic acids selected for the ability to bind individual identified targets, optionally including an amplification step to enable sequencing by routine methods (i.e., automated, capillary or gel-based methods rather than single-molecule sequencing as described in Example 20, vide supra). The instant methods are not directed, as is the prior art, toward determining or imaging the interaction of DNA-binding proteins with naturally occurring nucleic acids (i.e., DNA or RNA). Nor are the instant methods directed toward measuring the binding and/or effect of a drug on biological DNA or RNA. Nor does the present invention provide methods to screen or select heretofore unknown drugs or libraries for the ability to interact with DNA or RNA. Rather, and contrary to prior art teachings, methods disclosed in this example are specifically directed toward the identification of individual synthetic nucleic acids capable of specifically binding selected nonoligonucleotide molecules, particularly ligands, receptors, structural molecules and effector molecules, having no heretofore known affinity for naturally occurring RNA or DNA. In addition, the instant methods enable the characterization and selection of an identified target-binding nucleic acid (i.e., an aptamer) based upon the binding force as measured by SPM, preferably AFM, of the aptamer-target interaction. In addition, methods are provided for removing an individual, selected aptamer from its bound target (i.e., dissociating the aptamer-target complex) and transporting the aptamer to a sequencing apparatus or amplification vessel. The selected aptamer is then amplified or sequenced, preferably first amplified and then sequenced, enabling synthesis of the defined sequence segment (e.g., at nanomolar scale) for routine characterization of binding affinity and specificity (e.g., by modified ELISA). Provided aptamer binding to the selected target molecule is found to be specific (i.e., the aptamer specifically binds the selected target), the selected aptamer sequence is produced by large-scale synthesis, preferably as a defined sequence segment comprising a synthetic heteropolymer and/or an aptameric multimolecular device.

Among the many possible SPM configurations that can be applied to aptamer selection using SPM for single-molecule detection, four particularly preferred protocols are described herein. In each protocol, AFM is used as the proximal probe technique of choice, though it will be apparent to one of skill in the art that STM and/or hybrid probe techniques can also be used. The four preferred protocols represent the four possible combinations of two basic reagent architectures and two different sequencing subroutines. The two reagent architectures are 1) target immobilized on substrate (i.e., AFM slide), and 2) target immobilized on AFM tip. The two sequencing paths are a) single-molecule sequencing (e.g., by fluorescence) without prior amplification, and b) single-molecule amplification followed by conventional sequencing. The four basic protocols are therefore: 1a) single-molecule AFM detection of aptamer bound to substrate-immobilized target followed by single-molecule sequencing, 1b) single-molecule AFM detection of aptamer bound to substrate-immobilized target followed by single-molecule amplification and conventional sequencing, 2a) single-molecule AFM detection of aptamer bound to AFM tip-immobilized target followed by single-molecule sequencing, and 2b) single-molecule AFM detection of aptamer bound to AFM tip-immobilized target followed by single-molecule amplification and conventional sequencing.

Binding of a synthetic nucleic acid (i.e., a selected aptamer) to an AFM substrate-immobilized target molecule is detected as follows. The identified target molecule, human thyrocalcitonin (Sigma Chemical Company, St. Louis Mo.), is dissolved in Tris buffer (pH 7.4) at a concentration of 25–250 ug/ml and spotted onto a freshly cleaved mica surface. After a 5–50 minute incubation, the surface is rinsed thoroughly with buffer, dried under nitrogen and probed with a NANOSCOPE® II AFM (Digital Instruments, Santa Barbara Calif.) by raster-scanning a sharp silicon nitride probe attached to a 100×20×1.0 micron cantilever over the sample surface in accordance with the manufacturer's recommendations. This instrument has a maximum scan range of approximately 10×10 microns. Image resolution (i.e., lines per image and points per line) varies with scan speed and image size. Images obtained by scanning 500×500 nm demonstrate thyrocalcitonin molecule densities in the range of 10–100 molecules per square micron, depending on the coating concentration and time. Following imaging, the substrate is rinsed in buffer and dried under nitrogen. A mixture of nucleic acid molecules comprising a 50-nucleotide randomized region flanked by PCR primer-annealing sequences is incubated with slivers of freshly cleaved mica to remove substrate-binding nucleic acids. A twenty microliter aliquot of clarified supernatant of the mica-counterselected solution is spotted onto the rinsed, thyrocalcitonin-modified substrate. After a 10-minute incubation, the substrate is rinsed, dried under nitrogen, and scanned again using the NANOSCOPE® SPM. After identification of a nucleic acid-thyrocalcitonin complex (as determined by increased topological height compared with immobilized thyrocalcitonin scans), the scan is stopped and the tip-substrate feedback turned off. A loading force is then titrated from about 0.01 micronewtons (uN) to the 10–100 uN range, depending on the apparent binding force of the nucleic acid-thyrocalcitonin complex. To extract the bound nucleic acid molecule (i.e., the anti-thyrocalcitonin aptamer with flanking primer-annealing sequences), one line scan is performed at a loading force (e.g., 0.1–10 uN) determined to dislodge the bound nucleic acid molecule. The probe tip with attached nucleic acid molecule is then retracted from the substrate-target surface and transferred to a microfuge tube containing PCR primers and enzymes in 10 µl of amplification buffer. The extracted thyrocalcitonin-binding nucleic acid molecule is then amplified and sequenced.

The propensity of the AFM probe tip (which has a slightly negative surface charge in water) to adsorb nucleic acid molecules during scanning and extraction phases may be altered by modifying the probe tip with coupling agents having positively or negatively charged functional groups. Since the probe tip (e.g., silicon nitride), nucleic acid and mica substrate are all typically negatively charged, nonspecific binding is not a significant problem. Optimal adhesive forces between the probe tip and sample nucleic acid molecule may be achieved through use of divalent cations, cationic lipids and/or nonaqueous probing solutions. The mica surface may also be modified, e.g., by deposition and evaporation of neutral or near-neutral coatings and/or hydrophobic or hydrophilic groups. Alternatively, modified-nucleotide and/or backbone-modified nucleic acid libraries comprising neutral or near-neutral nucleic acids may be used to maximize specific aptamer-target binding and minimize nonspecific adhesive forces among the sample, probe tip and mica substrate.

To ensure more permanent attachment of the selected target (to either the AFM substrate or probe tip), e.g., to select a high affinity nucleic acid-target complex requiring a large loading force for probe-induced dissociation, the target is covalently immobilized. For example, primary amines can be thiolated in a borate buffer (pH 8.0) using Traut's reagent (2-iminothiolane-HCl; Pierce Chemical Company, Rockford Ill.). After desalting, the thiol-modified target is covalently bonded to a substrate comprising gold freshly evaporated on mica, optionally using a nebulizer to spray the target onto the substrate. Alternative substrates and immobilization protocols for achieving relatively homogeneous distribution, stable attachment and desired coverage (i.e., surface density) of different types of molecules are known in the art. For single-molecule detection and single-molecule sequencing, the protocol is modified as follows. The sample library comprises nucleic acids prepared with fluorescently tagged nucleotides comprising a 50-nucleotide randomized sequence and a 50-nucleotide fixed region (to facilitate imaging). Thyrocalcitonin immobilization, nucleic acid binding, AFM scanning and nucleic acid extraction are performed as in the preceding paragraph, but the selected and dislodged nucleic acid is transferred with the probe tip to a microfuge tube containing 10 µl of sequencing buffer and unloaded by reversing polarity of the tip. The sequencing buffer containing the fluorescently tagged, isolated nucleic acid is then aspirated to the flow cell of a cytometer capable of single-fluorophore detection, and the nucleic acid is suspended at 37° C. in the flow stream. Tagged nucleotides are cleaved sequentially by exonuclease and identified by laser-induced fluorescence as they pass through the excitation laser beam.

For nucleic acid selection protocols relying on AFM probe-immobilized target, thyrocalcitonin is attached to the silicon nitride probe tip by passive adsorption in 10 mM sodium phosphate buffer (pH 7.4). Alternatively, the probe surface is first modified with a silane coupling agent (e.g., 4-aminobutyldimethylmethoxysilane; United Chemical Technologies, Bristol Pa.). Thyrocalcitonin is then covalently attached using a homobifunctional crosslinker (e.g., glutaraldehyde) or heterobifunctional crosslinker (e.g., SULFO-SMCC or EDC; Pierce Chemical) or, optionally, site-directed attachment via the amine terminus (e.g., by mild periodate oxidation) or the carboxyl terminus (e.g., by reverse proteolysis in the presence of the dihydrazide of carbonic acid to produce a C-terminal hydrazo group). Mica-counterselected nucleic acid libraries are prepared and applied to freshly cleaved mica substrate as described in the preceding paragraphs. Scanning of the sample is performed in a feedback mode until binding of nucleic acid to the tip-immobilized thyrotropin is detected. The probe tip is then retracted from the substrate-target surface, and the bound nucleic acid molecule is transferred either to a microfuge tube containing PCR primers and enzymes (i.e., for amplification and sequencing) or, in the case of fluorescently tagged nucleic acid, to a microfuge containing sequencing buffer (i.e., for single-molecule sequencing). Alternatively, thyrocalcitonin-modified tip-bound nucleic acids may be transferred, for single-molecule sequencing, directly to the flow cell of a sequencing cytometer apparatus.

To maximize imaging sensitivity for target-bound nucleic acids and to enhance discrimination between target-bound nucleic acids and uncomplexed immobilized targets, nucleic acids may be labeled with a detectable molecule (e.g., a protein or other macromolecule), preferably a signal-generating species (e.g., an enzyme, fluorophore, polymer, dye, colloid, nanoparticle or microparticle). Labeling may be accomplished during nucleic acid preparation, e.g., by using labeled or modified nucleotides during nucleic acid synthesis or by post-synthetic conjugation or modification of the nucleic acid. Alternatively, nucleic acids may be labeled after they are applied to the SPM substrate, e.g., using a secondary label (i.e., labeled binding partner) or dye such as an oligonucleotide-enzyme, oligonucleotide-gold or oligonucleotide-fluor conjugate, an oligonucleotide immobilized to a nanosphere or microsphere, a labeled anti-nucleic acid antibody or streptavidin conjugate, an intercalating dye or nucleic acid-binding substance. These labeling techniques can also be used to maximize library screening efficiency. Target-bound nucleic acids can be detected by low resolution scanning of large imaging fields (e.g., 1–10 square microns). High resolution scanning can then be used to extract bound nucleic acids from complexes located at coordinates identified in gross scans. Alternatively, conventional optical microscopy can be used for low resolution detection of labeled nucleic acid-target complexes, e.g., using bright-field, epi-fluorescent or confocal techniques. Having determined the position of a target-bound nucleic acid by visualizing an attached label (e.g., a latex or colloidal gold particle, dye or fluorophore) or a localized signal generated by an attached label (e.g., an insoluble colored or fluorescent product of a reporter enzyme), the operator can then zoom to high resolution with the SPM probe for scanning and extraction of the bound nucleic acid.

In a particularly preferred embodiment of single-molecule aptamer selection, a selected target comprises or is labeled with a first effector molecule, preferably a signal-generating species, optionally an enzyme or luminescent compound, more preferably a first fluorescent nanoparticle or microparticle having a first selected size, color or absorption or emission spectrum or property, hereafter referred to as a first fluorescent nanoparticle having a first spectral property. A mixture of nucleic acids is prepared or selected, preferably by automated chemical synthesis or by enzymatic synthesis, amplification or transcription of a library comprising nucleic acids having a randomized sequence and at least one fixed nucleotide or nucleotide sequence for conjugation, optionally comprising one or more fixed sequences for primer annealing and amplification. The nucleic acid mixture, preferably a random-sequence library and hereafter referred to as such, is counterselected against selection buffer comprising selected effector molecules, preferably (first and second) fluorescent nanoparticles or dyed microparticles. Nucleic acids comprising the random-sequence library are conjugated at a molar ratio of about 0.1–3.0 (molecules/particle), more preferably about 0.3–1.0 (molecules/particle), to a second effector molecule, preferably a signal-generating species, optionally an enzyme or luminescent compound, more preferably a second fluorescent nanoparticle or microparticle having a second selected size, color or absorption or emission spectrum or property using a modified fixed-sequence nucleotide or fixed nucleotide, preferably a 3' or 5' terminal amino, thiol or carboxyl group, more preferably a 5' aminolinker-modified nucleotide. The selected target, which is either itself an effector molecule (e.g., an enzyme, fluorophore, nanoparticle or dye polymer) or is conjugated to an effector molecule, hereafter presumed to be conjugated to a second fluorescent nanoparticle having a second spectral property, is incubated with the first fluorescent nanoparticle-conjugated, counterselected random-sequence library in selection buffer. Selection buffer conditions, particle conjugation and blocking conditions and first and second particle ratios are preselected to obviate nonspecific nanoparticle-nanoparticle interactions, and complete monodispersion of nanoparticles is ensured by sonication immediately before aptamer selection. Optionally, the selection incubation is doped with unconjugated nanoparticles having a third and advantageously white, black, opaque, transparent, or translucent spectral property to control against nonspecific or spurious interaction between first and second fluorescent nanoparticles. Individual aptamer-attached complexes comprising first and second fluorescent nanoparticles are selected by single-molecule detection, isolation and/or amplification methods known in the art, particularly using fluorescence microscopy and more particularly single-cell flow cytometry (e.g., Lewin et al. (1992) *Genomics* 13:44–48; Li et al. (1991) *Methods: Comp. Meth. Enzymol.* 2:49–59; Mirsky et al. (1993) *PCR Meth. Appl.* 2:333–340; Patterson et al. (1993) *Science* 260:976–979). A laser-based flow cytometer equipped with a single-cell deposition device, for example, is used to sort fluorescent nanoparticles and isolate aptamer-attached doublet nanoparticle complexes, preferably doublet complexes comprising functionally coupled donor and acceptor fluorescent nanoparticles, by multicolor fluorescence, advantageously fluorescence energy transfer of functionally coupled nanoparticle complexes. Fluorescent nanoparticles conjugated to nonsense oligonucleotide and to blocking protein (e.g., casein) are used as internal standards (e.g., for calibration and gating) and negative controls. Biotinylated casein-conjugated fluorescent donor nanoparticles (i.e., first nanoparticles) and streptavidin-conjugated acceptor nanoparticles (i.e., second nanoparticles) are used as positive controls for doublet nanoparticle complex formation and detection. To validate the selection procedure, positive controls are doped with negative controls at ratios ranging from $10^{-16}$ to $10^{1}$.

Alternatively, methods described in the preceding paragraph are modified for detection, isolation, amplification and/or sequencing using a combination of optical microscopy, optical trapping and/or SPM methods. Detection by SPM, for instance, is preferably achieved using targets and nucleic acids conjugated to particles differing in size, color and/or fluorescence. In a preferred embodiment, the efficiency of nucleic acid library selection is enhanced by screening multiple targets or target variants conjugated to different selected effector molecules, preferably a family of signal-generation species expressing variations in a selected type of detectable signal (e.g., size, color, photon absorption or emission, enzyme activity), advantageously nanoparticles and/or microparticles varying in either size or color or fluorescent properties. In a particularly preferred embodiment, efficiency is further enhanced by screening multiple targets, each distinctly labeled by a first family of signal-generating species (e.g., nanoparticles and microparticles of varying size) against multiple libraries of varying design, preferably a spectrum of diverse libraries representing differing regions of chemical and sequence space, advantageously a diverse library of chemically diverse random-sequence nucleic acid libraries, wherein the libraries comprise random-sequence nucleic acids having fixed-sequence nucleotides or fixed-position nucleotides conjugated to a second and optionally a third or fourth or Nth different family of signal-generation species expressing variations in a different type of detectable signal, preferably nanoparticles and microparticles varying, e.g., in color or fluorescence.

SPM imaging of binding events with molecular scale resolution is a potentially useful tool for high-throughput screening of diverse mixtures of compounds, e.g., combinatorial libraries. SPM provides a method of detecting a single binding event between a prospective ligand or receptor and a selected target, enabling efficient library construction and screening. Once detected, a target-bound ligand or receptor can be physically isolated from all other members of the library or mixture. But for lack of a method to characterize, preferably identify, a single detected molecule (i.e., to determine its chemical composition and structure), molecular detection and isolation by SPM would enable screening and selection of molecular libraries, e.g., combinatorial libraries, with unprecedented resolution and efficiency. However, because a general method does not yet exist to precisely and accurately characterize individual selected molecules (i.e., to determine the chemical identity of a selected molecule), the potential of SPM for selecting and characterizing compounds from chemical libraries has not been realized.

Methods of the instant example enable not only the detection of selected members comprising diverse mixtures of compounds, e.g., combinatorial libraries, but also structural characterization (i.e., sequencing) and functional analysis (e.g., detailed binding studies following large-scale synthesis) of selected nucleic acids. Unlike nonnucleotide molecules, a single nucleic acid molecule selected from a mixture by SPM can be amplified and sequenced to determine its chemical identity. Also, because its possible to sequence single nucleic acid molecules, e.g., using laser-induced fluorescence of tagged nucleotides (cf. Example 20, vide supra), hybrid SPM-sequencing techniques can be used to screen, select and characterize molecules comprising nucleic acid libraries on a single-molecule scale. In other words, the combination of single-molecule detection (e.g., using AFM) and single-molecule sequencing (e.g., using laser-induced fluorescence of dye-tagged nucleotides) provides a novel approach to detection, isolation and characterization of individual molecules from mixtures comprising synthetic nucleic acids, e.g., nucleic acid libraries and particularly highly diverse libraries of nucleic acids. This single-molecule selection and identification capability relies on single-molecule sequencing and/or single-molecule amplification of nucleic acids and therefore cannot be applied to libraries of nonnucleotide molecules (i.e., unless compound-specific nucleotide codes are generated during synthesis or nonnucleotides are conjugated to compound-specific oligonucleotide tags).

Methods described herein for identifying and sequencing defined sequence segments comprising aptamers can also be applied, with modification, to the selection and sequencing of defined sequence segments comprising nucleotide ligands and nucleotide receptors, e.g., by screening and selection of nucleotide-encoded chemical libraries and/or nucleotide-encoded libraries comprising modified nucleotides or nucleotide analogs. SPM-based nucleic acid selection and sequencing methods described herein therefore enable the detection, selection, and identification, optionally including amplification, of useful ligands and receptors from diverse mixtures of nucleotides, particularly libraries of nucleic acids comprising randomized sequences (i.e., for aptamer selection), libraries of nucleic acids comprising modified nucleotides or nucleotide analogs (i.e., for selection of nucleotide ligands or nucleotide receptors), or libraries of molecules whose synthesis, composition or structure is coded by an associated nucleotide sequence (i.e., nucleotide-encoded chemical libraries). The interaction of nucleotide ligands, nucleotide receptors and aptamers with selected target molecules may further be characterized by well known structure probing methods following amplification of defined sequence segments comprising the selected nucleotides.

Example 22

Aptamer Selection by Molecular Proximity

Light microscopy (e.g., confocal, fluorescent and brightfield), flow cytometry (e.g., fluorescence activated sorting), proximal probe techniques (e.g., AFM, STM, SFM, SECM) and/or optical trapping and manipulation (e.g., laser scanning, force fields and optical tweezers) can be used to discriminate two macromolecules, conjugates or particles attached by a nucleic acid from corresponding uncomplexed macromolecules, conjugates or particles. In a simple case, a first macromolecule or particle is conjugated to fixed sequences (or nucleotides) of nucleic acids comprising a randomized sequence library. SPM is then used to detect paired molecules resulting from a randomized sequence (i.e., aptamer) binding to a macromolecular target molecule or a target-macromolecule conjugate. For example, human serum albumin is conjugated to the amino-modified 5' termini of 36 mer RNAs comprising a library having 30-nucleotide randomized sequences. The library is then incubated with the target molecule HRP. The HRP-albumin complex is detected topographically by AFM, followed by amplification and/or sequencing of the complex-forming aptamer by methods described elsewhere herein (cf. Example 21, vide supra). Off-line amplification is accomplished by loading force-mediated aptamer extraction and transfer to a microfuge tube comprising primer(s) and enzymes in amplification buffer. On-site amplification is performed using in situ hybridization (e.g., Patterson et al. (1993) *Science* 260:976–979), optionally using degenerate oligonucleotide primers and/or primer extension. Thermal cycling (e.g.,. using PCR or LCR) or isothermal amplification (e.g., 3SR or CPR) may be used. Alternatively, the selected aptamer may be sequenced in situ by SPM (provided adequate resolution can be achieved) or, preferably, transferred to a single-molecule sequencing apparatus (e.g., a laser-driven nucleotide fluorescence detector). Aptamers or synthetic heteropolymers comprising the selected sequence are then produced by large-scale enzymatic or chemical synthesis (e.g., using PCR or and automated DNA synthesizer).

Improved detection can be achieved using a uniform nanoparticle (e.g., 20 nm latex or colloidal gold) in place of albumin to amplify the topographical signal. In this case, the target molecule is preferably also conjugated so that nucleic acid and target species are of similar size (i.e., for maximal discrimination of paired vs. unpaired molecules). Buffer and blocking conditions are optimized to obviate nonspecific particle and protein interactions. Counterselection is performed using the conjugated molecule(s) and/or particle(s) and buffer. In a variation of this molecular proximity selection method, a selected aptamer assembles two molecules or particles by hybridizing to one and specifically binding the other. The target is conjugated, e.g., to ferritin (i.e., a high molecular weight protein or polymer; alternatives include purified KLH or dextran). The nucleic acid library is synthesized with a fixed sequence capable of hybridizing to an oligonucleotide conjugated to a 20 nm uniform nanosphere. Nanosphere-binding and ferritin-binding nucleic acids are removed by counterselection. Library-target binding is performed in solution, and nanosphere-conjugated oligonucleotide is added prior to AFM imaging. Nanosphere-conjugated oligonucleotide hybridization to fixed sequences yields nucleic acid-hybridized nanospheres and nanosphere-aptamer-HRP-ferritin complexes. The nanosphere-aptamer-HRP-ferritin complex is discriminated topographically from nucleic acid-hybridized nanospheres and ferritin-HRP conjugates by AFM, and aptamers are isolated and sequenced as per Example 21 (vide supra).

Using selected molecules as reporters for single-molecule detection, proximity-based methods can be used to select and isolate one or more aptamers based upon user-defined selection criteria or thresholds. For example, by varying the size, density and/or surface charge of the reporters conjugated to target molecules and nucleic acids comprising a random-sequence library, an affinity threshold or set point can be established to select an individual aptamer or group of aptamers with desired binding strength. The aptamer binding strength required to assemble two nanospheres (i.e., target-nanosphere and aptamer-nanosphere conjugates) and remain bound throughout selection, detection and isolation steps increases exponentially with particle diameter. Affinity set points spanning more than four orders of magnitude can be established using as reporters uniform latex nanospheres having particle diameters ranging from 10–300 nm.

To select an aptamer with high affinity for the enzyme AP, a large-scale library is prepared comprising 90 mer RNA molecules having 30-nucleotide fixed hybridization sequences and 60-nucleotide randomized sequences. The 30-nucleotide fixed sequence is complementary to a 30 mer oligonucleotide immobilized to each of three batches of fluorescent red carboxylate-modified polystyrene nanospheres varying in particle diameter (20 nm, 50 nm and 100 nm). AP is conjugated to a first 32 mer oligonucleotide complementary to a second 32 mer oligonucleotide that is immobilized to each of three different batches (i.e., 20 nm, 50 nm and 100 nm particle diameter) of fluorescent green carboxylate-modified polystyrene nanospheres using a water-soluble carbodiimide. Nanospheres are thoroughly sonicated immediately before use and surface charge, immobilization protocol, blocking, concentration, and buffer conditions are optimized to obviate nonspecific particle-particle interactions, as determined by confocal fluorescence microscopy. The random-sequence library is counterselected against the different nanospheres and immobilized oligonucleotide preparations, and the mixture comprising surviving RNA molecules is incubated with the AP-oligonucleotide conjugate. Aliquots of the AP-oligonucleotide plus RNA mixture are pipetted into nine reaction vessels, and a complementary set of capture nanospheres is added to each vessel in a checkerboard design (i.e., one red RNA-reporter plus one green AP-reporter particle set per vessel; 3×3=9 particle diameter combinations). Confocal fluorescence microscopy is used to identify red-green particle complexes. AFM is used for proximity-based detection and isolation of aptamer-AP-attached particle complexes from each vessel. Individual tight-binding, aptamer-linked complexes are selected as those remaining intact with AFM extraction under probe-induced loading forces in the $10^{-6}$–$10^{-5}$ newton range. To explore diverse nucleic acid libraries for higher affinity aptamers, randomized sequence lengths can be increased to 100, 150 or 200 nucleotides, optionally even more than 200 nucleotides, preferably by ligating two or more nucleic acids comprising less than about 100 nucleotides each.

A parallel experimental design is applied at fixed particle size (20 nm red and green fluorescent nanospheres, as per the preceding paragraph) using carboxylate modified latex particles of varying surface charge and parking area. The repulsive force of negative surface charge on paired particle sets (i.e., red plus green fluorescent sets) is titrated against a random-sequence RNA library to select for individual aptamers with high AP-oligonucleotide binding strength. The influence of particle density is investigated using sub-micron diameter glass beads, silanized iron oxide particles and stabilized liposomal vesicles with polystyrene nanospheres as reference.

Alternative aptamer selection parameters include the macromolecular size, weight and density of selected molecules used as signal-generating species for single-molecule detection (e.g., via STM, AFM, laser scanning and optical trapping). These properties can be detected optically, topographically, or by changes in loading or discharge force accompanying association Dissociation or extraction of a selected target or target-aptamer complex by SPM or optical trapping methods, e.g., AFM or SPEC. In a preferred mode of operation, molecular proximity is used as a selection criterion detectable by the functional coupling (e.g., enzyme channeling, fluorescence energy transfer) resulting from aptamer-induced assembly of first and second selected molecules comprising a donor-acceptor pair.

Alternative embodiments of aptamer selection by molecular proximity rely on different methods for covalent, pseudoirreversible or specific binding of a first selected molecule, conjugate or particle to a first fixed sequence or nucleotide of nucleic acids comprising a random-sequence library. Binding of the second, randomized sequence to a second selected molecule (i.e., the selected target, optionally a conjugated selected target) results in assembly of a complex comprising at least three molecules (i.e., first and second selected molecules attached by the selected aptamer). Covalent attachment is preferably directed to a fixed 3' or 5' nucleotide and/or spacer sequence, preferably an amino-modified nucleotide, using a heterobifunctional crosslinker (e.g., SMCC, MBS, SPDP or the corresponding water-soluble sulfo-crosslinker). Specific binding of a first selected molecule to first fixed sequence or nucleotide may be accomplished, e.g., using an existing aptameric defined sequence segment specific for the first selected molecule, optionally a conjugate comprising the selected molecule. Alternatively, anti-digoxigenin/digoxigenin, nucleotide ligands or nucleotide receptors may be used. Pseudoirreversible binding may be achieved using avidin-biotin, streptavidin-biotin or hybridization of an oligonucleotide conjugate.

It will be apparent on reading the instant disclosure that an aptameric nucleic acid selected and characterized by molecular proximity of attached selected molecules comprises a synthetic heteropolymer. That is, the selected and identified aptamer comprises a first defined sequence segment capable of specifically binding a first selected molecule and a second defined sequence segment capable of specifically binding, hybridizing or covalently positioning a second selected molecule for detection. Methods described in the instant example therefore exploit the useful molecular positioning properties of synthetic heteropolymers as a selection criterion for detection, isolation and identification of individual aptamers.

Example 23

Aptamer Selection by Single-molecule Detection of Functional Coupling Between Donor and Acceptor Pairs Assembled by Random-sequence Nucleotides The detectability of two attached selected molecules, preferably two effector molecules, more preferably two signal-generating molecules and optionally two functionally coupled signal-generating species, provides a useful tool for selecting defined sequence segments, nucleotide ligands and nucleotide receptors for the ability to specifically recognize one or both of the selected molecules.

MOLECULAR MACHINES of the instant invention can perform useful work that depends on nucleotide-dependent molecular positioning of selected molecules, particularly ligands, receptors and effector molecules. Nucleotide-dependent molecular positioning provides a general approach for attaching two or more selected molecules to a nucleotide scaffold or template. In preferred aspects of the invention, nucleotide-dependent molecular positioning results in functional coupling between two selected molecules to generate an output which depends on the proximity of the selected molecules. For example, in a multimolecular transducer comprising the donor and acceptor fluorophores R-PE and R-PC bound to neighboring defined sequence segments of a synthetic heteropolymer, energy is transferred from donor (R-PE) to acceptor (R-PC) on excitation with an argon-ion laser.

Alternatively, a highly diverse mixture of nucleic acids (e.g., a library comprising $10^{13}$ to $10^{15}$ 60 mer RNA molecules) can be selected for individual RNA molecules capable of binding both a donor and an acceptor fluorophore using fluorescence microscopy with suitable excitation and emission filter sets. The practicality of selecting for a single RNA molecule capable of binding both donor and acceptor fluorophores is limited, however, by two constraints. First, the bound fluorophores must produce a sufficiently intense signal to enable detection of a single donor-acceptor pair. Fluorescent nanospheres and supramolecular light harvesting structures are useful in this regard. Second, the diversity of an RNA library must be sufficiently diverse to express at least one RNA molecule capable of binding both the donor and the acceptor fluorophore. If only one RNA molecule in $10^{10}$ has a useful affinity for a selected target molecule (i.e., a target comprising or attached to a donor fluorophore), then only about one in $10^{20}$ RNA molecules (i.e., $10^{-10} \times 10^{-10}$ molecules) is likely to bind both of two selected molecules (e.g., a donor and acceptor fluorophore) required for detection by functional coupling (i.e., fluorescence energy transfer). An RNA library comprising even $10^{15}$ or $10^{16}$ members is therefore highly unlikely to contain even a single member capable of binding both the donor and the acceptor fluorophore.

Methods described herein address both the detectability and diversity challenges that must be overcome to select an individual nucleic acid molecule for its ability to connect two signal-generating species, thus rendering them detectable. Single-molecule detectability is achieved by either using at least two highly intense signal-generating species as selected targets, by conjugating at least one selected target to a highly detectable signal-generating species or, more preferably, conjugating approximately each member of a diverse nucleic acid mixture to a highly detectable signal-generating species either covalently, by high-affinity specific binding (e.g., using streptavidin/biotin or anti-digoxigenin/digoxigenin) or by pseudoirreversible attachment (e.g., hybridization of an oligonucleotide/signal-generating species conjugate).

Diversity is addressed by attaching a first signal-generating species to approximately each member of the diverse nucleic acid mixture, e.g., by synthesizing each member of the mixture with a fixed modified nucleotide or defined sequence segment known to specifically bind the first signal-generating species (or a conjugate comprising the first signal-generating species) or by covalently attaching, specifically binding or pseudoirreversibly attaching (e.g., hybridizing) the first signal-generating species to approximately each member of the nucleic acid mixture. Attachment may be achieved, e.g., using a covalent crosslinking reagent, anti-digoxigenin/digoxigenin, streptavidin/biotin, or a hybridizable oligonucleotide-effector conjugate. In this way, the probability of identifying a member of the nucleic acid mixture capable of connecting the two signal-generating molecules is increased to approximately the likelihood of identifying a single RNA molecule capable of binding a single target molecule.

Screening and selection of a library comprising member nucleotides conjugated to a first (donor or acceptor) signal-generating species for binding to a second (donor or acceptor) signal-generating species is preferably accomplished by single-molecule detection, characterization, sequencing and/or amplification as described elsewhere herein (e.g., Example 22, vide supra). Prior to conjugation of random-sequence nucleotides comprising the library to a first (donor or acceptor) signal-generating species, the library is preselected or counterselected against the signal-generating species to remove unwanted random-sequence nucleic acids.

As an example of library selection by functional coupling between a conjugated donor and an aptamer-bound acceptor, random-sequence nucleotides are biotinylated and labeled with an FITC-streptavidin conjugate. R-PE-bound FITC-streptavidin-conjugated aptamers are then selected, optionally following column chromatography, by single-molecule detection of tightly coupled complexes, i.e., complexes having intense R-PE fluorescence (i.e., at about 575 nm) and lacking the characteristic fluorescein emission (I.e., at 515–520 nm). As will be apparent to the skilled artisan on reading the instant example, donor or acceptor signal-generating species (i.e., oxidoreductases, fluorophores, luminescent compounds) can be conjugated to fixed nucleotides or fixed sequences of nucleotides comprising a diverse library by attachment methods known in the art, e.g., hybridization of an oligonucleotide-effector conjugate, covalent conjugation using heterobifunctional crosslinkers, specific binding of labeled ligands or receptors (e.g., labeled anti-digoxigenin or avidin), incorporation of tagged nucleotides during nucleotide synthesis, chelation to metals comprising modified nucleotides, intercalation of dyes and/or fluorophores within duplex regions of partially or fully double-stranded nucleotides, enzymatic labeling, and the like.

Example 24

Prodrug Complexes for Use in Multimolecular Drug Delivery Systems

Prodrug complexes described in the instant example are not themselves MOLECULAR MACHINES. They are precursor compositions that can be used as selected molecules comprising triggered release and/or receptor-targeted multimolecular drug delivery systems of the invention. Alternatively, a prodrug complex may be used as a molecular recognition pair comprising a tethered molecular recognition device designed for drug delivery. The choice of a particular prodrug complex will depend on the particular indication and corresponding drug of choice. For a drug such as amphotericin B, primary advantages relate to safety, solubility and duration of therapeutic action. Amphotericin B has been in clinical use for over thirty years and, despite toxicity problems, remains the drug of choice for systemic fungal infections. One of its most serious adverse effects is renal toxicity, which occurs in up to one third of patients receiving therapeutically effective doses. Amphotericin B is insoluble in water, requiring controlled infusion of a colloidal suspension in neutral dextrose solution and precautionary monitoring of intravenous lines to ensure patency. To address toxicity and infusion problems, liposomal and/or lipid-complex formulations of amphotericin B are being developed. Amphotericin B is believed to act by mechanically disrupting cell membranes following preferential binding to ergosterol-containing fungal plasma membranes as opposed to cholesterol-rich mammalian cell membranes. Accordingly, the prodrug complex of the present invention provides a means for increasing selectivity for fungi by specifically partitioning drug from synthetic receptors to ergosterol-containing membranes, thereby reducing toxic effects on mammalian cells. Selection of a suitably hydrophilic (ionized) synthetic receptor also provides a stable, soluble dosage form to overcome the inconvenience, cost and risk of controlled infusion.

A prodrug complex comprising amphotericin B specifically bound to a synthetic receptor comprising amino acids, nucleotides, sugars and/or other small organic monomers is formulated.

Synthetic receptors useful in this formulation are identified through iterative screening and selection for specific binding attributes and physicochemical properties, preferably from a diverse pool of molecular candidates and more preferably from a combinatorial shape library. Classes of molecules (and corresponding mimetics) from which synthetic receptors may be selected include, without limitation, antibodies and engineered antibodies, oligonucleotides, oligosaccharides, peptides, organic polymers such as polyhydroxyalkanoates, polyphenols, poylphosphates and polysulfates, and derivatives, analogs or combinations thereof. Optimization of the solubility and circulating half-life of the prodrug complex is achieved through multifactorial selection from panels of synthetic receptors differing in molecular size and net charge (e.g., degree of ionization under physiologic conditions). The pharmacological half-life of dissociable drug is maximized by further selecting synthetic receptor candidates on the basis of relative affinity for amphotericin B compared with the apparent affinity of the drug for isolated fungal membranes.

A prodrug complex can also be used to stabilize a biopharmaceutical preparation, as illustrated below for an HIV-specific aptamer. The in vivo half-life and efficacy of a biopharmaceutical can be improved using prodrug complexes of the present invention. Biopharmaceutical classes amenable to this embodiment include, but are not limited to, peptides (e.g., hormones, releasing factors, molecular recognition units), proteins (e.g., monoclonal antibodies, recombinant antigens, hormones, interferons, colony stimulating factors), oligonucleotides (e.g., antisense, ribozymes, aptamers), oligosaccharides (e.g., cell adhesion molecules, immunomodulators, antiinfectives) and hybrid structures such as glycopeptides and glycolipids.

For example, an aptamer that specifically binds and inhibits HIV reverse transcriptase is protected against enzymatic degradation by administration in specifically bound form. The specific binding partner of the anti-HIV aptamer may be either a synthetic receptor selected from a combinatorial shape library or an oligonucleotide that hybridizes to the aptamer through Watson-Crick base pairing with a suitable degree of complementarity to yield quasistable hybrids that are dissociable in the presence of HIV reverse transcriptase. These oligonucleotides are generated by in vitro evolution from initial sequence segments complementary to different nucleotide sequences of the anti-HIV aptamer. In this embodiment, at least one HIV aptamer is selected for specific binding to a relatively conserved region of HIV reverse transcriptase from a randomized pool or combinatorial shape library comprising oligonucleotides generated by in vitro evolution. Potentially useful shape libraries include, without limitation, populations of polymeric conformers prepared from random combinations of amino acids, nucleotides, carbohydrates and other organic monomers. Selected synthetic receptors are first evaluated in vitro for effectiveness in protecting aptamers against enzymatic degradation through stability studies of corresponding prodrug complexes and control (unbound) aptamers. Synthetic receptors affording protection are then tested for their ability to efficiently deliver aptamers to therapeutic targets in vitro. Prodrug complexes comprising each selected aptamer specifically bound to each selected synthetic receptor are incubated alone and in combination with isolated preparations of HIV reverse transcriptase, and the rate, degree and duration of enzyme inhibition are compared with control conditions (enzyme alone, enzyme plus aptamer(s), enzyme plus synthetic receptor(s)). Selected prodrug complexes and combinations are then tested for safety and efficacy in preclinical and clinical studies.

Immobilized prodrug complexes can also be used to prolong the half-life of the therapeutic efficacy of the designer receptor-bound drug by increasing its circulating, as illustrated, e.g., by enhanced antithrombotic performance. Vascular thrombotic events associated with myocardial infarction, percutaneous transluminal coronary angioplasty (PTCA), stroke, peripheral arterial occlusion and venous thromboembolism, among other conditions, cause significant morbidity and mortality. Intense antithrombin and antiplatelet drug development efforts are underway to reduce the incidence of thrombotic events. Because rethrombosis occurs in 15% to 35% of treated patients, a major drug development focus for the treatment of acute myocardial infarction is maintaining vessel patency following thrombolytic therapy. Another major focus is reducing the incidence of restenosis following PTCA procedures from the historical rate of about 30%. Other important applications for antithrombin and antiplatelet agents include chronic maintenance of vessel patency following coronary artery bypass surgery and post-thromboembolitic stroke.

Pharmacological approaches to thrombosis include prostaglandins, calcium channel blockers and antifibrinogen agents; antagonists of platelet activating factor and glycoprotein (Gp) Ib, IIb and IIIa receptors; ticlopidine, which alters GP IIb/IIIa receptor expression; and inhibitors of cyclooxygenase, thrombin, phosphodiesterase and thromboxane synthetase. Significant evidence indicates that fibrinogen binding to the platelet Gp IIb/IIIa (adhesion) receptor is the final common pathway of platelet aggregation, suggesting the utility of effective Gp IIb/IIa receptor antagonists. CENTORX (Centocor; Malvern, Pa.) is a chimeric anti-7E3 Fab fragment with Gp IIb/IIIa receptor specificity. RGD and RGDS peptides bind the active site of the Gp IIb/IIIa receptor through the adhesive protein recognition sequences Arg-Gly-Asp and Arg-Gly-Asp-Ser, respectively, which are essential for fibrinogen-receptor interaction. However, the clinical and commercial potential of such antibodies and peptides as antithrombotics is limited by their unacceptably short half-lives. Platelet Gp Ib receptors interact with von Willebrand factor associated with damaged vascular endothelium to initiate platelet adhesion. Adhesion is followed by platelet aggregation which, in turn, leads to thrombus formation. Gp Ib receptor antagonists may therefore interrupt thrombus formation at an earlier point in the pathologic cascade than Gp IIb/IIIa receptor antagonists.

Administration of a drug specifically bound to an immobilized synthetic receptor as in the present invention can increase the circulating half-life and therapeutic efficacy of the drug, as exhibited by enhanced antithrombotic performance of a platelet receptor antagonist. For example, a therapeutic composition comprising a Gp IIb/IIIa receptor antagonist (e.g., RGDS peptide SK&F 106760 (SmithKline Beecham; Philadelphia, Pa.), Britistatin or Echistatin (both of Merck; Rahway, N.J.)) specifically bound to selected synthetic receptors operatively attached to red blood cells obtained by autologous or heterologous donation. Synthetic receptors are selected for specific binding to platelet Gp IIb/IIIa receptor antagonists in accordance with described elsewhere in this example (vide supra). Selected synthetic receptors are attached to red cell membranes either covalently (e.g., by chemical conjugation) or by noncovalent partitioning into the lipid bilayer following conjugation to a lipophilic carrier (e.g., a Zyn-Linker, glycolipid or synthetic phospholipid). Red cell-prodrug complexes are then prepared by addition of the Gp IIb/IIIa receptor antagonist to synthetic receptor-modified red cells. Prodrug-modified red cells, stored at 28° C. until use, are administered perioperatively by intravenous infusion.

Multi-prodrug complexes such as these are designed for therapeutic applications requiring prolonged therapeutic action at extracellular or external membrane receptors. Preferred embodiments favor distribution and retention of systemically administered drugs within particular physiologic compartments, such as the circulation or lymphatic system. Representative applications include, but are not limited to, cardiovascular, respiratory, endocrine, immune, hematologic and antiinfective therapeutics.

Immobilized prodrug complexes can also be designed to retain a topical therapeutic near the site of therapeutic action, as illustrated below for psoriasis, an autoimmune inflammatory disorder. Although the etiology and pathogenesis of psoriasis have not been fully elucidated, interactions among genetic, immunologic and environmental factors appear to be important. First-line therapy consists of lubricants, keratolytics and topical corticosteroids. Topical steroids are the primary treatment for mild psoriasis, but adverse effects are caused by diffusion of drug into the circulation. Severe psoriasis is not well managed by topical steroids which may induce tolerance, toxicity and side effects with chronic use.

Interleukins (IL) have been implicated in the pathogenesis of psoriasis. IL8, released during both acute and chronic phases of inflammatory diseases, causes both accumulation and activation of neutrophils which, in turn, produce cytotoxic agents. IL1, IL4 and IL7 have also been implicated in immune-mediated inflammatory diseases. Several companies (e.g., Repligen (Cambridge, Mass.), Immunex (Seattle, Wash.)) are developing soluble receptors of interleukins, particularly IL1 and IL8, as a means of scavenging released cytokines and interrupting the inflammatory cascade.

The prodrug complexes of the present invention provide a means of retaining topically administered anticytokine agents (e.g., soluble IL receptors or receptor antagonists) in prodrug form at sites of inflammation. Dissociation of active drug in proportion to local cytokine levels provides for target-dependent drug delivery.

For example, a prodrug complex comprising a soluble interleukin receptor (e.g., IL1 receptor, IL8 receptor) specifically bound to a selected synthetic receptor operatively attached to a liposome, lipid complex or lipophilic matrix in a topical cream, ointment or gel can be formulated. Because the synthetic receptor is selected for its ability to specifically bind a pathophysiologic receptor, it is considered a ligand or interleukin mimetic.

Selected synthetic receptors are attached to liposomes, lipid complexes or lipid matrices either by direct covalent attachment or by noncovalent association following conjugation to a lipophilic carrier. Synthetic receptor-modified liposomes, lipid complexes or lipid matrices are converted to immobilized prodrug complexes by incubation with drug (e.g., IL1 receptor, IL8 receptor). Immobilized prodrug complexes are then incorporated into a penetrating cream, gel or ointment which is applied topically to psoriatic lesions. Locally released interleukins (having a higher affinity than immobilized synthetic receptors for soluble IL receptors) compete with immobilized synthetic receptors (prodrug complexes) for specifically bound soluble IL receptors. Released interleukins are scavenged by soluble IL receptors which dissociate from immobilized prodrug complexes, thereby preventing cytokine-mediated recruitment and activation of neutrophils and interrupting the downstream inflammatory cascade.

Prodrug complexes comprising a drug which is a soluble receptor specifically bound to a synthetic receptor which is a ligand are useful in treating a number of different anatomically localized conditions, psoriasis being only one example. Preferably, prodrug complexes of this type are used for anatomically confined conditions involving locally proliferating, released or recruited therapeutic targets. Representative applications include localized infections, inflammatory, allergic and immune disorders.

For purposes of clarity of understanding, the foregoing invention has been described in some detail by way of illustration and example in conjunction with specific embodiments, although other aspects, advantages, modes of operation and modifications will be apparent to those skilled in the art to which the invention pertains. The foregoing description and examples are intended to illustrate, but not limit, the scope of the invention. Modifications of the above-described modes for carrying out the invention that are apparent to persons of skill in nucleic acid chemistry, molecular biology, biomedical research, veterinary, agricultural and environmental sciences, clinical medicine, diagnostics, pharmaceuticals, drug delivery, combinatorial chemistry, informatics, nanotechnology, materials science, semiconductors, micromachining, optics, electronics, immunology, clinical chemistry, electrochemistry, enzymology, fluorescence, luminescence, sensors, transducers, actuators, microelectromechanical systems, nanoelectromechanical systems, instrumentation and related fields are intended to be within the scope of the invention, which is limited only by the appended claims.

All publications and patent applications cited in this specification are indicative of the level of skill of those skilled in the art to which this invention pertains and are herein incorporated by reference to the same extent as if each individual publication or patent application was specifically and individually indicated to be incorporated by reference.

What is claimed is:

1. A method of detecting a single nonnaturally occurring oligonucleotide molecule capable of specifically binding to a selected nonoligonucleotide molecule comprising:
   (a) contacting a mixture comprising an assortment of nonnaturally occurring oligonucleotides with a selected nonoligonucleotide molecule; and
   (b) detecting a single nonnaturally occurring oligonucleotide molecule specifically bound to said selected nonoligonucleotide molecule by at least one of scanning probe microscopy, optical trapping or flow cytometry.

2. The method of claim 1 wherein said selected nonoligonucleotide molecule is not a DNA-binding protein.

3. The method of claim 1 wherein said mixture comprises a random-sequence assortment of oligonucleotides.

4. The method of claim 1 wherein said mixture comprises at least one of a nonrandom assortment of oligonucleotides, a nucleic acid library, a combinatorial library, or a nucleotide-encoded library.

5. The method of claim 1 wherein said mixture comprises an oligonucleotide produced by at least one of amplification, replication, transcription, or in vitro evolution.

6. The method of claim 1 wherein said single nonnaturally occurring oligonucleotide molecule further comprises a nonnucleotide molecule.

7. The method of claim 6 wherein the identity of said nonnucleotide molecule is encoded by a nucleotide sequence comprising said single nonnaturally occurring oligonucleotide molecule.

8. The method of claim 1 wherein said selected nonoligonucleotide molecule is immobilized on a solid support.

9. The method of claim 1 further comprising isolating said single nonnaturally occurring oligonucleotide molecule by at least one of removing said single nonnaturally occurring oligonucleotide molecule from said mixture, removing said single nonnaturally occurring oligonucleotide molecule from said selected nonoligonucleotide molecule, transporting said single nonnaturally occurring oligonucleotide molecule to a sequencing apparatus, or transporting said single nonnaturally occurring oligonucleotide molecule to an amplification vessel.

10. The method of claim 1 further comprising at least one of determining, amplifying, replicating, or transcribing a nucleotide sequence comprising said single nonnaturally occurring oligonucleotide molecule.

11. The method of claim 1 further comprising identifying said single nonnaturally occurring oligonucleotide molecule.

12. A method of detecting a single nonnaturally occurring oligonucleotide molecule capable of specifically binding to a selected nonoligonucleotide molecule comprising:
   (a) preparing a reaction mixture comprising a selected nonoligonucleotide molecule and a nonnaturally occurring oligonucleotide comprising an unknown nucleotide sequence; and
   (b) detecting a single nonnaturally occurring oligonucleotide molecule specifically bound to said selected nonoligonucleotide molecule by at least one of scanning probe microscopy, optical trapping or flow cytometry.

13. The method of claim 12 wherein said selected nonoligonucleotide molecule is not a DNA-binding protein.

14. The method of claim 12 further comprising isolating said single nonnaturally occurring oligonucleotide molecule by at least one of removing said single nonnaturally occurring oligonucleotide molecule from said mixture, removing said single nonnaturally occurring oligonucleotide molecule from said selected nonoligonucleotide molecule, transporting said single nonnaturally occurring oligonucleotide molecule to a sequencing apparatus, or transporting said single nonnaturally occurring oligonucleotide molecule to an amplification vessel.

15. The method of claim 12 further comprising at least one of determining, amplifying, replicating, or transcribing a nucleotide sequence comprising said single nonnaturally occurring oligonucleotide molecule.

16. A method of detecting a single nonnaturally occurring oligonucleotide molecule capable of specifically binding to a selected target that is not a DNA-binding protein comprising:
   (a) selecting a target that is not a DNA-binding protein;
   (b) contacting the selected target with a mixture comprising an assortment of nonnaturally occurring oligonucleotides; and
   (c) detecting a single nonnaturally occurring oligonucleotide molecule specifically bound to said selected target by at least one of scanning probe microscopy, optical trapping or flow cytometry.

17. The method of claim 16 wherein said mixture contains an oligonucleotide comprising an unknown nucleotide sequence.

18. The method of claim 16 further comprising isolating said single nonnaturally occurring oligonucleotide molecule by at least one of removing said single nonnaturally occurring oligonucleotide molecule from said mixture, removing said single nonnaturally occurring oligonucleotide molecule from said selected target, transporting said single nonnaturally occurring oligonucleotide molecule to a sequencing apparatus, or transporting said single nonnaturally occurring oligonucleotide molecule to an amplification vessel.

19. The method of claim 16 further comprising at least one of determining, amplifying, replicating, or transcribing a nucleotide sequence comprising said single nonnaturally occurring oligonucleotide molecule.

20. A method of detecting a single nonnaturally occurring oligonucleotide conjugate molecule capable of specifically binding to a selected nonoligonucleotide molecule, said method comprising:
   (a) preparing a reaction mixture comprising a selected nonoligonucleotide molecule and a plurality of different nonnaturally occurring oligonucleotide conjugates, each different nonnaturally occurring oligonucleotide conjugate comprising a different nonnucleotide moiety attached to an oligonucleotide; and
   (b) detecting a single nonnaturally occurring oligonucleotide conjugate molecule specifically bound to said selected nonoligonucleotide molecule by at least one of scanning probe microscopy, optical trapping or flow cytometry.

21. The method of claim 20 wherein said selected nonoligonucleotide molecule is not a DNA-binding protein.

22. The method of claim 20 wherein the identity of said nonnucleotide moiety is encoded by a nucleotide sequence comprising said single oligonucleotide conjugate.

23. The method of claim 20 further comprising isolating said single nonnaturally occurring oligonucleotide conjugate by at least one of removing said single nonnaturally occurring oligonucleotide conjugate from said mixture, removing said single nonnaturally occurring oligonucleotide conjugate from said selected nonoligonucleotide molecule, transporting said single nonnaturally occurring oligonucleotide conjugate to a sequencing apparatus, or transporting said single nonnaturally occurring oligonucleotide conjugate to an amplification vessel.

24. The method of claim 20 further comprising at least one of determining, amplifying, replicating, or transcribing a nucleotide sequence comprising said single nonnaturally occurring oligonucleotide conjugate.

25. A method of detecting a single nonoligonucleotide molecule comprising:
   (a) selecting a nonnaturally occurring oligonucleotide capable of specifically binding to a selected nonoligonucleotide molecule;
   (b) preparing a reaction mixture comprising said nonnaturally occurring oligonucleotide and said selected nonoligonucleotide molecule; and
   (c) detecting a single complex comprising said nonnaturally occurring oligonucleotide specifically bound to said selected nonoligonucleotide molecule by at least one of scanning probe microscopy, optical trapping or flow cytometry.

26. The method of claim 25 wherein said selected nonoligonucleotide molecule is not a DNA-binding protein.

27. The method of claim 25 wherein said nonnaturally occurring oligonucleotide further comprises a nonnucleotide molecule.

* * * * *